United States Patent
Campbell et al.

(10) Patent No.: US 9,796,733 B2
(45) Date of Patent: Oct. 24, 2017

(54) IMIDAZO-PYRAZINE DERIVATIVES USEFUL AS SOLUBLE GUANYLATE CYCLASE ACTIVATORS

(71) Applicant: Merck Sharp & Dohme Corp., Rahway, NJ (US)

(72) Inventors: Brian T. Campbell, Burlington, NJ (US); Guizhen Dong, Dayton, NJ (US); Joie Garfunkle, Metuchen, NJ (US); Alexander Kim, Morganville, NJ (US); Olga Ornoski, Teaneck, NJ (US); Dann L. Parker, Jr., Cranford, NJ (US); Subharekha Raghavan, Teaneck, NJ (US); Libo Xu, Bridgewater, NJ (US); Zhiquang Yang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/315,428

(22) PCT Filed: May 29, 2015

(86) PCT No.: PCT/US2015/033084
§ 371 (c)(1),
(2) Date: Dec. 1, 2016

(87) PCT Pub. No.: WO2015/187470
PCT Pub. Date: Dec. 10, 2015

(65) Prior Publication Data
US 2017/0107236 A1    Apr. 20, 2017

Related U.S. Application Data

(60) Provisional application No. 62/007,440, filed on Jun. 4, 2014.

(51) Int. Cl.
| | | |
|---|---|---|
| *C07D 487/04* | (2006.01) | |
| *C07D 519/00* | (2006.01) | |
| *A61K 31/519* | (2006.01) | |
| *A61K 45/06* | (2006.01) | |
| *A61K 31/5377* | (2006.01) | |
| *A61K 31/541* | (2006.01) | |

(52) U.S. Cl.
CPC .......... *C07D 519/00* (2013.01); *A61K 31/519* (2013.01); *A61K 31/5377* (2013.01); *A61K 31/541* (2013.01); *A61K 45/06* (2013.01)

(58) Field of Classification Search
CPC .................................................. C07D 487/04
See application file for complete search history.

(56) References Cited

U.S. PATENT DOCUMENTS

| | | |
|---|---|---|
| 6,743,798 B1 | 6/2004 | Straub et al. |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |
| 9,216,978 B2 | 12/2015 | Follmann et al. |
| 9,284,301 B2 | 3/2016 | Schmidt et al. |

(Continued)

FOREIGN PATENT DOCUMENTS

| | | |
|---|---|---|
| WO | WO2015088885 A1 | 6/2015 |
| WO | WO2015088886 A1 | 6/2015 |

OTHER PUBLICATIONS

Follmann, N. et al, The Chemistry and Biology of Soluble Guanylate Cyclase Stimulators and Activators, Angewandte Chemie-International Edition, 2013, pp. 9442-9462, vol. 52 Issue 36.

(Continued)

*Primary Examiner* — Bruck Kifle
(74) *Attorney, Agent, or Firm* — Eric A. Meade; Catherine D. Fitch

(57) ABSTRACT

A compound of Formula II or a pharmaceutically acceptable salt thereof, are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula II, or a pharmaceutically acceptable salt thereof, for their use in the therapy and prophylaxis of the abovementioned diseases and for preparing pharmaceuticals for this purpose, and to pharmaceutical preparations which comprise compounds of Formula II or a pharmaceutically acceptable salt thereof.

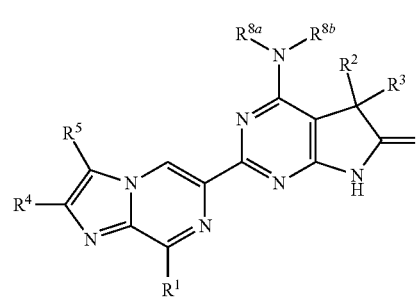

18 Claims, No Drawings

(56) References Cited

U.S. PATENT DOCUMENTS

| | | |
|---|---|---|
| 9,365,574 B2 | 6/2016 | Raghavan et al. |
| 2010/0222323 A1 | 9/2010 | Mitchell et al. |
| 2011/0218202 A1 | 9/2011 | Brockunier et al. |
| 2013/0072492 A1 | 3/2013 | Raghavan et al. |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2016/0145272 A1 | 5/2016 | Berger et al. |

OTHER PUBLICATIONS

International Search and Written Opinion for PCT/US2015/033084, mailed Aug. 14, 2015, 6 pages.

PubChem. Substance for SID 120484509, Retrieved from Internet Jul. 30, 2015. <URL: https://pubchem.ncbi.nih.gov/substance/120484509, Available Apr. 25, 2011, pp. 1-5.

IMIDAZO-PYRAZINE DERIVATIVES USEFUL AS SOLUBLE GUANYLATE CYCLASE ACTIVATORS

CROSS REFERENCE TO RELATED APPLICATIONS

This application is a U.S. National Phase application under 35 U.S.C. §371 of PCT Application No. PCT/US2015/033084, filed May 29, 2015, which claims priority under 35 U.S.C. §119(e) from U.S. Provisional Application No. 62/007,440, filed Jun. 4, 2013.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are each composed of an $\alpha$ and a $\beta$ subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of soluble guanylate cyclase and are therefore suitable for the therapy and prophylaxis of disorders which are associated with a low cGMP level.

SUMMARY OF THE INVENTION

The present invention relates to compounds which activate soluble guanylate cyclase and are valuable pharmaceutically active compounds for the therapy and prophylaxis of diseases, for example for cardiovascular diseases such as hypertension, heart failure, pulmonary hypertension, angina pectoris, diabetes, cardiac insufficiency, thrombosis, chronic kidney disease, fibrosis or atherosclerosis. The compounds of Formula I

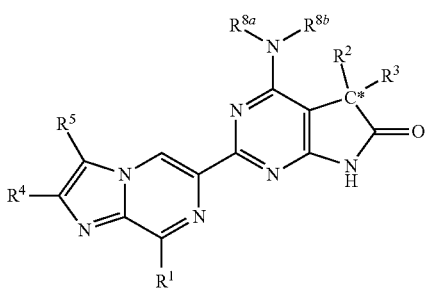

are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, to their use for the therapy and prophylaxis of the abovementioned diseases and for preparing pharmaceuticals for this purpose, and to pharmaceutical preparations which comprise compounds of Formula I.

DETAILED DESCRIPTION OF THE INVENTION

The present invention is directed to compounds having structural Formula I

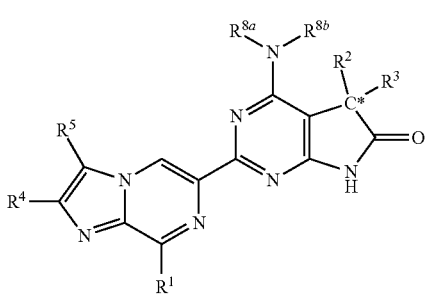

or a pharmaceutically acceptable salt thereof wherein C* indicates a potential chiral carbon atom;
$R^1$ is
(1) hydrogen,
(2) $(C_{1-6})$alkyl,
(3) halo$(C_{1-6})$alkyl,
(4) $(C_{1-6})$alkyl-$(C_{3-7})$cycloalkyl,
(5) $(C_{1-6})$alkyl-aryl, wherein aryl is unsubstituted or substituted by cyano, $(C_{3-6})$cycloalkyl, $(C_{1-6})$alkoxy, or one to three halo,
(6) aryl unsubstituted or substituted by cyano, $(C_{3-6})$cycloalkyl, $(C_{1-6})$alkoxy, or one to three halo, or
(7) $(C_{3-6})$cycloalkyl;
$R^2$ is
(1) $(C_{1-6})$alkyl,
(2) $(C_{1-6})$alkoxy, or
(3) $(C_{3-7})$cycloalkyl;
$R^3$ is
(1) $(C_{1-6})$alkyl,
(2) $(C_{3-6})$cycloalkyl,
(3) $CO_2(C_{1-6})$alkyl,
(4) $CONR^{6a}R^{6b}$,
(5) —N(H)C(O)$(C_{1-6})$alkyl,
(6) —N(H)$(C_{1-6})$alkyl,
(7) aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo,
(8) five- or six-membered heteroaryl containing one, two or three heteroatoms independently selected from N, O and S, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo, or
(9) $(C_{2-6})$alkynyl;
$R^4$ is
(1) hydrogen,
(2) $(C_{1-6})$alkyl,
(3) halo$(C_{1-6})$alkyl,
(4) halo$(C_{1-6})$alkoxy,
(5) $(C_{1-6})$alkoxy,
(6) $(C_{3-7})$cycloalkyl, or
(7) cyano;
$R^5$ is
(1) hydrogen,
(2) $(C_{1-6})$alkyl,
(3) halo$(C_{1-6})$alkyl,
(4) halo,
(5) amino,
(6) $(C_{1-3})$alkyl-aryl,
(7) $(C_{1-3})$alkyl-$(C_{3-6})$cycloalkyl,
(8) cyano, or
(9) —C(O)O—$(C_{1-3})$alkyl;
each $R^{6a}$ and $R^{6b}$ are independently
(1) hydrogen,
(2) $(C_{1-3})$alkyl, or
(3) $(C_{3-6})$cycloalkyl;
$R^{8a}$ and $R^{8b}$ are independently
(1) hydrogen,
(2) $(C_{1-6})$alkyl,
(3) halo$(C_{1-6})$alkyl,
(4) $(C_{1-6})$alkyl-C(O)—O—$(C_{1-6})$alkyl,
(5) $(C_{3-6})$cycloalkyl, unsubstituted or substituted by one to two halo,
(6) $(C_{1-3})$alkyl-$(C_{3-6})$cycloalkyl, or
(7) —$(C_{1-3})$alkyl-O—$(C_{1-3})$alkyl;
or $R^{8a}$ and $R^{8b}$ along with the nitrogen atom to which they are attach cyclize to form a 4- to 6-membered heterocyclyl containing one or two heteroatoms independently selected from N, O and S, wherein the heterocyclyl is unsubstituted or substituted by one to three $R^9$; and
$R^9$ is
(1) $(C_{1-3})$alkyl,
(2) halo,
(3) halo$(C_{1-3})$alkyl,
(4) $(C_{3-6})$cycloalkyl, or
(5) —S(O)$_2$—$(C_{1-3})$alkyl.
In one embodiment, the present invention is directed to compounds having structural Formula II:

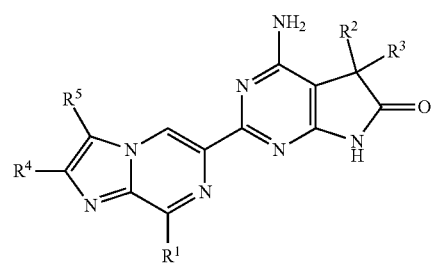

or a pharmaceutically acceptable salt thereof wherein:

$R^1$ is
(1) hydrogen,
(2) $(C_{1-6})$alkyl,
(3) halo$(C_{1-6})$alkyl,
(4) $(C_{1-6})$alkyl-$(C_{3-7})$cycloalkyl,
(5) $(C_{1-6})$alkyl-aryl, wherein aryl is unsubstituted or substituted by cyano, $(C_{3-6})$cycloalkyl, $(C_{1-6})$alkoxy, or one to three halo,
(6) aryl unsubstituted or substituted by cyano, $(C_{3-6})$cycloalkyl, $(C_{1-6})$alkoxy, or one to three halo, or
(7) $(C_{3-6})$cycloalkyl;

$R^2$ is
(1) $(C_{1-6})$alkyl,
(2) $(C_{1-6})$alkoxy, or
(3) $(C_{3-7})$cycloalkyl;

$R^3$ is
(1) $(C_{1-6})$alkyl,
(2) $(C_{3-6})$cycloalkyl,
(3) $CO_2(C_{1-6})$alkyl,
(4) $CONR^{6a}R^{6b}$,
(5) —N(H)C(O)$(C_{1-6})$alkyl,
(6) —N(H)$(C_{1-6})$alkyl,
(7) aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo,
(8) five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo, or
(9) $(C_{2-6})$alkynyl, $R^4$ is
(1) hydrogen,
(2) $(C_{1-6})$alkyl,
(3) halo$(C_{1-6})$alkyl,
(4) $(C_{1-6})$alkoxy,
(5) halo$(C_{1-6})$alkoxy,
(6) $(C_{3-7})$cycloalkyl, or
(7) cyano;

$R^5$ is
(1) hydrogen,
(2) $(C_{1-6})$alkyl,
(3) halo$(C_{1-6})$alkyl,
(4) halo,
(5) amino,
(6) $(C_{1-3})$alkyl-aryl,
(7) $(C_{1-3})$alkyl-$(C_{3-6})$cycloalkyl, or
(8) cyano; and each $R^{6a}$ and $R^{6b}$ are independently
(1) hydrogen,
(2) $(C_{1-3})$alkyl, or
(3) $(C_{3-6})$cycloalkyl.

In one embodiment of the present invention are compounds of Formula I wherein $R^1$ is hydrogen; $(C_{1-6})$alkyl; halo$(C_{1-6})$alkyl; $(C_{1-3})$alkyl-$(C_{3-6})$cycloalkyl; $(C_{1-3})$alkyl-aryl, wherein aryl is unsubstituted or substituted by cyano, $(C_{3-6})$cycloalkyl, $(C_{1-3})$alkoxy, or one to three fluoro; aryl unsubstituted or substituted by cyano, $(C_{3-6})$cycloalkyl, $(C_{1-3})$alkoxy, or one to three halo; or $(C_{3-6})$cycloalkyl. In one class of this embodiment, $R^{8a}$ is hydrogen; and $R^{8b}$ is hydrogen.

In one class of this embodiment, $R^1$ is $(C_{1-6})$alkyl or halo$(C_{1-6})$alkyl. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is hydrogen. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is $(C_{1-6})$alkyl. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is halo$(C_{1-6})$alkyl. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is $(C_{1-2})$alkyl-$(C_{3-6})$cycloalkyl. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is $(C_{1-3})$alkyl-aryl, wherein aryl is unsubstituted or substituted by cyano, $(C_{3-6})$cycloalkyl, $(C_{1-6})$alkoxy, or one to three fluoro. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is aryl unsubstituted or substituted by cyano, $(C_{3-6})$cycloalkyl, $(C_{1-6})$alkoxy, or one to three halo. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one class of this embodiment, $R^1$ is $(C_{3-6})$cycloalkyl. In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

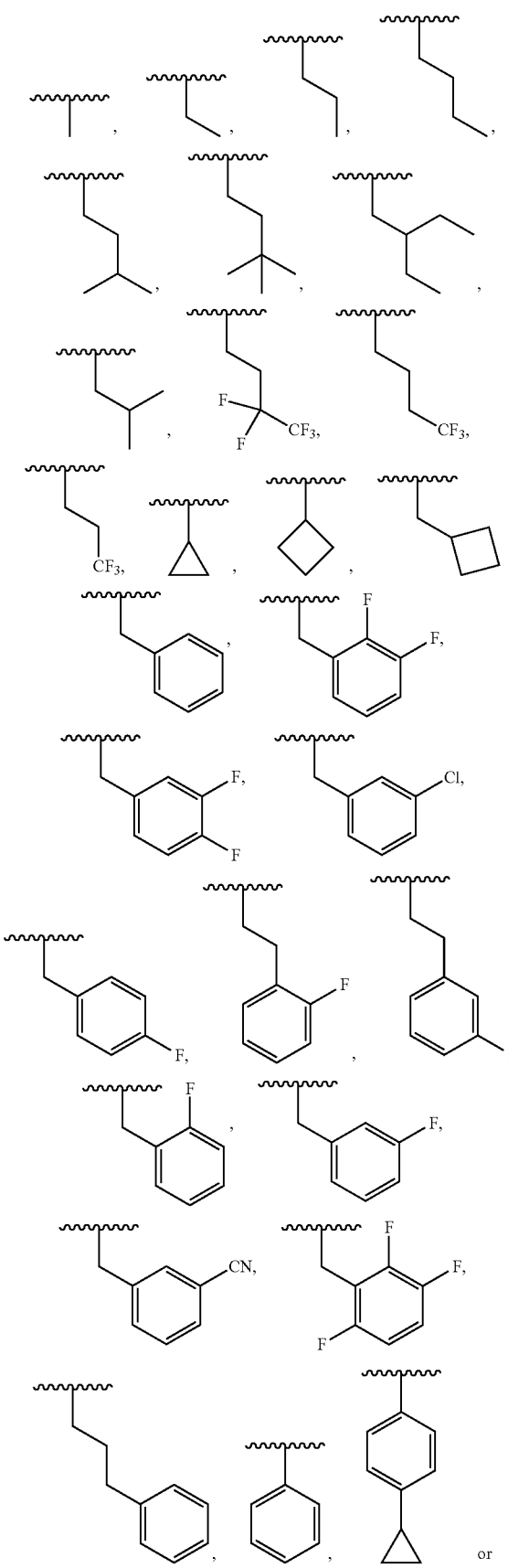

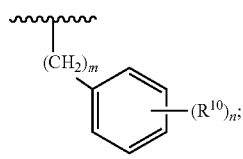

In one class of this embodiment, $R^1$ is hydrogen,
In one subclass of this class, $R^{8a}$ is hydrogen; and $R^{8b}$ is hydrogen. In a subclass of this class, $R^2$ is methyl, ethyl, isopropyl or cyclopropyl. In one sub-subclass of this subclass, $R^{8a}$ is hydrogen; and $R^{8b}$ is hydrogen. In a sub-subclass of this class, $R^4$ is hydrogen and $R^5$ is hydrogen. In one sub-sub-subclass of this sub-subclass, $R^{8a}$ is hydrogen; and $R^{8b}$ is hydrogen.

In one embodiment of the present invention are compounds of Formula I wherein $R^1$ is $R^{10}$ is cyano, $(C_{3-6})$cycloalkyl, $(C_{1-6})$alkoxy, or one to three halo; m is 1, 2, or 3; and n is 0, 1, 2, or 3. In one class of this embodiment, $R^{8a}$ is hydrogen; and $R^{8b}$ is hydrogen. In one class of this embodiment, $R^{10}$ is fluoro, chloro, cyano, cyclopropyl, or methoxy. In one subclass of this class, $R^a$ is hydrogen; and $R^{8b}$ is hydrogen. In one subclass of this class, n is 0, 1, 2 or 3 for fluoro or chloro and n is 0 or 1 for cyano, cyclopropyl or methoxy. In one sub-subclass of this subclass, $R^a$ is hydrogen; and $R^{8b}$ is hydrogen.

In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^a$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is In one class of this embodiment, $R^{8a}$ is hydrogen; and $R^{8b}$ is hydrogen. In one class of this embodiment, $R^3$ is $(C_{1-6})$ alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein R is

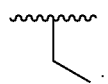

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

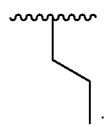

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

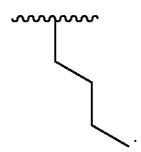 [SMILES: *CCCC]

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

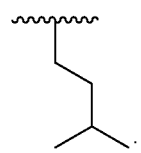 [SMILES: *CCC(C)C]

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$ alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is In one subclass of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is In one embodiment of the present invention are compounds of Formula I wherein $R^1$ is In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

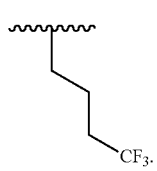CF₃.

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

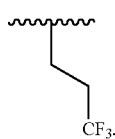CF₃.

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

.

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. In one subclass of this class, $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

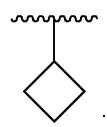.

In one class of this embodiment, $R^{8a}$ is hydrogen; and $R^{8b}$ is hydrogen. In one class of this embodiment, $R^3$ is $(C_{1-6})$alkyl. In one subclass of this class, $R^{8a}$ is hydrogen; and $R^{8b}$ is hydrogen. In one class of this embodiment, $R^3$ is $(C_{3-6})$cycloalkyl. In one subclass of this class, $R^{8a}$ is hydrogen; and $R^{8b}$ is hydrogen. In one class of this embodiment, $R^3$ is $CONR^{6a}R^{6b}$. $R^{8a}$ is hydrogen; and $R^{8b}$ is hydrogen. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one subclass of this class, $R^{8a}$ is hydrogen; and $R^{8b}$ is hydrogen. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one subclass of this class, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^1$ is

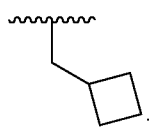 [SMILES: *CC1CCC1].

In one class of this embodiment, $R^3$ is $(C_{1-6})$alkyl. In one class of this embodiment, $R^3$ is $(C_{3-6})$cycloalkyl. In one class of this embodiment, $R^3$ is $CONR^{6a}R^{6b}$. In one class of this embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one class of this embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one class of this embodiment, $R^{8a}$ is hydrogen; and $R^{8b}$ is hydrogen. In one class of this embodiment, $R^3$ is $(C_{2-6})$alkynyl. In one subclass of this class, $R^{8a}$ is hydrogen; and $R^{8b}$ is hydrogen.

In one embodiment of the present invention are compounds of Formula I wherein $R^2$ is $(C_{1-6})$alkyl. In one class of this embodiment, $R^{8a}$ is hydrogen; and $R^{8b}$ is hydrogen. In one class of this embodiment, $R^2$ is $(C_{1-3})$alkyl. In one subclass of this class, $R^{8a}$ is hydrogen; and $R^{8b}$ is hydrogen. In one subclass of this class, $R^2$ is methyl, ethyl or isopropyl. In one sub-subclass of this subclass, $R^{8a}$ is hydrogen; and $R^{8b}$ is hydrogen.

In one embodiment of the present invention are compounds of Formula I wherein $R^2$ is $(C_{3-6})$cycloalkyl. In one class of this embodiment, $R^{8a}$ is hydrogen; and $R^{8b}$ is hydrogen. In one class of this embodiment, $R^2$ is cyclopropyl. In one subclass of this class, $R^{8a}$ is hydrogen; and $R^{8b}$ is hydrogen.

In one embodiment of the present invention are compounds of Formula I wherein $R^2$ is methyl, ethyl, isopropyl or cyclopropyl. In one class of this embodiment, $R^{8a}$ is hydrogen; and $R^{8b}$ is hydrogen.

In one embodiment of the present invention are compounds of Formula I wherein $R^3$ is $(C_{1-6})$alkyl. In one class of this embodiment, $R^{8a}$ is hydrogen; and $R^{8b}$ is hydrogen. In one embodiment, $R^3$ is $(C_{3-6})$cycloalkyl. In one class of this embodiment, $R^{8a}$ is hydrogen; and $R^{8b}$ is hydrogen. In one embodiment, $R^3$ is $CONR^{6a}R^{6b}$. In one class of this embodiment, $R^{8a}$ is hydrogen; and $R^{8b}$ is hydrogen. In one embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo. In one class of this embodiment, $R^{8a}$ is hydrogen; and $R^{8b}$ is hydrogen. In one embodiment, $R^3$ is five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one class of this embodiment, $R^{8a}$ is hydrogen; and $R^{8b}$ is hydrogen. In one embodiment, $R^3$ is $(C_{2-6})$alkynyl. In one class of this embodiment, $R^{8a}$ is hydrogen; and $R^{8b}$ is hydrogen.

In one embodiment of the present invention are compounds of Formula I wherein $R^3$ is $(C_{1-3})$alkyl; $(C_{3-6})$cycloalkyl; $CONR^{6a}R^{6b}$; phenyl unsubstituted or substituted by $(C_{1-3})$alkyl, halo$(C_{1-3})$alkyl, $(C_{1-3})$alkoxy, halo$(C_{1-3})$alkoxy, $(C_{3-6})$cycloalkyl, $CO_2(C_{1-3})$alkyl, $CONR^{6a}R^{6b}$, or one to three halo; five-membered heteroaryl containing one to three N, O or S heteroatoms, wherein heteroaryl is unsubstituted or substituted by $(C_{1-3})$alkyl, halo$(C_{1-3})$alkyl or $(C_{3-6})$cycloalkyl; 6-membered heteroaryl containing one to two N heteroatoms, wherein heteroaryl is unsubstituted or substituted by $(C_{1-3})$alkyl, halo $(C_{1-3})$alkyl, $(C_{1-3})$alkoxy, halo $(C_{1-3})$alkoxy, $(C_{3-6})$cycloalkyl or halo, or $(C_{2-3})$alkynyl; and each $R^{6a}$ and $R^{6b}$ are independently hydrogen or $(C_{1-3})$alkyl. In one class of this embodiment, $R^{8a}$ is hydrogen; and $R^{8b}$ is hydrogen.

In one embodiment, $R^3$ is $(C_{1-3})$alkyl, $(C_{3-6})$cycloalkyl, $(C_{2-6})$alkynyl or $CONR^{6a}R^{6b}$. In one class of this embodiment, $R^2$ is methyl, ethyl, isopropyl or cyclopropyl. In one class of this embodiment, $R^3$ is

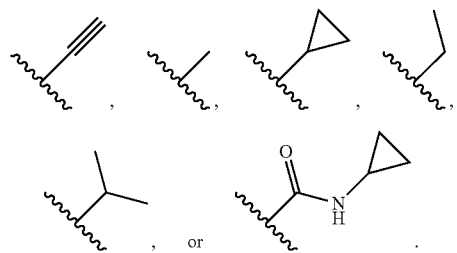

In one subclass of this class, $R^2$ is methyl, ethyl, isopropyl or cyclopropyl. In one sub-subclass of this subclass, $R^{8a}$ is hydrogen; and $R^{8b}$ is hydrogen.

In one embodiment, $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo; or five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo. In one class of this embodiment, $R^2$ is methyl, ethyl, isopropyl or cyclopropyl. In one class of this embodiment, $R^3$ is

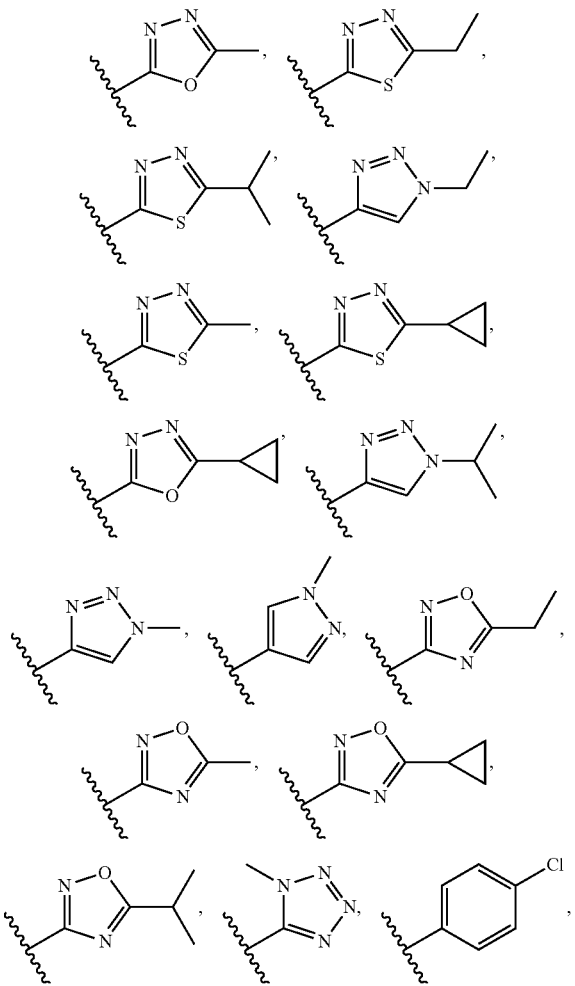

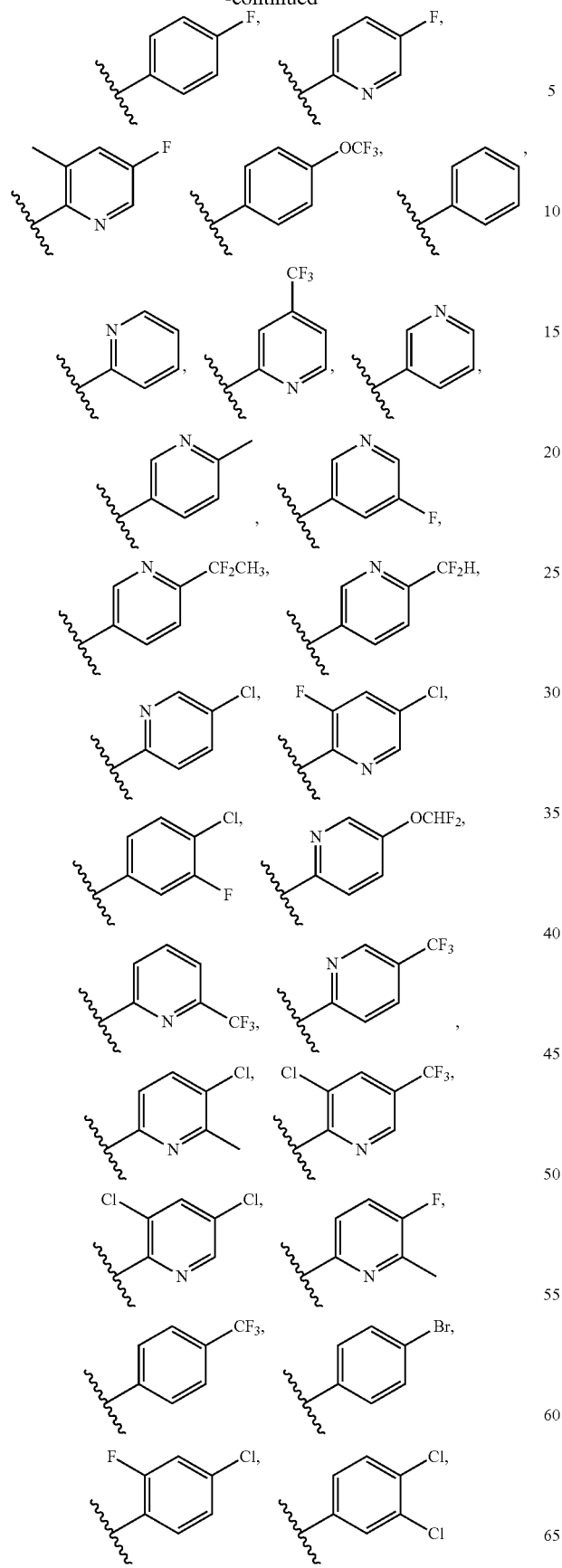
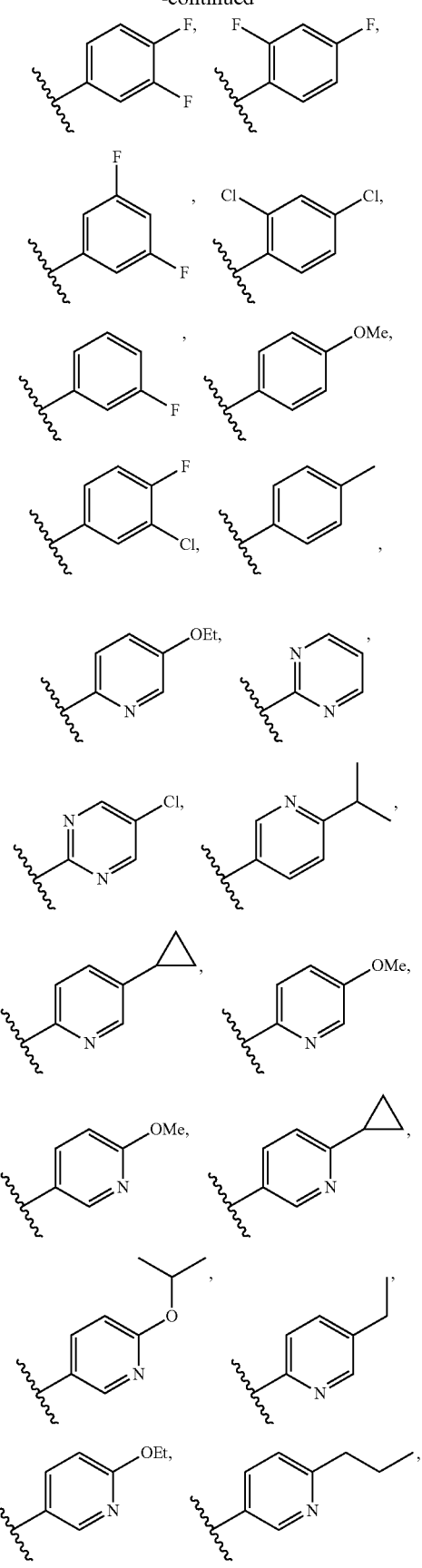

-continued
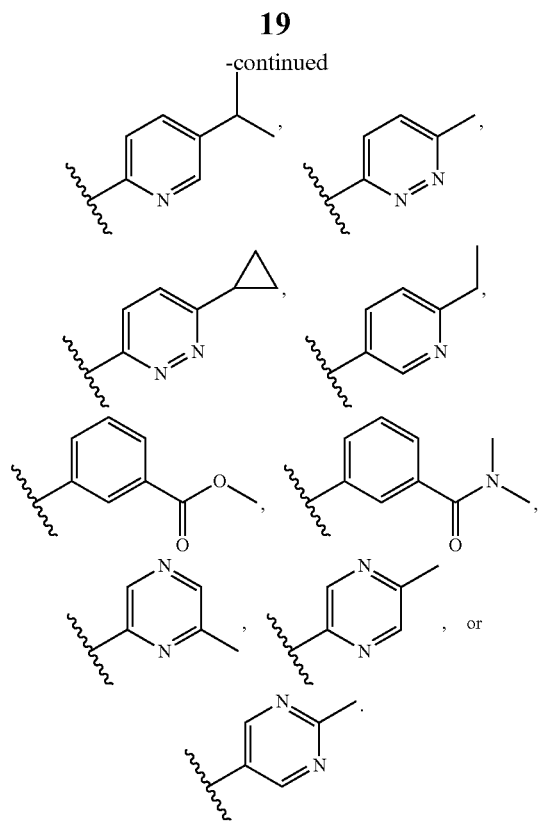
In one subclass of this class, R² is methyl, ethyl, isopropyl or cyclopropyl. In one sub-subclass of this subclass, $R^{8a}$ is hydrogen; and $R^{8b}$ is hydrogen.
In one subclass of this class,
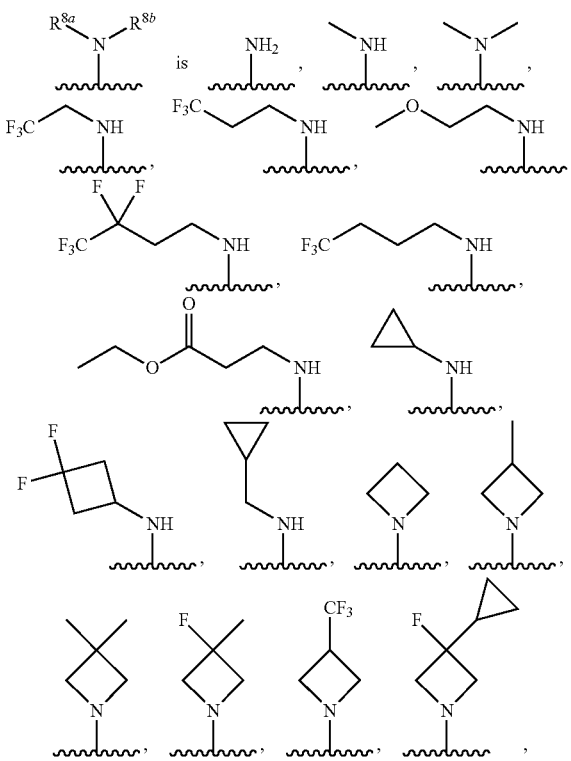
-continued
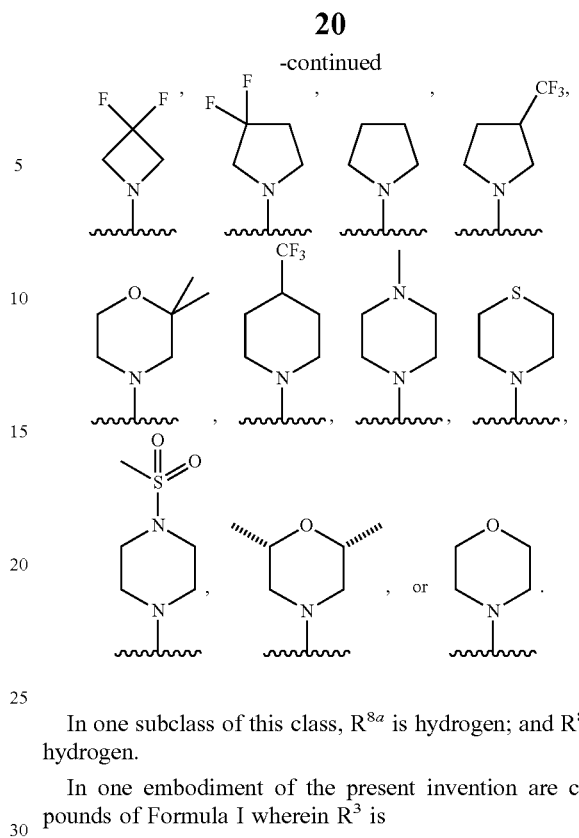
In one subclass of this class, $R^{8a}$ is hydrogen; and $R^{8b}$ is hydrogen.
In one embodiment of the present invention are compounds of Formula I wherein R³ is
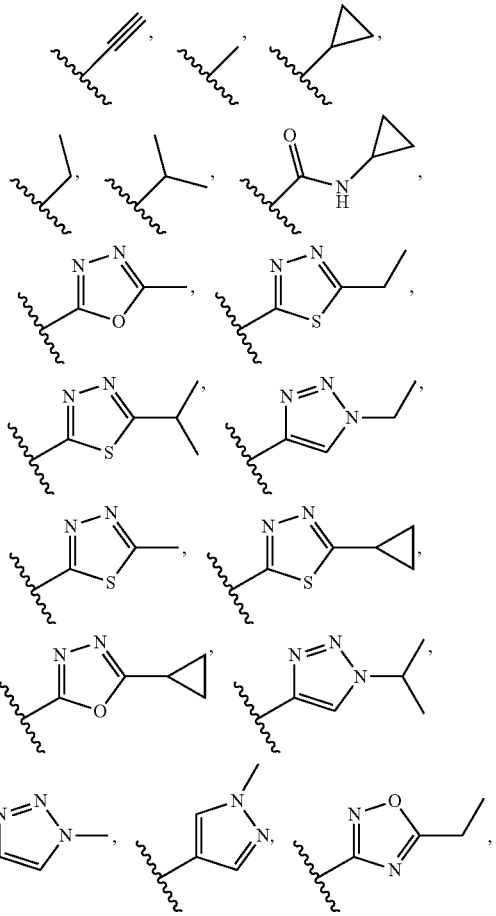

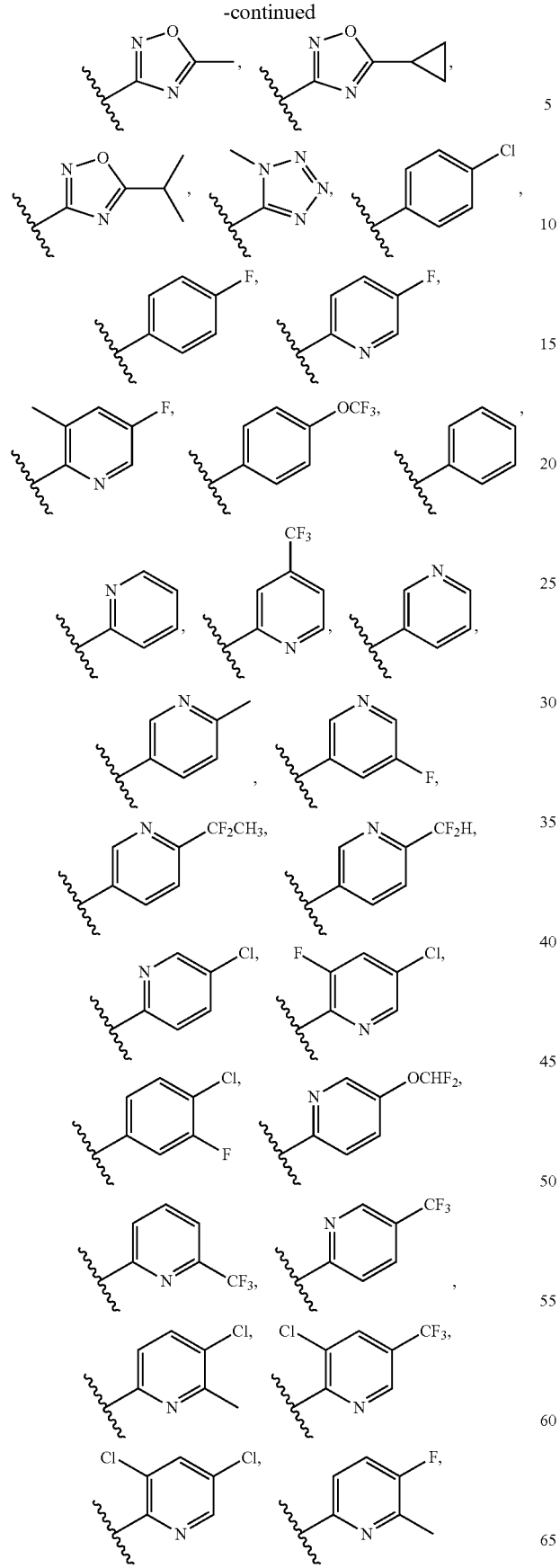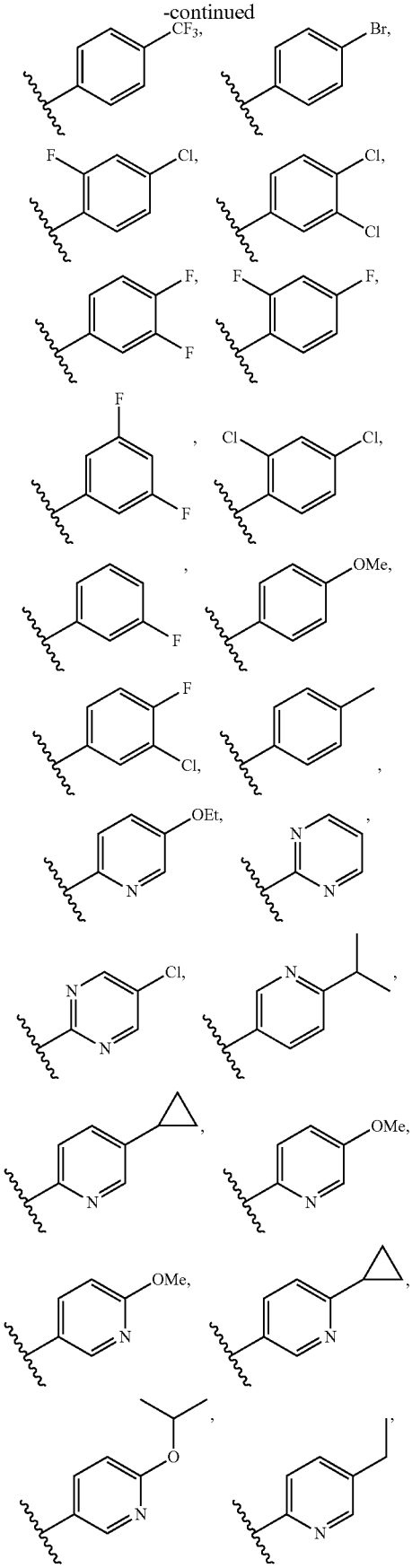

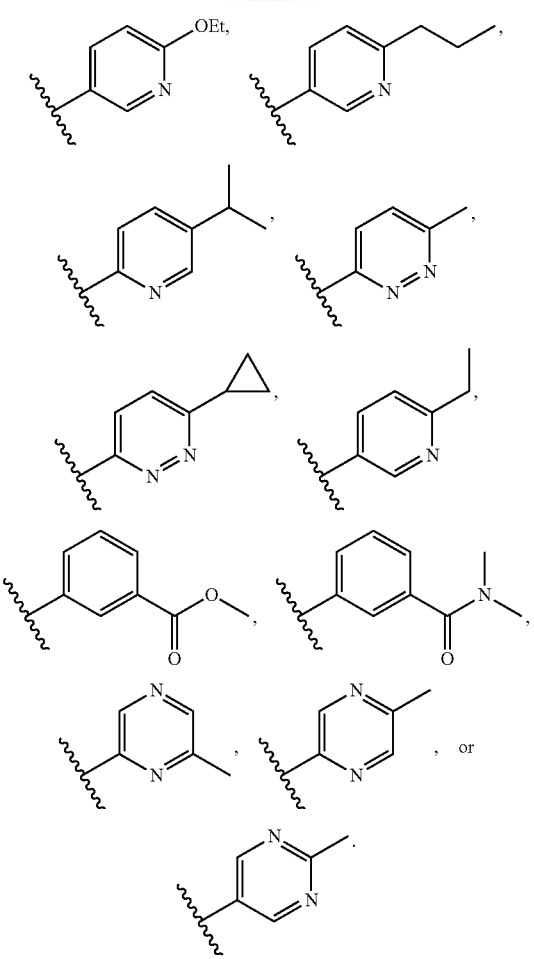
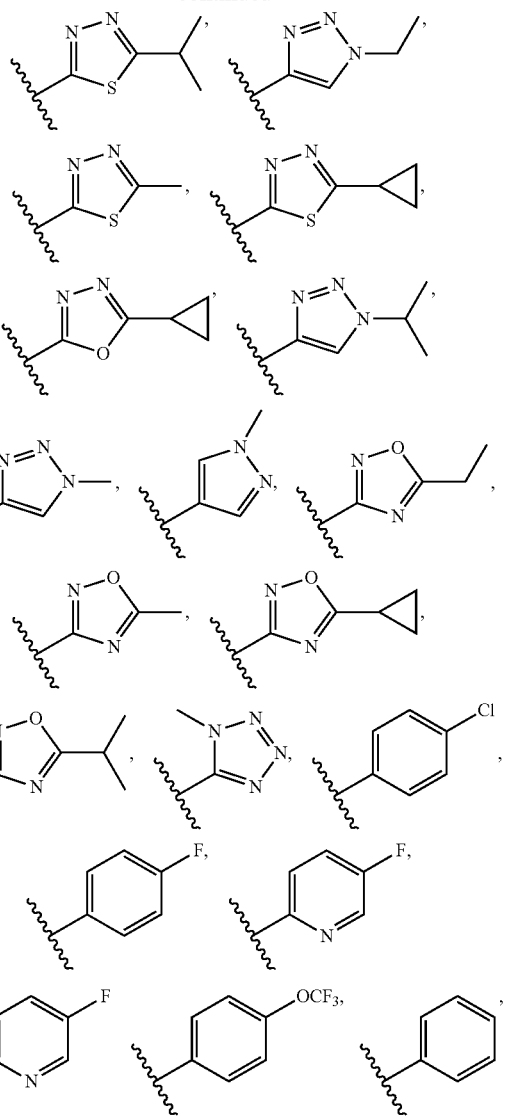
In one class of this embodiment, $R^{8a}$ is hydrogen; and $R^{8b}$ is hydrogen.
In one class of this embodiment, $R^3$ is
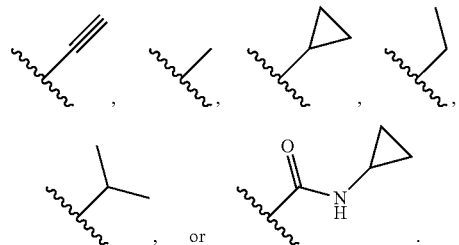
In one subclass of this class, $R^{8a}$ is hydrogen; and $R^{8b}$ is hydrogen.
In one class of this embodiment, $R^3$ is
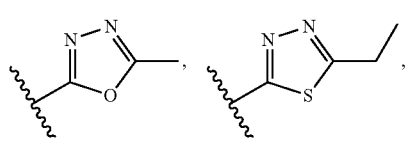

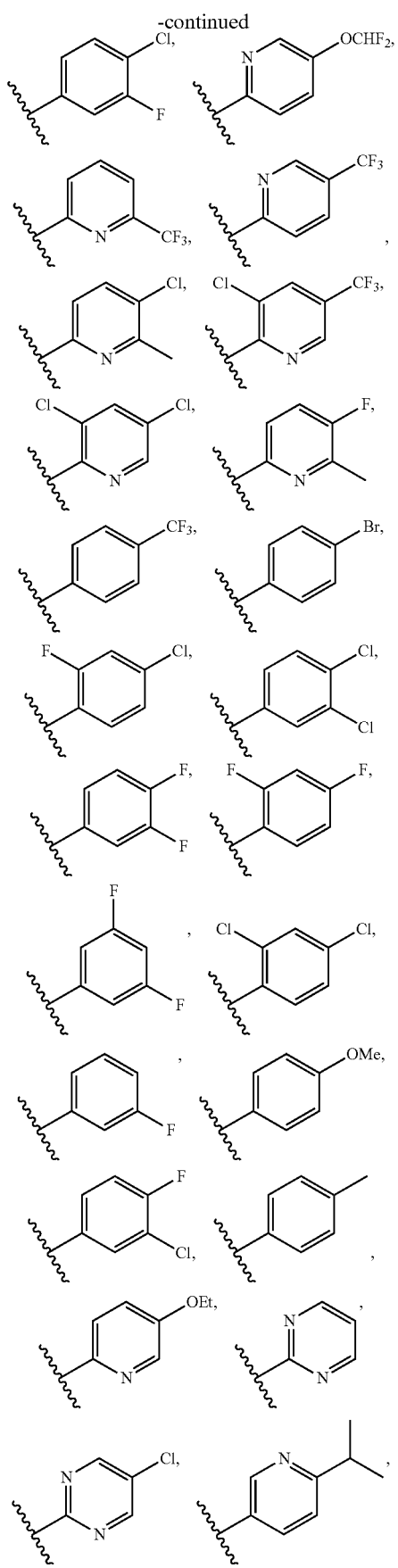
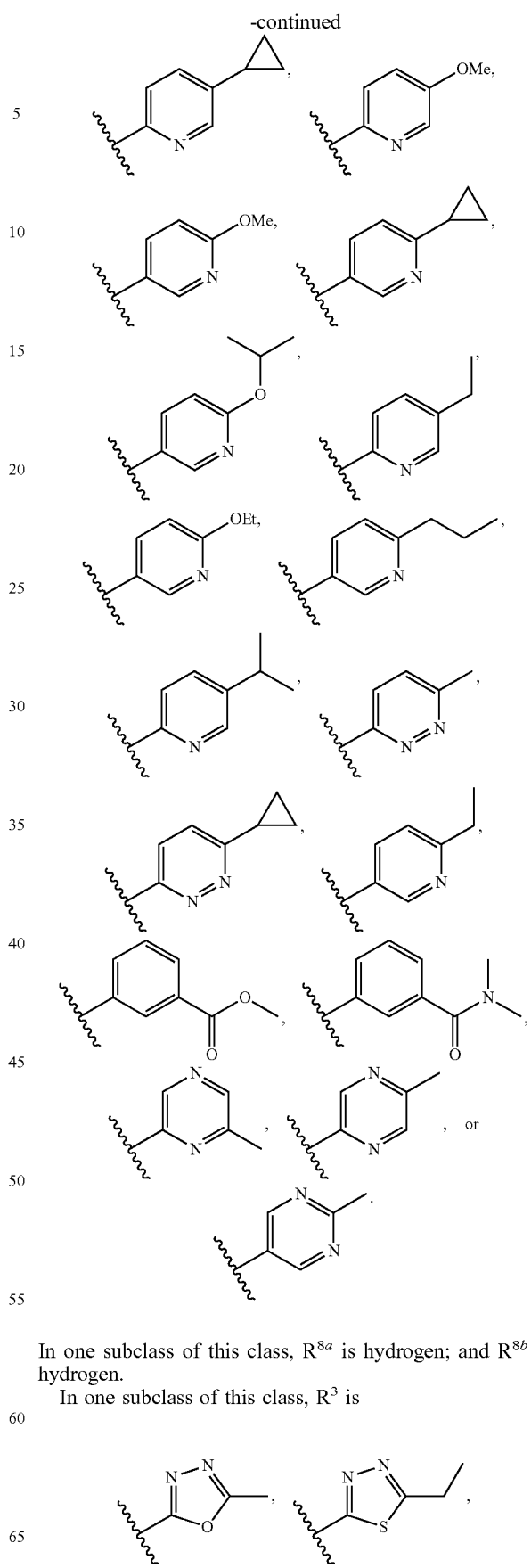
In one subclass of this class, $R^{8a}$ is hydrogen; and $R^{8b}$ is hydrogen.
In one subclass of this class, $R^3$ is

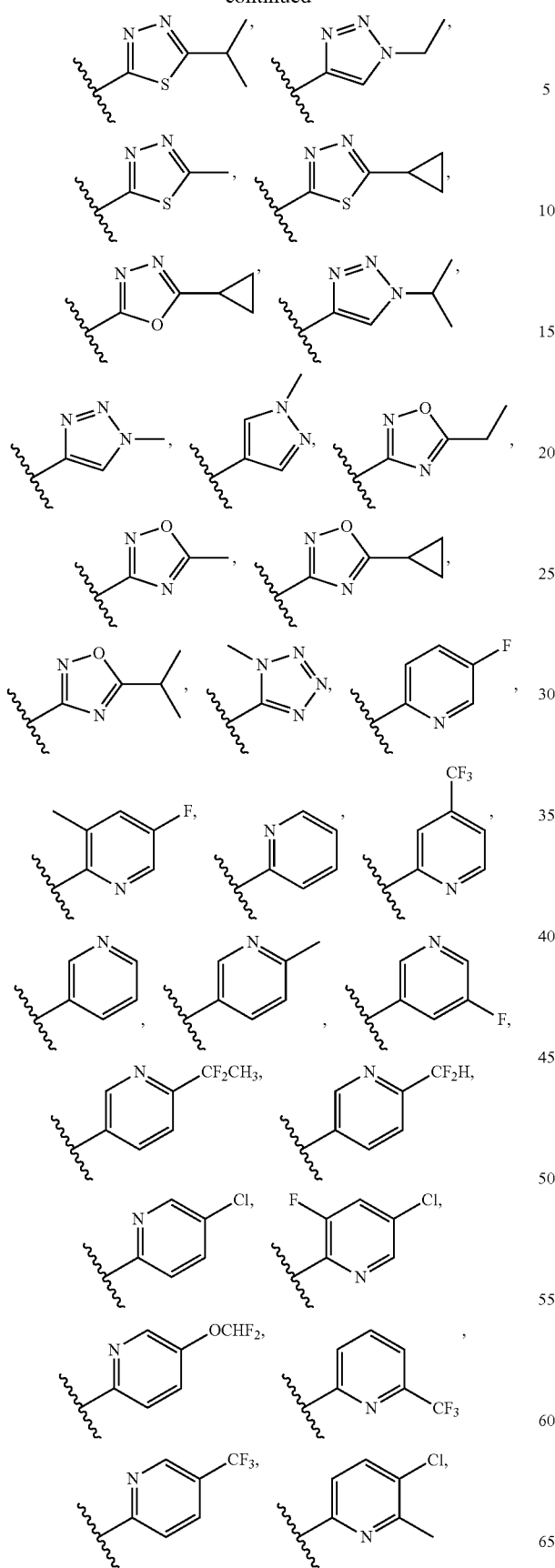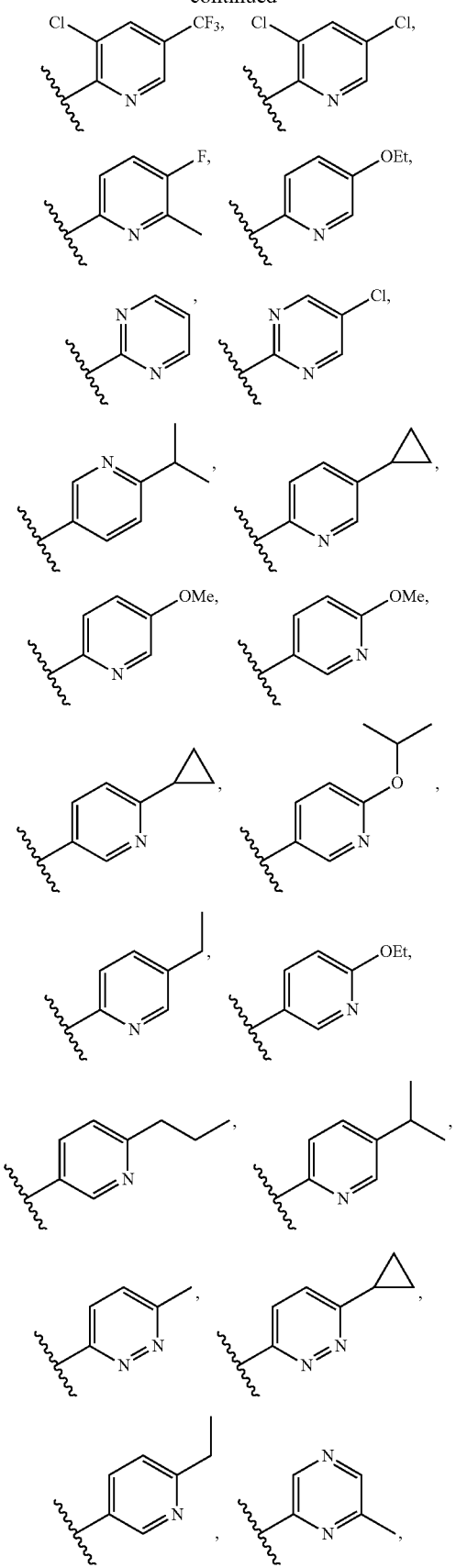

-continued
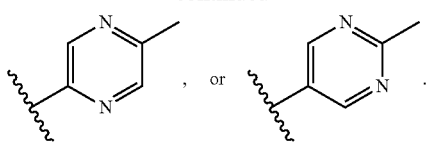
In one sub-subclass of this subclass, $R^{8a}$ is hydrogen; and $R^{8b}$ is hydrogen.
In one subclass of this class, $R^3$ is
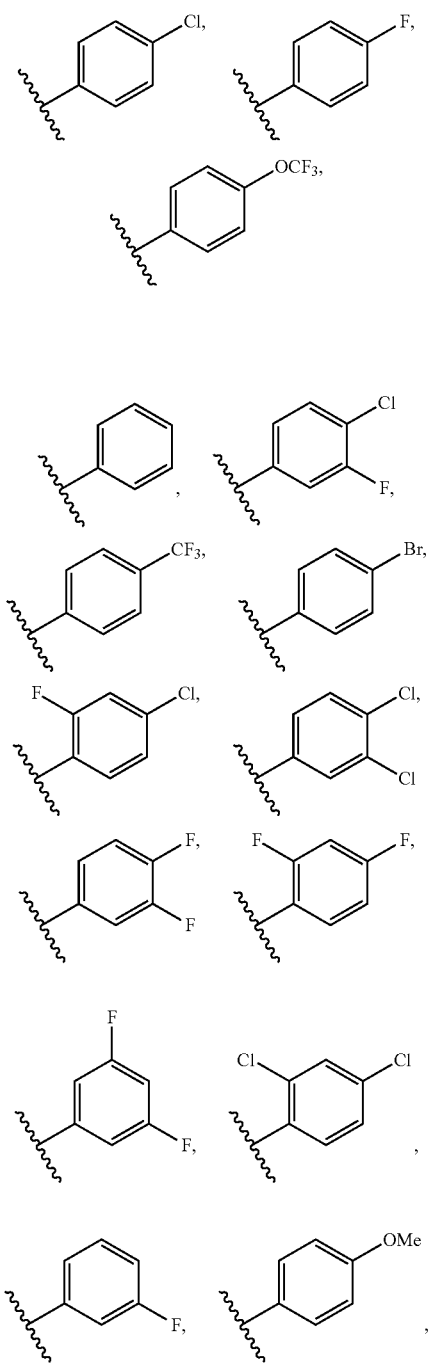
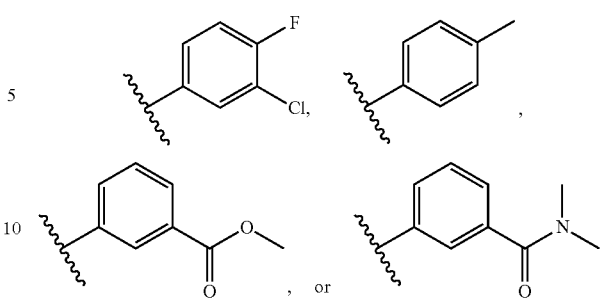
In one sub-subclass of this subclass, $R^{8a}$ is hydrogen; and $R^{8b}$ is hydrogen.
In one embodiment of the present invention are compounds of Formula I wherein
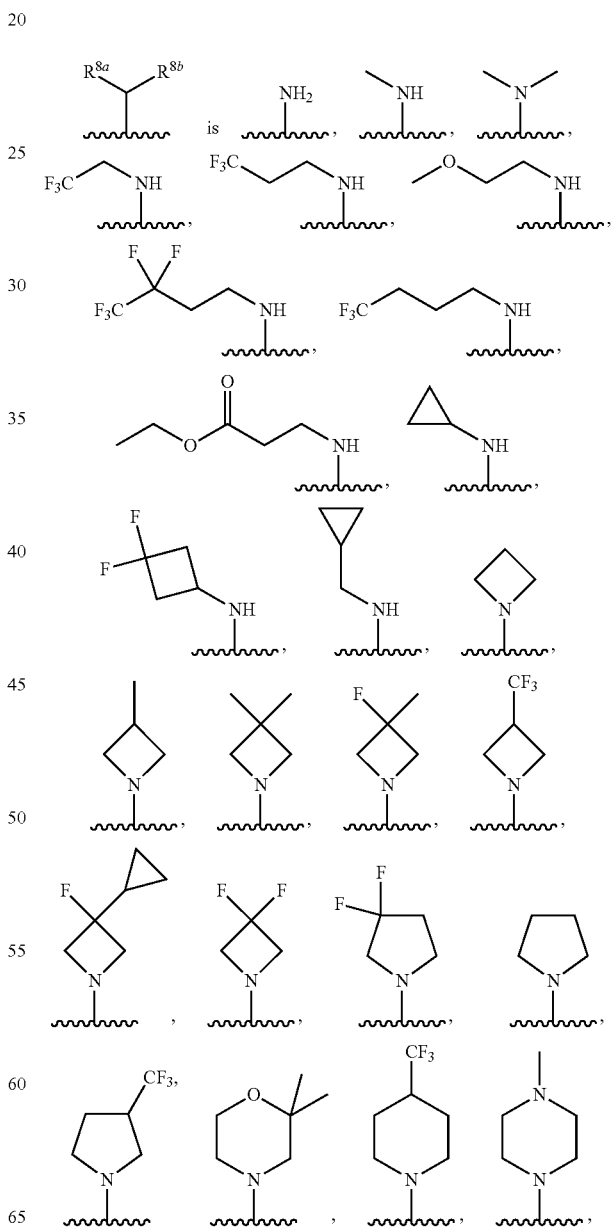

-continued

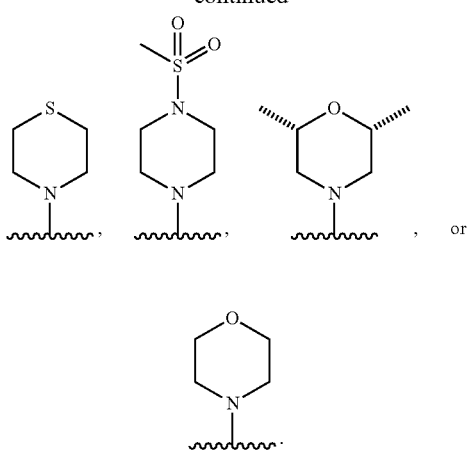

In one class of this embodiment,

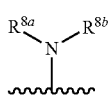

is NH$_2$.

In one class of this embodiment,

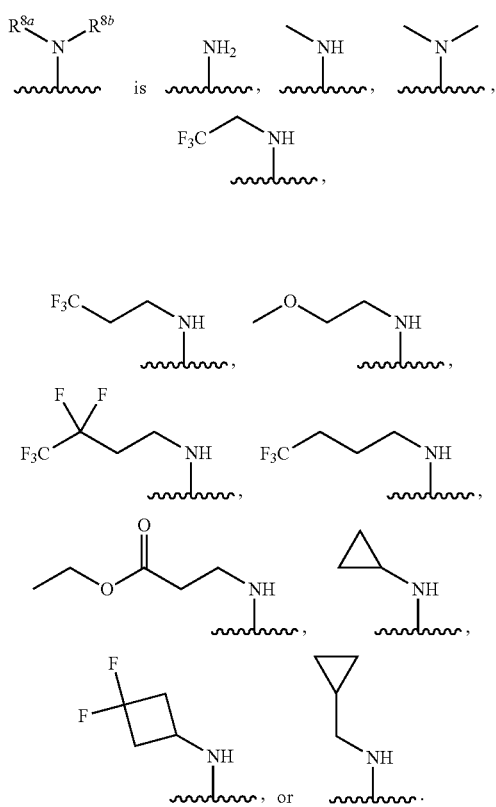

In one class of this embodiment,

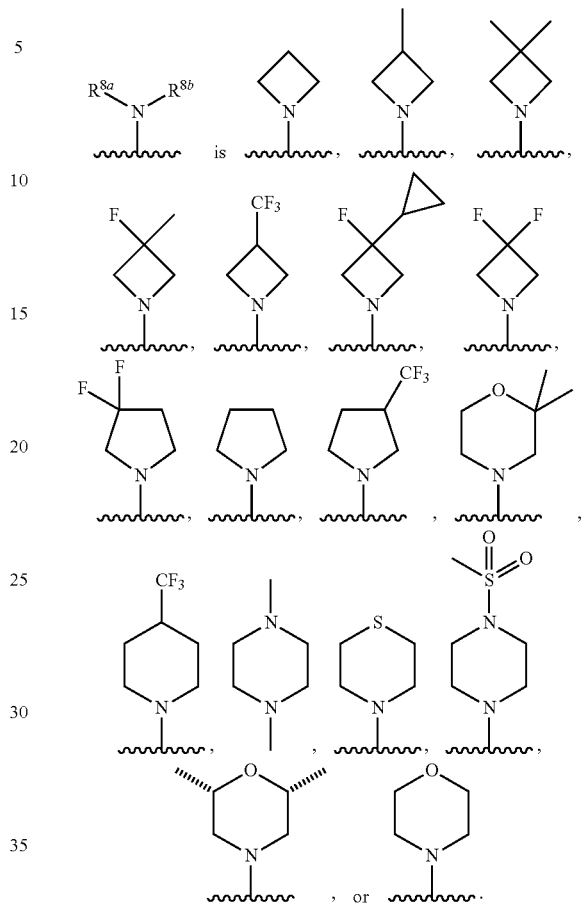

In one embodiment, $R^{8a}$ is hydrogen. In one class of this embodiment, $R^{8b}$ is $(C_{1-6})$alkyl. In one class of this embodiment, $R^{8b}$ is halo$(C_{1-6})$alkyl. In one class of this embodiment, $R^{8b}$ is $(C_{1-6})$alkyl-C(O)—O—$(C_{1-6})$alkyl. In one class of this embodiment, $R^{8b}$ is $(C_{3-6})$cycloalkyl, unsubstituted or substituted by one to two halo. In one class of this embodiment, $R^{8b}$ is $(C_{1-3})$alkyl-$(C_{3-6})$cycloalkyl. In one class of this embodiment, $R^{8b}$ is —$(C_{1-3})$alkyl-O—$(C_{1-3})$alkyl.

In one embodiment, $R^{8a}$ and $R^{8b}$ along with the nitrogen atom to which they are attach cyclize to form a 4- to 6-membered heterocyclyl containing one or two heteroatoms independently selected from N, O and S, wherein the heterocyclyl is unsubstituted or substituted by one to three $R^9$.

In one embodiment, $R^4$ is hydrogen. In one class of this embodiment, $R^{8a}$ is hydrogen; and $R^{8b}$ is hydrogen. In one embodiment, $R^4$ is $(C_{1-3})$alkyl. In one class of this embodiment, $R^{8a}$ is hydrogen; and $R^{8b}$ is hydrogen. In one embodiment, $R^4$ is halo$(C_{1-3})$alkyl. In one class of this embodiment, $R^{8a}$ is hydrogen; and $R^{8b}$ is hydrogen. In one embodiment, $R^4$ is $(C_{1-3})$alkoxy. In one class of this embodiment, $R^{8a}$ is hydrogen; and $R^{8b}$ is hydrogen. In one embodiment, $R^4$ is halo$(C_{1-3})$alkoxy. In one class of this embodiment, $R^{8a}$ is hydrogen; and $R^{8b}$ is hydrogen. In one embodiment, $R^4$ is $(C_{3-6})$cycloalkyl. In one class of this embodiment, $R^{8a}$ is hydrogen; and $R^{8b}$ is hydrogen. In one embodiment, $R^4$ is cyano. In one class of this embodiment, $R^{8a}$ is hydrogen; and $R^{8b}$ is hydrogen.

In one embodiment, $R^4$ is hydrogen, $(C_{1-3})$alkyl, $(C_{1-3})$alkoxy, $(C_{3-6})$cycloalkyl, or cyano. In one class of this embodiment, $R^{8a}$ is hydrogen; and $R^{8b}$ is hydrogen. In one class of this embodiment, $R^4$ is hydrogen, methyl, ethyl, methoxy, trifluoromethyl, cyclopropyl, or cyano. In one subclass of this class, $R^{8a}$ is hydrogen; and $R^{8b}$ is hydrogen. In one embodiment, $R^5$ is hydrogen, methyl, ethyl, bromo, chloro, amino, —$CH_2$-cyclohexyl, or benzyl. In one class of this embodiment, $R^{8a}$ is hydrogen; and $R^{8b}$ is hydrogen.

In one embodiment, $R^4$ is hydrogen. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one embodiment, $R^5$ is benzyl. In one class of this embodiment, $R^{8a}$ is hydrogen; and $R^{8b}$ is hydrogen.

In one embodiment, $R^4$ is methyl. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, $R^4$ is ethyl. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, $R^4$ is methoxy. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, $R^4$ is trifluoromethyl. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, $R^4$ is cyclopropyl. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, $R^4$ is cyano. In one class of this embodiment, $R^{8a}$ is hydrogen; and $R^{8b}$ is hydrogen. In one class of this embodiment, $R^5$ is hydrogen. In one subclass of this class, $R^{8a}$ is hydrogen; and $R^{8b}$ is hydrogen. In one class of this embodiment, $R^5$ is methyl. In one subclass of this class, $R^{8a}$ is hydrogen; and $R^{8b}$ is hydrogen. In one class of this embodiment, $R^5$ is ethyl. In one subclass of this class, $R^{8a}$ is hydrogen; and $R^{8b}$ is hydrogen. In one class of this embodiment, $R^5$ is bromo. In one subclass of this class, $R^{8a}$ is hydrogen; and $R^{8b}$ is hydrogen. In one class of this embodiment, $R^5$ is chloro. In one subclass of this class, $R^{8a}$ is hydrogen; and $R^{8b}$ is hydrogen. In one class of this embodiment, $R^5$ is amino. In one subclass of this class, $R^{8a}$ is hydrogen; and $R^{8b}$ is hydrogen. In one class of this embodiment, $R^5$ is $CH_2$-cyclohexyl. In one subclass of this class, $R^{8a}$ is hydrogen; and $R^{8b}$ is hydrogen. In one class of this embodiment, $R^5$ is benzyl. In one subclass of this class, $R^{8a}$ is hydrogen; and $R^{8b}$ is hydrogen.

In one embodiment, the invention relates to compounds of Formula I-a:

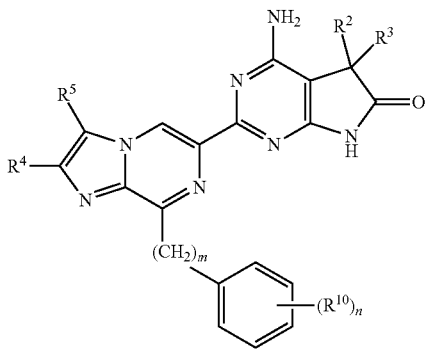

I-a or a pharmaceutically acceptable salt thereof, wherein $R^2$, $R^3$, $R^4$, $R^5$, $R^{10}$, m and n are as previously defined.

In one embodiment, the invention relates to compounds of Formula I-b:

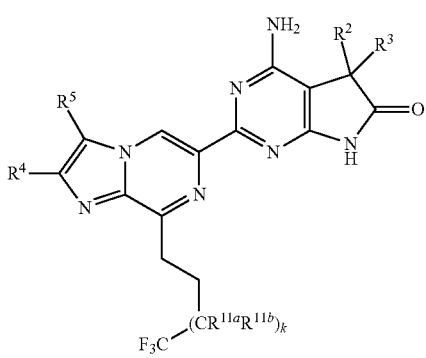

I-b or a pharmaceutically acceptable salt thereof, wherein k is 0 or 1; $R^{11a}$ and $R^{11b}$ are independently hydrogen or fluoro; and $R^2$, $R^3$, $R^4$ and $R^5$ are as previously defined.

In one embodiment, the invention relates to compounds of Formula I-c:

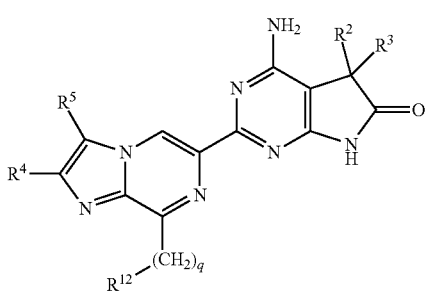

I-c or a pharmaceutically acceptable salt thereof, wherein q is 0, 1 or 2; $R^{12}$ is $(C_{1-6})$alkyl, or $(C_{3-7})$cycloalkyl; and $R^2$, $R^3$, $R^4$ and $R^5$ are as previously defined. In one class of this embodiment, $R^{12}$ is $CH_3$, $—CH(CH_2CH_3)_2$, $—CH(CH_3)_2$, $—C(CH_3)_3$, cyclohexyl, cyclobutyl, or cyclopropyl. In one subclass of this class, $R^{12}$ is $CH_3$. In one subclass of this class, $R^{12}$ is $—CH(CH_2CH_3)_2$. In one subclass of this class, $R^{12}$ is $—CH(CH_3)_2$. In one subclass of this class, $R^{12}$ is $—C(CH_3)_3$. In one subclass of this class, $R^{12}$ is cyclohexyl. In one subclass of this class, $R^{12}$ is cyclobutyl. In one subclass of this class, $R^{12}$ is cyclopropyl.

In one embodiment of this invention are compounds of Formula I, wherein the compounds exist as S and R enantiomers with respect to C*. In one class of this embodiment, the compounds of Formula I exist as an S enantiomer with respect to C*. In one class of this embodiment, the compounds of Formula I exist as a R enantiomer with respect to C*.

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I, including but not limited to Formulas I-a to I-c, or II.

As used herein except where noted, "alkyl" is intended to include both branched- and straight-chain saturated aliphatic hydrocarbon groups having the specified number of carbon atoms when noted. Commonly used abbreviations for alkyl groups are used throughout the specification, e.g. methyl may be represented by conventional abbreviations including "Me" or $CH_3$ or a symbol that is an extended bond without a defined terminal group, e.g., a methyl substituent on phenyl may be represented as:

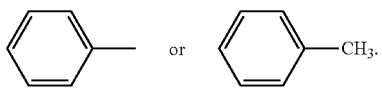

Ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. A phrase like or similar to "$C_{1-6}$ alkyl unsubstituted or substituted with 1-3 fluorine atoms" refers to alkyl groups having 0, 1, 2 or 3 fluorine atoms wherein each fluorine is attached to one or more carbon atoms.

The term "cycloalkyl" means a cyclized alkyl ring (i.e., a carbocycle) containing no heteroatoms. Examples of cycloalkyl include cyclopropyl (cPr or cyPr), cyclobutyl (cBu or cyBu), cyclopentyl, cyclohexyl, cycloheptyl, decahydronaphthyl and the like. In an embodiment, cycloalkyl is cyclopropyl or cyclobutyl, and particularly cyclopropyl.

Alkyl, alkenyl, alkynyl and cycloalkyl are each intended to include such carbon moieties containing isotopic forms of hydrogen (H) such as protium ($^1H$), for example but not limited to $—CH_3$, and/or deuterium ($^2H$, also denoted herein as D), for example but not limited to $-CD_3$.

"Heteroaryl" unless otherwise indicated, means a mono- or bicyclic aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyrimidyl, pyridazinyl, pyrazinyl, and the like. Heteroaryl also includes a bicyclic ring system comprised of a mono-heteroaryl ring fused to a heterocyclic ring or a cycloalkyl ring. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl," "heterocyclic," "heterocycle" or the like, unless otherwise indicated, means a 5- or 6-membered monocyclic non-aromatic or saturated ring containing at least one heteroatom selected from N, S and O, in which the point of attachment may be via an available carbon or nitrogen in the ring. Examples include, but are not limited to, pyrrolidinyl, piperidinyl, piperazinyl, morpholinyl, imidazolidinyl, 2,3-dihydrofuro(2,3-b)pyridyl, benzoxazinyl, oxetanyl, tetrahydrofuranyl or tetrahydropyranyl and the like. The terms also includes partially unsaturated monocyclic rings that are not aromatic, such as 2- or 4-pyridones attached through the nitrogen or N-substituted-(1H, 3H)-pyrimidine-2, 4-diones (N-substituted uracils). The terms also include such moieties in charged form, e.g., piperidinium.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^1$, $R^2$, etc.) occurs more than one time in any constituent or in Formula I or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^6$, are permitted on any available carbon atom in the ring to which the variable is attached. When a moiety is noted as being "optionally substituted" in Formulas I to I-c or II, or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formulas I to I-c or II may contain one or more asymmetric centers and can thus occur as racemates and racemic mixtures, single enantiomers, diastereoisomeric mixtures and individual diastereoisomers. Centers of asymmetry that are present in the compounds of Formula I to I-c or II can all independently of one another have S configuration or R configuration. The compounds of this invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formulas I to I-c or II.

Compounds of structural Formulas I to I-c or II may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formulas I to I-c or II may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formulas I to I-c or II described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I to I-c or II of the present invention.

In the compounds of structural Formulas I to I-c or II, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formulas I to I-c or II and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formulas I to I-c or II, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formulas I to I-c or II are meant to also include the pharmaceutically acceptable salts thereof, and also salts that are not pharmaceutically acceptable when they are used as precursors to the free compounds or their pharmaceutically acceptable salts or in other synthetic manipulations. The compounds of the present invention, including the compounds of the Examples, also includes all salts of the compounds of Formulas I to I-c or II which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formulas I to I-c or II simultaneously contain acidic and basic groups in the molecule the invention also includes, in addition to the salt forms mentioned, inner salts or betaines (zwitterions). Salts can be obtained from the compounds of Formulas I to I-c or II by customary methods which are known to the person skilled in the art, for example by combination with an organic or inorganic acid or base in a solvent or dispersant, or by anion exchange or cation exchange from other salts. The present invention also includes all salts of the compounds of Formula I to I-c or II which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I to I-c or II, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise.

The present invention also relates to processes for the preparation of the compounds of Formulas I to I-c which are described in the following and by which the compounds of the invention are obtainable.

The compounds of Formulas I to I-c or II according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formulas I to I-c or II can be examined, for example, in the activity assay described below.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formulas I to I-c or II are, for example, cardiovascular diseases, such as endothelial dysfunction, diastolic dysfunction, atherosclerosis, hypertension, heart failure, pulmonary hypertension, which includes pulmonary arterial hypertension (PAH), stable and unstable angina pectoris, thromboses, restenoses, myocardial infarction, strokes, cardiac insufficiency, fibrosis or pulmonary hypertonia, or, for example, erectile dysfunction, asthma bronchiale, chronic kidney insufficiency and diabetes. Compounds of Formulas I to I-c or II can additionally be used in the therapy of cirrhosis of the liver and also for improving a restricted memory performance or ability to learn.

The compounds of Formulas I to I-c or II and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A subject of the present invention therefore also are the compounds of Formulas I to I-c or II and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of Formulas I to I-c or II and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formulas I to I-c or II and/or its pharmaceutically acceptable salts in the pharmaceutical preparations normally is from 0.1 to 200 mg, preferably from 1 to 200 mg, per dose, but depending on the type of the pharmaceutical preparation it can also be higher. The pharmaceutical preparations usually comprise 0.5 to 90 percent by weight of the compounds of Formulas I to I-c or II and/or their pharmaceutically acceptable salts. The preparation of the pharmaceutical preparations can be carried out in a manner known per se. For this purpose, one or more compounds of Formulas I to I-c or II and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formulas I to I-c or II and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formulas I to I-c or II and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formulas I to I-c or II. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formulas I to I-c or II activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formulas I to I-c or II and salts thereof can furthermore be employed, as already mentioned above, as intermediates for the preparation of other pharmaceutically active compounds.

One or more additional pharmacologically active agents may be administered in combination with a compound of Formulas I to I-c or II. An additional active agent (or agents) is intended to mean a pharmaceutically active agent (or agents) that is active in the body, including pro-drugs that convert to pharmaceutically active form after administration, which are different from the compound of Formulas I to I-c or II, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formulas I to I-c or II in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S), 5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe); HDL-raising drugs, (e.g., niacin and nicotinic acid receptor agonists, and extended-release versions thereof; MK-524A, which is a combination of niacin extended-release and the DP-1 antagonist MK-524); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211); inhibitors of acyl coenzyme A: diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I to I-c or II are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula I at the same positions on the structures.

SCHEME 1

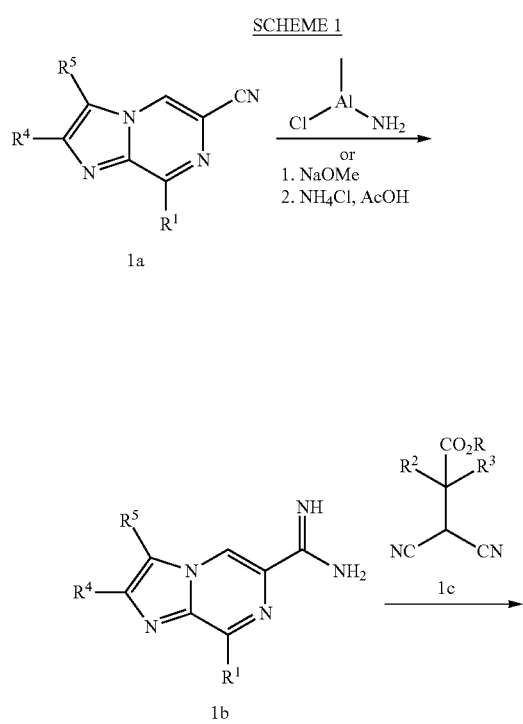

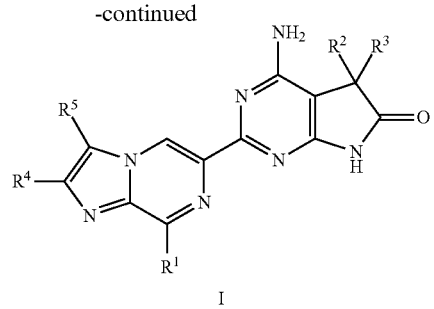

Compounds of Formula I can be prepared from the nitrile precursor (1a) as outlined in Scheme 1. Conversion of the imidazo[1,2-a]pyrazine nitrile 1a to the amidine intermediate 1b can be accomplished with a reagent such as amino(chloro)methylaluminum, prepared from trimethylaluminum and ammonium chloride, in a non-polar solvent such as toluene at elevated temperature as described by Garigipati, R. S. et al *Tetrahedron Letters* 1990, 31(14), 1969. The nitrile 1a can also be converted to the amidine 1b by using sodium methoxide in methanol to form the imidate which can then be transformed to the amidine 1b using ammonium chloride and acetic acid as described by Pinner, A. et al, *Ber. Dtsch. Chem. Ges.* 1877, 10, 1889. Treatment of the amidine 1b with a suitable malononitrile intermediate 1c in an alcoholic solvent such as t-BuOH, EtOH, or MeOH, in the presence of a suitable base such as $NaHCO_3$, $KHCO_3$, $Na_2CO_3$ at elevated temperature provides compounds with Formula I. The reactions in Scheme 1 may also be carried out on the corresponding ester of compound 1a, and corresponding methyl, ethyl, or propyl esters of compound 1c.

SCHEME 2

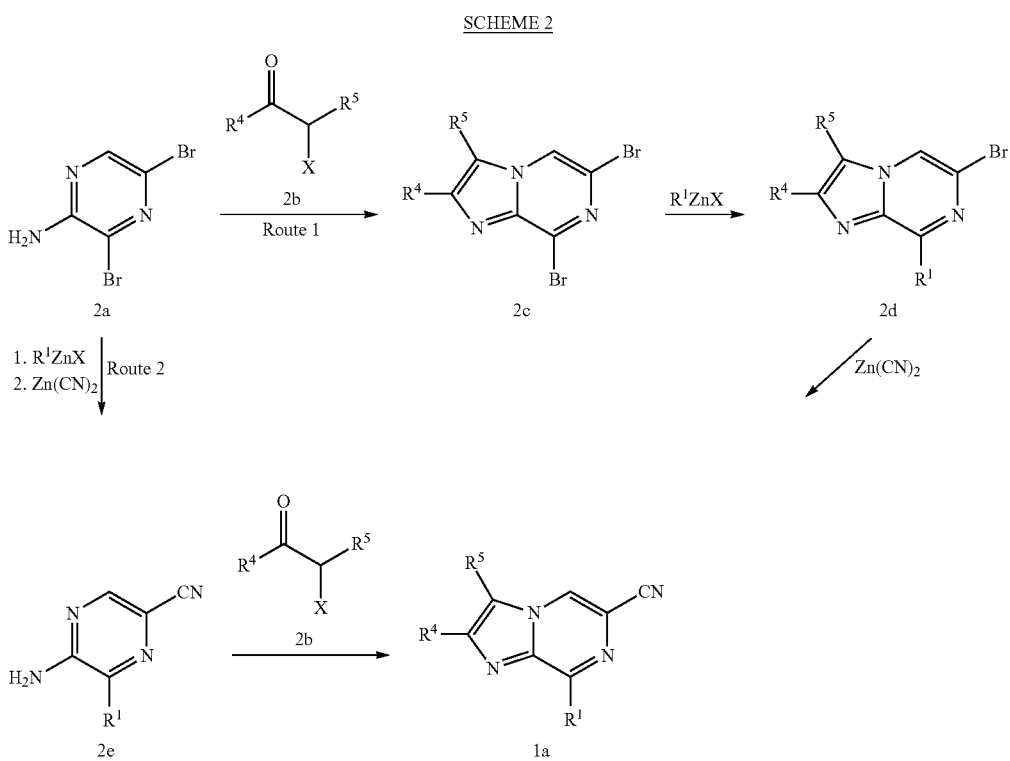

X = halo

The nitrile intermediate 1a can be prepared by two different routes as depicted in Scheme 2. In Route 1, 3,5-dibromopyrazin-2-amine (2a) can be treated with a suitable alpha haloketone reagent (2b) to afford the dibromo intermediate 2c. The dibromo intermediate 2c can be coupled to an alkylzinc reagent R₁ZnX using a palladium catalyst such as Pd(PPh₃)₂Cl₂ to give compound 2d, which can be transformed into the nitrile intermediate 1a using Zn(CN)₂ and a palladium catalyst such as Pd(dppf)Cl₂ at an elevated temperature. Alternatively in Route 2, 3,5-dibromopyrazin-2-amine (2a) can be coupled first to an alkylzinc reagent R₁ZnX using a palladium catalyst such as Pd(PPh₃)₂Cl₂, followed by treatment with Zn(CN)₂ and a palladium catalyst such as Pd(dppf)Cl₂ at an elevated temperature to afford the nitrile intermediate 2e. Compound 2e can be cyclized with a suitable alpha haloketone reagent (2b) to afford the nitrile intermediate 1a.

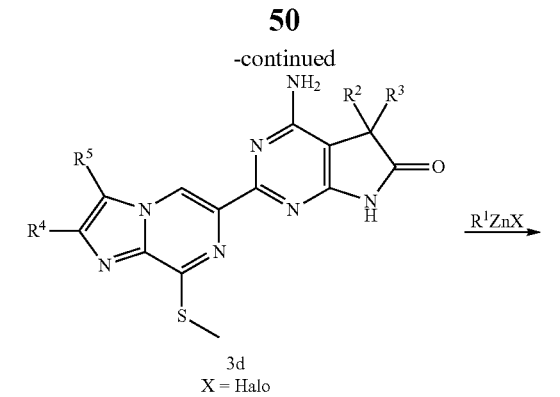

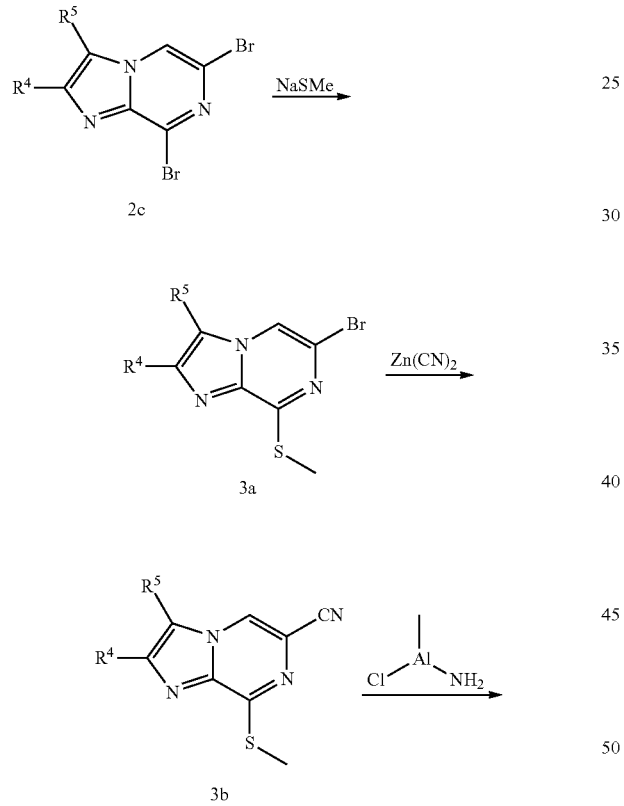

Alternatively, compounds of Formula I can be prepared as depicted in Scheme 3. The dibromo intermediate (2c) from Scheme 2 can be converted to the thiomethyl intermediate (3a) by nucleophilic displacement using sodium thiomethoxide as described by Belanger, D. B. et al. *Bioorg. Med. Chem. Lett.* 2010, 20, 5170. Compound 3b can be obtained by treatment of the intermediate 3a with a reagent such as Zn(CN)₂ in the presence of a suitable palladium catalyst such as Pd(dppf)Cl₂. The nitrile intermediate (3b) can be transformed to the amidine intermediate (3c) and subsequently cyclized with a suitable malononitrile reagent (1c) to afford the thiomethyl intermediate (3d) as described in Scheme 1. Treatment of the thiomethyl intermediate (3d) with an appropriate alkylzinc reagent in the presence of a suitable catalyst system such as Xantphos biaryl precatalyst affords compounds of Formula I.

SCHEME 4

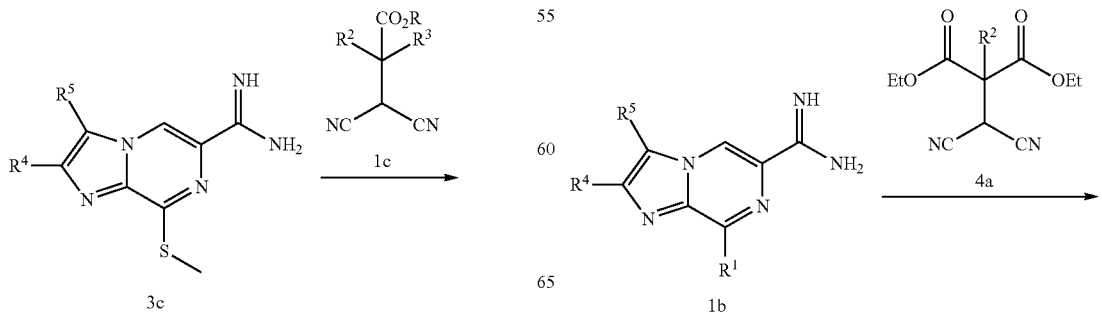

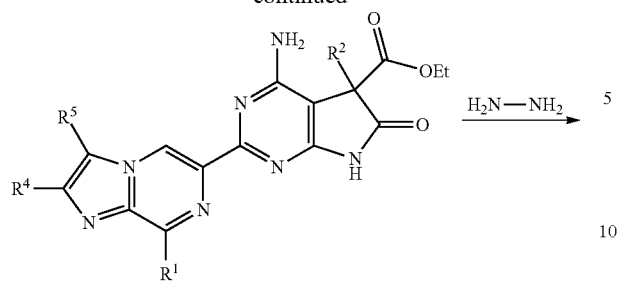

4b

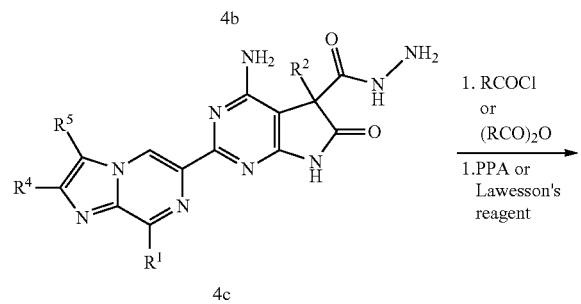

4c

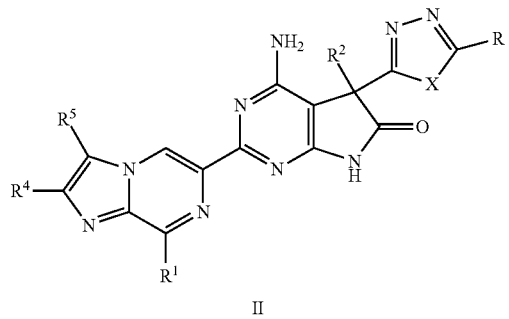

II

X = O or S

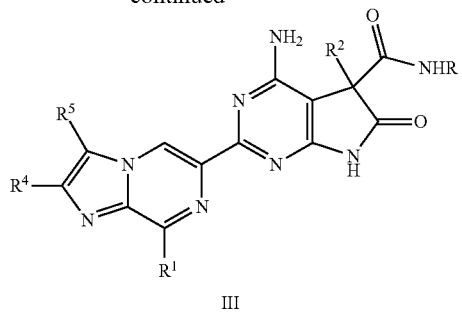

III

In one embodiment of the present invention, compounds of the Formula III may be prepared from the ester intermediate 4b as depicted in Scheme 5. Thus, treatment of the ester intermediate 4b with a suitable amine reagent $RNH_2$ either neat or in a polar solvent such as DMF at elevated temperatures affords compounds of Formula III.

SCHEME 6

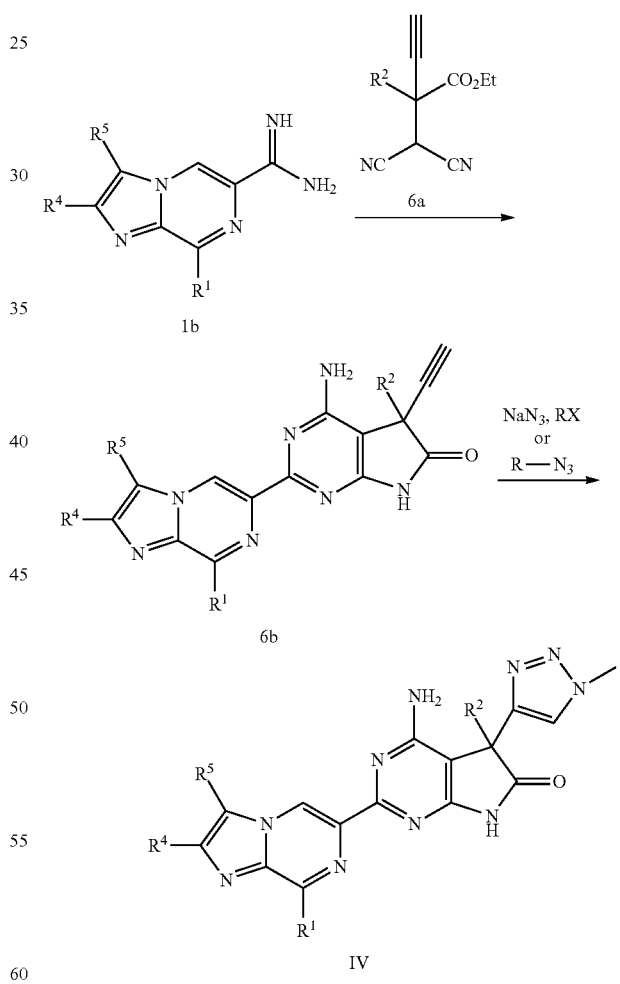

In one embodiment of the present invention, compounds with Formula II may be prepared by the sequence depicted in Scheme 4. The amidine intermediate 1b from Scheme 1 can be cyclized with a suitable diester-malononitrile intermediate (4a) to afford compound 4b. Treatment of the ester intermediate (4b) with hydrazine affords the acyl hydrazide intermediate (4c), which can be acylated with a suitable acylating reagent bearing the desired $R_6$ substitution and subsequently can be cyclized to form a 1,3,4-oxadiazole (X=O, Formula II) in the presence of a suitable condensing reagent such as phosphoric acid (PPA), or a 1,3,4-thiadiazole (X=S, Formula II) using Lawesson's reagent.

SCHEME 5

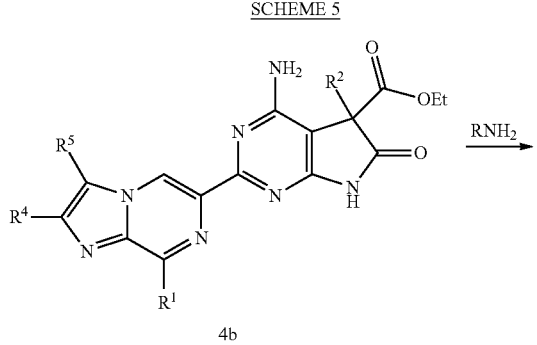

4b

In one embodiment of the present invention, compounds with Formula IV may be prepared by the sequence outlined in Scheme 6. The amidine intermediate 1b from Scheme 1 can be treated with a suitable malononitrile reagent 6a under similar conditions described for Scheme 1 to afford the alkyne intermediate 6b. The alkyne intermediate 6b can be further transformed into 1,2,3-triazoles with Formula IV by treatment with a suitable alkyl azide that is either commercially available or formed in situ from sodium azide and an alkyl bromide in the presence of a suitable copper source such as CuBr.

with a suitable malononitrile intermediate (1c) affords intermediate 7d, which can be converted to compound Ia by using methods familiar to those skilled in the art. One such method involves the treatment of 7d with a suitable coupling partner such as an alkyl zinc bromide or dialkyl zinc, in the presence of a suitable catalyst such as Pd(dppf)Cl$_2$ to afford compounds with Formula Ia.

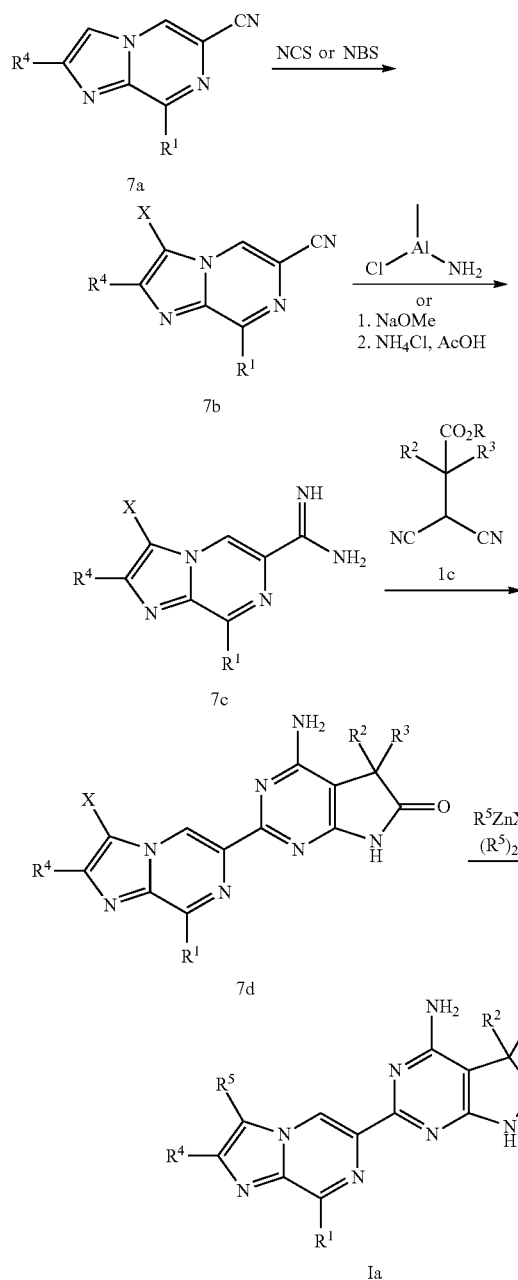

In another embodiment of the present invention, compounds of Formula Ia can be prepared by the sequences as depicted in Scheme 7A. Thus, the nitrile intermediate (7a), which is a specific form of imidazo[1,2-a]pyrazine intermediate 1a, can be halogenated using NCS, NBS, or a suitable halogenation reagent thereof. The halo-intermediate 7b can be transformed into the amidine intermediate 7c using procedures described in Scheme 1. Subsequent cyclization Alternatively, compounds of Formula Ia can be prepared by the reaction sequence as depicted in Scheme 7B. Thus, intermediate 7b can be treated with an alkyl zinc bromide or a dialkyl zinc reagent using a suitable palladium catalyst such as Pd(dppf)Cl$_2$ to afford intermediate 7e, which can be transformed to compounds of Formula Ia via intermediate 7f and the reaction with 1c as described in Scheme 1.

SCHEME 8

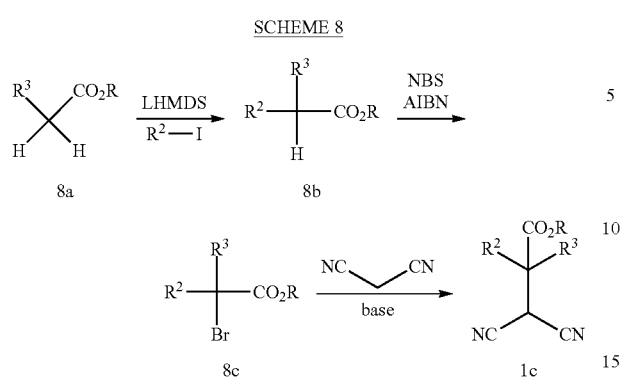

The preparation of compound 1c is outlined in Scheme 8. Deprotonation of ester 8a using a suitable base such as LiHMDS, NaHMDS, NaH or LDA in a solvent such as THF or DMF followed by treatment with an alkyl iodide affords the intermediate 8b. Treatment of intermediate 8b with a suitable brominating reagent such as NBS and AIBN in a solvent such as carbon tetrachloride at refluxing temperatures affords intermediate 8c. Intermediate 8c can be transformed to compound 1c by reaction with malononitrile in the presence of a suitable base such as NaH, t-BuOK, $K_2CO_3$ or DBU in a solvent such as THF or DMF at ambient temperature or at elevated temperature. The synthetic sequence depicted in Scheme 8 can also be similarly used to prepare the corresponding ethyl or propyl esters of compound 1c.

SCHEME 9

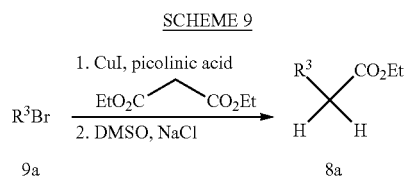

The ester (8a) can be prepared according to Scheme 9 from the corresponding carboxylic acid by one skilled in the art. The ester (8a) may also be prepared by the α-arylation/heteroarylation of esters as described by Buchwald, S. L. et al *Organic Letters* 2009, 11(8), 1773; or by Shen, H. C. et al *Organic Letters* 2006, 8(7), 1447. Commercially available aryl bromides can be converted to compound 8a (depicted as the ethyl ester) by the reaction with diethyl malonate in the presence of a suitable catalyst system such as CuI and picolinic acid, followed by decarboxylation at elevated temperature.

SCHEME 10

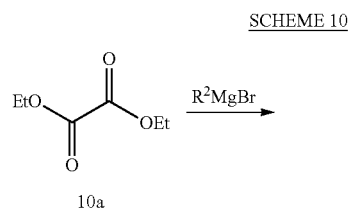

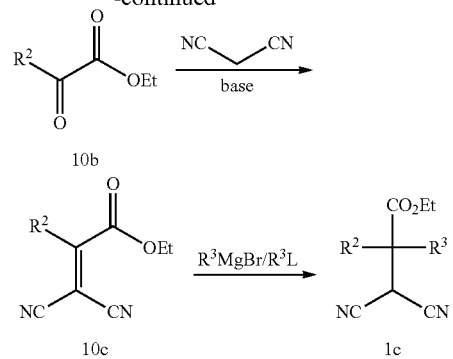

In addition to the method described in Scheme 8, intermediates 1c, depicted as the ethyl ester, may also be prepared as shown in Scheme 10. Thus, treatment of diethyl oxalate with a suitable aryl magnesium bromide (with or without lithium chloride additive) or the lithiate of heteroaryl reagents derived via metal-halogen exchange in a suitable solvent such as THF affords compound 10b. Treatment of compound 10b with malononitrile and a suitable base such as piperidine in a solvent such as EtOH at elevated temperature affords compound 10c. Compound 10c, upon treatment with a suitable alkyl magnesium bromide (with or without lithium chloride additive) in a solvent such as THF affords compound 1c. The reaction sequence could also be carried out by treating compound 10a with an alkyl magnesium bromide to afford compound 10b in which R2 is alkyl, and treating compound 10c with an aryl magnesium bromide, either commercial or generated in situ from the bromide precursor, or the lithiate of heteroaryl reagents derived via metal-halogen exchange in a suitable solvent such as THF to afford compound 1c.

Compounds with N-alkyl substitutions in which $R^6$ and $R^7$ are not hydrogen can be prepared as shown in Scheme 11. Treatment of I with a suitable diazotizing reagent such as tert-butyl nitrite or isopentyl nitrite in a non-polar solvent such as 1,2-DCE or DMF in the presence of excess copper (II) chloride or copper(II) bromide can provide the respective halogenated intermediate 11a. Treatment of the halogen intermediate (11a) with an excess of amine $HNR^6R^7$ in a suitable solvent, such as 1,2-DCE, DMF, DMA, MeOH or THF, with or without a base additive at elevated temperatures may result in the conversion of 11 to compounds of formula Ia.

SCHEME 11

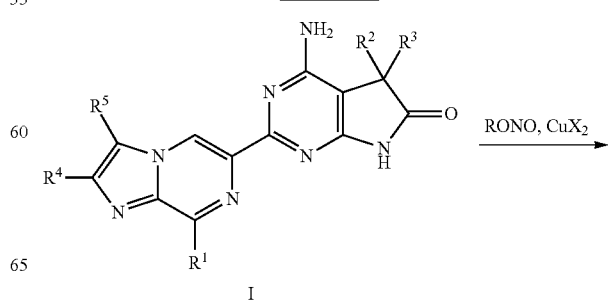

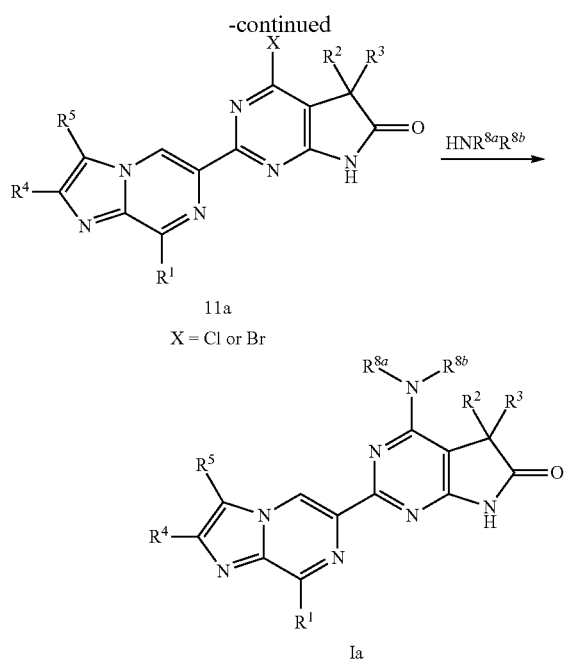

11a
X = Cl or Br

Ia

Compounds of the present invention possess an asymmetric center at the carbon bearing the $R^2/R^3$ substituent which can be either R or S configuration. These enantiomeric mixtures may be separated or resolved to single enantiomers using methods familiar to those skilled in the art. For example, compounds of the present invention may be resolved to the pure isomers by using chiral SFC chromatography. Racemic material can be resolved to enantiomerically pure compounds whenever possible and at any step in the route. Characterization data may be of the chiral or racemic material. Unless otherwise noted, the examples in the present invention are enantiomerically pure isomers (R or S). Biochemical assay data is listed for the more active enantiomer if only one of the enantiomers is active.

The independent synthesis of diastereomers and enantiomers or their chromatographic separations may be achieved as known in the art by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated: AcOH=acetic acid; AIBN=2,2'-azobisisobutyronitrile; bp, b.p.=boiling point; br s=broad singlet; Bu=butyl; t-Bu=tert-butyl; BuLi=butyllithium; tBuOH, tert-BuOH=tert-butanol; tBuOK=potassium tert-butoxide; CDCl₃=deuterated chloroform; CELITE=diatomaceous earth; CF₃=trifluoromethyl; cGMP=cyclic guanosine monophosphate; conc, conc.=concentrated; Cs₂CO₃=cesium carbonate; CuI=copper(I) iodide; DBU=1,8-Diazabicyclo[4.3.0]undec-7-ene; DCM, CH₂Cl₂=dichloromethane; DIEA=diisopropylethylamine; DMA, DMAC=N,N-dimethylacetamide; DMF=N,N-dimethylformamide; DMSO=dimethylsulfoxide; dppf=1,1'-bis(diphenylphosphino)ferrocene; EAB=egg albumin; EBSS=Earle's balanced salt solution; equiv, eq.=equivalent(s); Et=ethyl; EtOAc=ethyl acetate; EtOH=ethanol; GTP=guanosine triphosphate; h, hr=hour; HATU=1-[bis(dimethylamino)methylene]-1H-1,2,3-triazolo[4,5-b]pyridinium 3-oxid hexafluorophosphate; HOBt=Hydroxybenzotriazole; HPLC=High pressure liquid chromatography; Int.=intermediate iPr=isopropyl; IPA, i-PrOH=isopropanol; LCMS, LC/MS=liquid chromatography-mass spectrometry; LDA=lithium diisopropylamide; LiHMDS, LHMDS=lithium bis(trimethylsilyl)amide; MeOH=methanol; min, min.=minute; Me=methyl; mp, m.p.=melting point; mpk=milligrams per kilogram; NaOMe=sodium methoxide; NaSMe=sodium thiomethoxide; NCS=N-chloro succinmide; NMP=N-methylpyrrolidone; NBS=N-bromo succinmide; NaHMDS=sodium bis(trimethylsilyl)amide; NMR=nuclear magnetic resonance; N.D.=not determined; PDA=photodiode array; Pd(dppf)Cl₂=dichloro((1,1'-bis(diphenylphosphino)ferrocene) palladium (II); Pd(PPh₃)₂Cl₂=dichlorobis(triphenylphosphine) palladium(II) or bis(triphenylphosphine) palladium (II) chloride; Pd₂(dba)₃=tris(dibenzylideneacetone)dipalladium (O); Ph=phenyl; PPA=polyphosphoric acid; Pr=propyl; psig=pounds per square inch gauge; PTFE=polytetrafluoroethylene; PTLC, prep TLC=preparative thin layer chromatography; PyBOP=(benzotriazol-1-yloxy) tripyrrolidinophosphonium hexafluorophosphate; rt=retention time; RP-HPLC=reverse phase HPLC; RT=room temperature; sat., sat'd=saturated; SFC=supercritical fluid chromatography; sGC=soluble guanylate cyclase; TFA=trifluoroacetic acid; TFAA=trifluoroacetic anhydride; TLC=thin layer chromatography; THF=tetrahydrofuran; VCD=vibrational circular dichroism; v, v/v=volume, volume to volume; w, w/w=weight, weight to weight.

The following examples are provided to more fully illustrate the present invention, and shall not be construed as limiting the scope in any manner. Unless stated otherwise, the following conditions were employed. All operations were carried out at room or ambient temperature (RT), that is, at a temperature in the range 18-25° C. Reactions are generally done using commercially available anhydrous solvents under an inert atmosphere, either nitrogen or argon. Microwave reactions were done using a BIOTAGE Initiator™ or CEM Explorer® system. Evaporation of solvent was carried out using a rotary evaporator under reduced pressure (4.5-30 mmHg) with a bath temperature of up to 50° C. The course of reactions was followed by thin layer chromatography (TLC) and/or tandem high performance liquid chromatography (HPLC) followed by electron spray mass spectroscopy (MS), herein termed LCMS, and any reaction times are given for illustration only. The structure of all final compounds was assured by at least one of the following techniques: MS or proton nuclear magnetic resonance (1H NMR) spectrometry, and the purity was assured by at least one of the following techniques: TLC or HPLC. ¹H NMR spectra were recorded on either a Varian Unity or a Varian Inova instrument at 400, 500 or 600 MHz using the indicated solvent. When line-listed, NMR data is in the form of delta values for major diagnostic protons, given in parts per million (ppm) relative to residual solvent peaks (multiplicity and number of hydrogens). Conventional abbreviations used for signal shape are: s. singlet; d. doublet (apparent); t. triplet (apparent); m. multiplet; br. broad; etc. MS data were recorded on a Waters Micromass unit, interfaced with a Hewlett-Packard (AGILENT 1100) HPLC instrument, and operating on MASSLYNX/OpenLynx software. Electrospray ionization was used with positive (ES+) or negative ion (ES−) detection; and diode array detection. Purification of compounds by preparative reverse phase HPLC was performed on a GILSON system using a YMC-Pack Pro C18 column (150×20 mm i.d.) eluting at 20 mL/min with a water/acetonitrile (0.1% TFA) gradient (typically 5% acetonitrile to 95% acetonitrile) using a SUNFIRE Prep C18 OBD 5 µM column (100×30 mm i.d.) eluting at 50 mL/min with a water/acetonitrile (0.1% TFA) gradient. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm (SiO$_2$), or on a BIOTAGE SiO$_2$ cartridge system using the BIOTAGE Horizon and BIOTAGE SP-1 systems; or a Teledyne Isco SiO$_2$ cartridge using the COMBIFLASH Rf system. Chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), uM (micromolar), nM (nanomolar), ca (circa/about).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any Intermediates described below may be referred to herein by their number preceded by "I—." For illustration, in the example titled "Intermediate 2," the racemic parent title compound would be referred to as Intermediate 39 (or 1-39), and the separated stereoisomers are noted as Intermediates 39A and 39B (or I-39A and I-39B). In some examples, compounds having a chiral center were derived synthetically from a single isomer intermediate; e.g., Example 63 was made using stereoisomer I-58A. Absolute stereochemistry (R or S) of each of the separated isomers was not determined, unless specifically described. An asterisk (*) may be used in a chemical structure drawing that indicates the location of a chiral center.

Absolute stereochemistry of separate stereoisomers in the Examples and Intermediates was not determined unless stated otherwise in an Example or Intermediate synthesis.

Intermediate 1

8-[(4-Fluorophenyl)methyl]imidazo[1,2-a]pyrazine-6-carboximidamide

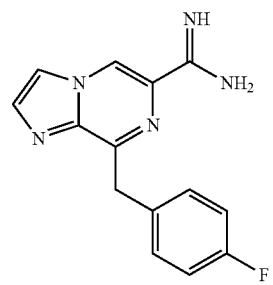 [SMILES: N=C(N)c1cn2ccnc2c(Cc2ccc(F)cc2)n1]

Step A—(4-Fluorobenzyl)zinc(II) bromide

Zinc (4.90 g, 75.0 mmol) and THF (50 mL) were added to a flask, which was purged with an atmosphere of nitrogen. 1,2-Dibromoethane (0.47 g, 2.50 mmol) was added dropwise and the mixture was warmed at 50° C. The mixture was stirred for 10 min at 50° C., and then chlorotrimethylsilane (0.27 g, 2.50 mmol) was added dropwise and the mixture was cooled to ambient temperature. After 10 min the reaction was further cooled to 0° C., and 1-(bromomethyl)-4-fluorobenzene (9.45 g, 50.0 mmol) was added. The mixture was stirred for 15 min at 0° C., then 2 h at ambient temperature. The mixture was directly used in the next step without further purification.

Step B—6-Bromo-8-(4-fluorobenzyl)imidazo[1,2-a]pyrazine

Into a flask purged with an inert atmosphere of nitrogen were placed 6,8-dibromoimidazo[1,2-a]pyrazine (9.2 g, 33.2 mmol), Pd(PPh$_3$)$_2$Cl$_2$ (466 mg, 0.66 mmol), and a solution of the intermediate from Step A (87 mL) in THF (87 mL). The resulting mixture was stirred for 1 h at 40° C. Upon completion, the reaction was quenched by the addition of saturated aqueous ammonium chloride. The resulting solution was extracted with EtOAc (3×) and the organic layers were combined. The organic layer was washed with brine, dried over anhydrous sodium sulfate and filtered. The filtrate was concentrated in vacuo to dryness. The residue was purified by silica gel chromatography with EtOAc:petroleum ether (40-60%) to afford the title compound.

Step C—8-[(4-Fluorophenyl)methyl]imidazo[1,2-a]pyrazine-6-carbonitrile

Into a flask purged with an inert atmosphere of nitrogen was placed the intermediate from Step B (8.1 g, 26 mmol), zinc cyanide (3.4 g, 29 mmol), dppf (2.9 g, 5.3 mmol), Pd$_2$(dba)$_3$ (2.7 g, 3.0 mmol), zinc metal (860 mg, 13.2 mmol), and DMA (200 mL). The resulting solution was stirred for 20 min at 120° C. Upon completion, the reaction mixture was cooled to ambient temperature. The resulting solution was diluted with EtOAc:CH$_2$Cl$_2$:MeOH (2:1:1, 200 mL). The solid was filtered through a pad of celite, and the resulting mixture was concentrated under vacuum. The residual material was diluted with water (500 mL) and then extracted with EtOAc (3×). The combined organic layer was washed with brine (2×), dried over anhydrous sodium sulfate and filtered. The filtrate was concentrated in vacuo to dryness. The residue was purified by silica gel chromatography with EtOAc:petroleum ether (50-70%) to afford the title compound.

Step D—8-[(4-Fluorophenyl)methyl]imidazo[1,2-a]pyrazine-6-carboximidamide

Into a 3-necked round-bottom flask, purged with an inert atmosphere of nitrogen, was placed ammonium chloride (4.5 g, 84 mmol) in toluene (79.3 mL). This was followed by the dropwise addition of a solution of trimethyl aluminum (31.7 mL, 2M, toluene) at 0° C. The reaction was slowly warmed to ambient temperature for 1 h. To this was added the intermediate from Step C (2.0 g, 7.9 mmol). The resulting mixture was stirred for 3 h at 100° C. Upon completion, the reaction mixture was cooled to 0° C. and quenched by the addition of MeOH: CH$_2$Cl$_2$ (1:1). The solid was filtered through a pad of celite, and the resulting mixture was concentrated under vacuum. The resulting material was diluted with EtOAc, and the pH value of the solution was adjusted to pH 10 with sodium hydroxide (1 N). The solution was extracted with EtOAc (3×) and the organic layers were combined. The resulting mixture was washed with brine, dried over anhydrous sodium sulfate and filtered. The filtrate was concentrated in vacuo to dryness. This afforded the title compound, which was used without further purification. m/z=270.1 (M+H).

Using a similar procedure for the preparation of intermediate 1, the following intermediates in Table 1 were prepared.

TABLE 1

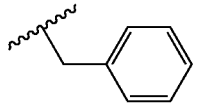 [SMILES: *Cc1ccccc1]

| Int. | R$^1$ | m/z (M + H) |
|---|---|---|
| I-2 | 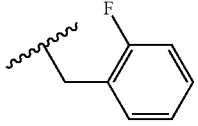 [SMILES: *Cc1ccccc1F] | 252.2 |
| I-3 | 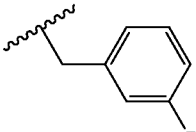 | 270.1 |
| I-4 | 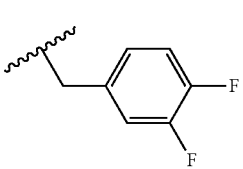 [SMILES: *Cc1ccc(F)c(F)c1] | 270.1 |
| I-5 | 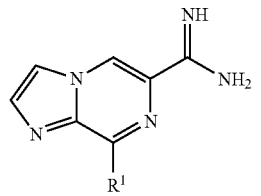 | 288.1 |

TABLE 1-continued

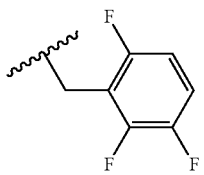 [SMILES: *Cc1c(F)ccc(F)c1F]

| Int. | R$^1$ | m/z (M + H) |
|---|---|---|
| I-6 | 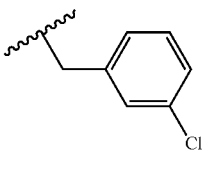 [SMILES: *Cc1cccc(Cl)c1] | 306.1 |
| I-7 | 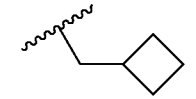 [SMILES: *CC1CCC1] | 286 |
| I-8 | 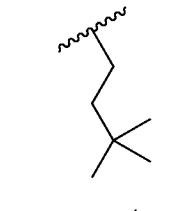 | 230.1 |
| I-9 | 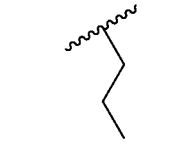 [SMILES: *CCC] | 246.0 |
| I-10 | 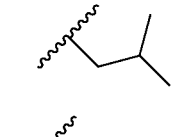 | 204.0 |
| I-11 |  | 218.2 |
| I-12 | 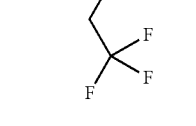 | 218.0 |
| I-13 | 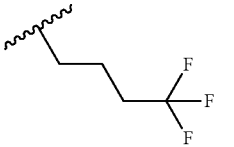 [SMILES: *CCCC(F)(F)F] | 258.0 |
| I-14 |  | 272.2 |

TABLE 1-continued

| Int. | R¹ | m/z (M + H) |
|---|---|---|
| I-15 | | 307.9 |
| I-107 | | 190.2 |

Intermediate 16

3-Chloro-8-(3,3,4,4,4-pentafluorobutyl)imidazo[1,2-a]pyrazine-6-carboximidamide

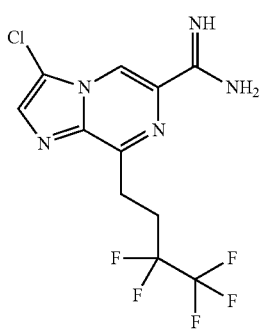 [SMILES: N=C(N)c1cn2c(Cl)cnc2c(CCC(F)(F)C(F)(F)F)n1]

Step A—3-Chloro-8-(3,3,4,4,4-pentafluorobutyl)imidazo[1,2-a]pyrazine-6-carbonitrile Into a flask, purged with an inert atmosphere of nitrogen, were placed 8-(3,3,4,4,4-pentafluorobutyl)imidazo[1,2-a]pyrazine-6-carbonitrile (250 mg, 0.86 mmol), which was prepared in accordance with intermediate 1 Steps A-C, NCS (127 mg, 0.95 mmol), and DMF (4.3 mL). The reaction was warmed at 35° C. for 16 h. Upon completion, the reaction was quenched with H₂O. The resulting solution was extracted with EtOAc (3x) and the combined organic layers were extracted with brine. The organic layer was dried over anhydrous sodium sulfate, the solid was filtered, and the filtrate was concentrated in vacuo to dryness. The residue was purified by silica gel chromatography with EtOAc:hexanes (10-100%) to afford the title compound.

Step B—3-Chloro-8-(3,3,4,4,4-pentafluorobutyl)imidazo[1,2-a]pyrazine-6-carboximidamide The title compound was prepared from the intermediate from Step A using the procedure described to prepare intermediate 1-Step D. m/z=341.9 (M+H).

Intermediate 17

3-Bromo-8-(3,3,4,4,4-pentafluorobutyl)imidazo[1,2-a]pyrazine-6-carboximidamide

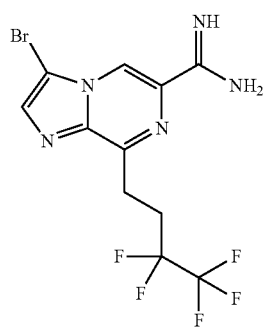

Step A—3-Bromo-8-(3,3,4,4,4-pentafluorobutyl)imidazo[1,2-a]pyrazine-6-carbonitrile The title compound was prepared from 8-(3,3,4,4,4-pentafluorobutyl)imidazo[1,2-a]pyrazine-6-carbonitrile, which was prepared in accordance with intermediate 1 Steps A-C, by using a procedure similar to that described to prepare intermediate 16-Step A.

Step B—3-Bromo-8-(3,3,4,4,4-pentafluorobutyl)imidazo[1,2-a]pyrazine-6-carboximidamide The title compound was prepared from the intermediate from Step A using the procedure described to prepare intermediate 1-Step D. m/z=387.9 (M+H).

Intermediate 18

3-Ethyl-8-(3,3,4,4,4-pentafluorobutyl)imidazo[1,2-a]pyrazine-6-carboximidamide

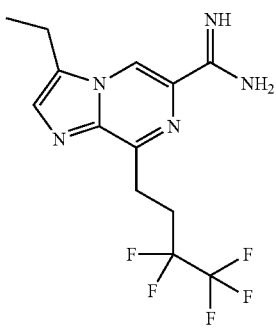 [SMILES: CCc1cnc2c(CCC(F)(F)C(F)(F)F)nc(C(=N)N)cn12]

Step A—3-Ethyl-8-(3,3,4,4,4-pentafluorobutyl)imidazo[1,2-a]pyrazine-6-carbonitrile Into a flask were added 3-bromo-8-(3,3,4,4,4-pentafluorobutyl)imidazo[1,2-a]pyrazine-6-carbonitrile (1.00 g, 2.71 mmol, intermediate 17-Step A) and Pd(dppf)Cl$_2$ (198 mg, 0.27 mmol). The system was evacuated and refilled with nitrogen (3×). DMA (13.5 mL) and diethylzinc (2.71 mL, 2.71 mmol, 1.0 M) were added and the reaction was warmed at 80° C. for 0.5 h. Upon completion, the reaction was cooled to ambient temperature, diluted with EtOAc and quenched with the addition of saturated aqueous sodium bicarbonate. The mixture was filtered through a pad of CELITE. The layers were separated and the resulting aqueous layer was extracted with EtOAc (2×). The organic layers were combined, and dried over anhydrous sodium sulfate. The solid was filtered and the filtrate was concentrated in vacuo to dryness. The residue was purified by silica gel chromatography with EtOAc:hexanes (10-80%) to afford the title compound.

Step B—3-Ethyl-8-(3,3,4,4,4-pentafluorobutyl)imidazo[1,2-a]pyrazine-6-carboximidamide The title compound was prepared from the intermediate from Step A using the procedure described to prepare intermediate 1-Step D. m/z=336.0 (M+H).

Intermediate 19

8-(3-Fluorobenzyl)-2-(trifluoromethyl)imidazo[1,2-a]pyrazine-6-carboximidamide

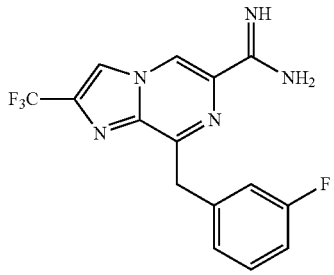 [SMILES: N=C(N)c1cn2cc(C(F)(F)F)nc2c(Cc2cccc(F)c2)n1]

Step A—6,8-Dibromo-2-(trifluoromethyl)imidazo[1,2-a]pyrazine

Into a flask was placed a solution of 3,5-dibromopyrazin-2-amine (20 g, 79 mmol) in DMA (100 mL), and 3-bromo-1,1,1-trifluoropropan-2-one (37.7 g, 197.4 mmol). The resulting solution was stirred 16 h at 90° C. The reaction was quenched by the addition of saturated aqueous sodium bicarbonate (400 mL). The resulting solution was extracted with EtOAc (3×) and the organic layers were combined. The resulting mixture was washed with brine (2×), dried over anhydrous sodium sulfate and filtered. The filtrate was concentrated in vacuo to dryness. The residue was purified by silica gel chromatography with EtOAc:petroleum ether (1:5) to afford the title compound.

Step B—6-Bromo-8-(3-fluorobenzyl)-2-(trifluoromethyl)imidazo[1,2-a]pyrazine

Into a flask, purged with an inert atmosphere of nitrogen, was placed the intermediate from Step A (2.0 g, 5.8 mmol), Pd(PPh$_3$)$_2$Cl$_2$ (400 mg, 0.60 mmol), and (3-fluorobenzyl)zinc(II) bromide (10 mL, 0.5N in THF). The resulting mixture was stirred for 1 h at 40° C. The reaction was then quenched by the addition of saturated aqueous ammonium chloride (4 mL). The resulting solution was extracted with EtOAc (3×) and the organic layers were combined. The resulting mixture was washed with brine, dried over anhydrous sodium sulfate and filtered. The filtrate was concentrated in vacuo to dryness. The residue was purified by silica gel chromatography with EtOAc:petroleum ether (1:5) to afford the title compound.

Step C—8-(3-Fluorobenzyl)-2-(trifluoromethyl)imidazo[1,2-a]pyrazine-6-carbonitrile Into a flask, purged with an inert atmosphere of nitrogen, was placed the intermediate from Step B (1.0 g, 2.7 mmol), zinc cyanide (847 mg, 7.20 mmol), dppf (133 mg, 0.24 mmol), and Pd$_2$(dba)$_3$ (0.11 g, 0.11 mmol) in DMF (20 mL). The resulting mixture was stirred for 2 h at 120° C. The reaction was then quenched by the addition of brine (50 mL). The resulting mixture was extracted with EtOAc (3×) and the organic layers were combined. The resulting mixture was washed with brine, dried over anhydrous sodium sulfate, and filtered. The filtrate was concentrated in vacuo to dryness. The residue was purified by silica gel chromatography with CH$_2$Cl$_2$:petroleum ether (10-80%) to afford the title compound.

Step D—8-(3-fluorobenzyl)-2-(trifluoromethyl)imidazo[1,2-a]pyrazine-6-carboximidamide Into a 3-necked round-bottom flask purged with an inert atmosphere of nitrogen, was placed ammonium chloride (1.5 g, 28 mmol) in toluene (40 mL). This was followed by the dropwise addition of trimethyl aluminum (9 mL, 18 mmol, 2 N) at 0° C. The resulting mixture was stirred for 30 min with warming to ambient temperature. To this was added the intermediate from Step C (710 mg, 2.22 mmol). The resulting solution stirred for an additional 3 h while the temperature was maintained at 100° C. The reaction mixture was then cooled to 0° C. and quenched by the addition of DCM:MeOH (1:1, 100 mL). The solids were filtered and washed with DCM:MeOH (1:1, 3×). The filtrate was collected and concentrated under vacuum. The pH value of the solution was adjusted to 9 with sodium hydroxide (4 N). The resulting solution was extracted with EtOAc (3×) and the organic layers were combined, and dried over sodium sulfate. The solid was filtered and the filtrate was concentrated in vacuo to dryness to afford the title compound. $^1$H NMR (400 MHz, DMSO-d$_6$) δ 9.23 (1H, s), 8.85 (1H, s), 7.41-7.14 (6H, m), 7.09-7.04 (1H, m), 4.55 (2H, s). m/z=338 (M+H).

Using a similar procedure for the preparation of intermediate 1919, the following intermediates in Table 2 were prepared.

TABLE 2

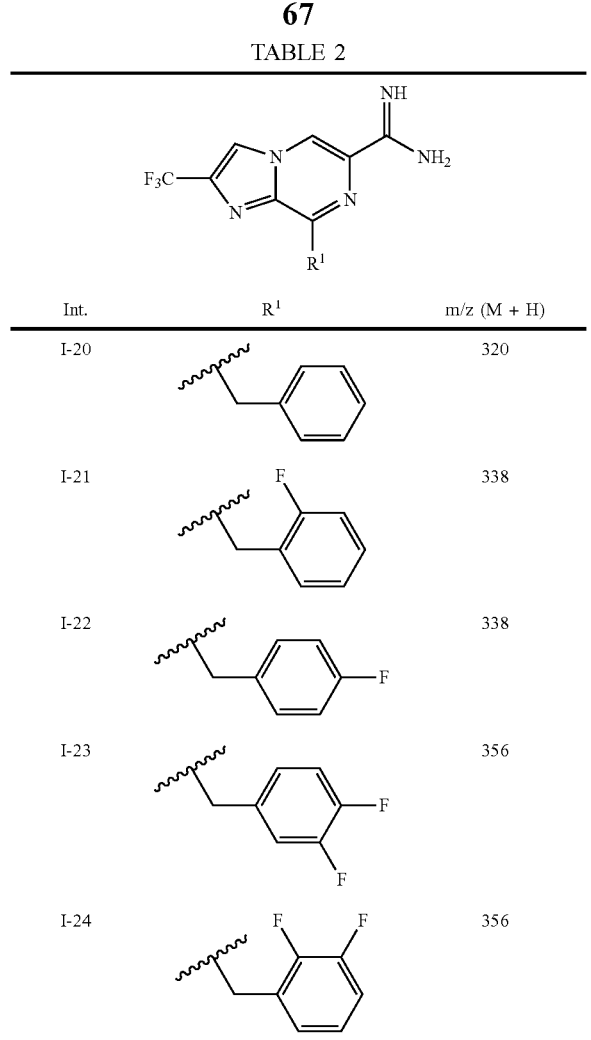

| Int. | R[1] | m/z (M + H) |
|---|---|---|
| I-20 | benzyl | 320 |
| I-21 | 2-fluorobenzyl | 338 |
| I-22 | 4-fluorobenzyl | 338 |
| I-23 | 3,4-difluorobenzyl | 356 |
| I-24 | 2,3-difluorobenzyl | 356 |

Intermediate 25

Imidazo[1,2-a]pyrazine-6-carboximidamide

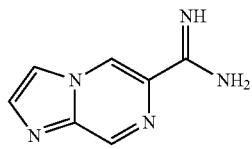 [SMILES: N=C(N)c1cn2ccnc2cn1]

Step A—Imidazo[1,2-a]pyrazine-6-carbonitrile

Into a flask, purged with an inert atmosphere of nitrogen, was placed 5-aminopyrazine-2-carbonitrile (0.69 ml, 8.33 mmol) and EtOH (36.2 ml). To this was added 2-bromo-1,1-diethoxyethane (2.58 ml, 16.6 mmol) and HBr in water (6.59 mL, 58.3 mmol). The mixture was warmed at 85° C. for 4 h. Upon completion, the reaction was diluted with EtOAc (50 mL), cooled to 0° C., and slowly quenched with saturated aqueous NaHCO₃ until the pH was adjusted to 9. The resulting solution was extracted with EtOAc (3×), and the organic layers were combined and dried over anhydrous sodium sulfate. The solid was filtered and the filtrate was concentrated in vacuo to dryness. The crude mixture was tritrated with DCM: hexanes (1:1). The liquid was decanted and the solid was dried to completion to afford the title compound.

Step B—Imidazo[1,2-a]pyrazine-6-carboximidamide

Into a flask, purged with an inert atmosphere of nitrogen, was placed the intermediate from Step A (1.05 g, 7.26 mmol) and MeOH (36.3 mL). Sodium methoxide (2.18 mL, 7.98 mmol) was added and after 5 min. the reaction became homogeneous. After 1.5 h, ammonium chloride (0.43 g, 7.98 mmol) and acetic acid (4.15 mL, 72.6 mmol) were added and the reaction was warmed at 70° C. After 2.5 h, the reaction was cooled to room temperature and concentrated in vacuo to dryness. This afforded the acetate salt of the title compound, which was used without further purification. m/z=162.1 (M+H).

Intermediate 26

8-Phenylimidazo[1,2-a]pyrazine-6-carboximidamide

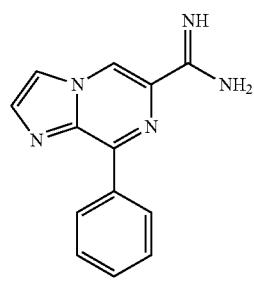 [SMILES: N=C(N)c1cn2ccnc2c(-c2ccccc2)n1]

Step A—6-Bromo-8-phenylimidazo[1,2-a]pyrazine

Into a flask, purged with an inert atmosphere of nitrogen, was placed 5-bromo-3-phenylpyrazin-2-amine (300 mg, 1.20 mmol) in EtOH (5.22 mL). 2-Bromo-1,1-diethoxyethane (372 μl, 2.40 mmol) and HBr in water (950 μl, 8.40 mmol) were added. The mixture was warmed at 85° C. After 2.5 h, the reaction was cooled to ambient temperature and diluted with EtOAc. The mixture was further cooled to 0° C. and slowly quenched with saturated aqueous NaHCO₃ until the pH was adjusted to 9. The resulting solution was extracted with EtOAc (3×). The organic layers were combined and dried over anhydrous sodium sulfate. The solid was filtered and the filtrate was concentrated in vacuo to dryness. The residue was purified by silica gel chromatography with EtOAc:hexanes (0-70%) to afford the title compound.

Step B—8-Phenylimidazo[1,2-a]pyrazine-6-carbonitrile

Into a vial was placed the intermediate from Step A (235 mg, 0.86 mmol), zinc cyanide (101 mg, 0.86 mmol), and Pd(dppf)Cl₂ (70.0 mg, 0.09 mmol), which was secured with a pierce-able cap. The sealed vial was evacuated and refilled with N₂ (3×). DMA (3.4 mL) was added, and the reaction was warmed at 120° C. After 24 h, the reaction was diluted with EtOAc and quenched with saturated aqueous NaHCO₃. The mixture was filtered through a pad of celite. The resulting solution was extracted with EtOAc (3×) and the organic layers were combined, and dried over anhydrous sodium sulfate. The solid was filtered and the filtrate was concentrated in vacuo to dryness. The residue was purified by silica gel chromatography with EtOAc:hexanes (0-80%) to afford the title compound.

Step C—8-Phenylimidazo[1,2-a]pyrazine-6-carboximidamide

Into a vial, purged with an inert atmosphere of nitrogen, was placed the intermediate from Step B (29 mg, 0.13 mmol) and Toluene (0.6 mL). To this was added amino(methyl)aluminum chloride (1.3 mL, 0.658 mmol, 0.5 M in toluene) and the resulting mixture was warmed at 100° C. After 16 h, the reaction mixture was cooled to 0° C. The reaction was quenched by the addition of MeOH:DCM (1:4, 15 mL). The solid was filtered through a pad of celite. The resulting eluent was concentrated in vacuo to dryness. This resulted in the HCl salt of the title compound. m/z=238.1 (M+H).

Intermediate 27

2-Methyl-8-(3,3,4,4,4-pentafluorobutyl)imidazo[1,2-a]pyrazine-6-carboximidamide

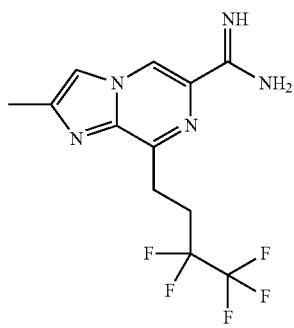 [SMILES: Cc1cn2cc(C(=N)N)nc(CCC(F)(F)C(F)(F)F)c2n1]

Step A—5-Amino-6-(3,3,4,4,4-pentafluorobutyl)pyrazine-2-carbonitrile

Into a flask, purged with an inert atmosphere of nitrogen, was placed 3,5-dibromopyrazin-2-amine (15.0 g, 59.3 mmol) and Pd(PPh$_3$)$_2$Cl$_2$ (4.16 g, 5.90 mmol). To this was added DMA (50 mL) and the mixture was stirred for 20 min before addition of (3,3,4,4,4-pentafluorobutyl)zinc(II) iodide in DMA (163 mL, 119 mmol), which was prepared similarly to intermediate 1—Step A. The reaction mixture was warmed at 40° C. After 16 h, zinc cyanide (4.88 g, 41.5 mmol) was added to the reaction mixture, which was warmed at 120° C. Upon completion, the reaction was cooled to ambient temperature, quenched with pH 7 buffer and EtOAc. The mixture was filtered through a pad of celite. The subsequent organic layer was separated and the aqueous layer was washed with EtOAc. The organic layers were combined, washed with brine, and dried over anhydrous sodium sulfate. The solid was filtered and the filtrate was concentrated in vacuo to dryness. The residue was purified by silica gel chromatography with EtOAc:hexanes (0-100%) to afford the title compound.

Step B—2-Methyl-8-(3,3,4,4,4-pentafluorobutyl)imidazo[1,2-a]pyrazine-6-carbonitrile Into a vial purged with an inert atmosphere of nitrogen, was placed the intermediate from Step A (500 mg, 1.88 mmol) and DMA (3.7 mL). 1-Chloropropan-2-one (0.75 mL, 9.39 mmol) was added and the reaction was warmed at 120° C. for 32 h. Upon completion, the reaction was cooled to ambient temperature, diluted with EtOAc and quenched with saturated aqueous NaHCO$_3$. The subsequent organic layer was separated and the aqueous layer was washed with EtOAc. The organic layers were combined, washed with brine, and dried over anhydrous sodium sulfate. The solid was filtered and the filtrate was concentrated in vacuo to dryness. The residue was purified by silica gel chromatography with EtOAc:hexanes (0-60%) to afford the title compound.

Step C—2-Methyl-8-(3,3,4,4,4-pentafluorobutyl)imidazo[1,2-a]pyrazine-6-carboximidamide The title compound was prepared from the intermediate from Step B using the procedure described to prepare intermediate 1—Step D. m/z=322.3 (M+H).

Using a similar procedure for the preparation of intermediate 27, the following intermediates in Table 3 were prepared. If additives or solvents were altered the difference is noted in Table 3.

TABLE 3

| Int. | R$^1$ | R$^4$ | R$^5$ | Cyclization additive | Cyclization reagent | m/z (M + H) |
|---|---|---|---|---|---|---|
| I-28 | (pentafluorobutyl) | Et | H | None | 1-bromobutan-2-one | 336.0 |

TABLE 3-continued
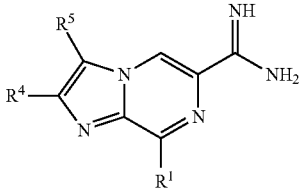
| Int. | R¹ | R⁴ | R⁵ | Cyclization additive | Cyclization reagent | m/z (M + H) |
|---|---|---|---|---|---|---|
| I-29 | 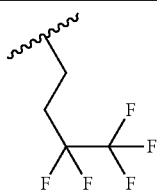 | CF₃ | H | None | 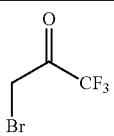 | 376.0 |
| I-30 | 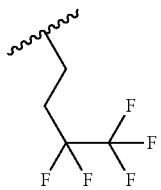 [SMILES: *CCC(F)(F)C(F)(F)F] | 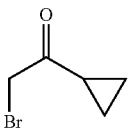 | H | None | 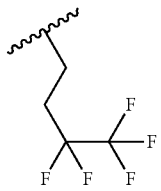 [SMILES: *CCC(F)(F)C(F)(F)F] | 348.0 |
| I-31 | 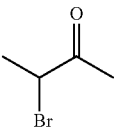 | Me | Me | None | 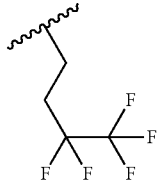 [SMILES: *CCC(F)(F)C(F)(F)F] | 336.0 |
| I-32 | 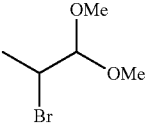 | H | Me | HBr in EtOH | 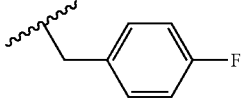 [SMILES: *Cc1ccc(F)cc1] | 322.1 |
| I-33 | 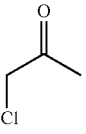 | Me | H | NMP, 200° C. | 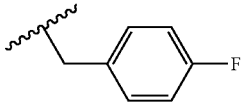 [SMILES: *Cc1ccc(F)cc1] | 284.0 |
| I-34 | 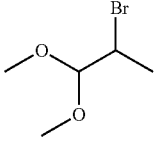 | H | Me | NMP, 200° C. | 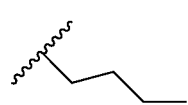 [SMILES: *CCCC] | 267.0 |
| I-35 | 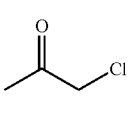 | Me | H | NMP, 200° C. | 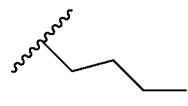 [SMILES: *CCCC] | 232.3 |
| I-36 | 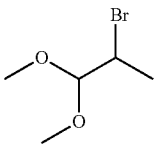 | H | Me | NMP, 200° C. |  | 323.0 |

Intermediate 37

2-Methoxy-8-(3,3,4,4,4-pentafluorobutyl)imidazo[1,2-a]pyrazine-6-carboximidamide

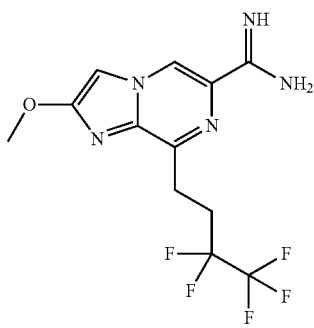 [SMILES: COc1cn2cc(C(=N)N)nc(CCC(F)(F)C(F)(F)F)c2n1]

Step A—2-Hydroxy-8-(3,3,4,4,4-pentafluorobutyl)imidazo[1,2-a]pyrazine-6-carbonitrile Into a vial, purged with an inert atmosphere of nitrogen, was placed the product of intermediate 27 Step A (5-amino-6-(3,3,4,4,4-pentafluorobutyl)pyrazine-2-carbonitrile) (0.35 g, 1.32 mmol) and DMA (5.3 mL). Bromoacetic acid (0.82 g, 5.92 mmol) was added and the reaction was warmed at 110° C. for 16 h. Upon completion, the reaction was cooled to ambient temperature, diluted with EtOAc and quenched with saturated aqueous NaHCO$_3$. The subsequent organic layer was separated and the aqueous layer was washed with EtOAc. The organic layers were combined, washed with brine (3×), and dried over anhydrous sodium sulfate. The solid was filtered and the filtrate was concentrated in vacuo to dryness. The crude mixture was tritrated with CH$_2$Cl$_2$:acetone (1:1). The liquid was decanted and the solid was dried to completion to afford the title compound, used without further purification.

Step B—2-Methoxy-8-(3,3,4,4,4-pentafluorobutyl)imidazo[1,2-a]pyrazine-6-carbonitrile Into a vial, purged with an inert atmosphere of nitrogen, was placed the intermediate from Step A (25.0 mg, 0.08 mmol), iodomethane (7.66 µL, 0.12 mmol), cesium carbonate (66.5 mg, 0.20 mmol), and DMF (408 µL). After 1 h, the reaction was diluted with EtOAc and extracted with H$_2$O and brine (2×). The combined aqueous layer was washed with EtOAc (2×). The organic layers were combined and dried over anhydrous sodium sulfate. The solid was filtered, and the filtrate was concentrated in vacuo to dryness. The residue was purified by silica gel chromatography with EtOAc:hexanes (0-60%) to afford the title compound.

Step C—2-Methoxy-8-(3,3,4,4,4-pentafluorobutyl)imidazo[1,2-a]pyrazine-6-carboximidamide The title compound was prepared from the intermediate from Step B using the procedure described to prepare intermediate 1—Step D. m/z=337.9 (M+H).

Intermediate 38

2-Methoxy-8-(4,4,4-trifluorobutyl)imidazo[1,2-a]pyrazine-6-carboximidamide

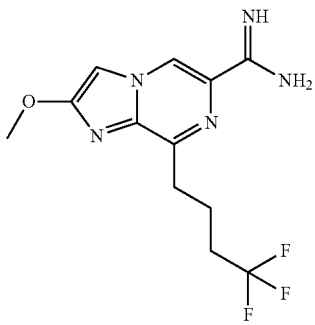 [SMILES: COc1cn2cc(C(=N)N)nc(CCCC(F)(F)F)c2n1]

Step A—5-amino-6-(4,4,4-trifluorobutyl)pyrazine-2-carbonitrile

Into a vial, purged with an inert atmosphere of nitrogen, was placed 3,5-dibromopyrazin-2-amine (1.7 g, 6.7 mmol) and Pd(PPh$_3$)$_2$Cl$_2$ (0.47 g, 0.67 mmol). To this was added THF (30 mL) and (4,4,4-trifluorobutyl)zinc(II) iodide in DMA (8.0 mL, 8.0 mmol, 1.0M, prepared similar to Intermediate 1-Step A). The reaction mixture was warmed at 40° C. After 16 h, zinc cyanide (0.5 g, 4.2 mmol) was added to the reaction mixture, which was then warmed at 120° C. Upon completion, the reaction was cooled to ambient temperature, quenched with pH 7 buffer and EtOAc. The mixture was filtered through a pad of celite. The subsequent organic layer was separated and the aqueous layer was washed with EtOAc. The organic layers were combined, washed with brine, and dried over anhydrous sodium sulfate. The solid was filtered and the filtrate was concentrated in vacuo to dryness. The residue was purified by silica gel chromatography with EtOAc:hexanes (10-50%) to afford the title compound.

Steps B—2-Methoxy-8-(4,4,4-trifluorobutyl)imidazo[1,2-a]pyrazine-6-carboximidamide Using a procedure similar to that described in Steps A-C of intermediate 37, the title compound was prepared from the intermediate from Step A. m/z=302.1 (M+H).

Intermediate 39, 39A, & 39B

Ethyl 3,3-dicyano-2-(5-fluoropyridin-2-yl)-2-methylpropanoate and the S and R Isomers Thereof

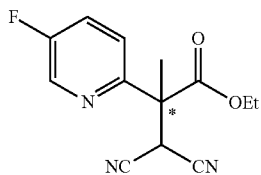 [SMILES: CCOC(=O)C(C)(c1ccc(F)cn1)C(C#N)C#N]

Step A—Diethyl 2-(5-fluoropyridin-2-yl)malonate

Into a flask, was placed 2-bromo-5-fluoropyridine (20.0 g, 114 mmol), 1,3-diethyl propanedioate (54.5 g, 340 mmol), picolinic acid (5.6 g, 45 mmol), $Cs_2CO_3$ (143 g, 438 mmol), CuI (4.3 g, 23 mmol), and dioxane (500 mL). The resulting solution was stirred for 12 h at 100° C. The resulting solution was quenched by the addition of water (300 mL). The resulting solution was extracted with EtOAc (2×), the organic layers combined and dried over anhydrous sodium sulfate, and concentrated in vacuo to dryness. The residue was purified by silica chromatography using EtOAc:petroleum ether (0-20%) to afford the title compound.

Step B—Ethyl 2-(5-fluoropyridin-2-yl)acetate

Into a 3-necked round-bottom flask, was placed the intermediate from Step A (46 g, crude), NaCl (20 g, 342 mmol), water (6 mL), and DMSO (90 mL). The resulting solution was stirred for 3 h at 180° C. Upon completion, the resulting solution was diluted with EtOAc, washed with water (5×) and the organic layer was dried over anhydrous sodium sulfate and concentrated in vacuo to dryness. The residue was purified by silica chromatography using EtOAc:petroleum ether (0-20%) to afford the title compound.

Step C—Ethyl 2-(5-fluoropyridin-2-yl)propanoate

Into a flask was placed THF (200 mL) and LiHMDS (45 mL, 1.0 M). This was followed by dropwise addition of the intermediate from Step B (7.5 g, 41 mmol) with stirring at 0° C. After stirring the resulting solution for 1 h, a solution of iodomethane (5.8 g, 41 mmol) in THF (10 mL) was added dropwise. The resulting solution was stirred for 3 h at 0° C. The reaction was then quenched by the addition of water. The resulting mixture was extracted with EtOAc (3×), the organic layers combined and dried over anhydrous sodium sulfate, and concentrated in vacuo to dryness. The residue was purified by silica chromatography using EtOAc:petroleum ether (0-20%) to afford the title compound.

Step D—Ethyl 2-bromo-2-(5-fluoropyridin-2-yl)propanoate

Into a flask was added the intermediate from Step C (1 g, 5 mmol) and THF (50 mL). This was followed by the addition of LiHMDS (5 mL, 1.0 M) dropwise with stirring at 78° C. The resulting solution was stirred for 30 min at 78° C. before NBS (1.2 g, 7.1 mmol) in THF (10 mL) was added, and the solution was warmed to ambient temperature and stirred for 1 h. The reaction was then quenched by the addition of water. The resulting solution was extracted with EtOAc (3×) and the organic layers combined and dried over anhydrous sodium sulfate. The solid was filtered and the eluent was concentrated in vacuo to dryness. The residue was purified by silica chromatography using EtOAc:petroleum ether (0-10%) to afford the title compound.

Step E—Ethyl 3,3-dicyano-2-(5-fluoropyridin-2-yl)-2-methylpropanoate

Into a flask was placed DMF (20 mL) and sodium hydride (260 mg, 6.50 mmol, 60%). This was followed by the addition of malononitrile (460 mg, 6.96 mmol) with stirring at 0° C. The resulting solution was stirred for 30 min at 0° C. To this was added the intermediate from Step D (950 mg, 3.44 mmol) in DMF dropwise with stirring at 0° C. The resulting solution was stirred for 1 h at ambient temperature. Upon completion, the resulting solution was quenched with water, and extracted with EtOAc. The organic layer was dried over anhydrous sodium sulfate and concentrated in vacuo to dryness. The residue was purified by silica chromatography using EtOAc:petroleum ether (0-20%). The racemic material was resolved using a chiral SFC (IA column) to afford isomers I-39A (faster eluting) and I-39B (slower eluting) of the title compound. $^1$H-NMR: (300 MHz, $CDCl_3$): δ 8.44-8.45 (1H, dd, J=0.9, 2.4 Hz), 7.47-7.57 (2H, m), 5.17 (1H, s), 4.19-4.29 (2H, m), 2.00 (3H, s), 1.22-1.27 (3H, t, J=6.9 Hz).

Using a similar procedure for the preparation of intermediate 39, the following intermediates in Table 4 were prepared. Some intermediates were commercially available at Step B and the synthesis could commence at Step C.

TABLE 4

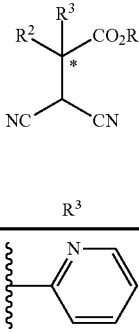

| Int. | Chiral Resolution Column | R² | R³ | R | m/z (M + H) or ¹H NMR |
|---|---|---|---|---|---|
| I-40A & B | CHIRALPAK IA | Me | 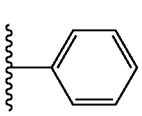 | Me | 230.2 |
| I-41A & B | CHIRALPAK AD | Me | 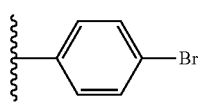 | Me | ¹H NMR (500 MHz, CDCl₃): δ 7.44-7.42 (3H, m), 7.38-7.36 (2H, m), 4.50 (1H, s), 3.80 (3H, s), 2.00 (3H, s). |
| I-42A & B | CHIRALPAK OJ | Me | (4-Br-phenyl) | Et | 319 [M − 1]⁻ |

TABLE 4-continued

Structure: R² and R³ on a carbon bearing CO₂R (chiral center *), with CH(CN)₂ group below.

| Int. | Chiral Resolution Column | R² | R³ | R | m/z (M + H) or ¹H NMR |
|---|---|---|---|---|---|
| I-43A & B | CHIRALPAK IA | Me | 2,4-dichlorophenyl | Et | ¹H NMR (400 MHz, CDCl₃): δ 7.53-7.42 (3H, m), 5.00 (1H, s), 4.30 (2H, q, J = 7.2 Hz), 2.08 (3H, s), 1.28 (3H, t, J = 7.2 Hz). |
| I-44A & B | Chiralcel OJ | Me | 4-chloro-2-fluorophenyl | Et | ¹H NMR (400 MHz, CDCl₃): δ 7.42 (1H, dd, J = 8.4, 8.4 Hz), 7.31 (1H, dd, J = 2.0, 9.2 Hz), 7.19 (1H, dd, J = 2.0, 11.6 Hz), 4.58 (1H, s), 4.31 (2H, q, J = 7.2 Hz), 2.01 (3H, s), 1.28 (3H, t, J = 7.2 Hz) |
| I-45A & B | CHIRALPAK AD | Me | 3,5-difluorophenyl | Et | 277 [M − 1]⁻ |
| I-46A & B | Chiralcel OJ | Me | 2,4-difluorophenyl | Et | ¹H NMR (300 MHz, CDCl₃): δ 7.50-7.42 (1H, m), 7.06-7.00 (1H, m), 6.94-6.87 (1H, m), 4.57 (1H, s), 4.31 (2H, q, J = 7.2 Hz), 2.01 (3H, s), 1.27 (3H, t, J = 7.2 Hz). |
| I-47 | racemic | Me | 3-fluorophenyl | Me | 1H NMR (500 MHz, CDCl₃): δ 7.43 (1 H, td, J = 8.11, 5.97 Hz), 7.07-7.16 (3 H, m), 4.49 (1 H, s), 3.82 (3 H, s), 2.00 (3 H, s). |
| I-48A & B | CHIRALPAK AD-H | Me | pyrimidin-2-yl | Me | 245.1 |
| I-49 | racemic | Me | 6-methylpyridazin-3-yl | Et | 259.1 |
| I-50 | racemic | Me | 6-cyclopropylpyridazin-3-yl | Et | 285.0 |
| I-51 | racemic | Me | 6-methylpyridin-3-yl | Et | 258 |
| I-52A & B | CHIRALPAK IA | Me | 5-chloropyridin-2-yl | Et | 278.2 |

TABLE 4-continued

| Int. | Chiral Resolution Column | R² | R³ | R | m/z (M + H) or ¹H NMR |
|---|---|---|---|---|---|
| I-53 | racemic | Me | 5-methoxypyridin-2-yl | Et | 274.1 |
| I-54A & B | CHIRALPAK IA | Me | 5-ethoxypyridin-2-yl | Et | 286.0 [M − H]⁻ |
| I-55A & B | CHIRALPAK AD | Me | 5-(difluoromethoxy)pyridin-2-yl | Et | 310.2 |
| I-108 | racemic | Me | 5-methyl-1,2,4-oxadiazol-3-yl | Me | 1H NMR (300 MHz, CDCl₃): δ 4.79 (1 H, s), 4.30 (2 H, q, J = 7.2 Hz), 2.64 (3 H, s), 2.08 (3 H, s), 1.27 (3H, t, J = 7.2 Hz) |
| I-109A & B | Chiralcel OJ | Me | 5-ethyl-1,2,4-oxadiazol-3-yl | Me | 263 |
| I-110 | racemic | Me | 5-isopropyl-1,2,4-oxadiazol-3-yl | Me | 277 |
| I-111 | racemic | Me | 5-cyclopropyl-1,2,4-oxadiazol-3-yl | Me | 275 |
| I-130 | racemic | Me | 5-(difluoromethyl)pyridin-2-yl | Me | 304 (M − 1) |
| I-131 | racemic | Me | 6-(1,1-difluoroethyl)pyridin-3-yl | Me | 308 |

Intermediate 56

Diethyl 2-cyclopropyl-2-(dicyanomethyl)malonate

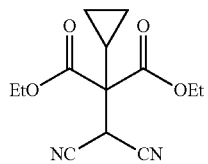

A THF (45.0 ml) solution of diethyl 2-(dicyanomethylene)malonate (prepared analogous to Sentman et. al. *J. Org. Chem.* 1982, 47, 4577) (4.50 ml, 4.50 mmol, 1M solution in benzene) was cooled to 0° C. and cyclopropylmagnesium bromide (9.00 ml, 4.50 mmol) and lithium chloride (0.191 g, 4.50 mmol) were added. The reaction was stirred at 0° C. for 2 h and then warmed to ambient temperature while stirring for an additional 2 h. The reaction was diluted with EtOAc and quenched with saturated ammonium chloride. The layers were separated and the organic layer was dried over anhydrous magnesium sulfate, filtered, and concentrated in vacuo to dryness. Purification by silica gel column chromatography using a EtOAc:hexanes gradient afforded the title compound. $^1$H NMR (500 MHz, CDCl$_3$): δ 4.41 (1H, s), 4.38-4.26 (4H, m), 1.52-1.45 (1H, m), 1.33 (6H, t, J=7.1 Hz), 0.86-0.79 (2H, m), 0.71-0.66 (2H, m).

Intermediate 57

Diethyl 2-(dicyanomethyl)-2-methylmalonate

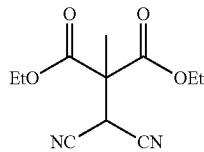

Using a similar procedure as described in intermediate 56, the following intermediate was prepared. $^1$H NMR (500 MHz, CDCl$_3$): δ 4.55 (1H, s), 4.28-4.39 (4H, m), 1.82 (3H, s), 1.34 (6H, t, J=7.12 Hz).

Intermediate 58, 58A, & 58B

Ethyl-2-(dicyanomethyl))-2-methylbut-3-ynoate and the S and R Isomers Thereof

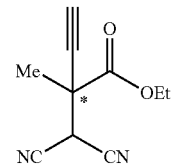

To a flask containing anhydrous LiCl (25.8 mg, 0.609 mmol) in THF (1 mL), was added a solution of ethynylmagnesium bromide (1.3 mL, 0.64 mmol, 0.5M in THF). The reaction was stirred at ambient temperature for 0.5 h. The resulting solution was then quickly added dropwise via syringe to a solution of ethyl 3,3-dicyano-2-methylprop-2-enoate (prepared according to Hagiware et. al. *Synthesis* 1974, 9, 669) (0.609 mL, 0.609 mmol, 1M solution in benzene) in THF (22.5 mL) at 10° C. The reaction was stirred for 10 min then quenched with saturated aqueous ammonium chloride and diluted with water and EtOAc. The layers were separated and the organic layer was dried over anhydrous sodium sulfate, and concentrated in vacuo to dryness. The residue was purified by silica gel chromatography using an EtOAc:hexanes gradient to afford the title product. The racemic material was resolved using chiral SFC (OJ-H column) to afford isomers I-58A (faster eluting) and I-58B (slower eluting). $^1$H NMR (500 MHz, CDCl$_3$): δ 4.34 (2H, q, J=7.2 Hz), 4.31 (1H, s), 2.66 (1H, s), 1.80 (3H, s), 1.35 (3H, t, J=7.1 Hz).

Using a similar procedure described for the synthesis of intermediate 58, the following compounds in Table 5 were prepared using either commercial starting reagents or from compounds known in the literature.

TABLE 5

Me—C(R³)(CO₂Et)—C*—CH(CN)(CN)

| Int. | Chiral Resolution Column | R³ | m/z (M + H) or $^1$H NMR |
|---|---|---|---|
| I-59A & B | CHIRALPAK AD | *N*-methylpyrazol-4-yl | 247.3 |
| I-60A & B | CHIRALPAK AD | 5-isopropylpyridin-2-yl | 286.1 |

TABLE 5-continued
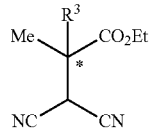
| Int. | Chiral Resolution Column | R³ | m/z (M + H) or ¹H NMR |
|---|---|---|---|
| I-61A & B | CHIRALPAK IA | 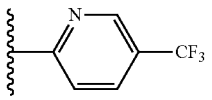 | 312.0 |
| I-62A & B | CHIRALPAK AS | 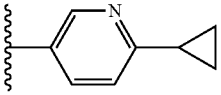 [SMILES: *c1ccc(C2CC2)nc1] | 284 |
| I-63 | CHIRALPAK AS | 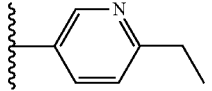 [SMILES: *c1ccc(CC)nc1] | 272.0 |
| I-64A & B | CHIRALPAK AS | 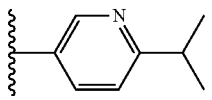 [SMILES: *c1ccc(C(C)C)nc1] | 286.0 |
| I-65A & B | CHIRALPAK AS | 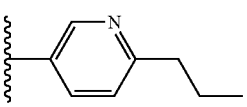 | 286 |
| I-66A & B | CHIRALPAK AS | 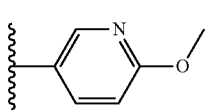 | 274.1 |
| I-67A & B | CHIRALPAK AS | 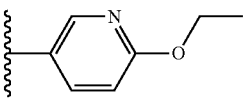 [SMILES: *c1ccc(OCC)nc1] | 288 |
| I-68A & B | CHIRALPAK AD | 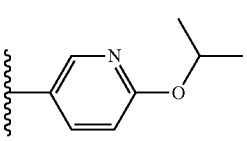 [SMILES: *c1ccc(OC(C)C)nc1] | 302.1 |
| I-69 | racemic | 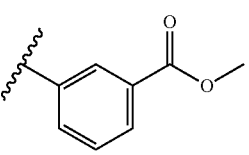 [SMILES: *c1cccc(C(=O)OC)c1] | ¹H NMR (500 MHz, CDCl₃): 8.09-8.13 (2H, m), 7.54-7.61 (2H, m), 4.57 (1H, s), 4.15 (2H, q, J = 7.1 Hz), 3.97 (3H, s), 2.07 (3H, s), 1.28 (3H, t, J = 7.2 Hz) |
| I-70 | racemic |  | ¹H NMR (300 MHz, CDCl₃): δ 4.31 (2H, q, J = 7.2 Hz), 4.23 (1H, s), 2.21-2.11 (1H, m), 1.52 (3H, s), 1.33 (3H, t, J = 7.2 Hz), 1.07-0.98 (6H, m) |

Intermediate 71

Ethyl 2-(dicyanomethyl)-2-methylbutanoate and the S and R Isomers Thereof

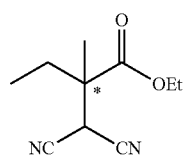

Step A—Ethyl 2-(dicyanomethylene) butanoate

Ethyl 2-oxobutanoate (15.0 g, 129 mmol) and malononitrile (12.8 g, 194 mmol) were added to a flask followed by the addition of 3-aminopropanoic acid (0.57 g, 6.46 mmol) as a solution in water (12.9 ml). Ethanol (12.9 ml) was added and the reaction was stirred for 2 h. The mixture was diluted with EtOAc and water. The layers were separated and the organic layer was dried over anhydrous sodium sulfate, filtered and concentrated in vacuo to dryness. Silica gel chromatography using an EtOAc:hexanes gradient afforded the title product.

Step B—Ethyl 2-(dicyanomethyl)-2-methylbutanoate

Methylmagnesium bromide (3.0 N, 4.2 mL, 12.6 mmol) was added dropwise to a mixture of the intermediate from Step A (1.5 g, 8.4 mmol) and LiCl (0.71 g, 16.8 mmol) in THF (15 mL) at 0° C. The mixture was stirred for 1 h at 0° C. The reaction was quenched with saturated aqueous ammonium chloride and extracted with EtOAc. The organic phase was washed with brine, dried over anhydrous magnesium sulfate, filtered, and concentrated. The residue was purified by silica gel chromatography using EtOAc:hexanes (50%) to afford the racemic title compound. $^1$H NMR (300 MHz, CDCl$_3$): δ 4.31 (2H, q, J=7.2 Hz), 4.19 (1H, s), 1.90 (2H, q, J=7.5 Hz), 1.53 (3H, s), 1.35 (3H, t, J=7.2 Hz), 0.91 (3H, t, J=7.5 Hz).

Using a similar procedure to that described for the synthesis of intermediate 71, the following compounds in Table 6 were prepared using either commercial starting reagents or from compounds known in the literature.

TABLE 6

| Int. | Chiral Resolution Column | R$^3$ | m/z (M + H) or $^1$H NMR |
|---|---|---|---|
| I-72 | N/A | (isobutyl) | $^1$H NMR(400 MHz, CDCl$_3$): δ 4.31(2H, q, J = 7.2 Hz), 4.24 (1H, s), 1.97 (4H, q, J = 7.2 Hz), 1.35 (3H, t, J = 7.2 Hz), 1.05 (6H, t, J = 7.2 Hz) |
| I-73A & B | PHENOMENEX Lux 5u Cellulose-3 | 4-Br-phenyl | 333 [M − 1]$^-$ |
| I-74A & B | Chiralcel OJ | 3-F-4-Cl-phenyl | 307 [M − 1]$^-$ |
| I-75A & B | Chiralcel OJ | 5-F-pyridin-2-yl | 276 |

Intermediate 76

Ethyl 3,3-dicyano-2-cyclopropyl-2-methylpropanoate and the S and R Isomers Thereof

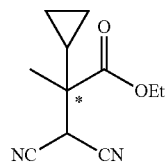

Step A—Ethyl 2-cyclopropyl-2-oxoacetate

Into a flask was placed a solution of diethyl oxalate (28.5 g, 195 mmol) in THF (200 mL) which was cooled at 78° C.

Cyclopropylmagnesium bromide (150 mL, 150 mmol, THF) was added dropwise, and the resulting solution was stirred for 2 h with warming to ambient temperature. The reaction was quenched by the addition of saturated aqueous ammonium chloride. The resulting solution was extracted with EtOAc (3×) and the organic layers were combined, washed with brine, dried over anhydrous sodium sulfate, and filtered. The filtrate was concentrated in vacuo to dryness. The residue was purified by silica gel chromatography with DCM:petroleum ether (40-60%) to afford the title compound.

Step B—Ethyl 3,3-dicyano-2-cyclopropylacrylate

Into a flask were placed the intermediate from Step A (5.6 g, 39 mmol), malononitrile (2.6 g, 39 mmol), EtOH (5 mL) and a solution of 3-aminopropanoic acid (175 mg) in water (5 mL). The resulting solution was stirred 16 h at ambient temperature. The reaction was quenched by the addition of water. The resulting solution was extracted with EtOAc (2×) and the organic layers were combined, washed with brine (2×), dried over anhydrous sodium sulfate, and filtered. The filtrate was concentrated in vacuo to dryness. The residue was purified by silica gel chromatography with EtOAc:petroleum ether (5-15%) to afford the title compound.

Step C—Ethyl 3,3-dicyano-2-cyclopropyl-2-methylpropanoate

Into a flask was placed a solution of the intermediate from Step B (1.0 g, 5.3 mmol) in THF (50 mL) which was cooled at 15° C. Methylmagnesium bromide (1.9 mL, THF) was added dropwise and the resulting solution was stirred for 1 h at 15° C. The reaction was quenched by the addition of saturated aqueous ammonium chloride. The resulting solution was extracted with EtOAc (3×) and the organic layers were combined, dried over anhydrous sodium sulfate, and filtered. The filtrate was concentrated in vacuo to dryness. The residue was purified by silica gel chromatography with DCM:petroleum ether (50%) to afford the racemic title compound. $^1$H NMR (300 MHz, CDCl$_3$): δ 4.31-4.20 (3H, m), 1.37 (3H, s), 1.32 (3H, t, J=7.2 Hz), 1.18-1.13 (1H, m), 0.74-0.57 (3H, m), 0.52-0.45 (1H, m).

Using a similar procedure to that described in Intermediate 76, the following compounds in Table 7 were prepared using either commercial starting reagents or from compounds known in the literature.

TABLE 7

| Int. | Chiral Resolution Column | R³ | R | m/z (M + H) or $^1$H NMR |
|---|---|---|---|---|
| I-77 | racemic | (sec-butyl group) | Et | $^1$H NMR (300 MHz, CDCl$_3$): δ 4.29-4.22 (3H, m), 1.99-1.81 (2H, m), 1.33 (3H, t, J = 7.2 Hz), 1.27-1.18 (1H, m), 1.00 (3H, t, J = 7.5 Hz), 0.79-0.64 (3H, m), 0.58-0.48 (1H, m) |
| I-78A & B | CHIRALPAK AS | 4-F-phenyl | Et | 285.0 [M − 1]⁻ |
| I-79A & B | CHIRALPAK IC | 4-Cl-phenyl | Et | 301.2 [M − 1]⁻ |
| I-80A & B | CHIRALPAK AD | 4-Br-phenyl | Et | 345 [M − 1]⁻ |
| I-81A & B | Chiralcel OJ | 3-F-4-Cl-phenyl | Et | 319 [M − 1]⁻ |
| I-82A & B | CHIRALPAK IA | 5-F-pyridin-2-yl | Et | 288.0 |

TABLE 7-continued

[Structure: cyclopropyl-C(R³)(CO₂R)-C*(CN)(CN) with stereocenter]

| Int. | Chiral Resolution Column | R³ | R | m/z (M + H) or ¹H NMR |
|---|---|---|---|---|
| I-112A & B | Chiralcel OJ | 4-OCF₃-phenyl | Me | ¹H NMR (400 MHz, CDCl₃): δ 7.52 (2H, d, J = 8.8 Hz), 7.28 (2H, d, J = 8.8 Hz), 4.45 (1H, s), 3.80 (3H, s), 1.60-1.72 (1H, m), 0.80-1.10 (4H, m), 0.50 (1H, m) |
| I-113A & B | Chiralcel OJ | 3,4-difluorophenyl | Me | 289 |
| I-114A & B | Chiralpak AD | 5-fluoropyridin-3-yl | Me | 274 |

Intermediate 83, 83A, & 83B

Methyl 2-(5-chloropyridin-2-yl)-3,3-dicyano-2-cyclopropylpropanoate

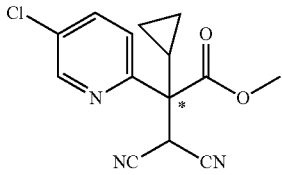 [SMILES: COC(=O)C(c1ccc(Cl)cn1)(C(C#N)C#N)C1CC1]

A solution of 2-bromo-5-chloropyridine (2.67 g, 13.9 mmol) in toluene (36.3 mL) and THF (9.08 mL) was placed into a flask under nitrogen atmosphere and cooled to 78° C. To this mixture was added t-butyl lithium (16.4 mL, 27.9 mmol, 1.7 M in THF) dropwise, and the resulting solution was stirred at 78° C. for 30 min. To this mixture was added a THF solution (1 mL) of ethyl 3,3-dicyano-2-cyclopropylacrylate (2.05 g, 11.6 mmol) (from Step B of I-76) dropwise and the resulting solution was slowly warmed up to 0° C. over 2 h. The reaction was quenched by the addition of ice-cold saturated aqueous ammonium chloride. The resulting solution was extracted with EtOAc (3×) and the organic layers were combined, washed with brine, dried over anhydrous sodium sulfate, and filtered. The filtrate was concentrated in vacuo to dryness. The residue was purified by silica gel chromatography with (EtOAc:EtOH 3:1)/Hexane (0-70%) to afford the title compound in its racemic form. The racemic material was resolved using chiral SFC (AD column) to afford isomers I-83A (faster eluting) and I83B (slower eluting) of the title compound. ¹H NMR (500 MHz, CDCl₃): δ 8.53 (1H, d, J=2.3 Hz), 7.78 (2H, m) 5.02 (s, 1H), 3.76 (3H, s), 0.96 (2H, m), 0.85 (2H, m), 0.55 (2H, m).

Using a similar procedure to that described in Intermediate 83, the following compounds in Table 8 were prepared using either commercial starting reagents or from compounds known in the literature.

TABLE 8

[Structure: cyclopropyl-C(R³)(CO₂CH₃)-C*(CN)(CN)]

| Int. | Chiral Resolution Column | R³ | m/z (M + H) or ¹H NMR |
|---|---|---|---|
| I-84A & B | Chiralcel OJ | 5-CF₃-pyridin-2-yl | 324.1 |

TABLE 8-continued
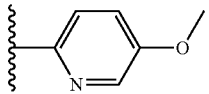
| Int. | Chiral Resolution Column | R³ | m/z (M + H) or ¹H NMR |
|---|---|---|---|
| I-115A & B | Chiralcel OJ | 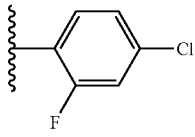 | 286 |
| I-116A & B | Chiralcel OJ | 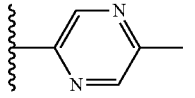 | ¹H NMR (300 MHz, CDCl₃): δ 7.75 (1H, t, J = 8.4 Hz), 7.36 (1H, d, J = 8.4 Hz), 7.11 (1H, d, J = 8.4 Hz), 4.61 (1H, s), 3.72 (3H, s), 1.60-1.70 (1H, m), 1.50 (1H, s), 0.85-0.94 (1H, m), 0.70-0.80 (1H, m), 0.51-0.62 (1H, m) |
| I-117 | racemic | 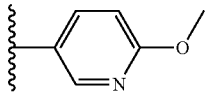 | 271.2 |
| I-118A & B | Chiralcel OJ | 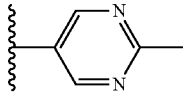 | 286 |
| I-119 | racemic | 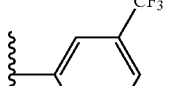 | 271.2 |
| I-120 | Racemic | 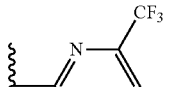 | 324.1 |
| I-121 | racemic | 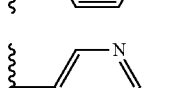 | 324.1 |
| I-122 | racemic |  | 256.1 |
| I-123 | racemic | 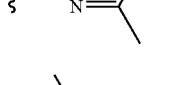 | 288.2 |
| I-124 | racemic | 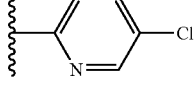 | 304.1 |
| I-125 | racemic | | 271.2 |

TABLE 8-continued

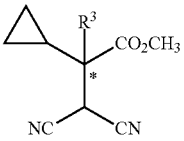

| Int. | Chiral Resolution Column | R³ | m/z (M + H) or ¹H NMR |
|---|---|---|---|
| I-126 | racemic | 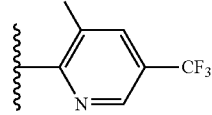 (3-Cl, 5-CF₃ pyridin-2-yl) | 358.1 |
| I-127 | racemic | 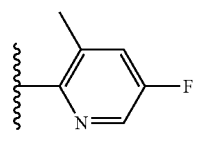 (3-F, 5-Cl pyridin-2-yl) | 308.0 |
| I-128 | racemic | 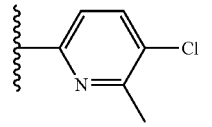 [SMILES: *c1ccc(Cl)c(C)n1] (3-methyl, 5-F pyridin-2-yl) | 288.2 |
| I-129 | racemic | 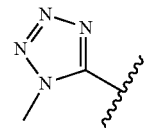 (3-Cl, 6-methyl pyridin-2-yl) | 304.1 |
| I-132 | racemic | 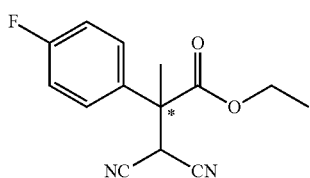 | 261 |

Intermediate 85, 85A, & 85B

Ethyl 3,3-dicyano-2-(4-fluorophenyl)-2-methylpropanoate and the S and R Isomers Thereof

[Structure of ethyl 3,3-dicyano-2-(4-fluorophenyl)-2-methylpropanoate]

Step A—Ethyl 2-(4-fluorophenyl)-2-oxoacetate

Into a flask was placed a solution of diethyl oxalate (28.5 g, 195 mmol) in THF (300 mL) which was cooled at 78° C. 4-Fluorophenylmagnesium bromide (150 mL, 1.0 M in THF) was added dropwise, and the resulting solution was stirred for 1.5 h with warming to ambient temperature. The reaction was quenched by the addition of saturated aqueous ammonium chloride. The resulting solution was extracted with EtOAc (3×) and the organic layers were combined, dried over anhydrous sodium sulfate, and filtered. The filtrate was concentrated in vacuo to dryness. The residue was purified by silica gel chromatography with EtOAc: petroleum ether (1%) to afford the title compound.

Step B—Ethyl 3,3-dicyano-2-(4-fluorophenyl)acrylate

Into a flask was placed the intermediate from Step A (28.0 g, 143 mmol), malononitrile (37.7 g, 571 mmol), piperidine (2.5 mL), and EtOH (125 mL). The resulting solution was stirred 16 h at reflux. Upon completion, the resulting mixture was concentrated under vacuum. The residue was purified by silica gel chromatography with EtOAc:petroleum ether (10%) to afford the title compound.

Step C—Ethyl 3,3-dicyano-2-(4-fluorophenyl)-2-methylpropanoate

Into a flask was placed the intermediate from Step B (3.0 g, 12 mmol), THF (50 mL), and lithium chloride (1.0 g, 23.6 mmol) which was cooled at 0° C. Subsequently, methylmagnesium bromide (7 mL) was added dropwise, and the resulting solution was stirred for 1 h at 0° C. The reaction was then quenched by the addition of water. The resulting solution was extracted with EtOAc (2×). The organic layers were combined, dried over anhydrous sodium sulfate, and filtered. The filtrate was concentrated in vacuo to dryness. The residue was purified by silica gel chromatography with EtOAc:petroleum ether (25%) to afford the title compound. The racemic material was resolved using chiral SFC (OJ column) to afford isomers I-85A (faster eluting) and I-85B (slower eluting) of the title compound. $^1$H NMR (300 MHz, CDCl$_3$): δ 7.40-7.33 (2H, m), 7.17-7.09 (2H, m), 4.45 (1H, s), 4.30 (2H, q, J=7.2 Hz), 1.99 (3H, s), 1.26 (3H, t, J=7.2 Hz).

Using a similar procedure to that described in Intermediate 85, the following compounds in Table 9 were prepared using either commercial starting reagents or from compounds known in the literature.

TABLE 9

| Int. | Chiral Resolution Column | R$^2$ | R$^3$ | m/z (M + H) or $^1$H NMR |
|---|---|---|---|---|
| I-86A & B | CHIRALPAK OJ | Me | 4-Cl-C$_6$H$_4$ | 275 [M − 1]$^-$ |
| I-87A & B | CHIRALPAK OJ | Me | 4-OCF$_3$-C$_6$H$_4$ | 325 [M − 1]$^-$ |
| I-88 | racemic | Me | 4-OMe-C$_6$H$_4$ | $^1$H NMR (400 MHz, CDCl$_3$): δ 7.31 (2H, d, J = 8.8 Hz), 6.96 (2H, d, J = 8.8 Hz), 4.48 (1H, s), 4.26 (2H, q, J = 7.2 Hz), 3.85 (3H, s), 1.99 (3H, s), 1.27 (3H, t, J = 7.2 Hz) |
| I-89 | racemic | Me | 4-Me-C$_6$H$_4$ | 255 [M − 1]$^-$ |
| I-90A & B | racemic & CHIRALPAK IA | Me | 4-CF$_3$-C$_6$H$_4$ | $^1$H NMR (400 MHz, DMSO-d$_6$): δ 7.89 (2H, d, J = 8.4 Hz), 7.67 (2H, d, J = 8.4 Hz) 5.83 (1H, s), 4.28 (2H, q, J = 7.2 Hz), 1.89 (3H, s), 1.19 (3H, t, J = 7.2 Hz) |
| I-91A & B | CHIRALPAK AD | Me | 3-F-4-Cl-C$_6$H$_3$ | 293 [M − 1]$^-$ |
| I-92 | racemic | Me | 3,4-diCl-C$_6$H$_3$ | $^1$H NMR (300 MHz, CDCl$_3$): δ 7.52 (1H, d, J = 8.4 Hz), 7.47 (1H, d, J = 2.4 Hz), 7.22 (1H, dd, J = 2.4, 8.4 Hz), 4.45 (1H, s), 4.30 (2H, q, J = 7.2 Hz), 1.98 (3H, s), 1.27 (3H, t, J = 7.2 Hz) |
| I-93A & B | PHENOMENEX PHENOMENEX Lux 5u Cellulose-3 | Me | 3-Cl-4-F-C$_6$H$_3$ | 293 [M − 1]$^-$ |
| I-94A & B | CHIRALPAK AD | Me | 3,4-diF-C$_6$H$_3$ | $^1$H NMR (300 MHz, CDCl$_3$): δ 7.31-7.12 (3H, m), 4.46 (1H, s), 4.31 (2H, q, J = 7.2 Hz), 1.99 (3H, s), 1.28 (3H, t, J = 7.2 Hz) |

TABLE 9-continued

| Int. | Chiral Resolution Column | R² | R³ | | m/z (M + H) or ¹H NMR |
|---|---|---|---|---|---|
| I-95A & B | PHENOMENEX PHENOMENEX Lux 5u Cellulose-3 | Et | | -Cl | ¹H NMR (300 MHz, CDCl₃): δ 7.44 (2H, d, J = 4.5 Hz), 7.31 (2H, d, J = 4.5 Hz), 4.45 (1H, s), 4.34 (2H, q, J = 7.2 Hz), 2.53-2.33 (2H, m), 1.31 (3H, t, J = 7.2 Hz), 1.06 (3H, t, J = 7.5 Hz) |
| I-96A & B | racemic & PHENOMENEX PHENOMENEX Lux 5u Cellulose-3 | Et | | -F | ¹H NMR (300 MHz, CDCl₃): δ 7.38-7.32 (2H, m), 7.18-7.11 (2H, m), 4.44 (1H, s), 4.31 (2H, q, J = 7.2 Hz), 2.55-2.30 (2H, m), 1.31 (3H, t, J = 7.2 Hz), 1.05 (3H, t, J = 7.5 Hz) |
| I-97 | racemic | iPr | | -Cl | ¹H NMR (400 MHz, CDCl₃): δ 7.45 (2H, d, J = 8.8 Hz), 7.32 (2H, d, J = 8.8 Hz), 4.72 (1H, s), 4.42 (2H, q, J = 7.2 Hz), 2.97-2.90 (1H, m), 1.38 (3H, t, J = 7.2 Hz), 1.10 (3H, d, J = 3.6 Hz), 1.09 (3H, d, J = 3.6 Hz) |
| I-133 | racemic | cBu | | -F | 301.0 |
| I-134 | racemic | cBu | | -Cl | ¹H NMR (500 MHz, CDCl₃): δ 7.40 (2H, d, J = 8.5 Hz), 7.20 (2H, d, J = 8.5 Hz), 4.38-4.49 (2H, m), 4.20 (1H, s), 3.45 (1H, m), 2.20-2.31 (2H, m), 2.05-2.11 (2H, m), 1.82-1.95 (2H, m), 1.76-1.79 (1H, m), 1.38 (3H, t, J = 7.5 Hz) |

Intermediate 98

Methyl 3,3-dicyano-2,2-dimethylpropanoate

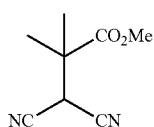

A 3 neck round bottom flask equipped with a mechanical stirrer, thermometer, condenser and nitrogen bubbler, was charged with malononitrile (251 g, 3.80 moles) and THF (2 L). Potassium t-butoxide (1M THF, 3.80 L, 3.80 mol) was then added. The mixture was stirred at 50° C. for 0.5 h. Methyl 2-bromoisobutyrate (688 g, 3.80 moles) was added and the reaction mixture was stirred overnight at 50° C. The reaction was partitioned between aqueous 1 N HCl and EtOAc. The organic phase was washed with brine, dried over anhydrous magnesium sulfate, filtered, and concentrated to afford the title compound. ¹H NMR (400 MHz, CD₃CN): δ 4.35 (1H, s) 3.73 (3H, s), 1.43 (6H, s).

Intermediate 99, 99A, & 99B

Ethyl 3,3-dicyano-2-(5-ethylpyridin-2-yl)-2-methyl-propanoate and the S and R Isomers Thereof

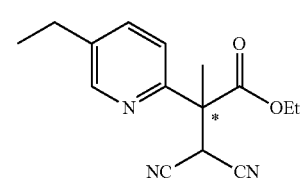 [SMILES: CCOC(=O)C(C)(c1ccc(CC)cn1)C(C#N)C#N]

Step A—Diethyl 2-(5-bromopyridin-2-yl)malonate

Into a 3-necked round-bottom flask, purged with an inert atmosphere of nitrogen, was placed 2,5-dibromopyridine (20 g, 84 mmol), copper(I) iodide (3.22 g, 16.9 mmol), picolinic acid (4.16 g, 33.8 mmol), cesium carbonate (110 g, 338 mmol), diethyl malonate (27.0 g, 169 mmol), and 1,4-dioxane (400 mL). The resulting mixture was stirred for 16 h at 100° C. The reaction was quenched by the addition of brine and the resulting solution was extracted with EtOAc (3×). The organic layers were combined, dried over anhydrous sodium sulfate, and filtered. The filtrate was concentrated in vacuo to dryness. The residue was purified by silica gel chromatography with EtOAc:petroleum ether (20%) to afford the title compound.

Step B—Ethyl 2-(5-bromopyridin-2-yl)acetate

Into a 3-necked round-bottom flask, purged with an inert atmosphere of nitrogen, was placed the intermediate from Step A (13.0 g, 41.1 mmol), sodium chloride (3.12 g, 53.5 mmol), water (9.6 mL) and DMSO (150 mL). The resulting mixture was stirred for 2 h at 150° C. The reaction was then quenched by the addition of brine and extracted with EtOAc (3×). The organic layers were combined, dried over anhydrous sodium sulfate, and filtered. The filtrate was concentrated in vacuo to dryness. The residue was purified by silica gel chromatography with EtOAc:petroleum ether (10%) to afford the title compound.

Step C—Ethyl 2-(5-ethylpyridin-2-yl)acetate

To a cold solution of the intermediate from Step B (3.0 g, 12 mmol) and Pd(PPh$_3$)$_2$Cl$_2$ (1.0 g, 1.2 mmol) in THF (30 mL) at 20° C. was added diethylzinc (12.3 mL, 12.3 mmol, 1 M) dropwise. The mixture was stirred for 1 h at 20° C. The reaction was quenched by adding water and extracted with EtOAc (2×). The organic layers were combined, dried over anhydrous sodium sulfate, and filtered. The filtrate was concentrated in vacuo to dryness. The residue was purified by silica gel chromatography with EtOAc:petroleum ether (0-20%) to afford the title compound.

Step D—Ethyl 3,3-dicyano-2-(5-ethylpyridin-2-yl)-2-methylpropanoate

The title compound in the racemic form was prepared from the intermediate from Step C following procedures described in steps CE of Intermediate 39. The racemic material was resolved using chiral SFC (AD column) to afford isomers I-99A (faster eluting) and I-99B (slower eluting) of the title compound. $^1$H NMR (300 MHz, CDCl$_3$): δ 8.41 (1H, d, J=1.5 Hz), 7.59 (1H, dd, J=2.1, 8.1 Hz), 7.41 (1H, d, J=8.1 Hz), 5.25 (1H, s), 4.24 (2H, q, J=7.2 Hz), 2.68 (2H, q, J=7.5 Hz), 1.99 (3H, s), 1.32 (3H, t, J=7.2 Hz), 1.24 (3H, t, J=7.2 Hz).

Intermediate 100, 100A, & 100B

Ethyl 3,3-dicyano-2-(5-cyclopropylpyridin-2-yl)-2-methylpropanoate and the S and R Isomers Thereof

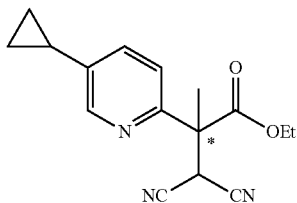 [SMILES: CCOC(=O)C(C)(c1ccc(C2CC2)cn1)C(C#N)C#N]

Step A—Ethyl 2-(5-cyclopropylpyridin-2-yl)acetate

Into a round-bottom flask, purged with an inert atmosphere of nitrogen, was placed ethyl 2-(5-bromopyridin-2-yl)acetate (the product of intermediate 99—Step B, 2.2 g, 9.0 mmol), cyclopropylboronic acid (1.0 g, 11 mmol), toluene (25 mL), water (2.5 mL), tricyclohexylphosphonium tetrafluoroborate (0.33 g, 0.90 mmol), potassium phosphate (6.70 g, 31.5 mmol), and diacetoxypalladium (0.10 g, 0.45 mmol). The resulting mixture was stirred for 16 h at 110° C. The reaction mixture was diluted with EtOAc, washed with water (2×) and brine (2×). The combined organic layers were dried over anhydrous sodium sulfate, and filtered. The filtrate was concentrated in vacuo to dryness. The residue was purified by silica gel chromatography with EtOAc:petroleum ether (0-20%) to afford the title compound.

Step B—Ethyl 3,3-dicyano-2-(5-cyclopropylpyridin-2-yl)-2-methylpropanoate

The title compound in the racemic form was prepared from the intermediate from Step A following procedures described in steps C E of intermediate 39. The racemic material was resolved using chiral SFC (IA column) to afford isomers I-100A (faster eluting) and I-100B (slower eluting) of the title compound. $^1$H NMR (300 MHz, CDCl$_3$): δ 8.36 (1H, s), 7.36-7.35 (2H, m), 5.23 (1H, s), 4.23 (2H, q, J=7.2 Hz), 1.97 (3H, s), 1.95-1.86 (1H, m), 1.26 (3H, t, J=7.2 Hz), 1.11-1.05 (2H, m), 0.79-0.72 (2H, m).

Intermediate 101A

4-Amino-5-(4-fluorophenyl)-5-methyl-2-(8-(methylthio)imidazo[1,2-a]pyrazin-6-yl)-5H-pyrrolo[2,3-d]pyrimidin-6(7H)-one and the S or R Isomers Thereof

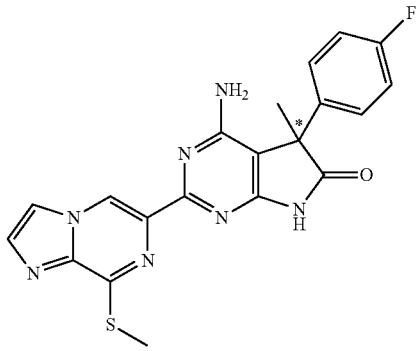 [SMILES: CSc1nc(-c2nc(N)c3c(n2)NC(=O)C3(C)c2ccc(F)cc2)cn2ccnc12]

Step A—8-(Methylthio)imidazo[1,2-a]pyrazine-6-carboximidamide

Into a flask, purged with an inert atmosphere of nitrogen, was placed 8-(methylthio)imidazo[1,2-a]pyrazine-6-carbonitrile (3.5 g, 18 mmol) and toluene (50 mL). To this was added amino(methyl)aluminum chloride (196 mL, 58.9 mmol, 0.3 M in toluene) and the resulting mixture was warmed at 80° C. After 16 h, the reaction mixture was cooled to 0° C. The reaction was quenched by the addition of MeOH:CH$_2$Cl$_2$ (1:4, 200 mL). The solid was filtered through a pad of celite, and the resulting eluent was concentrated in vacuo to dryness to afford the title compound as the HCl salt.

Step B—4-Amino-5-(4-fluorophenyl)-5-methyl-2-(8-(methylthio)imidazo[1,2-a]pyrazin-6-yl)-5H-pyrrolo[2,3-d]pyrimidin-6(7H)-one Into a vial, purged with an inert atmosphere of nitrogen, was placed t-BuOH (8.8 mL), the intermediate from Step A (425 mg, 2.05 mmol), intermediate 85A (656 mg, 2.67 mmol) and potassium bicarbonate (616 mg, 6.15 mmol). The heterogeneous mixture was stirred at 70° C. for 16 h. The reaction mixture was cooled to ambient temperature and quenched with H$_2$O (25 mL). The resulting solution was extracted with EtOAc (3×) and the organic layers were combined, and dried over anhydrous sodium sulfate. The solid was filtered and the filtrate was concentrated in vacuo to dryness. The residue was purified by silica gel chromatography with EtOAc:hexanes (20-100%) to afford the title compound. $^1$H-NMR: (500 MHz, acetone-d$_6$): δ 9.12 (1H, s), 8.10 (1H, s), 7.67 (1H, s), 7.43-7.40 (2H, m), 7.14-7.10 (2H, m), 2.80 (3H, s), 1.91 (3H, s); m/z=422.1 (M+H).

Using similar procedure to that described in intermediate 101, the following compounds in Table 10 were prepared using either commercial starting reagents or from compounds known in the literature.

TABLE 10

| Int. | R$^2$ | R$^3$ | Starting Int. | m/z (M + H) |
|---|---|---|---|---|
| I-102A | Me | ~phenyl-Cl | I-86A* | 438.0 |
| I-103B | cyclopropyl | ~phenyl-Cl | I-79B* | 464.0 |
| I-104B | Me | ~pyridyl-F | I-39B* | 423.1 |
| I-105A | Me | ~phenyl-OCF$_3$ | I-87A* | 488.0 |

Intermediates 106, 106A, & 106B

Ethyl 2-(2-chloropyrimidin-5-yl)-3,3-dicyano-2-cyclopropylpropanoate and the S and R Isomers Thereof

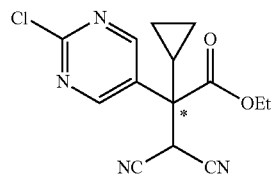

Step A—Ethyl 2-cyano-2-cyclopropylacetate

Into a 250-mL round-bottom flask purged and maintained with an inert atmosphere of nitrogen, were placed diethyl carbonate (29.1 g, 247 mmol), sodium hydride (15.29 g, 382 mmol), and toluene (80 ml). To this was added 2-cyclopropylacetonitrile (10 g, 123 mmol) in toluene (40 mL) dropwise with stirring at reflux, over a period of 30 min. The resulting mixture was stirred for 2 h at reflux. The reaction mixture was cooled to 0° C., and to this was added acetic acid (40 mL) dropwise with stirring, followed by water (100 mL). The resulting mixture was extracted with ethyl acetate (3×50 mL). The organic layers were combined, washed with brine (2×30 mL), dried over anhydrous sodium sulfate, and filtered. The filtrate was concentrated and distillation at reduced pressure (8690° C. at 10 mmHg) to affor the title compound.

Step B—Ethyl 2-cyclopropyl-3-ethoxy-3-iminopropanoate

Into a 50-mL 3-necked round-bottom flask, were placed intermediate from Step A (10 g, 65.3 mmol) and ethanol (20 ml). To this was introduced gaseous hydrogen chloride (2.86 g, 78 mmol) with stirring at 0° C. The resulting mixture was stirred for 16 h at ambient temperature. Ethanol was concentrated under vacuum without heating to affor the title compound.

Step C—Ethyl 3-amino-2-cyclopropyl-3-iminopropanoate

Into a 50-mL 3-necked round-bottom flask, were placed ethyl 2-cyclopropyl-3-ethoxy-3-iminopropanoate hydrochloride (15.5 g, 65.8 mmol) and ethanol (100 ml). To this was introduced gaseous ammonia (1.12 g, 65.8 mmol) with stirring at 0° C. The resulting mixture was stirred for 16 h at ambient temperature. Precipitates were removed by filtration, and the filtrate was concentrated in vacuo to afford the title compound.

Step D—Ethyl 2-(5-chloropyrimidin-2-yl)-2-cyclopropylacetate

Into a 4-mL vial, were placed ethyl 3-amino-2-cyclopropyl-3-iminopropanoate (200 mg, 1.175 mmol), 2-chloromalonaldehyde (225 mg, 2.115 mmol), and acetic acid (1 ml). To this was added sodium acetate (289 mg, 3.53 mmol) at ambient temperature in one portion. The resulting mixture was stirred for 16 h at 100° C. After cooling down, it was concentrated and quenched with saturated aqueous sodium bicarbonate (5 mL). The resulting mixture was extracted with ethyl acetate (3×10 mL). The organic layers were combined, washed with brine (5 mL), dried over anhydrous sodium sulfate, and filtered. The filtrate was concentrated under vacuum. The residue was purified by silica gel chromatography with ethyl acetate/petroleum ether (5%~20%) to affor the title compound.

Step E—Ethyl 2-(2-chloropyrimidin-5-yl)-3,3-dicyano-2-cyclopropylpropanoate

Into a 50-mL round-bottom flask purged and maintained with an inert atmosphere of nitrogen, were placed ethyl 2-(5-chloropyrimidin-2-yl)-2-cyclopropylacetate (300 mg, 1.246 mmol) and THF (20 mL). To this was added lithium bis(trimethylsilyl)amide (1.50 mL, 1.496 mmol, 1M in THF) dropwise with stirring at 0° C. The resulting mixture was stirred for 1 h at 0° C. To this was added NBS (333 mg, 1.870 mmol). The resulting mixture was stirred for 2 h at ambient temperature, and quenched by the addition of saturated $NH_4Cl$ solution (50 mL). The resulting mixture was extracted with EtOAc (3×50 mL), and the organic layers were combined, washed with brine (2×50 mL), dried over anhydrous sodium sulfate and filtrated. The filtrate was concentrated and purified by silica gel chromatography with EtOAc/petroleum ether (0-10%) to afford the title compound.

Step F—Ethyl 2-(2-chloropyrimidin-5-yl)-3,3-dicyano-2-cyclopropylpropanoate

Into a 50-mL round-bottom flask were placed ethyl 2-bromo-2-(5-chloropyrimidin-2-yl)-2-cyclopropylacetate (470 mg, 1.471 mmol), malononitrile (486 mg, 7.35 mmol), and DMSO (15 mL). To this was added potassium carbonate (457 mg, 3.31 mmol) in portions at ambient temperature. The resulting mixture was stirred for 16 h at ambient temperature. The reaction mixture was quenched by the addition of saturated aqueous ammonium chloride (100 mL) and extracted with ethyl acetate (3×20 mL). The organic layers were combined, washed with brine (20 mL), dried over anhydrous sodium sulfate, and filtered. The filtrate was concentrated and purified by silica gel chromatography with ethyl acetate/petroleum ether (5%-20%). To afford title compound. The racemic material was resolved using chiral HPLC (CHIRALCEL OJ) to afford isomers I-106A (faster eluting) and I-106B (slower eluting) of the title compound. LCMS m/z 305.0=(M+H).

Example 1A

4-Amino-5-(4-chlorophenyl)-2-(8-ethylimidazo[1,2-a]pyrazin-6-yl)-5-methyl-5H-pyrrolo[2,3-d]pyrimidin-6(7H)-one and the S or R Isomers Thereof

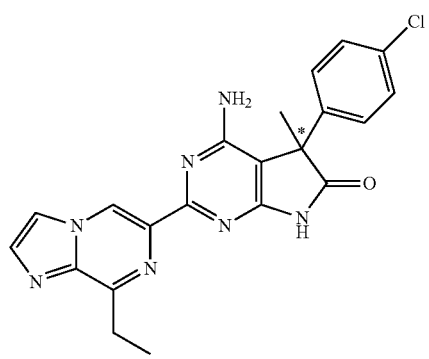 [SMILES: CCc1nc(-c2nc(N)c3c(n2)NC(=O)C3(C)c2ccc(Cl)cc2)cn2ccnc12]

Intermediate 102A (80 mg, 0.18 mmol) and Xantphos generation II precatalyst (16 mg, 0.02 mmol) were placed in an oven-dried vial under a nitrogen atmosphere. To this were added anhydousanhydous THF (1.0 mL) and a solution of diethylzinc in hexanes (2.2 mL, 1.1 mmol). The mixture was capped and warmed at 50° C. for 16 h. The reaction mixture was cooled and diluted with 10 mL of 1:1 MeOH:EtOAc and quenched with saturated aqueous $NaHCO_3$. The mixture was passed through a pad of celite and the filtrate was partitioned between EtOAc and water. The phases were separated and the organic layer was washed with brine, dried over anhydrous sodium sulfate, and concentrated in vacuo to dryness. The crude residue was purified by RP-HPLC with 10-50% acetonitrile:water (0.1% TFA), followed by basifying with saturated aqueous $NaHCO_3$ and extraction with EtOAc to afford the title compound. $^1$H NMR (500 MHz, $CD_3OD$): δ 9.37 (1H, s), 8.12 (1H, s), 7.83 (1H, s), 7.34-7.40 (4H, m), 3.24-3.26 (2H, m), 1.88 (3H, s), 1.49 (3H, t, J=7.60 Hz); m/z=420.1 (M+H).

Example 2A

4-Amino-5-(4-chlorophenyl)-5-methyl-2-(8-propylimidazo[1,2-a]pyrazin-6-yl)-5H-pyrrolo[2,3-d]pyrimidin-6(7H)-one and the S and/or R Isomers Thereof

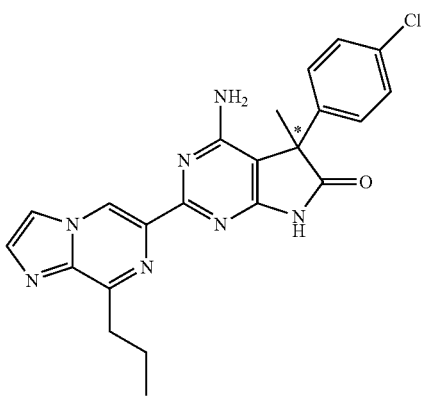 [SMILES: CCCc1nc(-c2nc(N)c3c(n2)NC(=O)C3(C)c2ccc(Cl)cc2)cn2ccnc12]

Intermediate 102A (80 mg, 0.18 mmol) and Xantphos generation II precatalyst (16 mg, 0.02 mmol) were added to an oven-dried vial which was capped, evacuated and refilled with nitrogen three times. A 0.5 M solution of propylzinc(II) bromide (2.2 mL, 1.1 mmol) was added and the reaction was warmed at 50° C. for 16 h. The reaction mixture was cooled, diluted with EtOAc, and quenched with saturated aqueous $NaHCO_3$. The mixture was passed through a pad of celite and the filtrate was partitioned between EtOAc and water. The phases were separated and the organic layer was washed with brine, dried over anhydrous sodium sulfate, and concentrated in vacuo to dryness. The crude residue was purified by RP-HPLC with 15-55% acetonitrile:water (0.1% TFA), followed by basifying with saturated aqueous $NaHCO_3$ and extraction with EtOAc to afford the title compound. $^1$H NMR (500 MHz, DMSO-$d_6$): δ 11.20 (1H, s), 9.18 (1H, s), 8.27 (1H, s), 7.78 (1H, s), 7.41 (2H, d, J=8.5 Hz), 7.27 (2H, d, J=8.5 Hz), 3.13 (2H, t, J=7.7 Hz), 1.89-1.84 (2H, m), 1.78 (3H, s), 0.98 (3H, t, J=7.4 Hz); m/z=434.1 (M+H).

TABLE 11

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 3A | 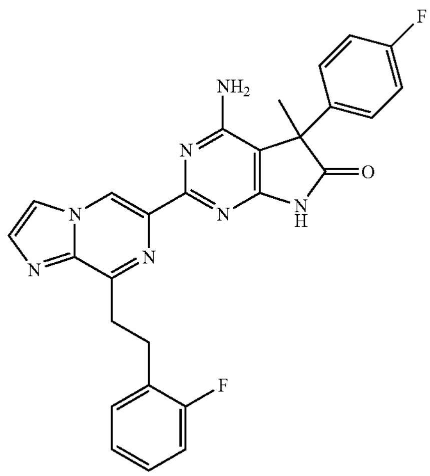 [SMILES: CC1(c2ccc(F)cc2)C(=O)Nc2nc(-c3cn4ccnc4c(CCc4ccccc4F)n3)nc(N)c21] | 4-amino-2-(8-(2-fluorophenethyl)imidazo[1,2-a]pyrazin-6-yl)-5-(4-fluorophenyl)-5-methyl-5H-pyrrolo[2,3-d]pyrimidin-6(7H)-one | I-101A | 498.1 |
| 4A | 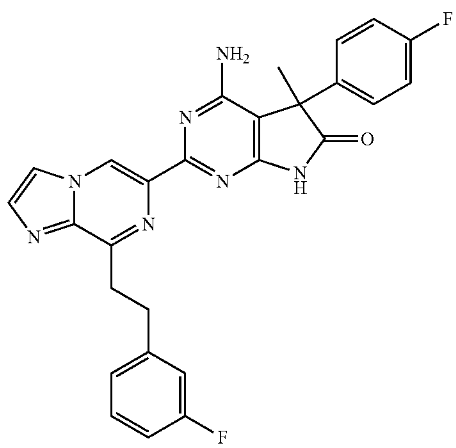 [SMILES: CC1(c2ccc(F)cc2)C(=O)Nc2nc(-c3cn4ccnc4c(CCc4cccc(F)c4)n3)nc(N)c21] | 4-amino-2-(8-(3-fluorophenethyl)imidazo[1,2-a]pyrazin-6-yl)-5-(4-fluorophenyl)-5-methyl-5H-pyrrolo[2,3-d]pyrimidin-6(7H)-one | I-101A | 498.1 |
| 5A | 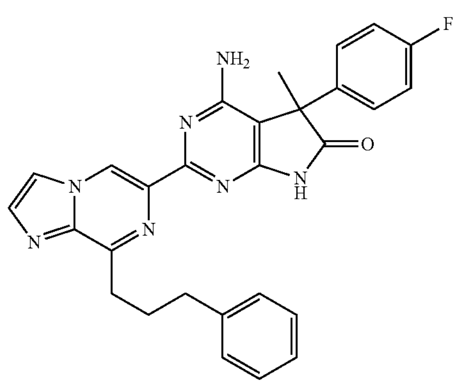 [SMILES: CC1(c2ccc(F)cc2)C(=O)Nc2nc(-c3cn4ccnc4c(CCCc4ccccc4)n3)nc(N)c21] | 6-(4-amino-5-(4-4-amino-5-(4-fluorophenyl)-5-methyl-2-(8-(3-phenylpropyl)imidazo[1,2-a]pyrazin-6-yl)-5H-pyrrolo[2,3-d]pyrimidin-6(7H)-one | I-101A | 494.2 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 6A | 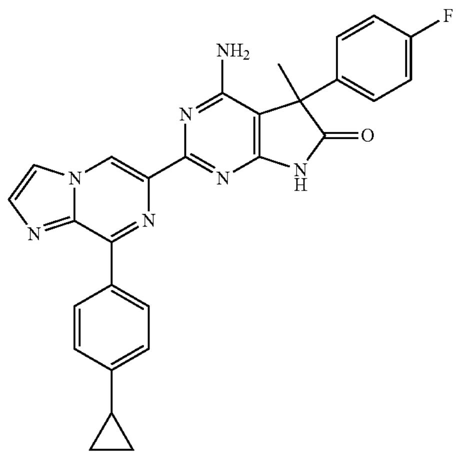 [SMILES: CC1(c2ccc(F)cc2)C(=O)Nc2nc(-c3cn4ccnc4c(-c4ccc(C5CC5)cc4)n3)nc(N)c21] | 4-amino-2-(8-(4-cyclopropylphenyl)imidazo[1,2-a]pyrazin-6-yl)-5-(4-fluorophenyl)-5-methyl-5H-pyrrolo[2,3-d]pyrimidin-6(7H)-one | I-101A | 492.1 |
| 7A | 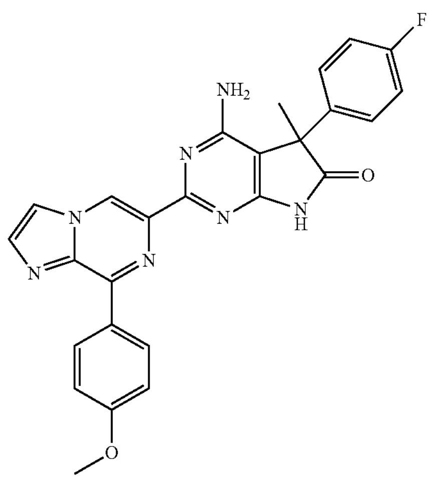 [SMILES: COc1ccc(-c2nc(-c3nc(N)c4c(n3)NC(=O)C4(C)c3ccc(F)cc3)cn3ccnc23)cc1] | 4-amino-5-(4-fluorophenyl)-2-(8-(4-methoxyphenyl)imidazo[1,2-a]pyrazin-6-yl)-5-methyl-5H-pyrrolo[2,3-d]pyrimidin-6(7H)-one | I-101A | 482.1 |
| 8A | 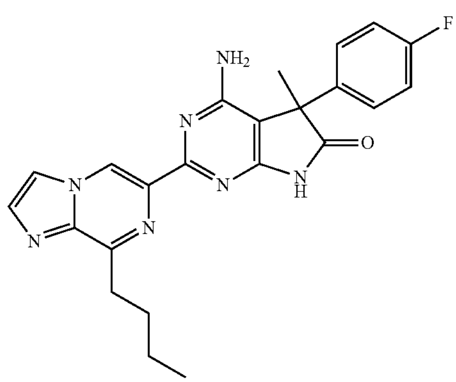 [SMILES: CCCCc1nc(-c2nc(N)c3c(n2)NC(=O)C3(C)c2ccc(F)cc2)cn2ccnc12] | 4-amino-2-(8-butylimidazo[1,2-a]pyrazin-6-yl)-5-(4-fluorophenyl)-5-methyl-5H-pyrrolo[2,3-d]pyrimidin-6(7H)-one | I-101A | 432.1 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 9A | 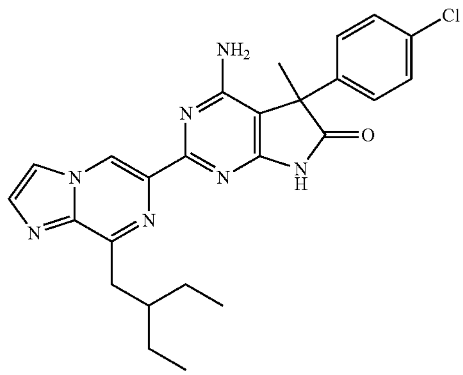 [SMILES: CCC(CC)Cc1nc(-c2nc(N)c3c(n2)NC(=O)C3(C)c2ccc(Cl)cc2)cn2ccnc12] | 4-amino-5-(4-chlorophenyl)-2-(8-(2-ethylbutyl)imidazo[1,2-a]pyrazin-6-yl)-5-methyl-5H-pyrrolo[2,3-d]pyrimidin-6(7H)-one | I-102A | 476.0 |
| 10A | 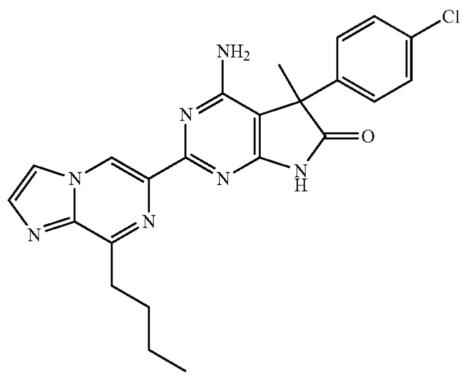 [SMILES: CCCCc1nc(-c2nc(N)c3c(n2)NC(=O)C3(C)c2ccc(Cl)cc2)cn2ccnc12] | 4-amino-2-(8-butylimidazo[1,2-a]pyrazin-6-yl)-5-(4-chlorophenyl)-5-methyl-5H-pyrrolo[2,3-d]pyrimidin-6(7H)-one | I-102A | 448.1 |
| 11B | 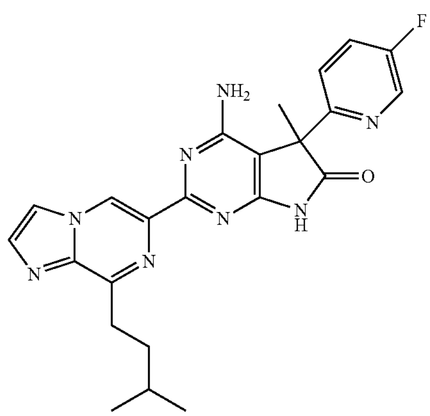 [SMILES: CC(C)CCc1nc(-c2nc(N)c3c(n2)NC(=O)C3(C)c2ccc(F)cn2)cn2ccnc12] | 4-amino-5-(5-fluoropyridin-2-yl)-2-(8-isopentylimidazo[1,2-a]pyrazin-6-yl)-5-methyl-5H-pyrrolo[2,3-d]pyrimidin-6(7H)-one | I-104B | 447.2 |
| 12A | 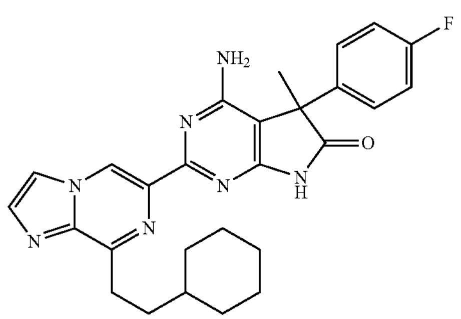 [SMILES: CC1(c2ccc(F)cc2)C(=O)Nc2nc(-c3cn4ccnc4c(CCC4CCCCC4)n3)nc(N)c21] | 4-amino-2-(8-(2-cyclohexylethyl)imidazo[1,2-a]pyrazin-6-yl)-5-(4-fluorophenyl)-5-methyl-5H-pyrrolo[2,3-d]pyrimidin-6(7H)-one | I-101A | 486.3 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 13A | 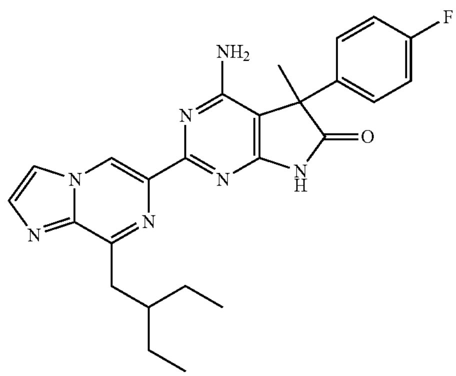 [SMILES: CCC(CC)Cc1nc(-c2nc(N)c3c(n2)NC(=O)C3(C)c2ccc(F)cc2)cn2ccnc12] | 4-amino-2-(8-(2-ethylbutyl)imidazo[1,2-a]pyrazin-6-yl)-5-(4-fluorophenyl)-5-methyl-5H-pyrrolo[2,3-d]pyrimidin-6(7H)-one | I-101A | 460.1 |
| 14A | 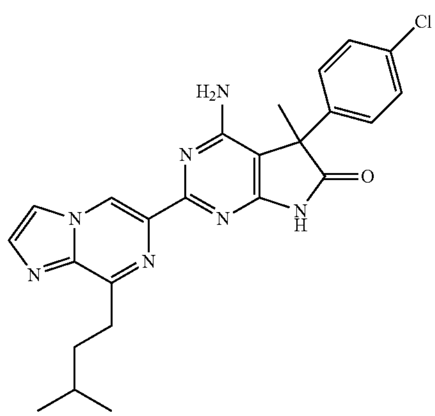 [SMILES: CC(C)CCc1nc(-c2nc(N)c3c(n2)NC(=O)C3(C)c2ccc(Cl)cc2)cn2ccnc12] | 4-amino-5-(4-chlorophenyl)-2-(8-isopentylimidazo[1,2-a]pyrazin-6-yl)-5-methyl-5H-pyrrolo[2,3-d]pyrimidin-6(7H)-one | I-102A | 462.0 |
| 15A | 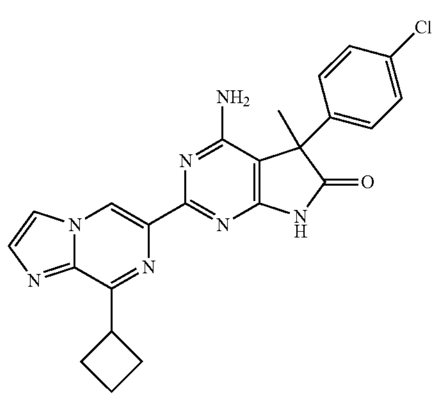 [SMILES: CC1(c2ccc(Cl)cc2)C(=O)Nc2nc(-c3cn4ccnc4c(C4CCC4)n3)nc(N)c21] | 4-amino-5-(4-chlorophenyl)-2-(8-cyclobutylimidazo[1,2-a]pyrazin-6-yl)-5-methyl-5H-pyrrolo[2,3-d]pyrimidin-6(7H)-one | I-102A | 446.1 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 16B | 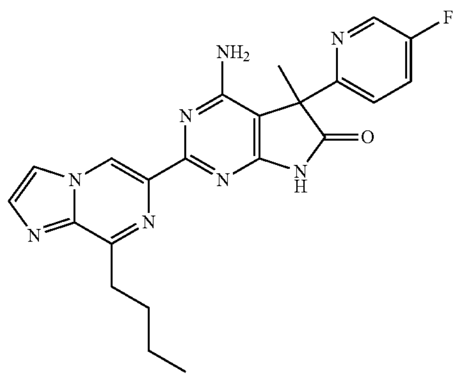 [SMILES: CCCCc1nc(-c2nc(N)c3c(n2)NC(=O)C3(C)c2ccc(F)cn2)cn2ccnc12] | 4-amino-2-(8-butylimidazo[1,2-a]pyrazin-6-yl)-5-(5-fluoropyridin-2-yl)-5-methyl-5H-pyrrolo[2,3-d]pyrimidin-6(7H)-one | I-104B | 433.1 |
| 17A | 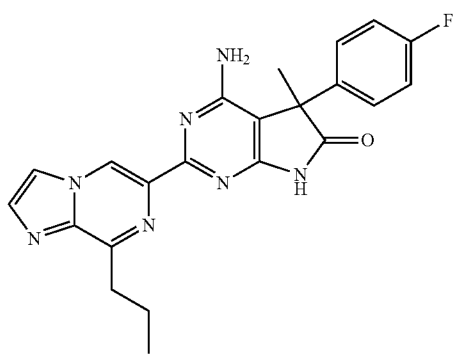 [SMILES: CCCc1nc(-c2nc(N)c3c(n2)NC(=O)C3(C)c2ccc(F)cc2)cn2ccnc12] | 4-amino-5-(4-fluorophenyl)-5-methyl-2-(8-propylimidazo[1,2-a]pyrazin-6-yl)-5H-pyrrolo[2,3-d]pyrimidin-6(7H)-one | I-101A | 418.1 |
| 18B | 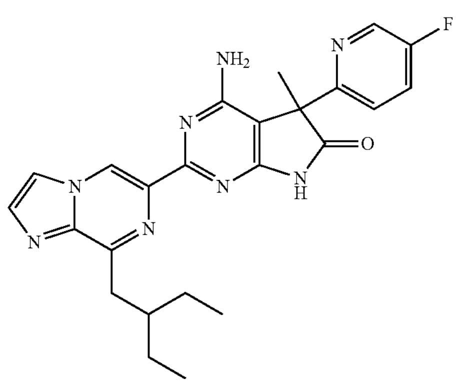 [SMILES: CCC(CC)Cc1nc(-c2nc(N)c3c(n2)NC(=O)C3(C)c2ccc(F)cn2)cn2ccnc12] | 4-amino-2-(8-(2-ethylbutyl)imidazo[1,2-a]pyrazin-6-yl)-5-(5-fluoropyridin-2-yl)-5-methyl-5H-pyrrolo[2,3-d]pyrimidin-6(7H)-one | I-104B | 461.1 |
| 19A | 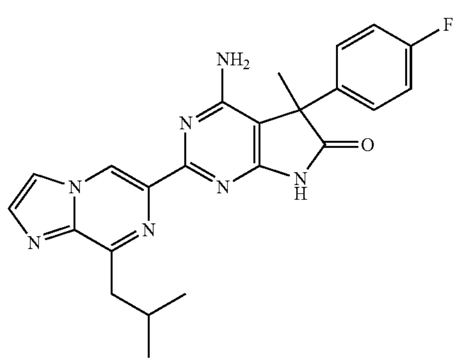 [SMILES: CC(C)Cc1nc(-c2nc(N)c3c(n2)NC(=O)C3(C)c2ccc(F)cc2)cn2ccnc12] | 4-amino-5-(4-fluorophenyl)-2-(8-isobutylimidazo[1,2-a]pyrazin-6-yl)-5-methyl-5H-pyrrolo[2,3-d]pyrimidin-6(7H)-one | I-101A | 432.2 |

TABLE 11-continued

Using similar similar procedures to that described in Examples 1-2, the following compounds in Table 11 were prepared.

| Ex. | Structure | IUPAC Name | Chiral starting material | MS (M + 1) |
|---|---|---|---|---|
| 20A | 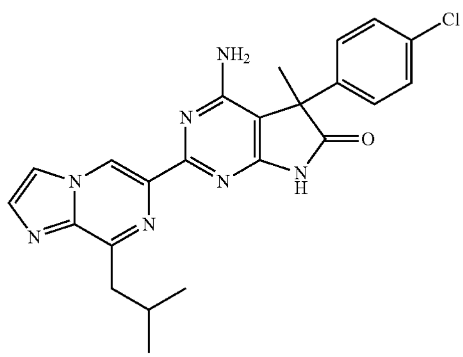 [SMILES: CC(C)Cc1nc(-c2nc(N)c3c(n2)NC(=O)C3(C)c2ccc(Cl)cc2)cn2ccnc12] | 4-amino-5-(4-chlorophenyl)-2-(8-isobutylimidazo[1,2-a]pyrazin-6-yl)-5-methyl-5H-pyrrolo[2,3-d]pyrimidin-6(7H)-one | I-102A | 448.1 |
| 21A | 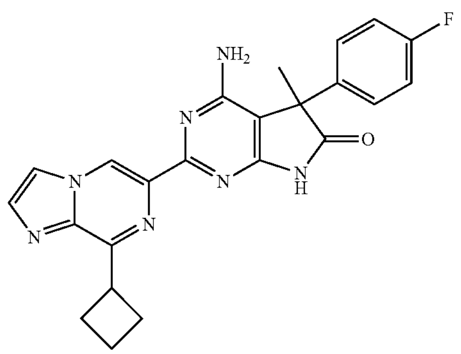 [SMILES: CC1(c2ccc(F)cc2)C(=O)Nc2nc(-c3cn4ccnc4c(C4CCC4)n3)nc(N)c21] | 4-amino-2-(8-cyclobutylimidazo[1,2-a]pyrazin-6-yl)-5-(4-fluorophenyl)-5-methyl-5H-pyrrolo[2,3-d]pyrimidin-6(7H)-one | I-101A | 430.1 |
| 22B | 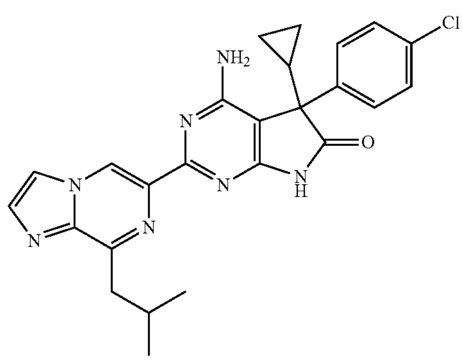 [SMILES: CC(C)Cc1nc(-c2nc(N)c3c(n2)NC(=O)C3(c2ccc(Cl)cc2)C2CC2)cn2ccnc12] | 4-amino-5-(4-chlorophenyl)-5-cyclopropyl-2-(8-isobutylimidazo[1,2-a]pyrazin-6-yl)-5H-pyrrolo[2,3-d]pyrimidin-6(7H)-one | I-103B | 474.1 |
| 23B | 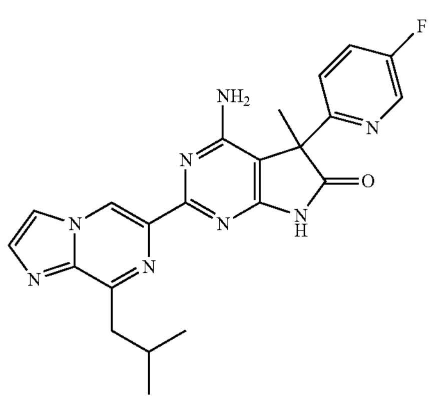 [SMILES: CC(C)Cc1nc(-c2nc(N)c3c(n2)NC(=O)C3(C)c2ccc(F)cn2)cn2ccnc12] | 4-amino-5-(5-fluoropyridin-2-yl)-2-(8-isobutylimidazo[1,2-a]pyrazin-6-yl)-5-methyl-5H-pyrrolo[2,3-d]pyrimidin-6(7H)-one | I-104B | 433.1 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 24A | 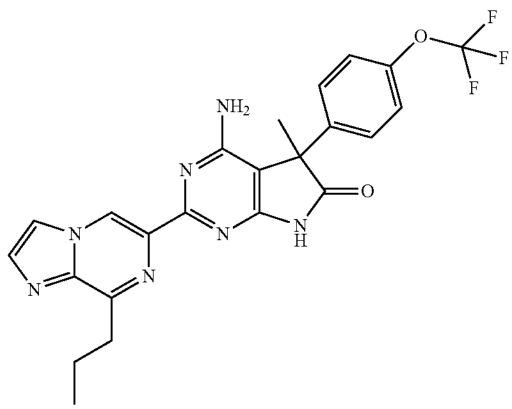 [SMILES: CCCc1nc(-c2nc(N)c3c(n2)NC(=O)C3(C)c2ccc(OC(F)(F)F)cc2)cn2ccnc12] | 4-amino-5-methyl-2-(8-propylimidazo[1,2-a]pyrazin-6-yl)-5-(4-(trifluoromethoxy)phenyl)-5H-pyrrolo[2,3-d]pyrimidin-6(7H)-one | I-105A | 484.2 |
| 25A | 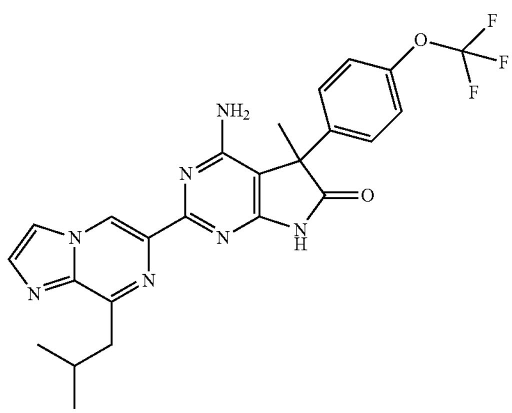 [SMILES: CC(C)Cc1nc(-c2nc(N)c3c(n2)NC(=O)C3(C)c2ccc(OC(F)(F)F)cc2)cn2ccnc12] | 4-amino-2-(8-isobutylimidazo[1,2-a]pyrazin-6-yl)-5-methyl-5-(4-(trifluoromethoxy)phenyl)-5H-pyrrolo[2,3-d]pyrimidin-6(7H)-one | I-105A | 498.0 |
| 26B | 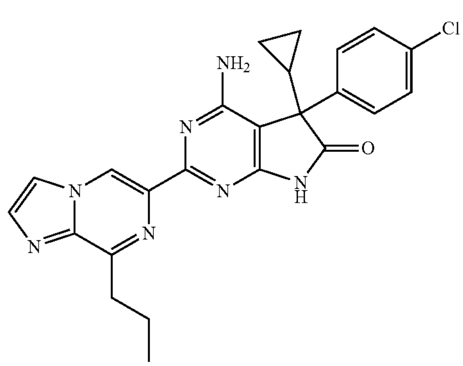 [SMILES: CCCc1nc(-c2nc(N)c3c(n2)NC(=O)C3(c2ccc(Cl)cc2)C2CC2)cn2ccnc12] | 4-amino-5-(4-chlorophenyl)-5-cyclopropyl-2-(8-propylimidazo[1,2-a]pyrazin-6-yl)-5H-pyrrolo[2,3-d]pyrimidin-6(7H)-one | I-103B | 460.1 |

TABLE 11-continued

Using simlarsimlar procedures to that described in Examples 1-2, the following compounds in Table 11 were prepared.

| Ex. | Structure | IUPAC Name | Chiral starting material | MS (M + 1) |
|---|---|---|---|---|
| 27B | 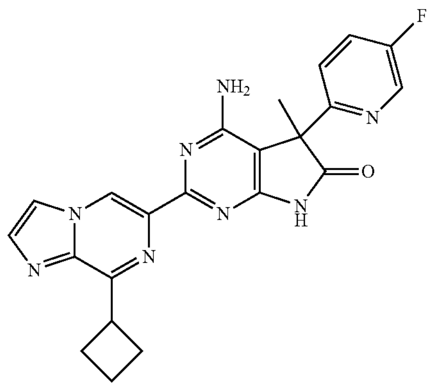 [SMILES: CC1(c2ccc(F)cn2)C(=O)Nc2nc(-c3cn4ccnc4c(C4CCC4)n3)nc(N)c21] | 4-amino-2-(8-cyclobutylimidazo[1,2-a]pyrazin-6-yl)-5-(5-fluoropyridin-2-yl)-5-methyl-5H-pyrrolo[2,3-d]pyrimidin-6(7H)-one | I-104B | 431.0 |
| 28A | 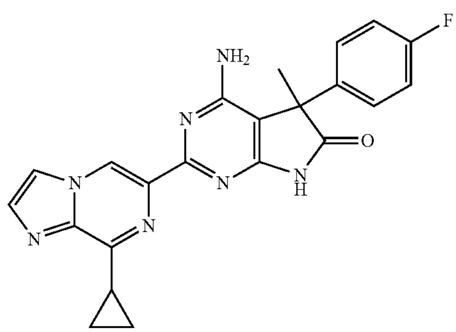 [SMILES: CC1(c2ccc(F)cc2)C(=O)Nc2nc(-c3cn4ccnc4c(C4CC4)n3)nc(N)c21] | 4-amino-2-(8-cyclopropylimidazo[1,2-a]pyrazin-6-yl)-5-(4-fluorophenyl)-5-methyl-5H-pyrrolo[2,3-d]pyrimidin-6(7H)-one | I-101A | 416.2 |

Example 29, 29A, & 29B

4-Amino-2-(8-(4-fluorobenzyl)imidazo[1,2-a]pyrazin-6-yl)-5-methyl-5-(5-methyl-1,3,4-oxadiazol-2-yl)-5H-pyrrolo[2,3-d]pyrimidin-6(7H)-one and the S and R Isomers Thereof

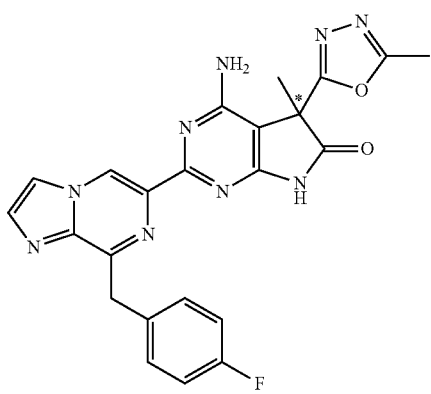 [SMILES: Cc1nnc(C2(C)C(=O)Nc3nc(-c4cn5ccnc5c(Cc5ccc(F)cc5)n4)nc(N)c32)o1]

Step A—Ethyl 4-amino-2-(8-(4-fluorobenzyl)imidazo[1,2-a]pyrazin-6-yl)-5-methyl-6-oxo-6,7-dihydro-5H-pyrrolo[2,3-d]pyrimidine-5-carboxylate Into a flask was placed Intermediate 1 (2.0 g, 7.4 mmol), Intermediate 57 (1.95 g, 8.19 mmol), potassium bicarbonate (0.82 g, 8.17 mmol) and tert-BuOH (40 mL). The resulting mixture was stirred for 16 h at 70° C. The reaction mixture was cooled to ambient temperature and quenched with water. The resulting solution was extracted with EtOAc (3×) and the organic layers were combined, and dried over anhydrous sodium sulfate. The solid was filtered and the filtrate was concentrated in vacuo to dryness. Purification by silica gel chromatography with EtOAc:petroleum ether (30-100%) afforded the title compound.

Step B—4-Amino-2-(8-(4-fluorobenzyl)imidazo[1,2-a]pyrazin-6-yl)-5-methyl-6-oxo-6,7-dihydro-5H-pyrrolo[2,3-d]pyrimidine-5-carbohydrazide Into a flask was placed the intermediate from Step A (2.9 g, 6.3 mmol) in MeOH (30 mL) and hydrazine hydrate (1.26 g, 25.2 mmol). The resulting mixture was stirred for 2 h at 70° C. The reaction mixture was concentrated in vacuo, and the residue was purified by silica gel chromatography with MeOH:DCM (10%) to afford the title compound.

Step C—N'-acetyl-4-amino-2-(8-(4-fluorobenzyl) imidazo[1,2-a]pyrazin-6-yl)-5-methyl-6-oxo-6,7-dihydro-5H-pyrrolo[2,3-d]pyrimidine-5-carbohydrazide To a solution of acetic acid (118 mg, 1.97 mmol) in DMF (25 mL) was added HATU (748 mg, 1.97 mmol) and triethylamine (271 mg, 2.68 mmol). The mixture was stirred at ambient temperature for 10 min, before the intermediate from Step B (800 mg, 1.79 mmol) was added. The resulting mixture was stirred for 16 h at ambient temperature. The reaction mixture was quenched with brine, and the resulting solid was collected by filtration. The solid was dried to afford the title compound.

Step D—4-Amino-2-(8-(4-fluorobenzyl)imidazo[1,2-a]pyrazin-6-yl)-5-methyl-5-(5-methyl-1,3,4-oxadiazol-2-yl)-5H-pyrrolo[2,3-d]pyrimidin-6(7H)-one Into a flask was placed the intermediate from Step C (350 mg, 0.72 mmol), polyphosphoric acid (5 mL) and 1,2-dichloroethane (5 mL). The resulting solution was stirred for 16 h at 80° C. The reaction mixture was cooled to ambient temperature and diluted with water. The pH value of the solution was adjusted to 8 with saturated aqueous sodium carbonate and the resulting mixture was extracted with EtOAc (3×). The organic layers were combined, washed with brine, dried over anhydrous sodium sulfate and concentrated in vacuo to dryness. The residue was purified by silica gel chromatography with EtOAc:petroleum ether (80-100%) to afford the title compound as a racemate. The racemic material was resolved using chiral SFC (AD column) to afford isomers Ex-29A (faster eluting) and Ex-29B (slower eluting) of the title compound. $^1$H NMR (400 MHz, CD$_3$OD): δ 9.41 (1H, s), 8.14 (1H, s), 7.85 (1H, s), 7.55-7.52 (2H, m), 7.01-6.95 (2H, m), 4.62 (2H, s), 2.57 (3H, s), 1.98 (3H, s); m/z=472.3 (M+H).

Example 30, 30A, & 30B

4-Amino-5-cyclopropyl-5-(5-ethyl-1,3,4-thiadiazol-2-yl)-2-(8-(3,3,4,4,4-pentafluorobutyl) imidazo[1,2-a]pyrazin-6-yl)-5H-pyrrolo[2,3-d]pyrimidin-6(7H)-one and the S and R Isomers Thereof

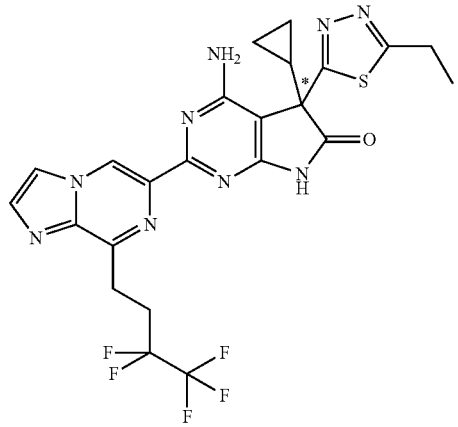 [SMILES: CCc1nnc(C2(C3CC3)C(=O)Nc3nc(-c4cn5ccnc5c(CCC(F)(F)C(F)(F)F)n4)nc(N)c32)s1]

Step A—4-Amino-5-cyclopropyl-6-oxo-2-[8-(3,3,4,4,4-pentafluorobutyl)imidazo[1,2-a]pyrazin-6-yl]-5H,6H,7H-pyrrolo[2,3-d]pyrimidine-5-carboxylate Into a flask, was placed Intermediate 15 (400 mg, 1.30 mmol), Intermediate 56 (413 mg, 1.56 mmol), KHCO$_3$ (156 mg, 1.56 mmol) and tert-BuOH (5 mL). The resulting mixture was stirred at 70° C. for 16 h. The reaction mixture was quenched with water, and extracted with EtOAc. The organic layer was washed with brine, dried over anhydrous sodium sulfate and concentrated in vacuo. The residue was purified by silica gel chromatography with EtOAc:petroleum ether (20%) to afford the title compound.

Step B—4-Amino-5-cyclopropyl-6-oxo-2-(8-(3,3,4,4-pentafluorobutyl)imidazo[1,2-a]pyrazin-6-yl)-6,7-dihydro-5H-pyrrolo[2,3-d]pyrimidine-5-carbohydrazide Into a flask was placed the intermediate from Step A (430 mg, 0.82 mmol), hydrazine hydrate (209 mg, 4.09 mmol) and MeOH (20 mL). The mixture was heated to reflux for 3 h and then concentrated in vacuo. The residue was purified by silica gel chromatography with MeOH:DCM (5%) to afford the title compound.

Step C—4-amino-5-cyclopropyl-6-oxo-2-(8-(3,3,4,4-pentafluorobutyl)imidazo[1,2-a]pyrazin-6-yl)-N'-propionyl-6,7-dihydro-5H-pyrrolo[2,3-d]pyrimidine-5-carbohydrazide A solution of the intermediate from Step B (180 mg, 0.35 mmol) in THF (5 mL) was added to a mixture of HATU (147 mg, 0.39 mmol), propanoic acid (29 mg, 0.39 mmol), triethylamine (0.1 mL, 0.72 mmol) and THF (10 mL). The resulting mixture was stirred for 12 h at ambient temperature. The reaction mixture was diluted with EtOAc, washed with water and brine, dried over anhydrous sodium sulfate, and concentrated in vacuo to dryness. The residue was purified by silica gel chromatography with MeOH:DCM (5%) to afford the title compound.

Step D—4-Amino-5-cyclopropyl-5-(5-ethyl-1,3,4-thiadiazol-2-yl)-2-(8-(3,3,4,4,4-pentafluorobutyl) imidazo[1,2-a]pyrazin-6-yl)-5H-pyrrolo[2,3-d]pyrimidin-6(7H)-one Into a flask, purged with an inert atmosphere of argon, was placed the intermediate from Step C (180 mg, 0.32 mmol), Lawesson's reagent (167 mg, 0.41 mmol), toluene (10 mL) and THF (1 mL). The resulting mixture was warmed to reflux for 12 h and then concentrated in vacuo. The residue was purified by silica gel chromatography with EtOAc:petroleum ether (20%) to afford the title compound as the racemate. The racemic material was resolved using chiral SFC (IB column) to afford isomers Ex-30A (faster eluting) and Ex-30B (slower eluting) of the title compound. $^1$H-NMR (300 MHz, CDCl$_3$) δ 9.20 (1H, s), 7.83 (1H, s), 7.77 (1H, s), 3.67-3.62 (2H, m), 3.11 (2H, q, J=7.5 Hz), 2.93-2.81 (2H, m), 1.69-1.60 (1H, m), 1.42 (3H, t, J=7.5 Hz), 0.71-0.51 (4H, m); m/z=566.1 (M+H).

Example 31A

4-Amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide and the S and R Isomers Thereof

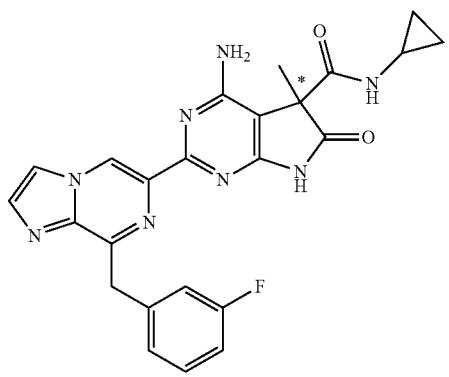 [SMILES: CC1(C(=O)NC2CC2)C(=O)Nc2nc(-c3cn4ccnc4c(Cc4cccc(F)c4)n3)nc(N)c21]

Step A—Ethyl 4-amino-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxylate The title compound was prepared from Intermediate 4 (90 mg, 0.33 mmol) and Intermediate 57 (80 mg, 0.33 mmol) using a similar procedure to that described in Example 30 Step A. The racemic material was resolved using chiral SFC (AD column) to afford isomers Ex-31A (faster eluting) and Ex-31B (slower eluting) of the title compound. m/z=462.1 (M+H).

Step B—4-Amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide A solution of isomer Ex-31A from Step A (31 mg, 0.067 mmol) and cyclopropylamine (237 µl, 3.36 mmol) in MeOH (0.5 mL) was warmed at reflux for 16 h. The crude residue was purified by RP-HPLC with 15-65% acetonitrile:water (0.1% TFA), followed by basifying with saturated aqueous NaHCO$_3$ and extraction with EtOAc to afford the title compound. $^1$H NMR (500 MHz, CD$_3$OD): δ 9.58 (1H, s), 8.25 (1H, s), 7.95 (1H, s), 7.22-7.30 (3H, m), 6.91 (1H, t, J=8.4 Hz), 4.66 (2H, s), 2.72 (1H, tt, J=7.2, 3.9 Hz), 1.80 (3H, s), 0.74-0.79 (2H, m), 0.57-0.61 (2H, m); m/z=473.1 (M+H).

TABLE 12

Using similarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 32A & B | 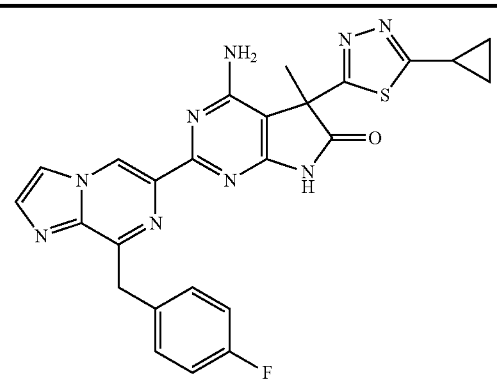 | 4-amino-5-(5-cyclopropyl-1,3,4-thiadiazol-2-yl)-2-(8-(4-fluorobenzyl)imidazo[1,2-a]pyrazin-6-yl)-5-methyl-5H-pyrrolo[2,3-d]pyrimidin-6(7H)-one | PHENOMEN EX Lux 5u Cellulose | 514.2 |
| 33A & B | 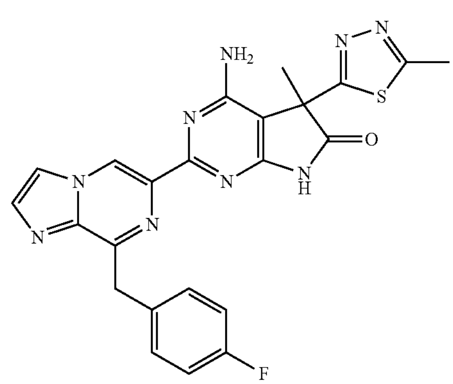 [SMILES: Cc1nnc(C2(C)C(=O)Nc3nc(-c4cn5ccnc5c(Cc5ccc(F)cc5)n4)nc(N)c32)s1] | 4-amino-2-(8-(4-fluorobenzyl)imidazo[1,2-a]pyrazin-6-yl)-5-methyl-5-(5-methyl-1,3,4-thiadiazol-2-yl)-5H-pyrrolo[2,3-d]pyrimidin-6(7H)-one | PHENOMEN EX Lux 5u Cellulose | 488.3 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 34A & B | 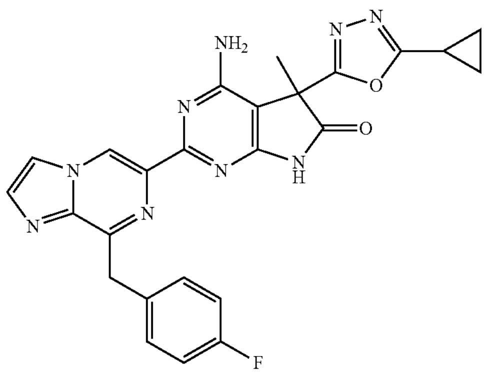 [SMILES: CC1(c2nnc(C3CC3)o2)C(=O)Nc2nc(-c3cn4ccnc4c(Cc4ccc(F)cc4)n3)nc(N)c21] | 4-amino-5-(5-cyclopropyl-1,3,4-oxadiazol-2-yl)-2-(8-(4-fluorobenzyl)imidazo[1,2-a]pyrazin-6-yl)-5-methyl-5H-pyrrolo[2,3-d]pyrimidin-6(7H)-one | CHIRALPAK AD | 498.1 |
| 35A | 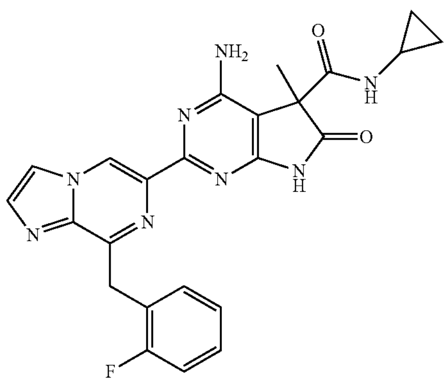 [SMILES: CC1(C(=O)NC2CC2)C(=O)Nc2nc(-c3cn4ccnc4c(Cc4ccccc4F)n3)nc(N)c21] | 4-amino-N-cyclopropyl-2-(8-(2-fluorobenzyl)imidazo[1,2-a]pyrazin-6-yl)-5-methyl-6-oxo-6,7-dihydro-5H-pyrrolo[2,3-d]pyrimidine-5-carboxamide | Similar intermediate to Ester Ex-31A* | 473.1 |
| 36A | 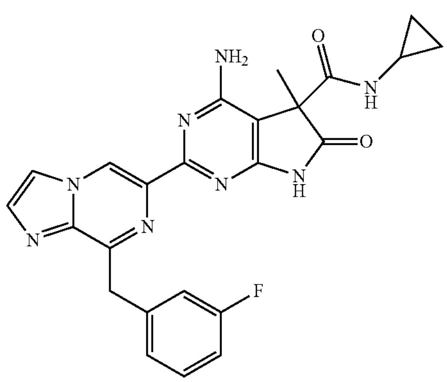 [SMILES: CC1(C(=O)NC2CC2)C(=O)Nc2nc(-c3cn4ccnc4c(Cc4cccc(F)c4)n3)nc(N)c21] | 4-amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide | Ester Ex-31A* | 473.1 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 36B | 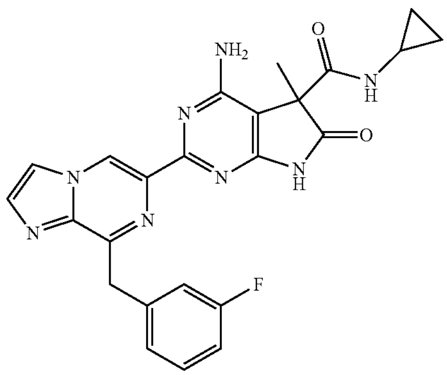 [SMILES: CC1(C(=O)NC2CC2)C(=O)Nc2nc(-c3cn4ccnc4c(Cc4cccc(F)c4)n3)nc(N)c21] | 4-amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide | Ester Ex-31B* | 473.1 |
| 38B | 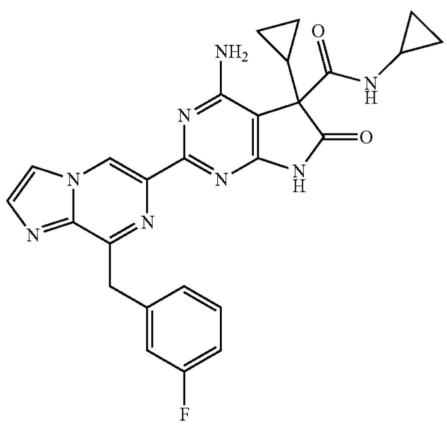 [SMILES: Nc1nc(-c2cn3ccnc3c(Cc3cccc(F)c3)n2)nc2c1C(C(=O)NC1CC1)(C1CC1)C(=O)N2] | 4-amino-N,5-dicyclopropyl-2-(8-(3-fluorobenzyl)imidazo[1,2-a]pyrazin-6-yl)-6-oxo-6,7-dihydro-5H-pyrrolo[2,3-d]pyrimidine-5-carboxamide | Similar intermediate to Ester Ex-31B* | 499.2 |
| 38A | 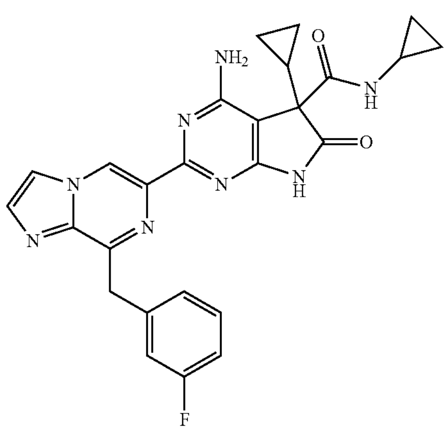 [SMILES: Nc1nc(-c2cn3ccnc3c(Cc3cccc(F)c3)n2)nc2c1C(C(=O)NC1CC1)(C1CC1)C(=O)N2] | 4-amino-N,5-dicyclopropyl-2-(8-(3-fluorobenzyl)imidazo[1,2-a]pyrazin-6-yl)-6-oxo-6,7-dihydro-5H-pyrrolo[2,3-d]pyrimidine-5-carboxamide | Similar intermediate to Ester Ex-31A* | 499.2 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 40B | 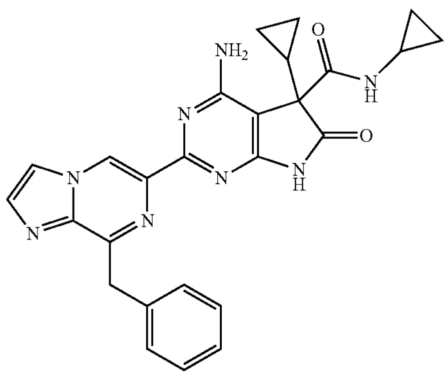 [SMILES: Nc1nc(-c2cn3ccnc3c(Cc3ccccc3)n2)nc2c1C(C(=O)NC1CC1)(C1CC1)C(=O)N2] | 4-amino-2-(8-benzylimidazo[1,2-a]pyrazin-6-yl)-N,5-dicyclopropyl-6-oxo-6,7-dihydro-5H-pyrrolo[2,3-d]pyrimidine-5-carboxamide | Similar intermediate to Ester Ex-31B* | 481.1 |
| 40A | 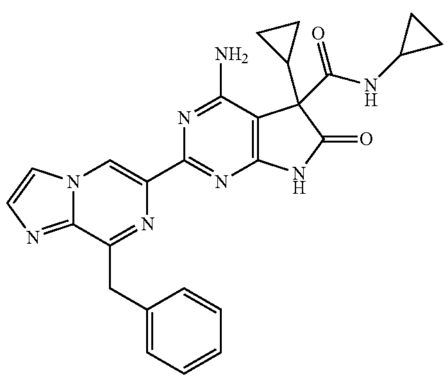 [SMILES: Nc1nc(-c2cn3ccnc3c(Cc3ccccc3)n2)nc2c1C(C(=O)NC1CC1)(C1CC1)C(=O)N2] | 4-amino-2-(8-benzylimidazo[1,2-a]pyrazin-6-yl)-N,5-dicyclopropyl-6-oxo-6,7-dihydro-5H-pyrrolo[2,3-d]pyrimidine-5-carboxamide | Similar intermediate to Ester Ex-31A* | 481.1 |
| 42B | 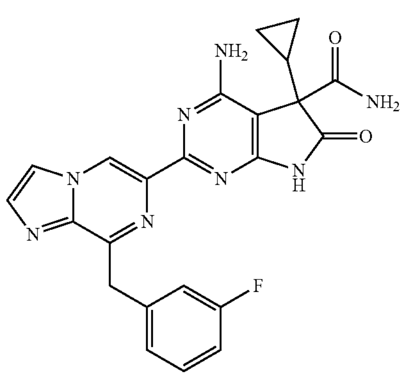 [SMILES: NC(=O)C1(C2CC2)C(=O)Nc2nc(-c3cn4ccnc4c(Cc4cccc(F)c4)n3)nc(N)c21] | 4-amino-5-cyclopropyl-2-(8-(3-fluorobenzyl)imidazo[1,2-a]pyrazin-6-yl)-6-oxo-6,7-dihydro-5H-pyrrolo[2,3-d]pyrimidine-5-carboxamide | Similar intermediate to Ester Ex-31B* | 459.0 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 43 | 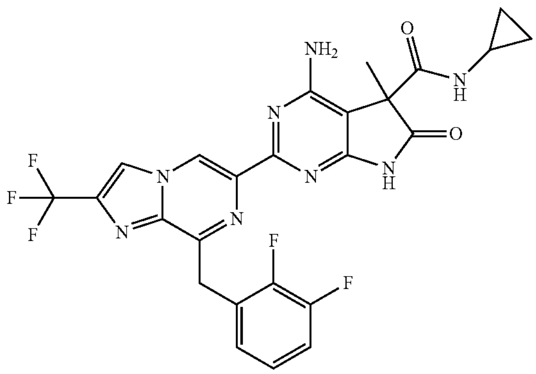 [SMILES: CC1(C(=O)NC2CC2)C(=O)Nc2nc(-c3cn4cc(C(F)(F)F)nc4c(Cc4cccc(F)c4F)n3)nc(N)c21] | 4-amino-N-cyclopropyl-2-(8-(2,3-difluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide | Ester separated on CHIRALPAK IA | 559.0 |
| 44 | 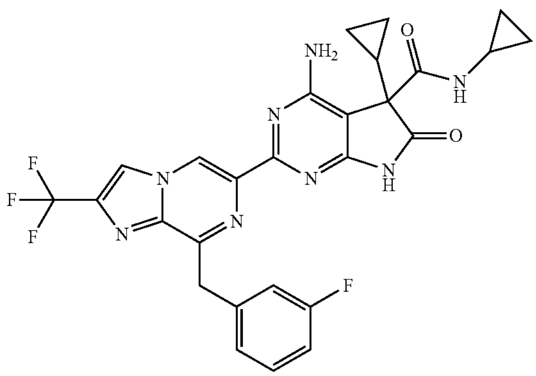 [SMILES: Nc1nc(-c2cn3cc(C(F)(F)F)nc3c(Cc3cccc(F)c3)n2)nc2c1C(C(=O)NC1CC1)(C1CC1)C(=O)N2] | 4-amino-N,5-dicyclopropyl-2-(8-(3-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide | Ester separated on CHIRALPAK IA | 567.0 |
| 45A & B | 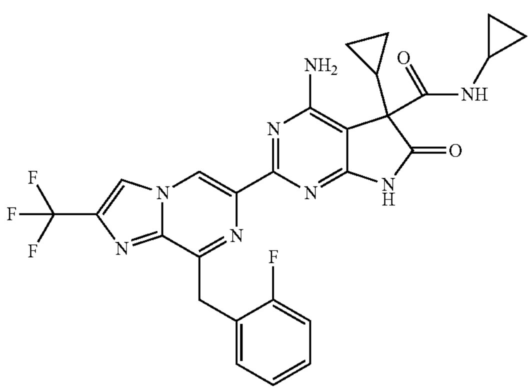 [SMILES: Nc1nc(-c2cn3cc(C(F)(F)F)nc3c(Cc3ccccc3F)n2)nc2c1C(C(=O)NC1CC1)(C1CC1)C(=O)N2] | 4-amino-N,5-dicyclopropyl-2-(8-(2-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide | Ester separated on CHIRALPAK IA | 567.2 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 46 | 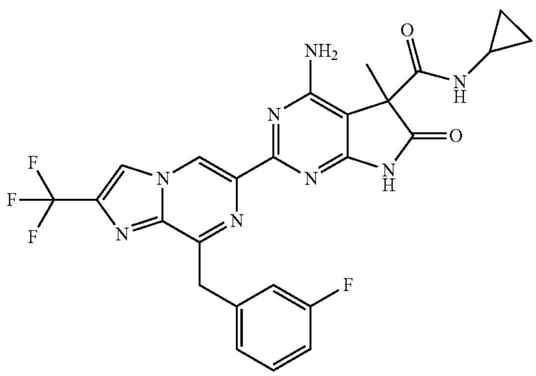 [SMILES: CC1(C(=O)NC2CC2)C(=O)Nc2nc(-c3cn4cc(C(F)(F)F)nc4c(Cc4cccc(F)c4)n3)nc(N)c21] | 4-amino-N-cyclopropyl-2-(8-(3-fluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide | Ester separated on CHIRALPAK IA | 541.2 |
| 47 | 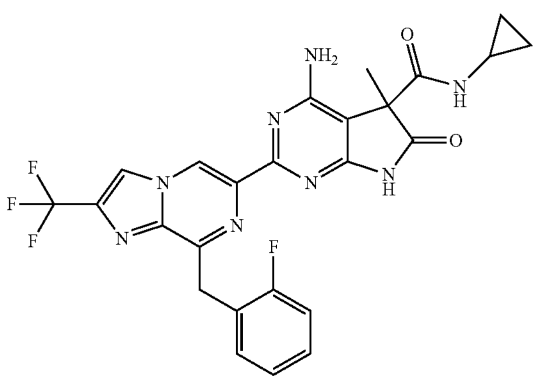 [SMILES: CC1(C(=O)NC2CC2)C(=O)Nc2nc(-c3cn4cc(C(F)(F)F)nc4c(Cc4ccccc4F)n3)nc(N)c21] | 4-amino-N-cyclopropyl-2-(8-(2-fluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide | Ester separated on CHIRALPAK IA | 541.3 |
| 48A | 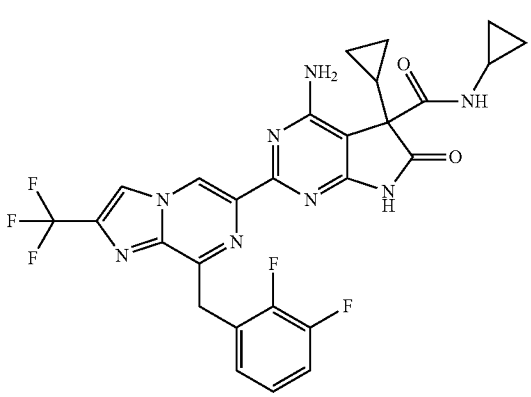 | 4-amino-N,5-dicyclopropyl-2-(8-(2,3-difluorobenzyl)-2-(trifluoromethyl)imidazo[1,2-a]pyrazin-6-yl)-6-oxo-6,7-dihydro-5H-pyrrolo[2,3-d]pyrimidine-5-carboxamide | Ester separated on CHIRALPAK IA | 585.0 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 50 | 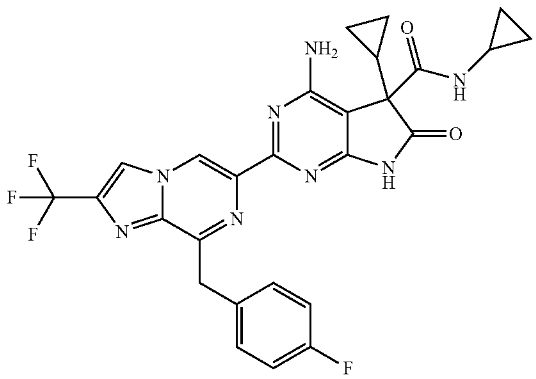 [SMILES: Nc1nc(-c2cn3cc(C(F)(F)F)nc3c(Cc3ccc(F)cc3)n2)nc2c1C(C(=O)NC1CC1)(C1CC1)C(=O)N2] | 4-amino-N,5-dicyclopropyl-2-(8-(4-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide | Ester separated on CHIRALPAK IA | 567.0 |
| 51 | 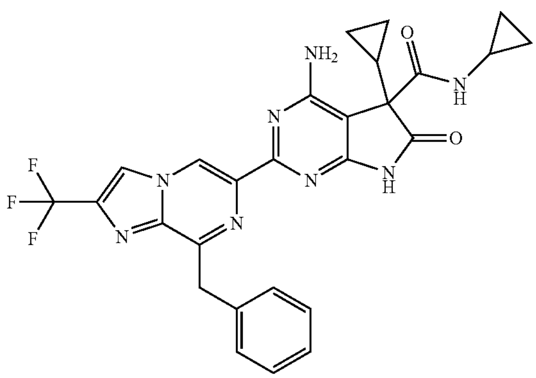 [SMILES: Nc1nc(-c2cn3cc(C(F)(F)F)nc3c(Cc3ccccc3)n2)nc2c1C(C(=O)NC1CC1)(C1CC1)C(=O)N2] | 4-amino-2-(8-benzyl-2-(trifluoromethyl)imidazo[1,2-a]pyrazin-6-yl)-N,5-dicyclopropyl-6-oxo-6,7-dihydro-5H-pyrrolo[2,3-d]pyrimidine-5-carboxamide | Ester separated on CHIRALPAK IA | 549.2 |
| 52 | 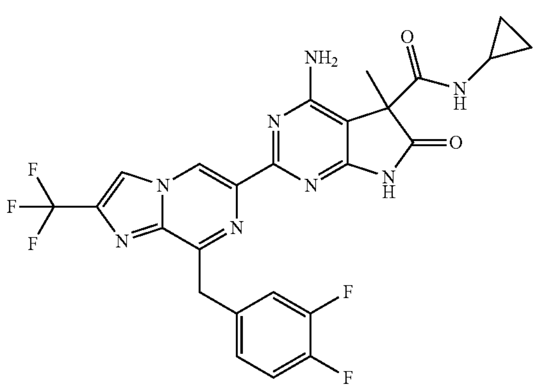 [SMILES: CC1(C(=O)NC2CC2)C(=O)Nc2nc(-c3cn4cc(C(F)(F)F)nc4c(Cc4ccc(F)c(F)c4)n3)nc(N)c21] | 4-amino-N-cyclopropyl-2-(8-(3,4-difluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide | Ester separated on CHIRALPAK IA | 559.0 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 53A & B | 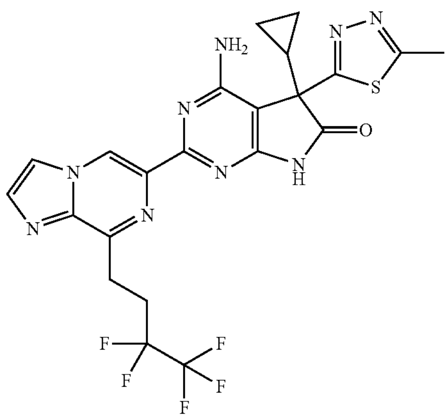 [SMILES: Cc1nnc(C2(C3CC3)C(=O)Nc3nc(-c4cn5ccnc5c(CCC(F)(F)C(F)(F)F)n4)nc(N)c32)s1] | 4-amino-5-cyclopropyl-5-(5-methyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 552.0 |
| 54A & B | 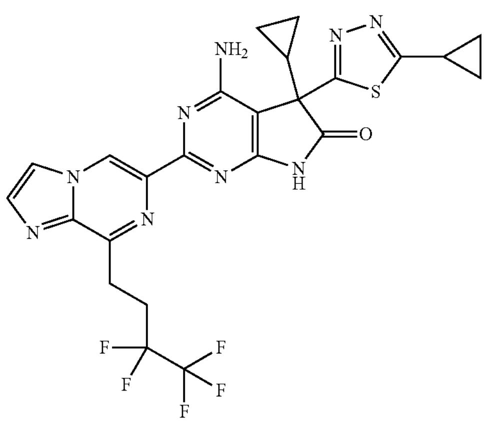 | 4-amino-5-cyclopropyl-5-(5-cyclopropyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 578.0 |
| 55A & B | 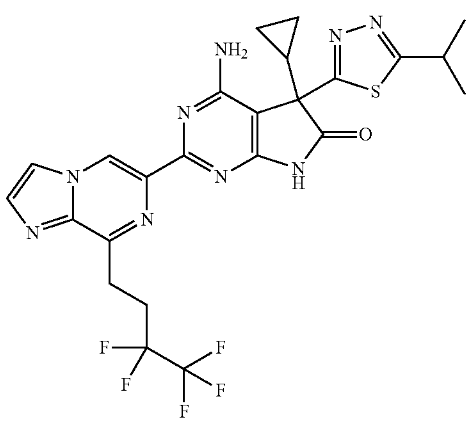 | 4-amino-5-cyclopropyl-5-(5-isopropyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IB | 580.1 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 56A & B | 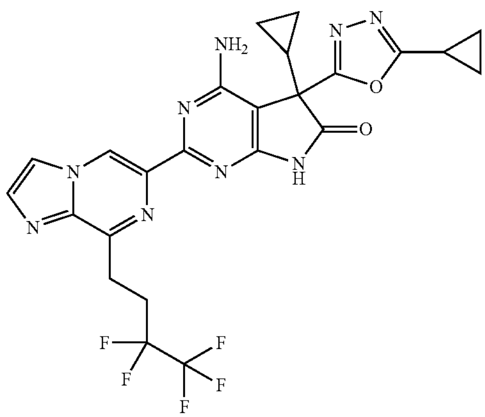 [SMILES: Nc1nc(-c2cn3ccnc3c(CCC(F)(F)C(F)(F)F)n2)nc2c1C(c1nnc(C3CC3)s1)(C1CC1)C(=O)N2] | 4-amino-5-cyclopropyl-5-(5-cyclopropyl-1,3,4-oxadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 561.9 |
| 57A & B | 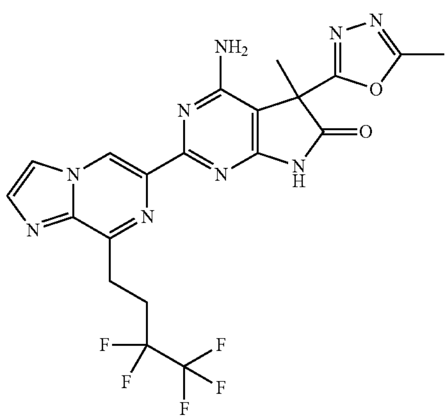 [SMILES: Cc1nnc(C2(C)C(=O)Nc3nc(-c4cn5ccnc5c(CCC(F)(F)C(F)(F)F)n4)nc(N)c32)o1] | 4-amino-5-methyl-5-(5-methyl-1,3,4-oxadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 510.2 |
| 58A & B | 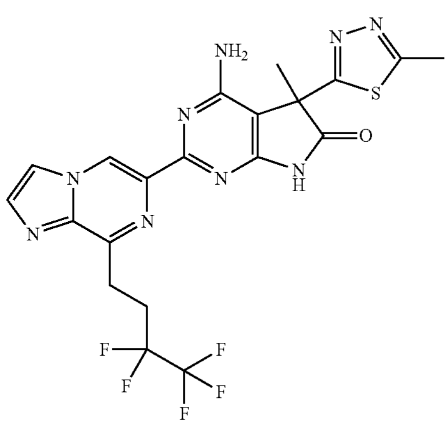 [SMILES: Cc1nnc(C2(C)C(=O)Nc3nc(-c4cn5ccnc5c(CCC(F)(F)C(F)(F)F)n4)nc(N)c32)s1] | 4-amino-5-methyl-5-(5-methyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 526.3 |

TABLE 12-continued

Using simlarsimlar procedures to that described in Examples 29-31, the following compounds in Table 12 were prepared.

| Ex. | Structure | IUPAC Name | Chiral separation condition or Starting Material | MS (M + 1) |
|---|---|---|---|---|
| 59A & B | 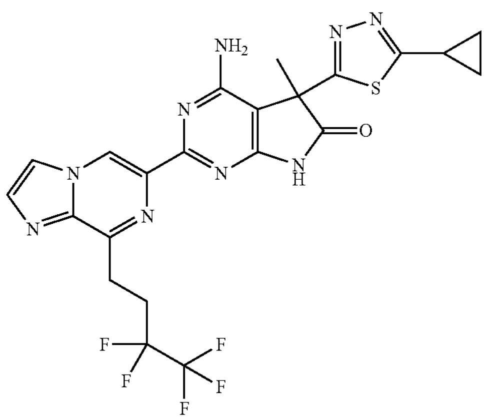 [SMILES: CC1(c2nnc(C3CC3)s2)C(=O)Nc2nc(-c3cn4ccnc4c(CCC(F)(F)C(F)(F)F)n3)nc(N)c21] | 4-amino-5-(5-cyclopropyl-1,3,4-thiadiazol-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AD | 552.0 |
| 60A & B | 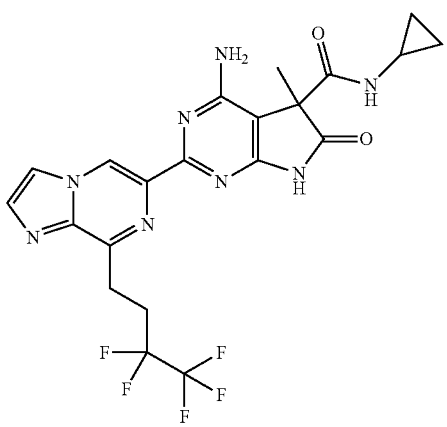 [SMILES: CC1(C(=O)NC2CC2)C(=O)Nc2nc(-c3cn4ccnc4c(CCC(F)(F)C(F)(F)F)n3)nc(N)c21] | 4-amino-N-cyclopropyl-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidine-5-carboxamide | CHIRALPAK AD | 511.5 |
| 61A & B | 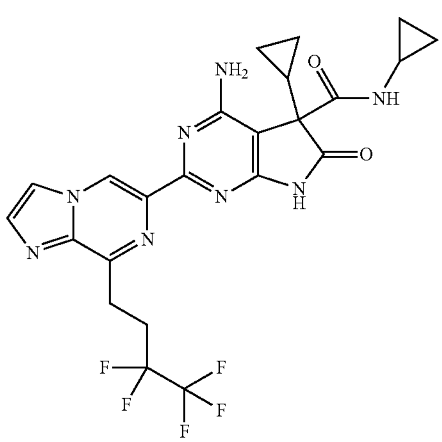 [SMILES: Nc1nc(-c2cn3ccnc3c(CCC(F)(F)C(F)(F)F)n2)nc2c1C(C(=O)NC1CC1)(C1CC1)C(=O)N2] | 4-amino-N,5-dicyclopropyl-6-oxo-2-(8-(3,3,4,4,4-pentafluorobutyl)imidazo[1,2-a]pyrazin-6-yl)-6,7-dihydro-5H-pyrrolo[2,3-d]pyrimidine-5-carboxamide | CHIRALPAK AD | 537.6 |

Example 63A

4-Amino-2-(8-(4-fluorobenzyl)imidazo[1,2-a]pyrazin-6-yl)-5-(1-isopropyl-1H-1,2,3-triazol-4-yl)-5-methyl-5H-pyrrolo[2,3-d]pyrimidin-6(7H)-one and the S and R Isomers Thereof

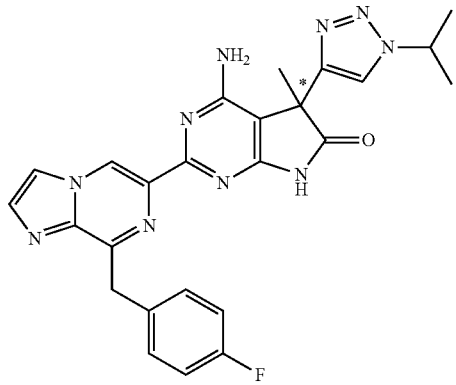 [SMILES: CC(C)n1cc(C2(C)C(=O)Nc3nc(-c4cn5ccnc5c(Cc5ccc(F)cc5)n4)nc(N)c32)nn1]

Step A—4-Amino-5-ethynyl-2-(8-(4-fluorobenzyl)imidazo[1,2-a]pyrazin-6-yl)-5-methyl-5H-pyrrolo[2,3-d]pyrimidin-6(7H)-one A flask was charged with Intermediate 1 (300 mg, 1.11 mmol), Intermediate 58-A (211 mg, 1.22 mmol), potassium bicarbonate (134 mg, 1.34 mmol) and tert-BuOH (6 mL). The resulting solution was stirred for 16 h at 70° C. Upon completion, the reaction was quenched by the addition of water. The resulting mixture was extracted with EtOAc (4×) and the organic layers were combined. The resulting solution was washed with brine, dried over anhydrous sodium sulfate, and filtered. The filtrate was concentrated in vacuo to dryness, and the residue purified by silica gel chromatography with MeOH:DCM (1-4%) to afford the title compound 63A.

Step B—4-Amino-2-(8-(4-fluorobenzyl)imidazo[1,2-a]pyrazin-6-yl)-5-(1-isopropyl-1H-1,2,3-triazol-4-yl)-5-methyl-5H-pyrrolo[2,3-d]pyrimidin-6(7H)-one To DMF (2.5 mL) in a flask wrapped in aluminum foil was added sodium azide (32 mg, 0.48 mmol) and 2-iodopropane (89 mg, 0.52 mmol), and the mixture was stirred for 16 h at ambient temperature. To the mixture was added the intermediate from Step A (80 mg, 0.19 mmol), water (1.5 mL), copper sulfate (13 mg, 0.081 mmol) and sodium ascorbate (38 mg, 0.19 mmol). The resulting solution was stirred for 3 days at 55° C. The reaction was then quenched by the addition of ammonium hydroxide. The resulting solution was extracted with EtOAc (4×), and the combined organic layers were washed with ammonium hydroxide (2×) and brine, dried over anhydrous sodium sulfate, and filtered. The filtrate was concentrated in vacuo to dryness and purified by RP-HPLC with 35-55% acetonitrile:water (0.1% TFA), followed by basifying with saturated aqueous $NaHCO_3$ and extraction with EtOAc to afford the title compound. $^1$H-NMR: (300 MHz, $CD_3OD$): δ 9.38 (1H, s), 8.12 (1H, d, J=1.2 Hz), 7.97 (1H, s), 7.83 (1H, d, J=0.9 Hz), 7.52 (2H, dd, J=5.4, 8.7 Hz), 6.97 (2H, dd, J=8.7, 8.7 Hz), 4.90-4.79 (1H, m), 4.60 (2H, s), 1.86 (3H, s), 1.58 (6H, d, J=1.8 Hz); m/z=499.4 (M+H).

TABLE 13

Using a similar procedure to that described in Examples 63, the following compounds in Table 13 were prepared.

| Ex. | Structure | IUPAC Name | Chiral separation column or Starting Material | MS (M + 1) |
|---|---|---|---|---|
| 64A | 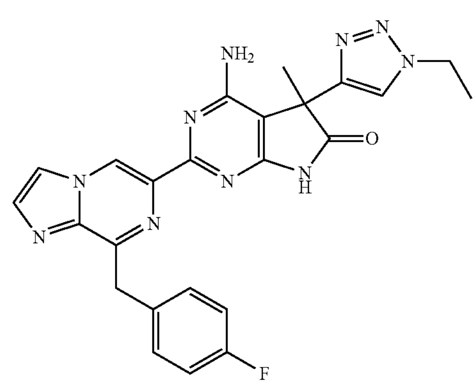 [SMILES: CCn1cc(C2(C)C(=O)Nc3nc(-c4cn5ccnc5c(Cc5ccc(F)cc5)n4)nc(N)c32)nn1] | 4-amino-5-(1-ethyl-1H-1,2,3-triazol-4-yl)-2-(8-(4-fluorobenzyl)imidazo[1,2-a]pyrazin-6-yl)-5-methyl-5H-pyrrolo[2,3-d]pyrimidin-6(7H)-one | Alkyne Ex-63A* | 485.4 |

TABLE 13-continued

Using a similar procedure to that described in Examples 63, the following compounds in Table 13 were prepared.

| Ex. | Structure | IUPAC Name | Chiral separation column or Starting Material | MS (M + 1) |
|---|---|---|---|---|
| 65A | 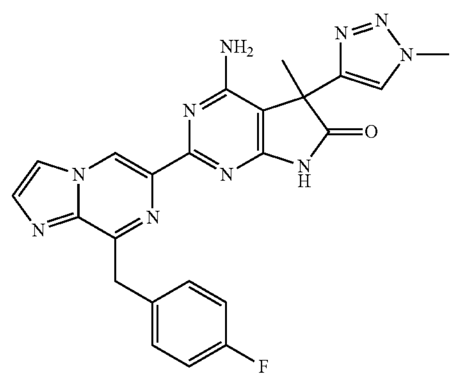 [SMILES: Cn1cc(C2(C)C(=O)Nc3nc(-c4cn5ccnc5c(Cc5ccc(F)cc5)n4)nc(N)c32)nn1] | 4-amino-2-(8-(4-fluorobenzyl)imidazo[1,2-a]pyrazin-6-yl)-5-methyl-5-(1-methyl-1H-1,2,3-triazol-4-yl)-5H-pyrrolo[2,3-d]pyrimidin-6(7H)-one | Alkyne Ex-63A* | 471.4 |
| 66A & B | 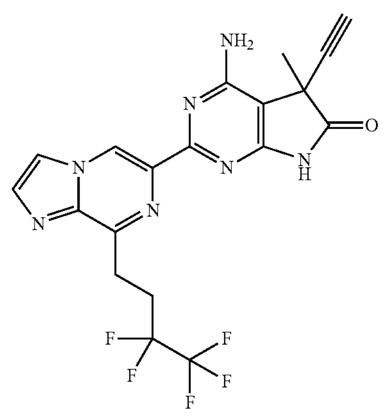 [SMILES: C#CC1(C)C(=O)Nc2nc(-c3cn4ccnc4c(CCC(F)(F)C(F)(F)F)n3)nc(N)c21] | 4-amino-5-ethynyl-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK OJ | 452.0 |
| 67A & B | 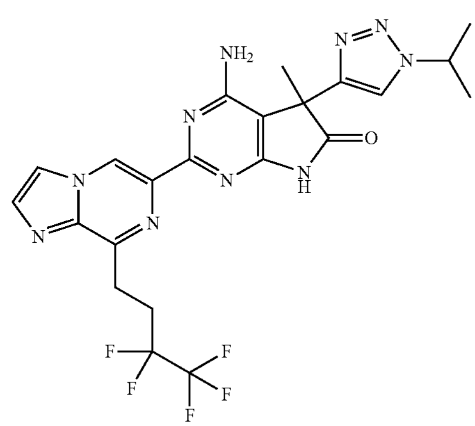 [SMILES: CC(C)n1cc(C2(C)C(=O)Nc3nc(-c4cn5ccnc5c(CCC(F)(F)C(F)(F)F)n4)nc(N)c32)nn1] | 4-amino-5-(1-isopropyl-1H-1,2,3-triazol-4-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AD | 537.1 |

Example 68A

4-Amino-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one and the S and R Isomers Thereof

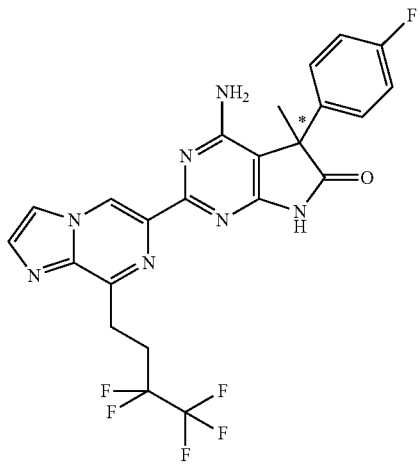 [SMILES: CC1(c2ccc(F)cc2)C(=O)Nc2nc(-c3cn4ccnc4c(CCC(F)(F)C(F)(F)F)n3)nc(N)c21]

Into a vial, purged with an inert atmosphere of nitrogen, was placed t-BuOH (1.0 mL), Intermediate 15 (31.5 mg, 0.10 mmol), Intermediate 85A (29.0 mg, 0.12 mmol) and potassium bicarbonate (30.8 mg, 0.30 mmol). The heterogeneous mixture was stirred at 80° C. for 16 h. The reaction mixture was cooled to ambient temperature and quenched with $H_2O$ (25 mL). The resulting solution was extracted with EtOAc (3×) and the organic layers were combined, and dried over anhydrous sodium sulfate. The solid was filtered and the filtrate was concentrated in vacuo to dryness. The crude residue was purified by RP-HPLC with 35-36% acetonitrile:water (0.1% TFA), followed by basifying with saturated aqueous $NaHCO_3$ and extraction with EtOAc to afford the title compound. $^1$H NMR: (600 MHz, $CD_3OD$): δ 9.33 (1H, s), 8.09 (1H, s), 7.79 (1H, s), 7.32 (2H, dd, J=8.6, 5.2 Hz), 7.03 (2H, t, J=8.6 Hz), 3.58-3.55 (2H, m), 2.95-2.86 (2H, m), 1.85 (3H, s); m/z=522.2 (M+H).

Example 69B

4-Amino-2-(8-(4-fluorobenzyl)imidazo[1,2-a]pyrazin-6-yl)-5-(5-fluoropyridin-2-yl)-5-methyl-5H-pyrrolo[2,3-d]pyrimidin-6(7H)-one and the S and R Isomers Thereof

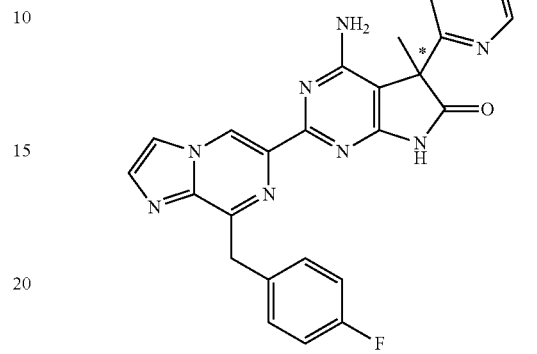

Into a vial, purged with an inert atmosphere of nitrogen, was placed t-BuOH (1.0 mL), Intermediate 1 (50.0 mg, 0.19 mmol), Intermediate 39B (58.2 mg, 0.22 mmol) and potassium bicarbonate (57.0 mg, 0.57 mmol). The heterogeneous mixture was stirred at 80° C. for 3.5 h. The reaction mixture was cooled to ambient temperature and quenched with $H_2O$ (25 mL). The resulting solution was extracted with EtOAc (3×) and the organic layers were combined, and dried over anhydrous sodium sulfate. The solid was filtered and the filtrate was concentrated in vacuo to dryness. The crude residue was purified by RP-HPLC with 10-50% acetonitrile:water (0.1% TFA), followed by basifying with saturated aqueous $NaHCO_3$ and extraction with EtOAc to afford the title compound. $^1$H NMR: (500 MHz, DMSO-$d_6$): δ 11.29 (1H, br s), 9.20 (1H, s), 8.52 (1H, d, J=3.01 Hz), 8.29 (1H, s), 7.81 (1H, s), 7.75 (1H, td, J=8.8, 3.0 Hz), 7.55 (1H, dd, J=8.9, 4.3 Hz), 7.43 (2H, dd, J=8.4, 5.6 Hz), 7.08 (2H, t, J=8.8 Hz), 6.53 (2H, s), 4.47 (2H, s), 1.80 (3H, s); m/z=485.1 (M+H).

TABLE 14

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 70 | 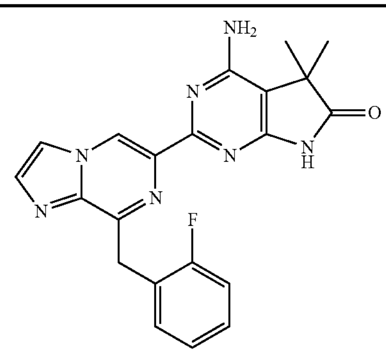 | 4-amino-2-(8-(2-fluorobenzyl)imidazo[1,2-a]pyrazin-6-yl)-5,5-dimethyl-5H-pyrrolo[2,3-d]pyrimidin-6(7H)-one | | 404.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 71 | 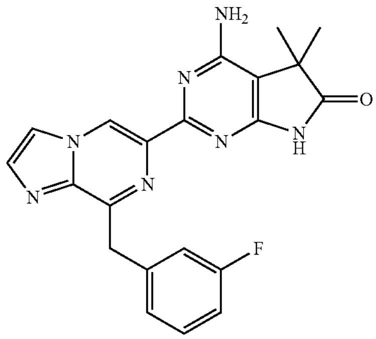 [SMILES: CC1(C)C(=O)Nc2nc(-c3cn4ccnc4c(Cc4cccc(F)c4)n3)nc(N)c21] | 4-amino-2-(8-(3-fluorobenzyl)imidazo[1,2-a]pyrazin-6-yl)-5,5-dimethyl-5H-pyrrolo[2,3-d]pyrimidin-6(7H)-one | | 404.1 |
| 72 | 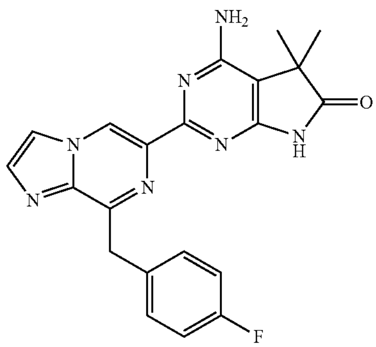 [SMILES: CC1(C)C(=O)Nc2nc(-c3cn4ccnc4c(Cc4ccc(F)cc4)n3)nc(N)c21] | 4-amino-2-(8-(4-fluorobenzyl)imidazo[1,2-a]pyrazin-6-yl)-5,5-dimethyl-5H-pyrrolo[2,3-d]pyrimidin-6(7H)-one | | 404.1 |
| 73 | 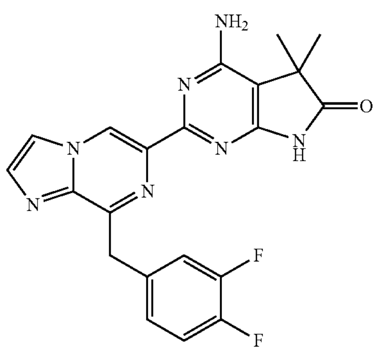 [SMILES: CC1(C)C(=O)Nc2nc(-c3cn4ccnc4c(Cc4ccc(F)c(F)c4)n3)nc(N)c21] | 4-amino-2-(8-(3,4-difluorobenzyl)imidazo[1,2-a]pyrazin-6-yl)-5,5-dimethyl-5H-pyrrolo[2,3-d]pyrimidin-6(7H)-one | | 422.1 |
| 74 | 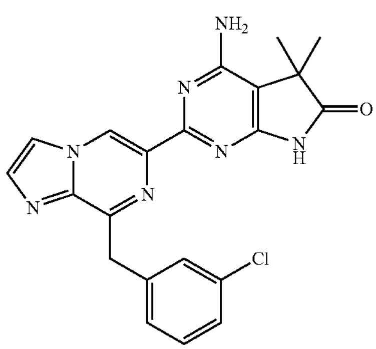 [SMILES: CC1(C)C(=O)Nc2nc(-c3cn4ccnc4c(Cc4cccc(Cl)c4)n3)nc(N)c21] | 4-amino-2-(8-(3-chlorobenzyl)imidazo[1,2-a]pyrazin-6-yl)-5,5-dimethyl-5H-pyrrolo[2,3-d]pyrimidin-6(7H)-one | | 420.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 75 | 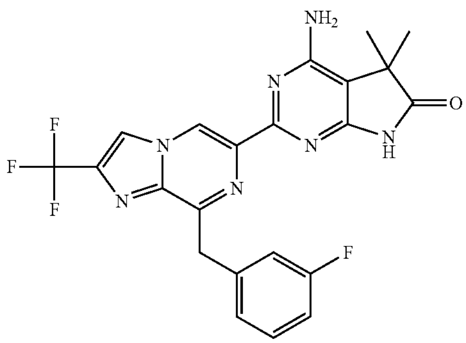 [SMILES: CC1(C)C(=O)Nc2nc(-c3cn4cc(C(F)(F)F)nc4c(Cc4cccc(F)c4)n3)nc(N)c21] | 4-amino-2-(8-(3-fluorobenzyl)-2-(trifluoromethyl)imidazo[1,2-a]pyrazin-6-yl)-5,5-dimethyl-5H-pyrrolo[2,3-d]pyrimidin-6(7H)-one | | 472.0 |
| 76 | 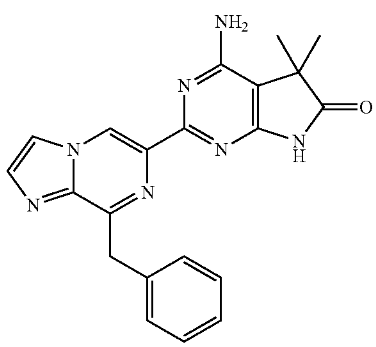 [SMILES: CC1(C)C(=O)Nc2nc(-c3cn4ccnc4c(Cc4ccccc4)n3)nc(N)c21] | 4-amino-2-(8-benzylimidazo[1,2-a]pyrazin-6-yl)-5,5-dimethyl-5H-pyrrolo[2,3-d]pyrimidin-6(7H)-one | | 386.0 |
| 77A & B | 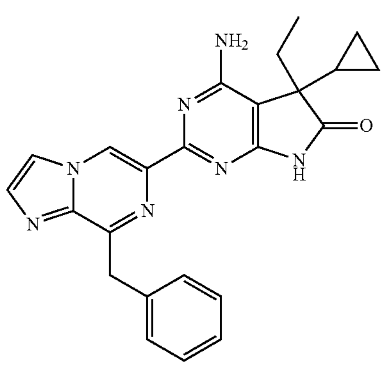 [SMILES: CCC1(C2CC2)C(=O)Nc2nc(-c3cn4ccnc4c(Cc4ccccc4)n3)nc(N)c21] | 4-amino-2-(8-benzylimidazo[1,2-a]pyrazin-6-yl)-5-cyclopropyl-5-ethyl-5H-pyrrolo[2,3-d]pyrimidin-6(7H)-one | CHIRALPAK IC | 426.2 |
| 79 | 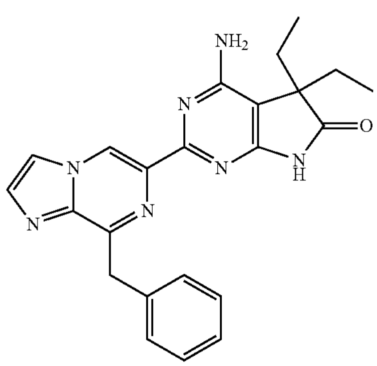 [SMILES: CCC1(CC)C(=O)Nc2nc(-c3cn4ccnc4c(Cc4ccccc4)n3)nc(N)c21] | 4-amino-2-(8-benzylimidazo[1,2-a]pyrazin-6-yl)-5,5-diethyl-5H-pyrrolo[2,3-d]pyrimidin-6(7H)-one | | 414.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 80A & B | 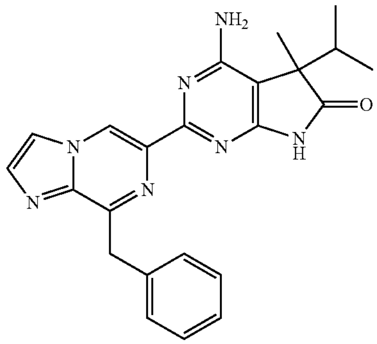 [SMILES: CC(C)C1(C)C(=O)Nc2nc(-c3cn4ccnc4c(Cc4ccccc4)n3)nc(N)c21] | 4-amino-2-(8-benzylimidazo[1,2-a]pyrazin-6-yl)-5-isopropyl-5-methyl-5H-pyrrolo[2,3-d]pyrimidin-6(7H)-one | CHIRALPAK IA | 414.2 |
| 82A & B | 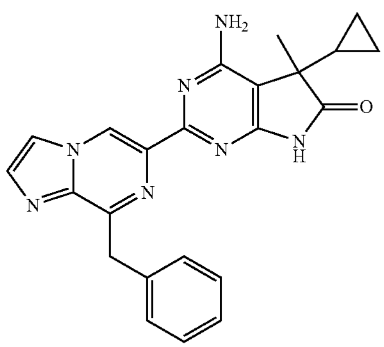 [SMILES: CC1(C2CC2)C(=O)Nc2nc(-c3cn4ccnc4c(Cc4ccccc4)n3)nc(N)c21] | 4-amino-2-(8-benzylimidazo[1,2-a]pyrazin-6-yl)-5-cyclopropyl-5-methyl-5H-pyrrolo[2,3-d]pyrimidin-6(7H)-one | CHIRALPAK AD | 412.1 |
| 84A & B | 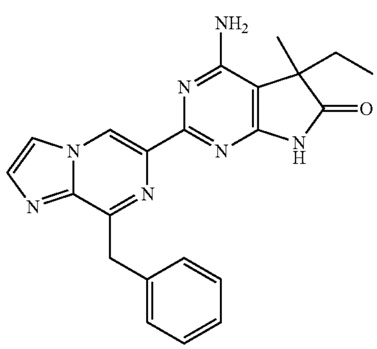 [SMILES: CCC1(C)C(=O)Nc2nc(-c3cn4ccnc4c(Cc4ccccc4)n3)nc(N)c21] | 4-amino-2-(8-benzylimidazo[1,2-a]pyrazin-6-yl)-5-ethyl-5-methyl-5H-pyrrolo[2,3-d]pyrimidin-6(7H)-one | CHIRALPAK IA | 400.0 |
| 86A & B | 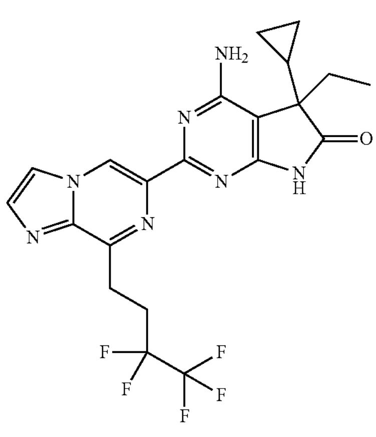 [SMILES: CCC1(C2CC2)C(=O)Nc2nc(-c3cn4ccnc4c(CCC(F)(F)C(F)(F)F)n3)nc(N)c21] | 4-amino-5-cyclopropyl-5-ethyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 482.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 87 | 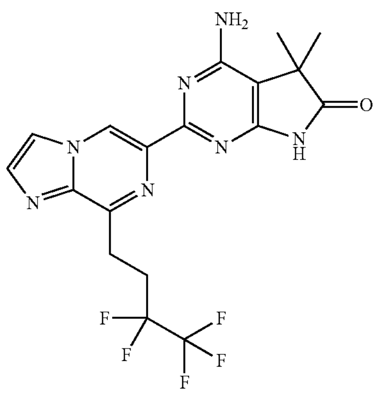 [SMILES: CC1(C)C(=O)Nc2nc(-c3cn4ccnc4c(CCC(F)(F)C(F)(F)F)n3)nc(N)c21] | 4-amino-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one | | 442.0 |
| 88B | 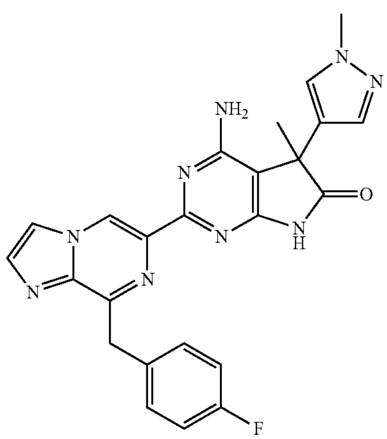 [SMILES: Cn1cc(C2(C)C(=O)Nc3nc(-c4cn5ccnc5c(Cc5ccc(F)cc5)n4)nc(N)c32)cn1] | 4-amino-2-(8-(4-fluorobenzyl)imidazo[1,2-a]pyrazin-6-yl)-5-methyl-5-(1-methyl-1H-pyrazol-4-yl)-5H-pyrrolo[2,3-d]pyrimidin-6(7H)-one | I-59B | 470.2 |
| 89A | 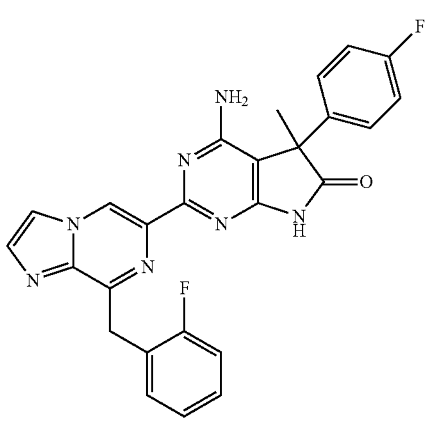 [SMILES: CC1(c2ccc(F)cc2)C(=O)Nc2nc(-c3cn4ccnc4c(Cc4ccccc4F)n3)nc(N)c21] | 4-amino-2-(8-(2-fluorobenzyl)imidazo[1,2-a]pyrazin-6-yl)-5-(4-fluorophenyl)-5-methyl-5H-pyrrolo[2,3-d]pyrimidin-6(7H)-one | I-85A* | 484.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|-----|-----------|------------|---------------------------------------------------|------------|
| 90A | 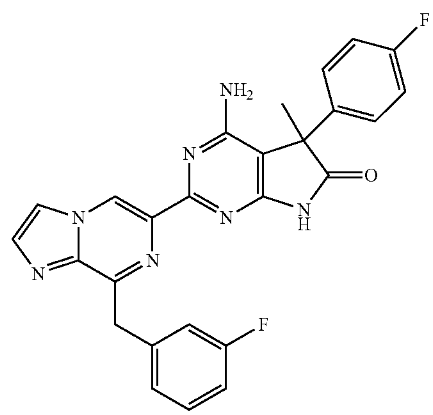 [SMILES: CC1(c2ccc(F)cc2)C(=O)Nc2nc(-c3cn4ccnc4c(Cc4cccc(F)c4)n3)nc(N)c21] | 4-amino-2-(8-(3-fluorobenzyl)imidazo[1,2-a]pyrazin-6-yl)-5-(4-fluorophenyl)-5-methyl-5H-pyrrolo[2,3-d]pyrimidin-6(7H)-one | I-85A* | 484.1 |
| 90B | 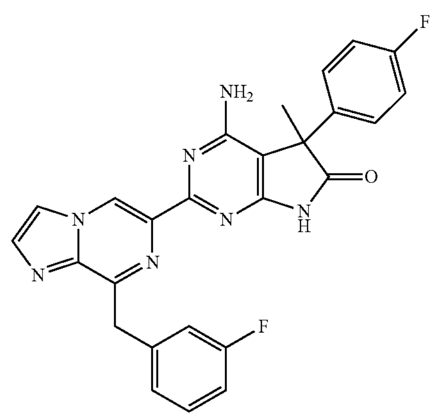 [SMILES: CC1(c2ccc(F)cc2)C(=O)Nc2nc(-c3cn4ccnc4c(Cc4cccc(F)c4)n3)nc(N)c21] | 4-amino-2-(8-(3-fluorobenzyl)imidazo[1,2-a]pyrazin-6-yl)-5-(4-fluorophenyl)-5-methyl-5H-pyrrolo[2,3-d]pyrimidin-6(7H)-one | I-85B* | 484.1 |
| 92A | 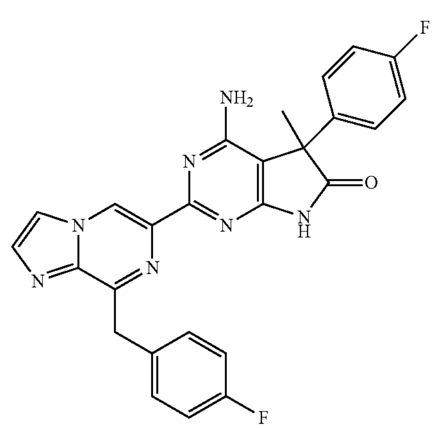 [SMILES: CC1(c2ccc(F)cc2)C(=O)Nc2nc(-c3cn4ccnc4c(Cc4ccc(F)cc4)n3)nc(N)c21] | 4-amino-2-(8-(4-fluorobenzyl)imidazo[1,2-a]pyrazin-6-yl)-5-(4-fluorophenyl)-5-methyl-5H-pyrrolo[2,3-d]pyrimidin-6(7H)-one | I-85A* | 484.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 93A | 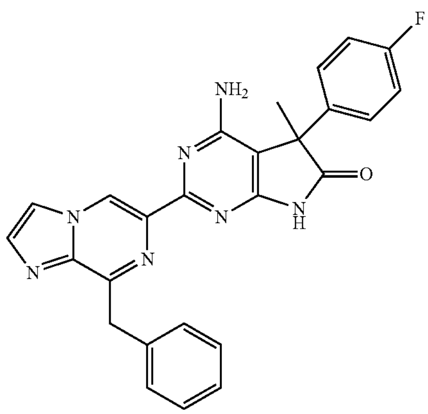 [SMILES: CC1(c2ccc(F)cc2)C(=O)Nc2nc(-c3cn4ccnc4c(Cc4ccccc4)n3)nc(N)c21] | 4-amino-2-(8-benzylimidazo[1,2-a]pyrazin-6-yl)-5-(4-fluorophenyl)-5-methyl-5H-pyrrolo[2,3-d]pyrimidin-6(7H)-one | I-85A* | 466.1 |
| 94A | 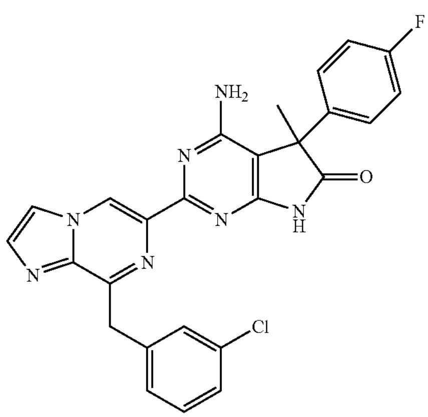 | 4-amino-2-(8-(3-chlorobenzyl)imidazo[1,2-a]pyrazin-6-yl)-5-(4-fluorophenyl)-5-methyl-5H-pyrrolo[2,3-d]pyrimidin-6(7H)-one | I-85A* | 500.0 |
| 95A | 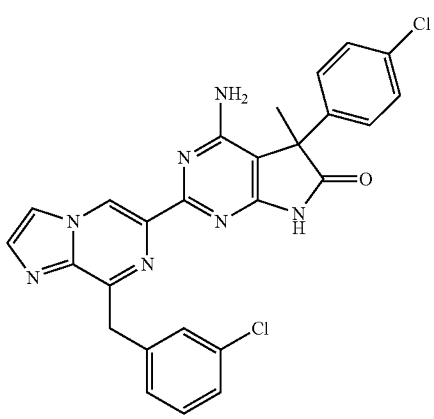 [SMILES: CC1(c2ccc(Cl)cc2)C(=O)Nc2nc(-c3cn4ccnc4c(Cc4cccc(Cl)c4)n3)nc(N)c21] | 4-amino-2-(8-(3-chlorobenzyl)imidazo[1,2-a]pyrazin-6-yl)-5-(4-chlorophenyl)-5-methyl-5H-pyrrolo[2,3-d]pyrimidin-6(7H)-one | I-86A* | 516 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 96A | 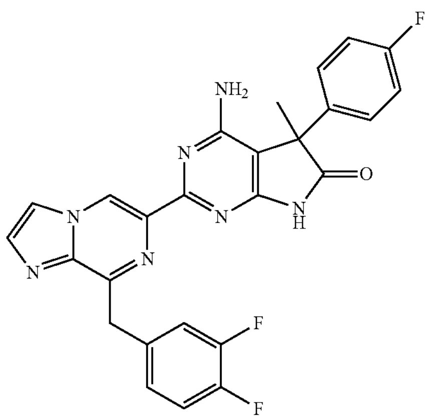 [SMILES: CC1(c2ccc(F)cc2)C(=O)Nc2nc(-c3cn4ccnc4c(Cc4ccc(F)c(F)c4)n3)nc(N)c21] | 4-amino-2-(8-(3,4-difluorobenzyl)imidazo[1,2-a]pyrazin-6-yl)-5-(4-fluorophenyl)-5-methyl-5H-pyrrolo[2,3-d]pyrimidin-6(7H)-one | I-85A* | 502.1 |
| 97A | 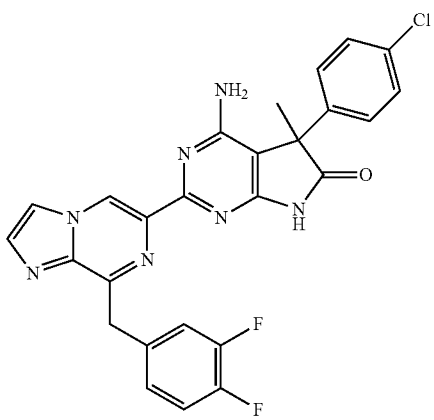 [SMILES: CC1(c2ccc(Cl)cc2)C(=O)Nc2nc(-c3cn4ccnc4c(Cc4ccc(F)c(F)c4)n3)nc(N)c21] | 4-amino-5-(4-chlorophenyl)-2-(8-(3,4-difluorobenzyl)imidazo[1,2-a]pyrazin-6-yl)-5-methyl-5H-pyrrolo[2,3-d]pyrimidin-6(7H)-one | I-86A* | 518.1 |
| 98A | 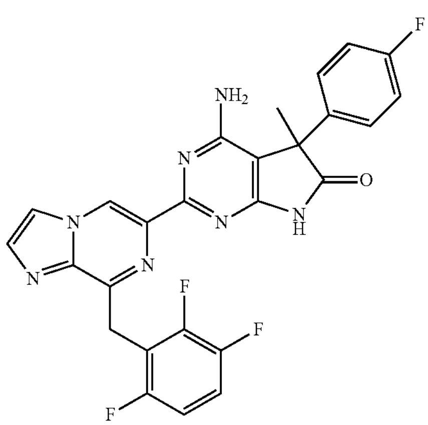 [SMILES: CC1(c2ccc(F)cc2)C(=O)Nc2nc(-c3cn4ccnc4c(Cc4c(F)ccc(F)c4F)n3)nc(N)c21] | 4-amino-5-(4-fluorophenyl)-5-methyl-2-(8-(2,3,6-trifluorobenzyl)imidazo[1,2-a]pyrazin-6-yl)-5H-pyrrolo[2,3-d]pyrimidin-6(7H)-one | I-85A* | 520.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 99A | 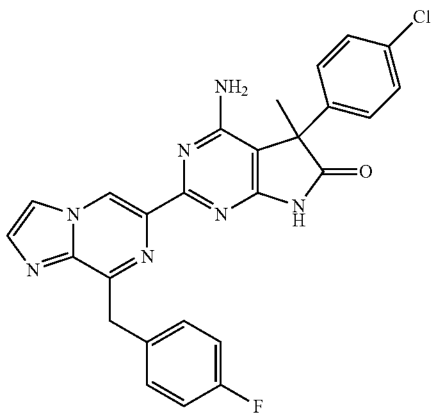 [SMILES: CC1(c2ccc(Cl)cc2)C(=O)Nc2nc(-c3cn4ccnc4c(Cc4ccc(F)cc4)n3)nc(N)c21] | 4-amino-5-(4-chlorophenyl)-2-(8-(4-fluorobenzyl)imidazo[1,2-a]pyrazin-6-yl)-5-methyl-5H-pyrrolo[2,3-d]pyrimidin-6(7H)-one | I-86A* | 500.1 |
| 100B | 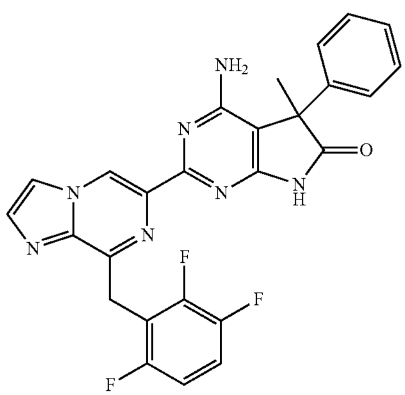 [SMILES: CC1(c2ccccc2)C(=O)Nc2nc(-c3cn4ccnc4c(Cc4c(F)ccc(F)c4F)n3)nc(N)c21] | 4-amino-5-methyl-5-phenyl-2-(8-(2,3,6-trifluorobenzyl)imidazo[1,2-a]pyrazin-6-yl)-5H-pyrrolo[2,3-d]pyrimidin-6(7H)-one | I-41B* | 502.0 |
| 101B | 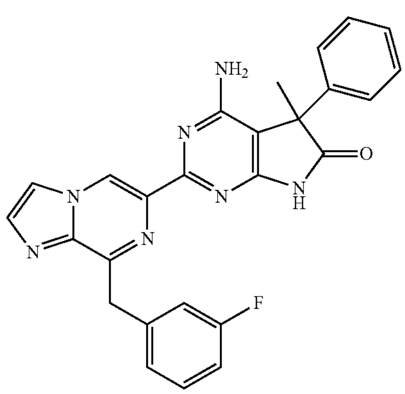 [SMILES: CC1(c2ccccc2)C(=O)Nc2nc(-c3cn4ccnc4c(Cc4cccc(F)c4)n3)nc(N)c21] | 4-amino-2-(8-(3-fluorobenzyl)imidazo[1,2-a]pyrazin-6-yl)-5-methyl-5-phenyl-5H-pyrrolo[2,3-d]pyrimidin-6(7H)-one | I-41B* | 466.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 102B | 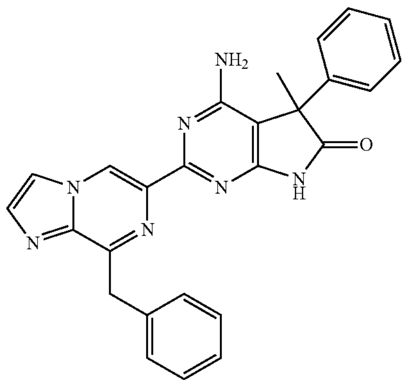 [SMILES: CC1(c2ccccc2)C(=O)Nc2nc(-c3cn4ccnc4c(Cc4ccccc4)n3)nc(N)c21] | 4-amino-2-(8-benzylimidazo[1,2-a]pyrazin-6-yl)-5-methyl-5-phenyl-5H-pyrrolo[2,3-d]pyrimidin-6(7H)-one | I-41B* | 448.0 |
| 103B | 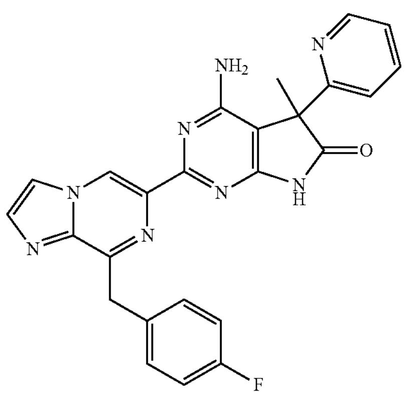 [SMILES: CC1(c2ccccn2)C(=O)Nc2nc(-c3cn4ccnc4c(Cc4ccc(F)cc4)n3)nc(N)c21] | 4-amino-2-(8-(4-fluorobenzyl)imidazo[1,2-a]pyrazin-6-yl)-5-methyl-5-(pyridin-2-yl)-5H-pyrrolo[2,3-d]pyrimidin-6(7H)-one | I-40B* | 467.1 |
| 104A | 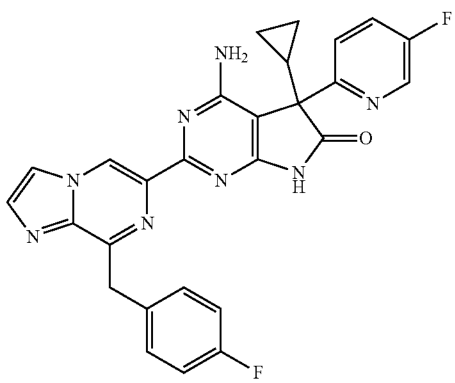 [SMILES: Nc1nc(-c2cn3ccnc3c(Cc3ccc(F)cc3)n2)nc2c1C(c1ccc(F)cn1)(C1CC1)C(=O)N2] | 4-amino-5-cyclopropyl-2-(8-(4-fluorobenzyl)imidazo[1,2-a]pyrazin-6-yl)-5-(5-fluoropyridin-2-yl)-5H-pyrrolo[2,3-d]pyrimidin-6(7H)-one | I-82A* | 511.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 105A & B | 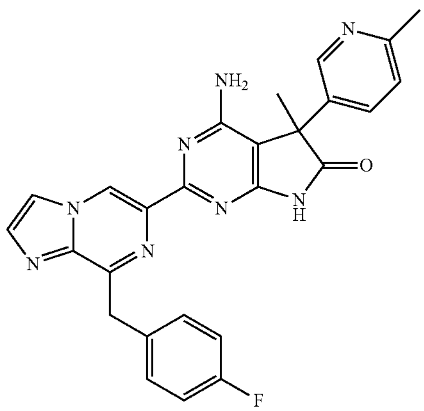 [SMILES: Cc1ccc(C2(C)C(=O)Nc3nc(-c4cn5ccnc5c(Cc5ccc(F)cc5)n4)nc(N)c32)cn1] | 4-amino-2-(8-(4-fluorobenzyl)imidazo[1,2-a]pyrazin-6-yl)-5-methyl-5-(6-methylpyridin-3-yl)-5H-pyrrolo[2,3-d]pyrimidin-6(7H)-one | CHIRALPAK IB | 481.1 |
| 106A | 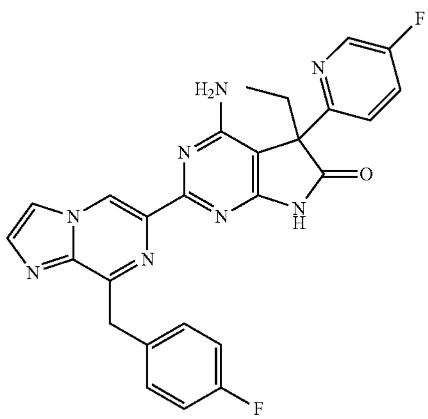 [SMILES: CCC1(c2ccc(F)cn2)C(=O)Nc2nc(-c3cn4ccnc4c(Cc4ccc(F)cc4)n3)nc(N)c21] | 4-amino-5-ethyl-2-(8-(4-fluorobenzyl)imidazo[1,2-a]pyrazin-6-yl)-5-(5-fluoropyridin-2-yl)-5H-pyrrolo[2,3-d]pyrimidin-6(7H)-one | I-75A* | 499.2 |
| 107A | 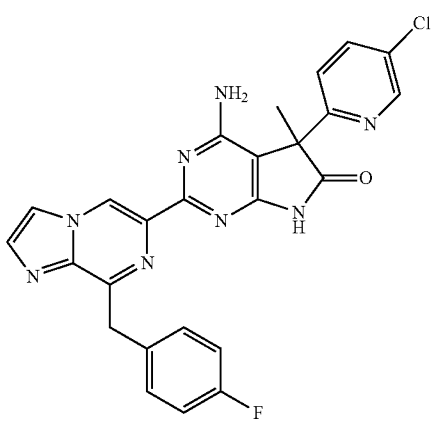 [SMILES: CC1(c2ccc(Cl)cn2)C(=O)Nc2nc(-c3cn4ccnc4c(Cc4ccc(F)cc4)n3)nc(N)c21] | 4-amino-5-(5-chloropyridin-2-yl)-2-(8-(4-fluorobenzyl)imidazo[1,2-a]pyrazin-6-yl)-5-methyl-5H-pyrrolo[2,3-d]pyrimidin-6(7H)-one | I-52A* | 501.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 108A & B | 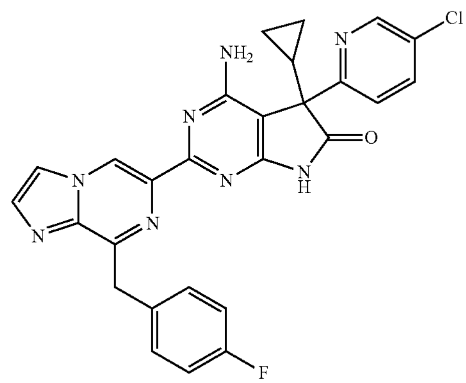 [SMILES: Nc1nc(-c2cn3ccnc3c(Cc3ccc(F)cc3)n2)nc2c1C(c1ccc(Cl)cn1)(C1CC1)C(=O)N2] | 4-amino-5-(5-chloropyridin-2-yl)-5-cyclopropyl-2-(8-(4-fluorobenzyl)imidazo[1,2-a]pyrazin-6-yl)-5H-pyrrolo[2,3-d]pyrimidin-6(7H)-one | CHIRALPAK OJ | 527.1 |
| 109A & B | 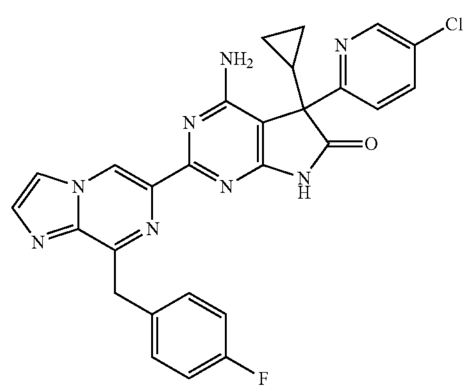 [SMILES: Nc1nc(-c2cn3ccnc3c(Cc3ccc(F)cc3)n2)nc2c1C(c1ccc(Cl)cn1)(C1CC1)C(=O)N2] | 4-amino-5-(5-chloropyridin-2-yl)-5-cyclopropyl-2-(8-(4-fluorobenzyl)imidazo[1,2-a]pyrazin-6-yl)-5H-pyrrolo[2,3-d]pyrimidin-6(7H)-one | CHIRALPAK OJ | 527.1 |
| 110A & B | 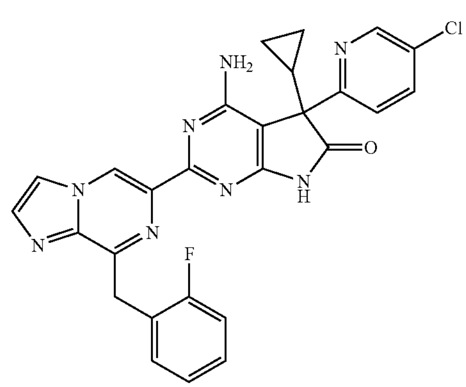 [SMILES: Nc1nc(-c2cn3ccnc3c(Cc3ccccc3F)n2)nc2c1C(c1ccc(Cl)cn1)(C1CC1)C(=O)N2] | 4-amino-5-(5-chloropyridin-2-yl)-5-cyclopropyl-2-(8-(2-fluorobenzyl)imidazo[1,2-a]pyrazin-6-yl)-5H-pyrrolo[2,3-d]pyrimidin-6(7H)-one | CHIRALPAK IC | 527.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 111A &B | 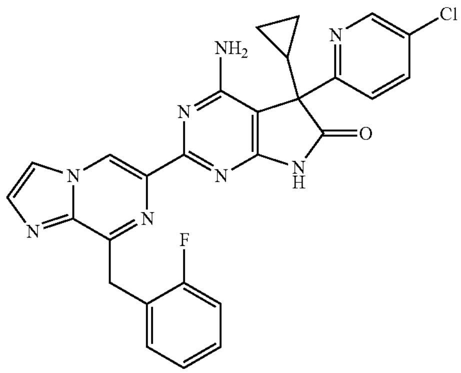 [SMILES: Nc1nc(-c2cn3ccnc3c(Cc3ccccc3F)n2)nc2c1C(c1ccc(Cl)cn1)(C1CC1)C(=O)N2] | 4-amino-5-(5-chloropyridin-2-yl)-5-cyclopropyl-2-(8-(2-fluorobenzyl)imidazo[1,2-a]pyrazin-6-yl)-5H-pyrrolo[2,3-d]pyrimidin-6(7H)-one | CHIRALPAK IC | 527.1 |
| 112A | 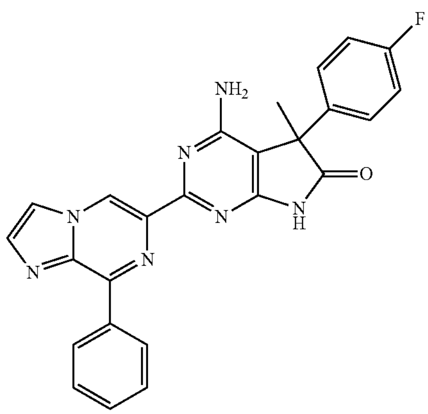 [SMILES: CC1(c2ccc(F)cc2)C(=O)Nc2nc(-c3cn4ccnc4c(-c4ccccc4)n3)nc(N)c21] | 4-amino-5-(4-fluorophenyl)-5-methyl-2-(8-phenylimidazo[1,2-a]pyrazin-6-yl)-5H-pyrrolo[2,3-d]pyrimidin-6(7H)-one | I-85A* | 452.2 |
| 113B | 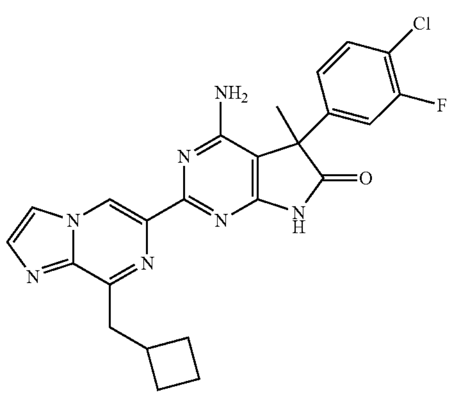 [SMILES: CC1(c2ccc(Cl)c(F)c2)C(=O)Nc2nc(-c3cn4ccnc4c(CC4CCC4)n3)nc(N)c21] | 4-amino-5-(4-chloro-3-fluorophenyl)-2-(8-(cyclobutylmethyl)imidazo[1,2-a]pyrazin-6-yl)-5-methyl-5H-pyrrolo[2,3-d]pyrimidin-6(7H)-one | I-91B* | 478.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 114A | 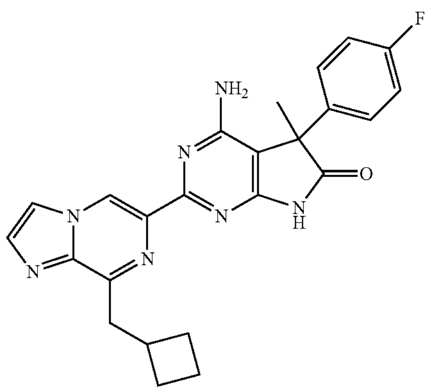 [SMILES: CC1(c2ccc(F)cc2)C(=O)Nc2nc(-c3cn4ccnc4c(CC4CCC4)n3)nc(N)c21] | 4-amino-2-(8-(cyclobutylmethyl)imidazo[1,2-a]pyrazin-6-yl)-5-(4-fluorophenyl)-5-methyl-5H-pyrrolo[2,3-d]pyrimidin-6(7H)-one | I-85A* | 444.4 |
| 115B | 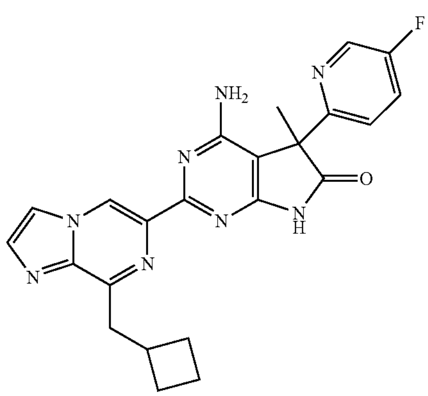 [SMILES: CC1(c2ccc(F)cn2)C(=O)Nc2nc(-c3cn4ccnc4c(CC4CCC4)n3)nc(N)c21] | 4-amino-2-(8-(cyclobutylmethyl)imidazo[1,2-a]pyrazin-6-yl)-5-(5-fluoropyridin-2-yl)-5-methyl-5H-pyrrolo[2,3-d]pyrimidin-6(7H)-one | I-39B* | 445.1 |
| 116A | 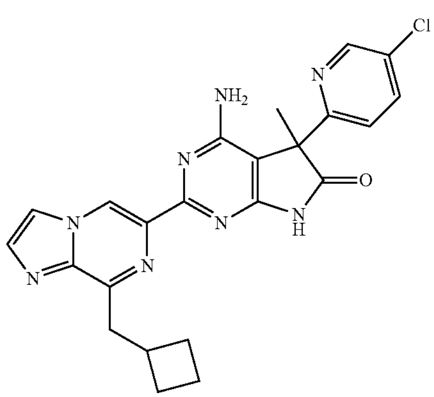 [SMILES: CC1(c2ccc(Cl)cn2)C(=O)Nc2nc(-c3cn4ccnc4c(CC4CCC4)n3)nc(N)c21] | 4-amino-5-(5-chloropyridin-2-yl)-2-(8-(cyclobutylmethyl)imidazo[1,2-a]pyrazin-6-yl)-5-methyl-5H-pyrrolo[2,3-d]pyrimidin-6(7H)-one | I-52A* | 461.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 117A | 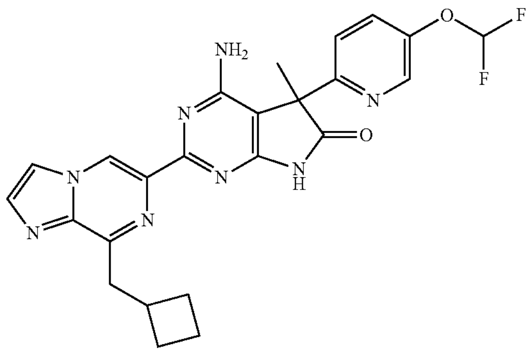 [SMILES: CC1(c2ccc(OC(F)F)cn2)C(=O)Nc2nc(-c3cn4ccnc4c(CC4CCC4)n3)nc(N)c21] | 4-amino-2-(8-(cyclobutylmethyl)imidazo[1,2-a]pyrazin-6-yl)-5-(5-(difluoromethoxy)pyridin-2-yl)-5-methyl-5H-pyrrolo[2,3-d]pyrimidin-6(7H)-one | I-55A* | 493.2 |
| 118A | 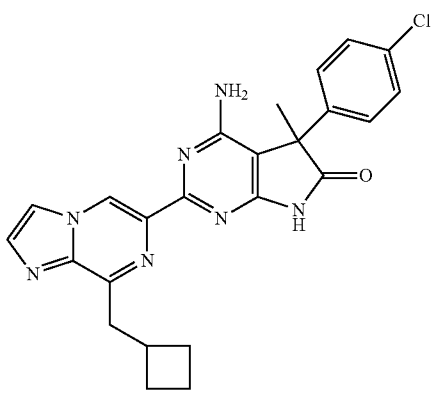 [SMILES: CC1(c2ccc(Cl)cc2)C(=O)Nc2nc(-c3cn4ccnc4c(CC4CCC4)n3)nc(N)c21] | 4-amino-5-(4-chlorophenyl)-2-(8-(cyclobutylmethyl)imidazo[1,2-a]pyrazin-6-yl)-5-methyl-5H-pyrrolo[2,3-d]pyrimidin-6(7H)-one | I-86A* | 460.1 |
| 119B | 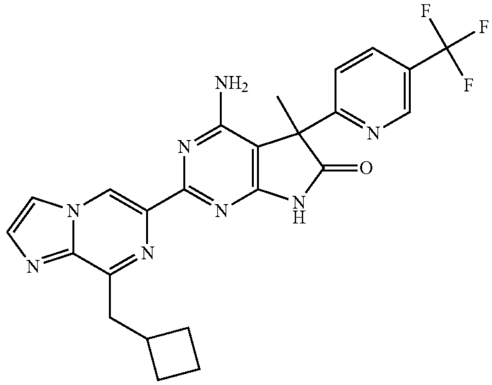 [SMILES: CC1(c2ccc(C(F)(F)F)cn2)C(=O)Nc2nc(-c3cn4ccnc4c(CC4CCC4)n3)nc(N)c21] | 4-amino-2-(8-(cyclobutylmethyl)imidazo[1,2-a]pyrazin-6-yl)-5-methyl-5-(5-(trifluoromethyl)pyridin-2-yl)-5H-pyrrolo[2,3-d]pyrimidin-6(7H)-one | I-61B* | 495.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 120A | 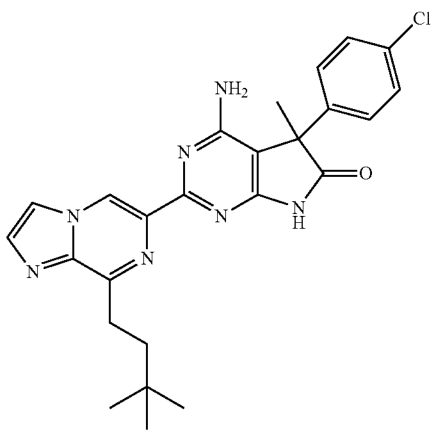 [SMILES: CC(C)(C)CCc1nc(-c2nc(N)c3c(n2)NC(=O)C3(C)c2ccc(Cl)cc2)cn2ccnc12] | 4-amino-5-(4-chlorophenyl)-2-(8-(3,3-dimethylbutyl)imidazo[1,2-a]pyrazin-6-yl)-5-methyl-5H-pyrrolo[2,3-d]pyrimidin-6(7H)-one | I-86A* | 476.1 |
| 121A | 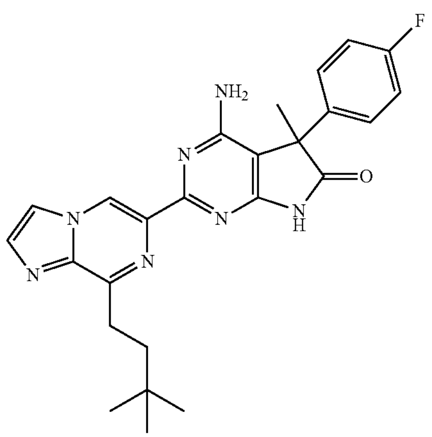 [SMILES: CC(C)(C)CCc1nc(-c2nc(N)c3c(n2)NC(=O)C3(C)c2ccc(F)cc2)cn2ccnc12] | 4-amino-2-(8-(3,3-dimethylbutyl)imidazo[1,2-a]pyrazin-6-yl)-5-(4-fluorophenyl)-5-methyl-5H-pyrrolo[2,3-d]pyrimidin-6(7H)-one | I-85A* | 460.2 |
| 122B | 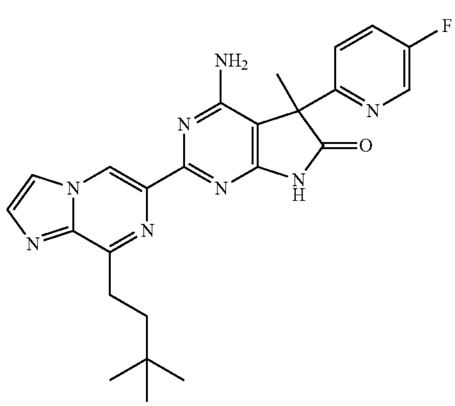 [SMILES: CC(C)(C)CCc1nc(-c2nc(N)c3c(n2)NC(=O)C3(C)c2ccc(F)cn2)cn2ccnc12] | 4-amino-2-(8-(3,3-dimethylbutyl)imidazo[1,2-a]pyrazin-6-yl)-5-(5-fluoropyridin-2-yl)-5-methyl-5H-pyrrolo[2,3-d]pyrimidin-6(7H)-one | I-39B* | 461.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 123A | 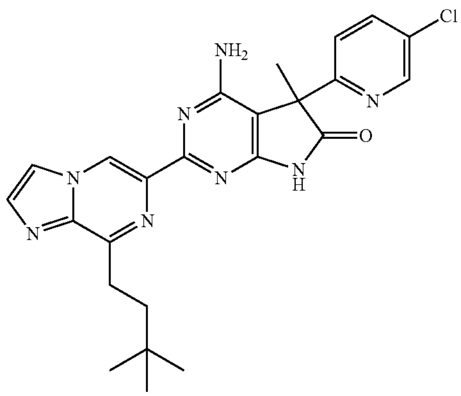 [SMILES: CC(C)(C)CCc1nc(-c2nc(N)c3c(n2)NC(=O)C3(C)c2ccc(Cl)cn2)cn2ccnc12] | 4-amino-5-(5-chloropyridin-2-yl)-2-(8-(3,3-dimethylbutyl)imidazo[1,2-a]pyrazin-6-yl)-5-methyl-5H-pyrrolo[2,3-d]pyrimidin-6(7H)-one | I-52A* | 477.1 |
| 124B | 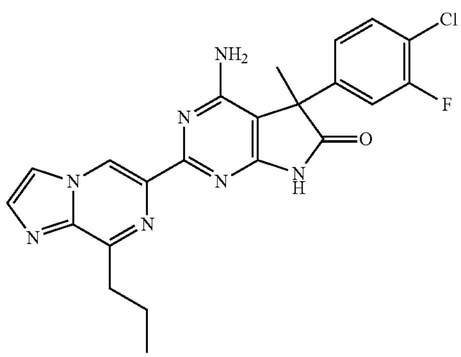 [SMILES: CCCc1nc(-c2nc(N)c3c(n2)NC(=O)C3(C)c2ccc(Cl)c(F)c2)cn2ccnc12] | 4-amino-5-(4-chloro-3-fluorophenyl)-5-methyl-2-(8-propylimidazo[1,2-a]pyrazin-6-yl)-5H-pyrrolo[2,3-d]pyrimidin-6(7H)-one | I-91B* | 452.1 |
| 125A | 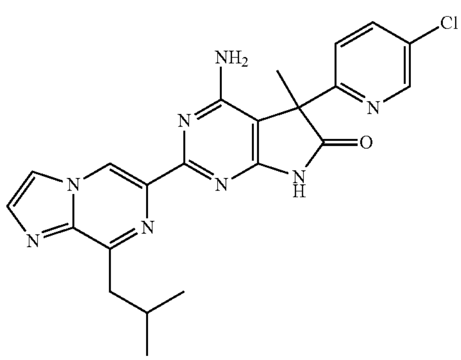 [SMILES: CC(C)Cc1nc(-c2nc(N)c3c(n2)NC(=O)C3(C)c2ccc(Cl)cn2)cn2ccnc12] | 4-amino-5-(5-chloropyridin-2-yl)-2-(8-isobutylimidazo[1,2-a]pyrazin-6-yl)-5-methyl-5H-pyrrolo[2,3-d]pyrimidin-6(7H)-one | I-52A* | 449.3 |
| 126A & B | 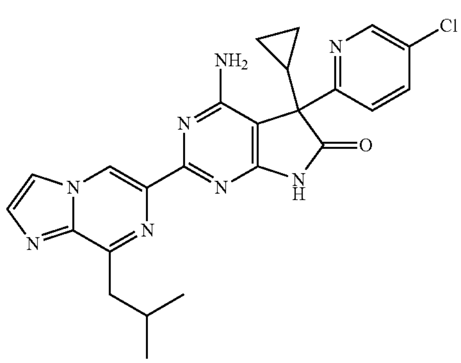 [SMILES: CC(C)Cc1nc(-c2nc(N)c3c(n2)NC(=O)C3(c2ccc(Cl)cn2)C2CC2)cn2ccnc12] | 4-amino-5-(5-chloropyridin-2-yl)-5-cyclopropyl-2-(8-isobutylimidazo[1,2-a]pyrazin-6-yl)-5H-pyrrolo[2,3-d]pyrimidin-6(7H)-one | CHIRALPAK IC | 475.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 127A | 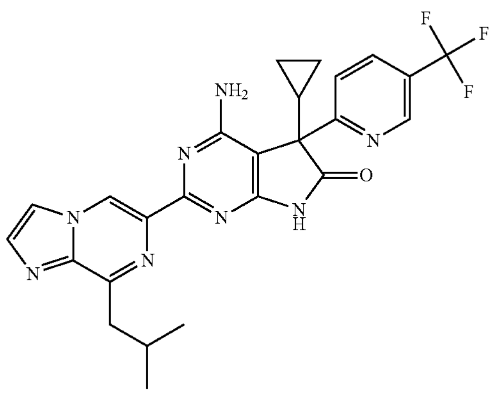 [SMILES: CC(C)Cc1nc(-c2nc(N)c3c(n2)NC(=O)C3(c2ccc(C(F)(F)F)cn2)C2CC2)cn2ccnc12] | 4-amino-5-cyclopropyl-2-(8-isobutylimidazo[1,2-a]pyrazin-6-yl)-5-(5-(trifluoromethyl)pyridin-2-yl)-5H-pyrrolo[2,3-d]pyrimidin-6(7H)-one | I-84A* | 509.3 |
| 128B | 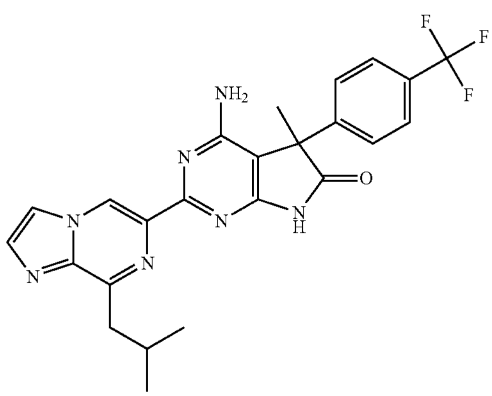 [SMILES: CC(C)Cc1nc(-c2nc(N)c3c(n2)NC(=O)C3(C)c2ccc(C(F)(F)F)cc2)cn2ccnc12] | 4-amino-2-(8-isobutylimidazo[1,2-a]pyrazin-6-yl)-5-methyl-5-(4-(trifluoromethyl)phenyl)-5H-pyrrolo[2,3-d]pyrimidin-6(7H)-one | I-90B* | 482.3 |
| 129A | 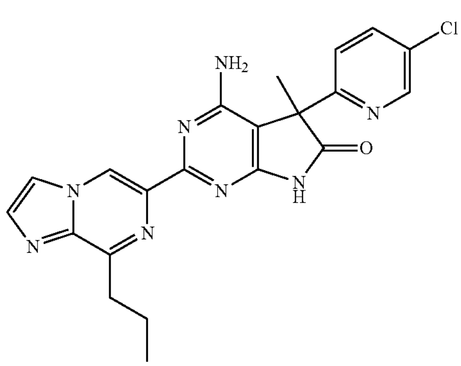 [SMILES: CCCc1nc(-c2nc(N)c3c(n2)NC(=O)C3(C)c2ccc(Cl)cn2)cn2ccnc12] | 4-amino-5-(5-chloropyridin-2-yl)-5-methyl-2-(8-propylimidazo[1,2-a]pyrazin-6-yl)-5H-pyrrolo[2,3-d]pyrimidin-6(7H)-one | I-52A* | 435.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 130A | 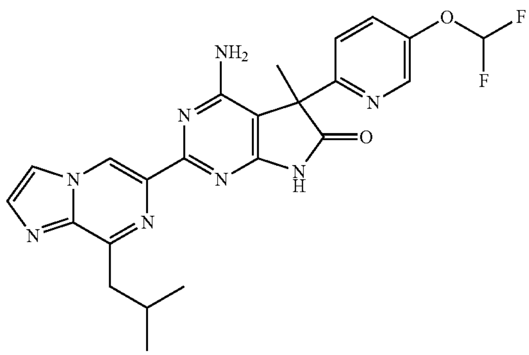 [SMILES: CC(C)Cc1nc(-c2nc(N)c3c(n2)NC(=O)C3(C)c2ccc(OC(F)F)cn2)cn2ccnc12] | 4-amino-5-(5-(difluoromethoxy)pyridin-2-yl)-2-(8-isobutylimidazo[1,2-a]pyrazin-6-yl)-5-methyl-5H-pyrrolo[2,3-d]pyrimidin-6(7H)-one | I-55A* | 481.3 |
| 131B | 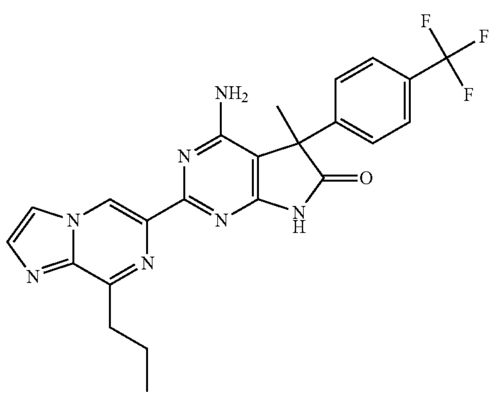 [SMILES: CCCc1nc(-c2nc(N)c3c(n2)NC(=O)C3(C)c2ccc(C(F)(F)F)cc2)cn2ccnc12] | 4-amino-5-methyl-2-(8-propylimidazo[1,2-a]pyrazin-6-yl)-5-(4-(trifluoromethyl)phenyl)-5H-pyrrolo[2,3-d]pyrimidin-6(7H)-one | I-90B* | 468.4 |
| 132B | 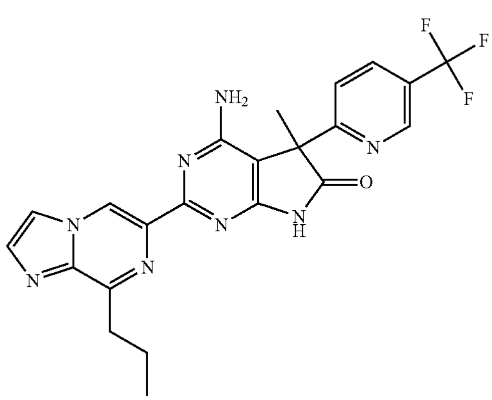 [SMILES: CCCc1nc(-c2nc(N)c3c(n2)NC(=O)C3(C)c2ccc(C(F)(F)F)cn2)cn2ccnc12] | 4-amino-5-methyl-2-(8-propylimidazo[1,2-a]pyrazin-6-yl)-5-(5-(trifluoromethyl)pyridin-2-yl)-5H-pyrrolo[2,3-d]pyrimidin-6(7H)-one | I-61B* | 469.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 133A | 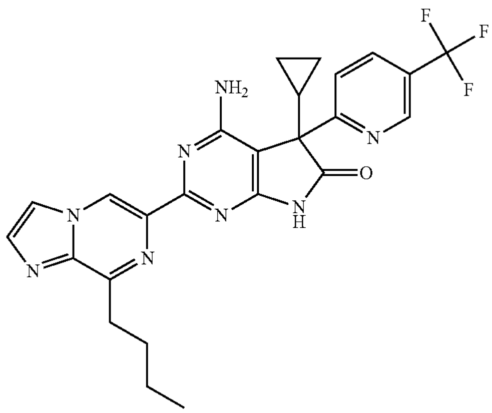 [SMILES: CCCCc1nc(-c2nc(N)c3c(n2)NC(=O)C3(c2ccc(C(F)(F)F)cn2)C2CC2)cn2ccnc12] | 4-amino-2-(8-butylimidazo[1,2-a]pyrazin-6-yl)-5-cyclopropyl-5-(5-(trifluoromethyl)pyridin-2-yl)-5H-pyrrolo[2,3-d]pyrimidin-6(7H)-one | I-84A* | 509.0 |
| 134A | 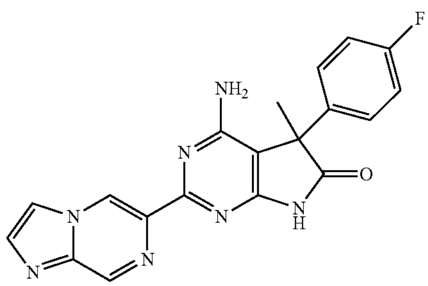 [SMILES: CC1(c2ccc(F)cc2)C(=O)Nc2nc(-c3cn4ccnc4cn3)nc(N)c21] | 4-amino-5-(4-fluorophenyl)-2-(imidazo[1,2-a]pyrazin-6-yl)-5-methyl-5H-pyrrolo[2,3-d]pyrimidin-6(7H)one | I-85A* | 376.0 |
| 135A | 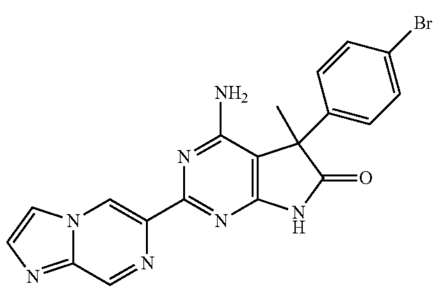 [SMILES: CC1(c2ccc(Br)cc2)C(=O)Nc2nc(-c3cn4ccnc4cn3)nc(N)c21] | 4-amino-5-(4-bromophenyl)-2-(imidazo[1,2-a]pyrazin-6-yl)-5-methyl-5H-pyrrolo[2,3-d]pyrimidin-6(7H)-one | I-42A* | 438.0 |
| 136A | 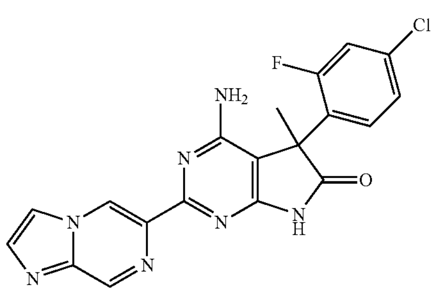 [SMILES: CC1(c2ccc(Cl)cc2F)C(=O)Nc2nc(-c3cn4ccnc4cn3)nc(N)c21] | 4-amino-5-(4-chloro-2-fluorophenyl)-2-(imidazo[1,2-a]pyrazin-6-yl)-5-methyl-5H-pyrrolo[2,3-d]pyrimidin-6(7H)-one | I-44A* | 410.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 137A & B | 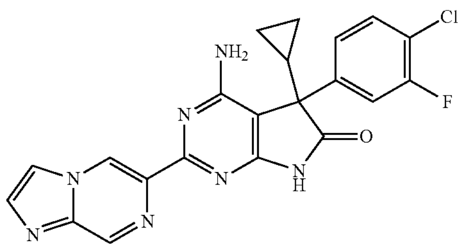 [SMILES: Nc1nc(-c2cn3ccnc3cn2)nc2c1C(c1ccc(Cl)c(F)c1)(C1CC1)C(=O)N2] | 4-amino-5-(4-chloro-3-fluorophenyl)-5-cyclopropyl-2-(imidazo[1,2-a]pyrazin-6-yl)-5H-pyrrolo[2,3-d]pyrimidin-6(7H)-one | CHIRALPAK IC | 436.3 |
| 138A & B | 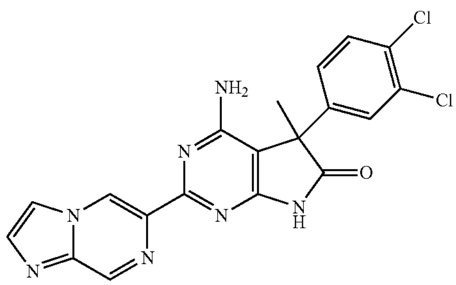 [SMILES: CC1(c2ccc(Cl)c(Cl)c2)C(=O)Nc2nc(-c3cn4ccnc4cn3)nc(N)c21] | 4-amino-5-(3,4-dichlorophenyl)-2-(imidazo[1,2-a]pyrazin-6-yl)-5-methyl-5H-pyrrolo[2,3-d]pyrimidin-6(7H)-one | CHIRALPAK AD | 426.0 |
| 139A | 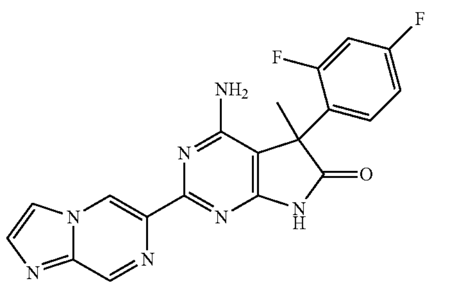 [SMILES: CC1(c2ccc(F)cc2F)C(=O)Nc2nc(-c3cn4ccnc4cn3)nc(N)c21] | 4-amino-5-(2,4-difluorophenyl)-2-(imidazo[1,2-a]pyrazin-6-yl)-5-methyl-5H-pyrrolo[2,3-d]pyrimidin-6(7H)-one | I-46A* | 394.0 |
| 140B | 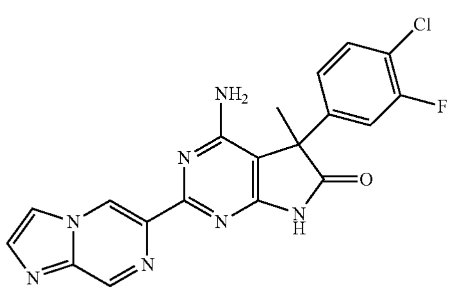 [SMILES: CC1(c2ccc(Cl)c(F)c2)C(=O)Nc2nc(-c3cn4ccnc4cn3)nc(N)c21] | 4-amino-5-(4-chloro-3-fluorophenyl)-2-(imidazo[1,2-a]pyrazin-6-yl)-5-methyl-5H-pyrrolo[2,3-d]pyrimidin-6(7H)-one | I-91B* | 410 |
| 141B | 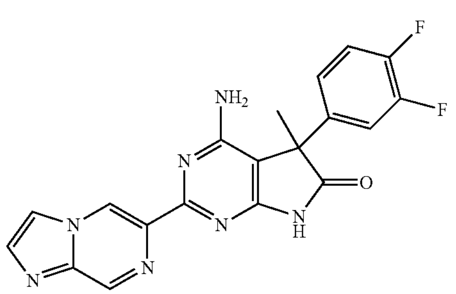 | 4-amino-5-(3,4-difluorophenyl)-2-(imidazo[1,2-a]pyrazin-6-yl)-5-methyl-5H-pyrrolo[2,3-d]pyrimidin-6(7H)-one | I-94B* | 394 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 142B | 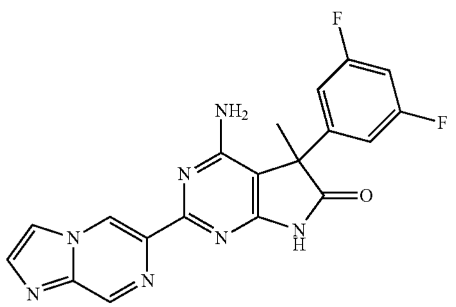 [SMILES: CC1(c2cc(F)cc(F)c2)C(=O)Nc2nc(-c3cn4ccnc4cn3)nc(N)c21] | 4-amino-5-(3,5-difluorophenyl)-2-(imidazo[1,2-a]pyrazin-6-yl)-5-methyl-5H-pyrrolo[2,3-d]pyrimidin-6(7H)-one | I-45B* | 394.2 |
| 143B | 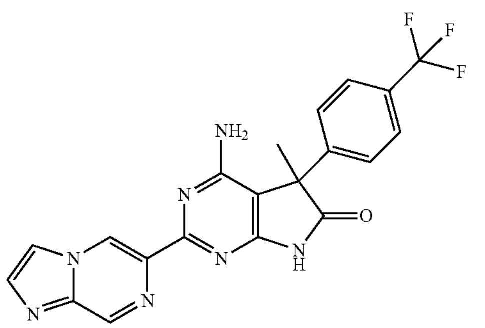 [SMILES: CC1(c2ccc(C(F)(F)F)cc2)C(=O)Nc2nc(-c3cn4ccnc4cn3)nc(N)c21] | 4-amino-2-(imidazo[1,2-a]pyrazin-6-yl)-5-methyl-5-(4-(trifluoromethyl)phenyl)-5H-pyrrolo[2,3-d]pyrimidin-6(7H)-one | I-90B* | 426.1 |
| 144A | 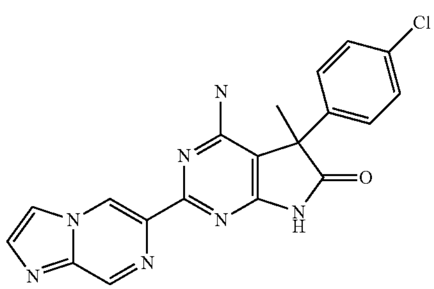 [SMILES: CC1(c2ccc(Cl)cc2)C(=O)Nc2nc(-c3cn4ccnc4cn3)nc(N)c21] | 4-amino-5-(4-chlorophenyl)-2-(imidazo[1,2-a]pyrazin-6-yl)-5-methyl-5H-pyrrolo[2,3-d]pyrimidin-6(7H)-one | I-86A* | 392.0 |
| 145A | 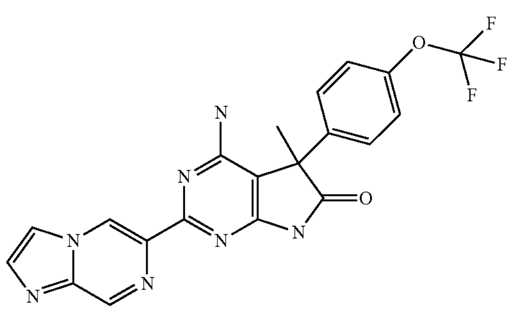 [SMILES: CC1(c2ccc(OC(F)(F)F)cc2)C(=O)Nc2nc(-c3cn4ccnc4cn3)nc(N)c21] | 4-amino-2-(imidazo[1,2-a]pyrazin-6-yl)-5-methyl-5-(4-(trifluoromethoxy)phenyl)-5H-pyrrolo[2,3-d]pyrimidin-6(7H)-one | I-87A* | 442 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 146B | 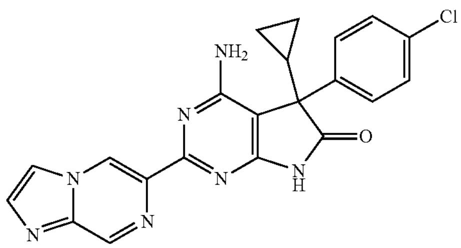 [SMILES: Nc1nc(-c2cn3ccnc3cn2)nc2c1C(c1ccc(Cl)cc1)(C1CC1)C(=O)N2] | 4-amino-5-(4-chlorophenyl)-5-cyclopropyl-2-(imidazo[1,2-a]pyrazin-6-yl)-5H-pyrrolo[2,3-d]pyrimidin-6(7H)-one | I-79B* | 418 |
| 147A | 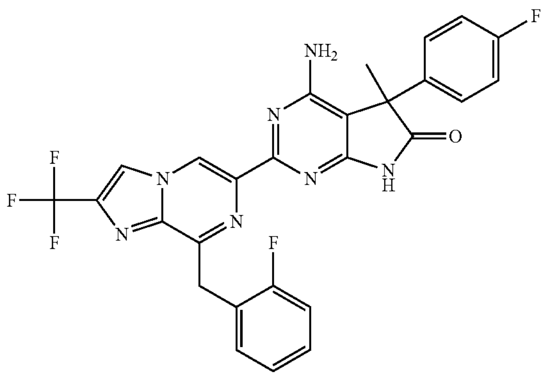 | 4-amino-2-(8-(2-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 552.2 |
| 148A | 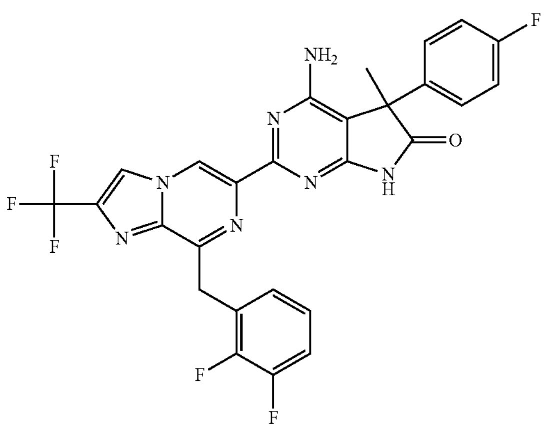 [SMILES: CC1(c2ccc(F)cc2)C(=O)Nc2nc(-c3cn4cc(C(F)(F)F)nc4c(Cc4cccc(F)c4F)n3)nc(N)c21] | 4-amino-2-(8-(2,3-difluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 569.9 |
| 149A | 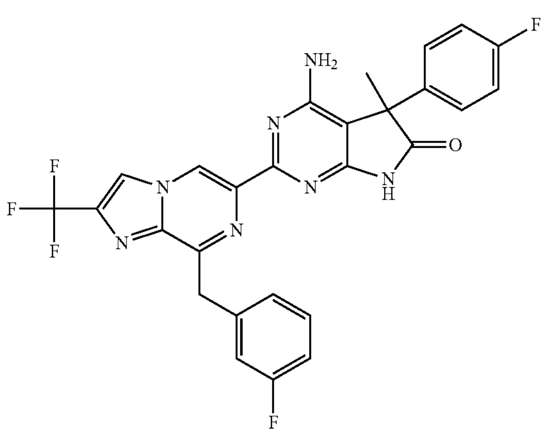 [SMILES: CC1(c2ccc(F)cc2)C(=O)Nc2nc(-c3cn4cc(C(F)(F)F)nc4c(Cc4cccc(F)c4)n3)nc(N)c21] | 4-amino-2-(8-(3-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 552.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 150A | 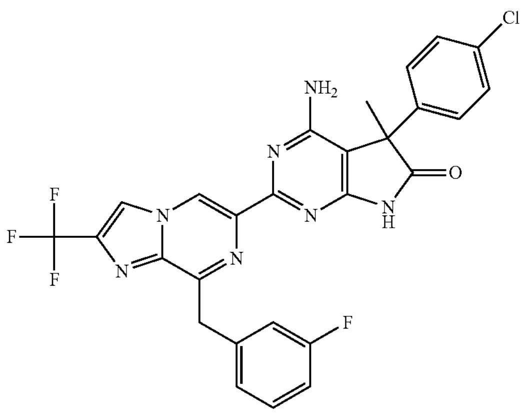 [SMILES: CC1(c2ccc(Cl)cc2)C(=O)Nc2nc(-c3cn4cc(C(F)(F)F)nc4c(Cc4cccc(F)c4)n3)nc(N)c21] | 4-amino-5-(4-chlorophenyl)-2-(8-(3-fluorobenzyl)-2-(trifluoromethyl)imidazo[1,2-a]pyrazin-6-yl)-5-methyl-5H-pyrrolo[2,3-d]pyrimidin-6(7H)-one | I-86A* | 568.2 |
| 151A | 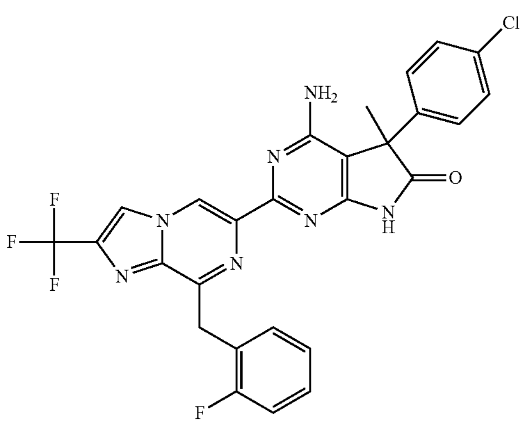 [SMILES: CC1(c2ccc(Cl)cc2)C(=O)Nc2nc(-c3cn4cc(C(F)(F)F)nc4c(Cc4ccccc4F)n3)nc(N)c21] | 4-amino-5-(4-chlorophenyl)-2-(8-(2-fluorobenzyl)-2-(trifluoromethyl)imidazo[1,2-a]pyrazin-6-yl)-5-methyl-5H-pyrrolo[2,3-d]pyrimidin-6(7H)-one | I-86A* | 568.0 |
| 152A | 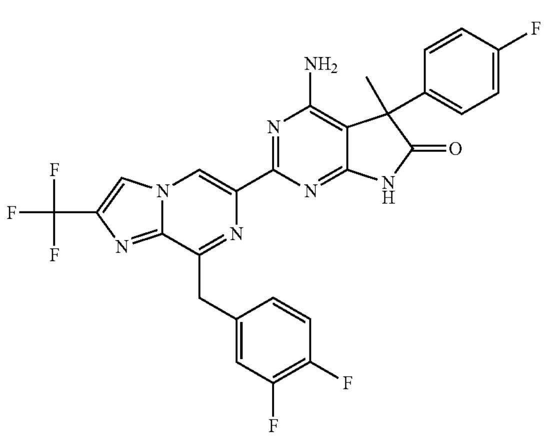 [SMILES: CC1(c2ccc(F)cc2)C(=O)Nc2nc(-c3cn4cc(C(F)(F)F)nc4c(Cc4ccc(F)c(F)c4)n3)nc(N)c21] | 4-amino-2-(8-(3,4-difluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 570.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 153A | 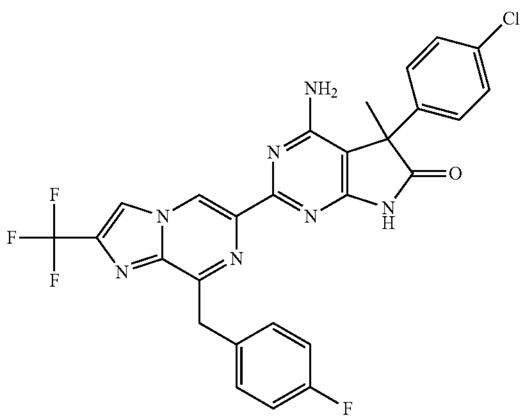 [SMILES: CC1(c2ccc(Cl)cc2)C(=O)Nc2nc(-c3cn4cc(C(F)(F)F)nc4c(Cc4ccc(F)cc4)n3)nc(N)c21] | 4-amino-5-(4-chlorophenyl)-2-(8-(4-fluorobenzyl)-2-(trifluoromethyl)imidazo[1,2-a]pyrazin-6-yl)-5-methyl-5H-pyrrolo[2,3-d]pyrimidin-6(7H)-one | I-86A* | 568 |
| 154A | 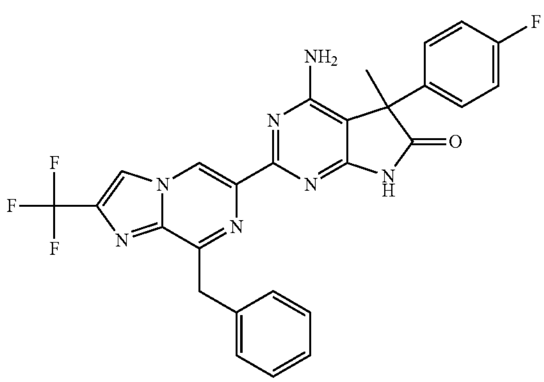 [SMILES: CC1(c2ccc(F)cc2)C(=O)Nc2nc(-c3cn4cc(C(F)(F)F)nc4c(Cc4ccccc4)n3)nc(N)c21] | 4-amino-2-(8-benzyl-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 534.2 |
| 155A | 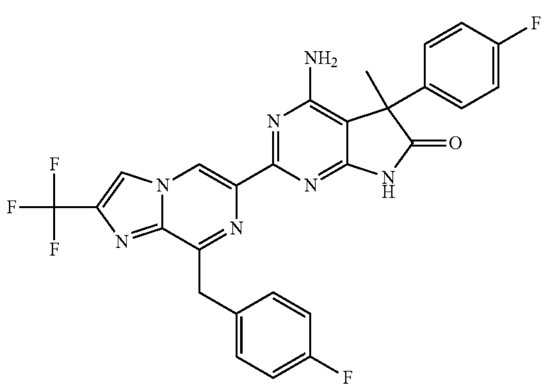 [SMILES: CC1(c2ccc(F)cc2)C(=O)Nc2nc(-c3cn4cc(C(F)(F)F)nc4c(Cc4ccc(F)cc4)n3)nc(N)c21] | 4-amino-2-(8-(4-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one | I-85A* | 552.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 156A | 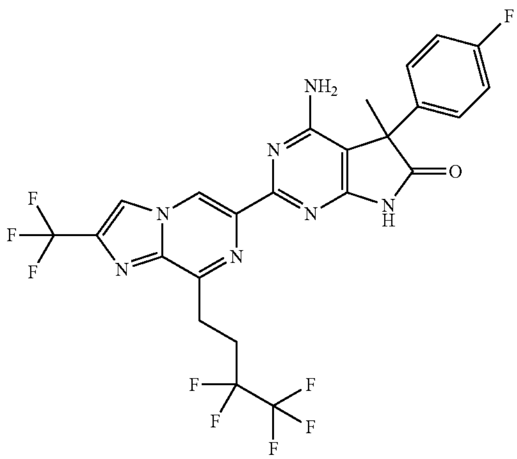 [SMILES: CC1(c2ccc(F)cc2)C(=O)Nc2nc(-c3cn4cc(C(F)(F)F)nc4c(CCC(F)(F)C(F)(F)F)n3)nc(N)c21] | 4-amino-5-(4-fluorophenyl)-5-methyl-2-(8-(3,3,4,4,4-pentafluorobutyl)-2-(trifluoromethyl)imidazo[1,2-a]pyrazin-6-yl)-5H-pyrrolo[2,3-d]pyrimidin-6(7H)-one | I-85A* | 590.2 |
| 157A | 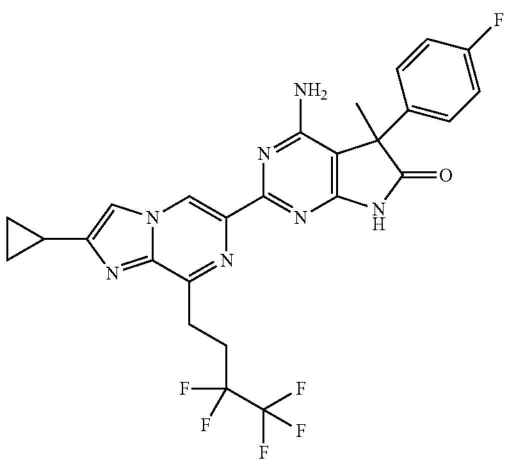 [SMILES: CC1(c2ccc(F)cc2)C(=O)Nc2nc(-c3cn4cc(C5CC5)nc4c(CCC(F)(F)C(F)(F)F)n3)nc(N)c21] | 4-amino-2-(2-cyclopropyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 562.0 |
| 158B | 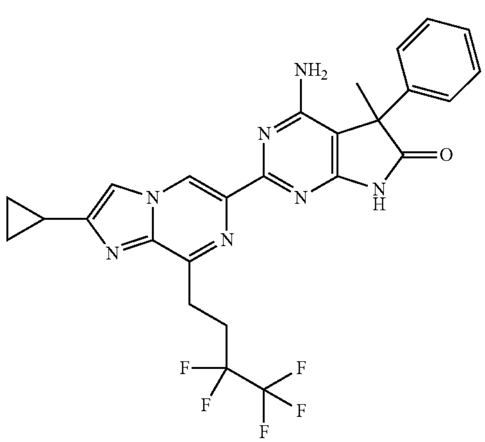 [SMILES: CC1(c2ccccc2)C(=O)Nc2nc(-c3cn4cc(C5CC5)nc4c(CCC(F)(F)C(F)(F)F)n3)nc(N)c21] | 4-amino-2-(2-cyclopropyl-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one | I-41B* | 544.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 159A | 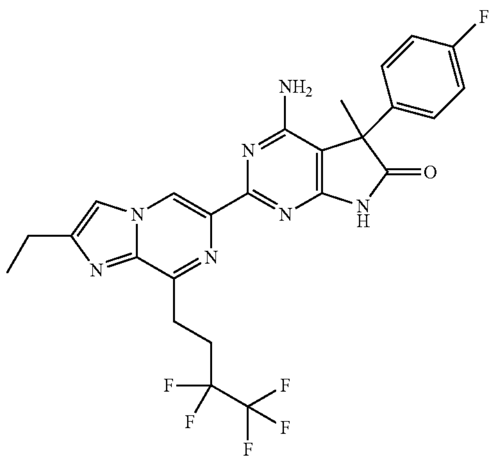 [SMILES: CCc1cn2cc(-c3nc(N)c4c(n3)NC(=O)C4(C)c3ccc(F)cc3)nc(CCC(F)(F)C(F)(F)F)c2n1] | 4-amino-2-(2-ethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 550.0 |
| 160B | 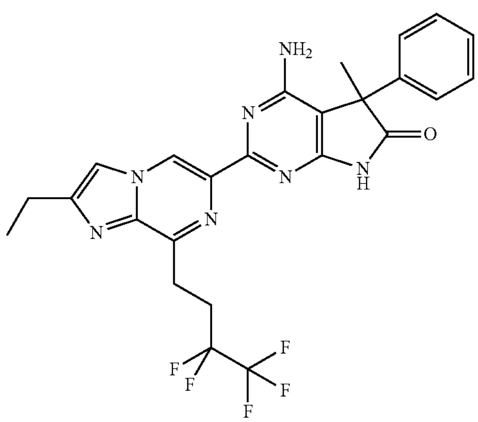 [SMILES: CCc1cn2cc(-c3nc(N)c4c(n3)NC(=O)C4(C)c3ccccc3)nc(CCC(F)(F)C(F)(F)F)c2n1] | 4-amino-2-(2-ethyl-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one | I-41B* | 532.1 |
| 161A | 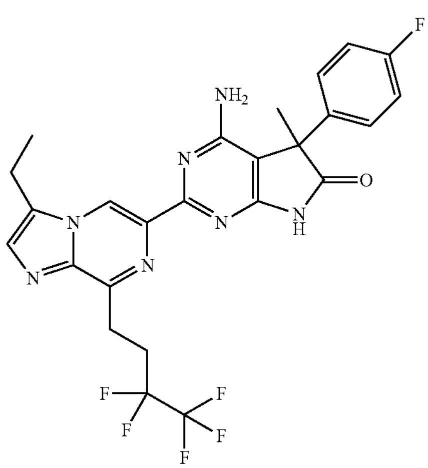 [SMILES: CCc1cnc2c(CCC(F)(F)C(F)(F)F)nc(-c3nc(N)c4c(n3)NC(=O)C4(C)c3ccc(F)cc3)cn12] | 4-amino-2-(3-ethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 550.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 162B | 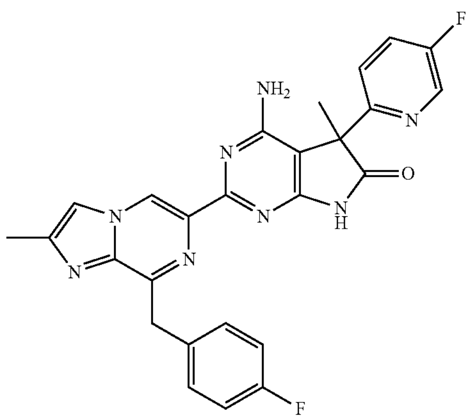 [SMILES: Cc1cn2cc(-c3nc(N)c4c(n3)NC(=O)C4(C)c3ccc(F)cn3)nc(Cc3ccc(F)cc3)c2n1] | 4-amino-2-(8-(4-fluorobenzyl)-2-methylimidazo[1,2-a]pyrazin-6-yl)-5-(5-fluoropyridin-2-yl)-5-methyl-5H-pyrrolo[2,3-d]pyrimidin-6(7H)-one | I-39B* | 499.1 |
| 163B | 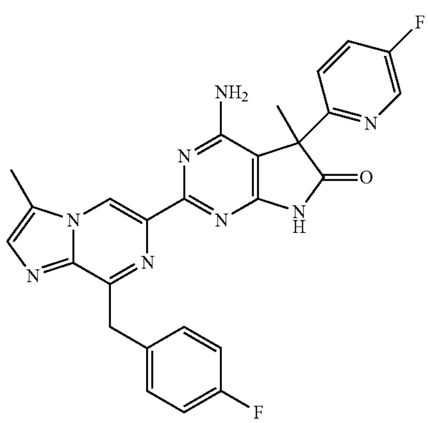 [SMILES: Cc1cnc2c(Cc3ccc(F)cc3)nc(-c3nc(N)c4c(n3)NC(=O)C4(C)c3ccc(F)cn3)cn12] | 4-amino-2-(8-(4-fluorobenzyl)-3-methylimidazo[1,2-a]pyrazin-6-yl)-5-(5-fluoropyridin-2-yl)-5-methyl-5H-pyrrolo[2,3-d]pyrimidin-6(7H)-one | I-39B* | 499.1 |
| 164B | 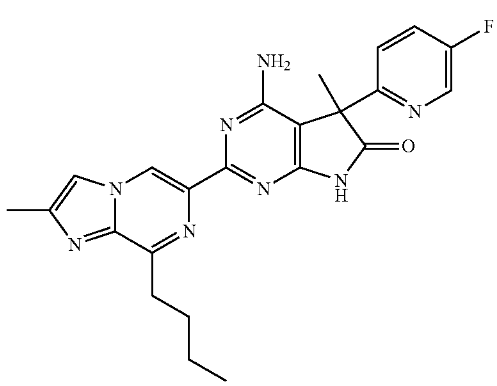 [SMILES: CCCCc1nc(-c2nc(N)c3c(n2)NC(=O)C3(C)c2ccc(F)cn2)cn2cc(C)nc12] | 4-amino-2-(8-butyl-2-methylimidazo[1,2-a]pyrazin-6-yl)-5-(5-fluoropyridin-2-yl)-5-methyl-5H-pyrrolo[2,3-d]pyrimidin-6(7H)-one | I-39B* | 447.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 165B | 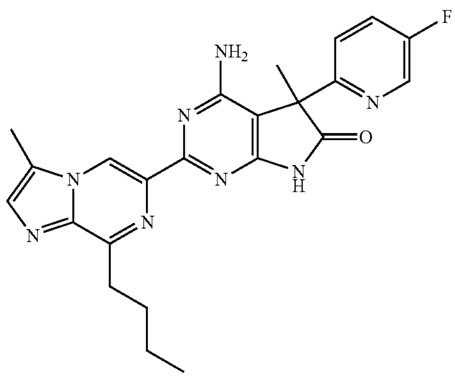 [SMILES: CCCCc1nc(-c2nc(N)c3c(n2)NC(=O)C3(C)c2ccc(F)cn2)cn2c(C)cnc12] | 4-amino-2-(8-butyl-3-methylimidazo[1,2-a]pyrazin-6-yl)-5-(5-fluoropyridin-2-yl)-5-methyl-5H-pyrrolo[2,3-d]pyrimidin-6(7H)-one | I-39B* | 447.2 |
| 166B | 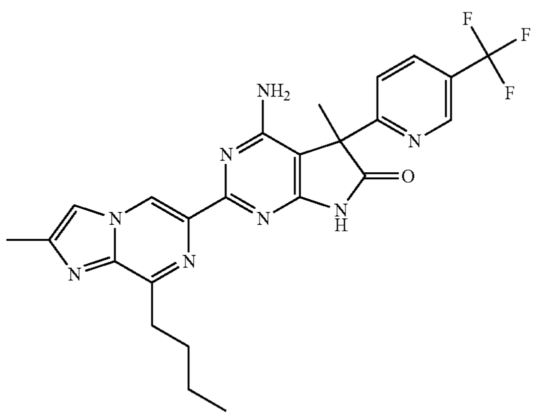 [SMILES: CCCCc1nc(-c2nc(N)c3c(n2)NC(=O)C3(C)c2ccc(C(F)(F)F)cn2)cn2cc(C)nc12] | 4-amino-2-(8-butyl-2-methylimidazo[1,2-a]pyrazin-6-yl)-5-methyl-5-(5-(trifluoromethyl)pyridin-2-yl)-5H-pyrrolo[2,3-d]pyrimidin-6(7H)-one | I-61B* | 497.2 |
| 167B | 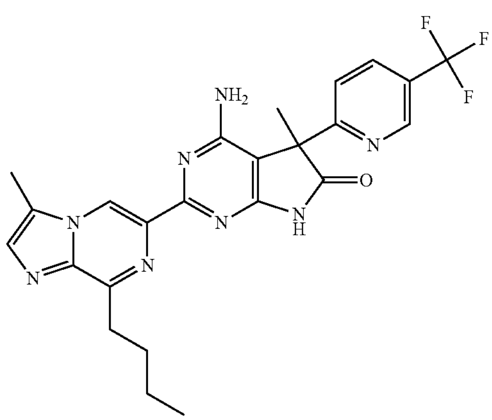 [SMILES: CCCCc1nc(-c2nc(N)c3c(n2)NC(=O)C3(C)c2ccc(C(F)(F)F)cn2)cn2c(C)cnc12] | 4-amino-2-(8-butyl-3-methylimidazo[1,2-a]pyrazin-6-yl)-5-methyl-5-(5-(trifluoromethyl)pyridin-2-yl)-5H-pyrrolo[2,3-d]pyrimidin-6(7H)-one | I-61B* | 497.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 168A | 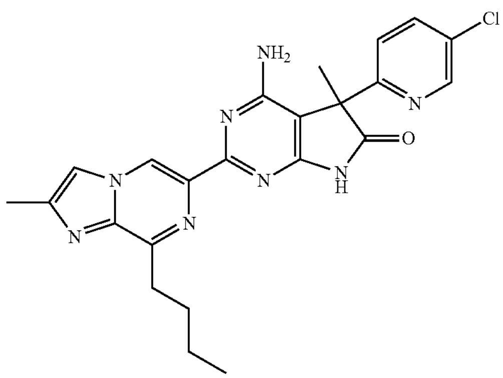 [SMILES: CCCCc1nc(-c2nc(N)c3c(n2)NC(=O)C3(C)c2ccc(Cl)cn2)cn2cc(C)nc12] | 4-amino-2-(8-butyl-2-methylimidazo[1,2-a]pyrazin-6-yl)-5-(5-chloropyridin-2-yl)-5-methyl-5H-pyrrolo[2,3-d]pyrimidin-6(7H)-one | I-52A* | 463.2 |
| 169A | 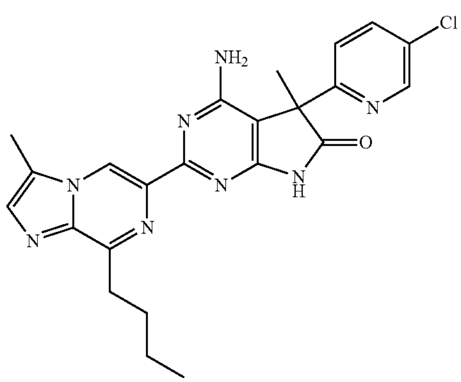 [SMILES: CCCCc1nc(-c2nc(N)c3c(n2)NC(=O)C3(C)c2ccc(Cl)cn2)cn2c(C)cnc12] | 4-amino-2-(8-butyl-3-methylimidazo[1,2-a]pyrazin-6-yl)-5-(5-chloropyridin-2-yl)-5-methyl-5H-pyrrolo[2,3-d]pyrimidin-6(7H)-one | I-52A* | 463.0 |
| 170A | 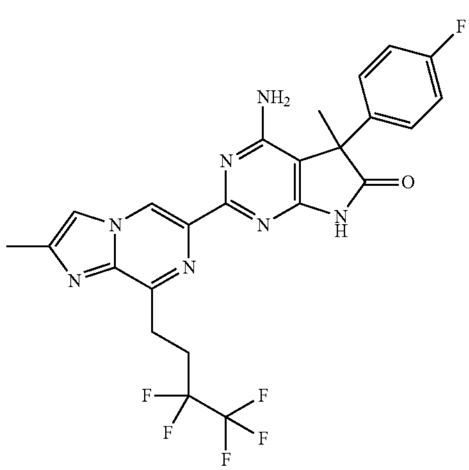 [SMILES: Cc1cn2cc(-c3nc(N)c4c(n3)NC(=O)C4(C)c3ccc(F)cc3)nc(CCC(F)(F)C(F)(F)F)c2n1] | 4-amino-5-(4-fluorophenyl)-5-methyl-2-(2-methyl-8-(3,3,4,4,4-pentafluorobutyl)imidazo[1,2-a]pyrazin-6-yl)-5H-pyrrolo[2,3-d]pyrimidin-6(7H)-one | I-85A* | 536.5 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 171A | 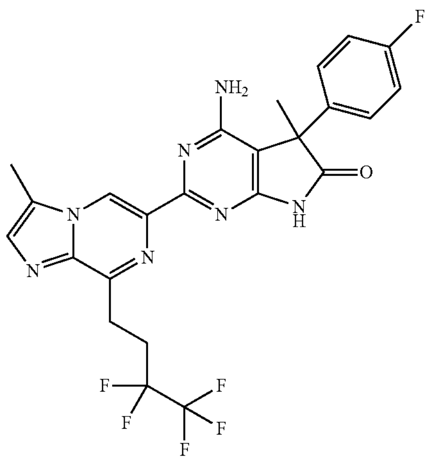 [SMILES: Cc1cnc2c(CCC(F)(F)C(F)(F)F)nc(-c3nc(N)c4c(n3)NC(=O)C4(C)c3ccc(F)cc3)cn12] | 4-amino-5-(4-fluorophenyl)-5-methyl-2-(3-methyl-8-(3,3,4,4,4-pentafluorobutyl)imidazo[1,2-a]pyrazin-6-yl)-5H-pyrrolo[2,3-d]pyrimidin-6(7H)-one | I-85A* | 536.0 |
| 172B | 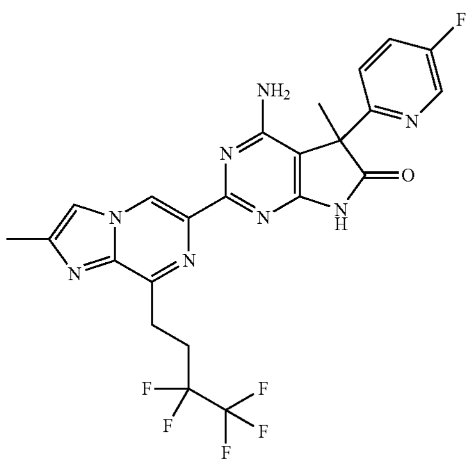 [SMILES: Cc1cn2cc(-c3nc(N)c4c(n3)NC(=O)C4(C)c3ccc(F)cn3)nc(CCC(F)(F)C(F)(F)F)c2n1] | 4-amino-5-(5-fluoropyridin-2-yl)-5-methyl-2-(2-methyl-8-(3,3,4,4,4-pentafluorobutyl)imidazo[1,2-a]pyrazin-6-yl)-5H-pyrrolo[2,3-d]pyrimidin-6(7H)-one | I-39B* | 537.0 |
| 173B | 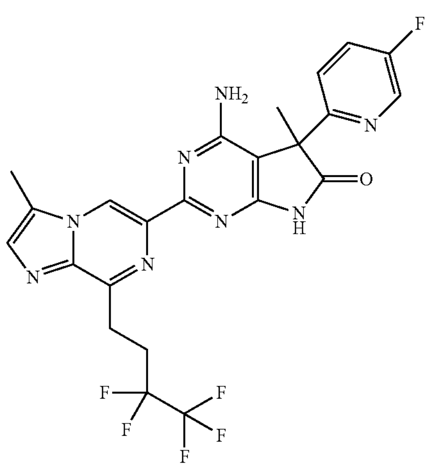 | 4-amino-5-(5-fluoropyridin-2-yl)-5-methyl-2-(3-methyl-8-(3,3,4,4,4-pentafluorobutyl)imidazo[1,2-a]pyrazin-6-yl)-5H-pyrrolo[2,3-d]pyrimidin-6(7H)-one | I-39B* | 537.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 174A | 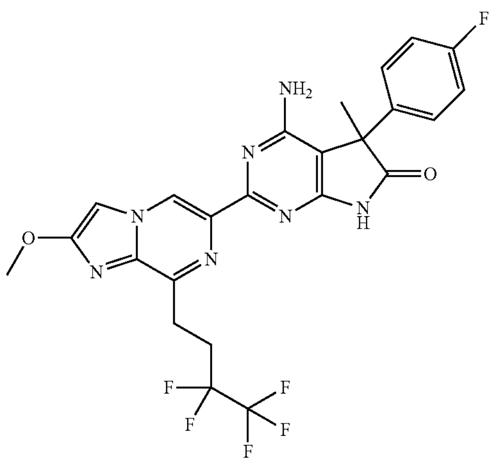 [SMILES: COc1cn2cc(-c3nc(N)c4c(n3)NC(=O)C4(C)c3ccc(F)cc3)nc(CCC(F)(F)C(F)(F)F)c2n1] | 4-amino-5-(4-fluorophenyl)-2-(2-methoxy-8-(3,3,4,4,4-pentafluorobutyl)imidazo[1,2-a]pyrazin-6-yl)-5-methyl-5H-pyrrolo[2,3-d]pyrimidin-6(7H)-one | I-85A* | 552.0 |
| 175B | 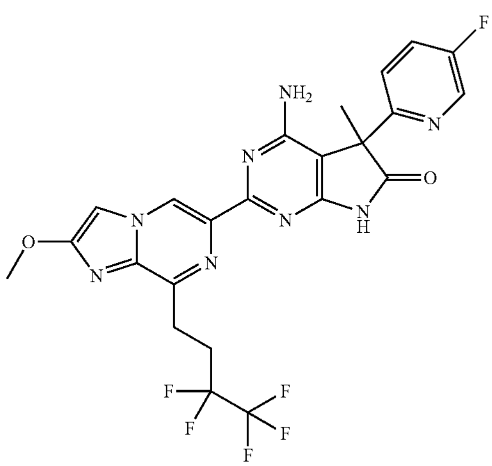 [SMILES: COc1cn2cc(-c3nc(N)c4c(n3)NC(=O)C4(C)c3ccc(F)cn3)nc(CCC(F)(F)C(F)(F)F)c2n1] | 4-amino-5-(5-fluoropyridin-2-yl)-2-(2-methoxy-8-(3,3,4,4,4-pentafluorobutyl)imidazo[1,2-a]pyrazin-6-yl)-5-methyl-5H-pyrrolo[2,3-d]pyrimidin-6(7H)-one | I-39B* | 553.0 |
| 176A | 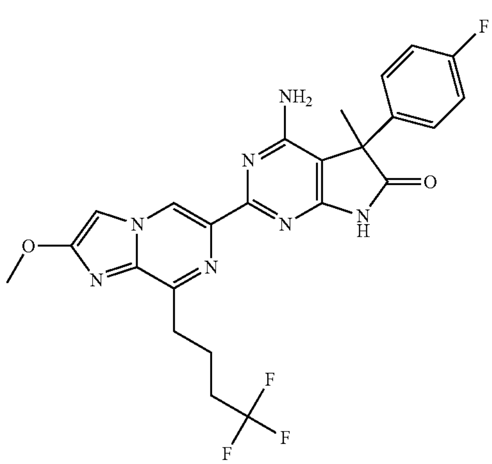 [SMILES: COc1cn2cc(-c3nc(N)c4c(n3)NC(=O)C4(C)c3ccc(F)cc3)nc(CCCC(F)(F)F)c2n1] | 4-amino-5-(4-fluorophenyl)-2-(2-methoxy-8-(4,4,4-trifluorobutyl)imidazo[1,2-a]pyrazin-6-yl)-5-methyl-5H-pyrrolo[2,3-d]pyrimidin-6(7H)-one | I-85A* | 516.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 177A | 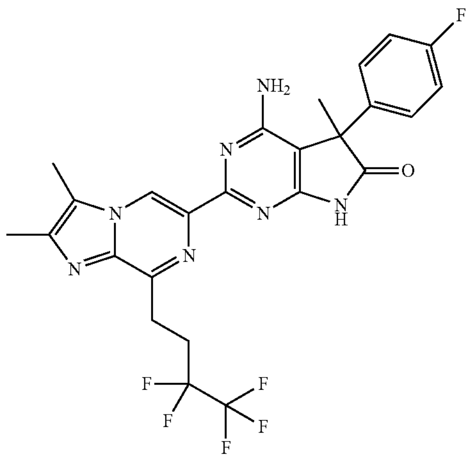 [SMILES: Cc1nc2c(CCC(F)(F)C(F)(F)F)nc(-c3nc(N)c4c(n3)NC(=O)C4(C)c3ccc(F)cc3)cn2c1C] | 4-amino-2-(2,3-dimethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 550.0 |
| 178B | 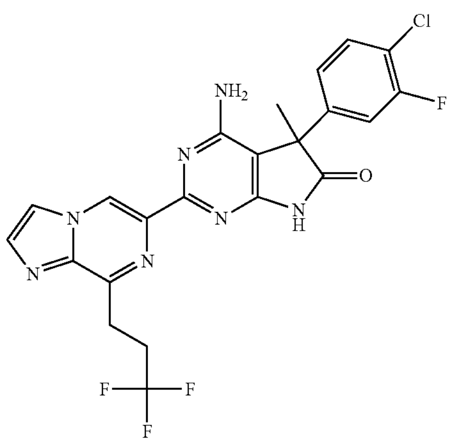 | 4-amino-5-(4-chloro-3-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-91B* | 506.2 |
| 179A | 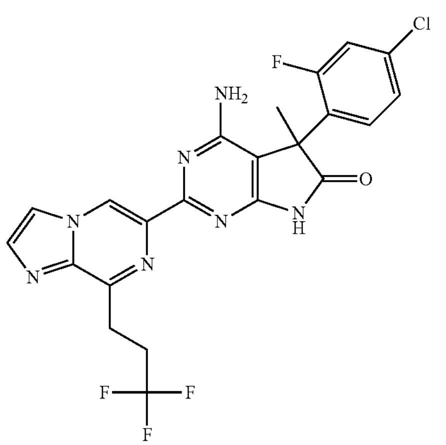 [SMILES: CC1(c2ccc(Cl)cc2F)C(=O)Nc2nc(-c3cn4ccnc4c(CCC(F)(F)F)n3)nc(N)c21] | 4-amino-5-(4-chloro-2-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-44A* | 506.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 180A | 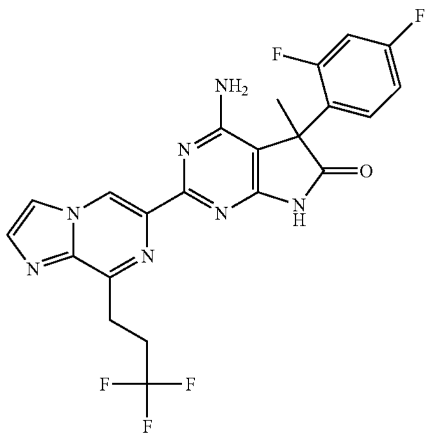 [SMILES: CC1(c2ccc(F)cc2F)C(=O)Nc2nc(-c3cn4ccnc4c(CCC(F)(F)F)n3)nc(N)c21] | 4-amino-5-(2,4-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-46A* | 490 |
| 181A | 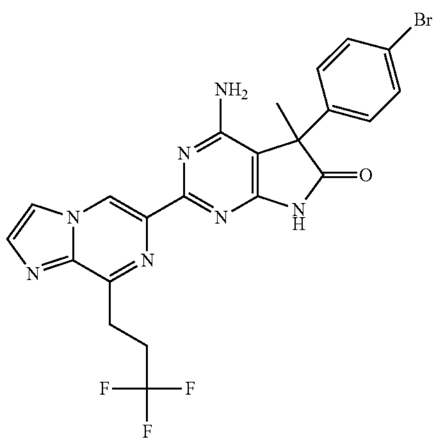 [SMILES: CC1(c2ccc(Br)cc2)C(=O)Nc2nc(-c3cn4ccnc4c(CCC(F)(F)F)n3)nc(N)c21] | 4-amino-5-(4-bromophenyl)-5-methyl-2-(8-(3,3,3-trifluoropropyl)imidazo[1,2-a]pyrazin-6-yl)-5H-pyrrolo[2,3-d]pyrimidin-6(7H)-one | I-42A* | 532.0 534.0 |
| 182A | 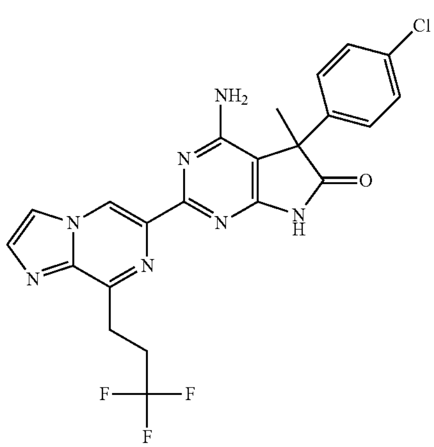 [SMILES: CC1(c2ccc(Cl)cc2)C(=O)Nc2nc(-c3cn4ccnc4c(CCC(F)(F)F)n3)nc(N)c21] | 4-amino-5-(4-chlorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-86A* | 488.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 183B | 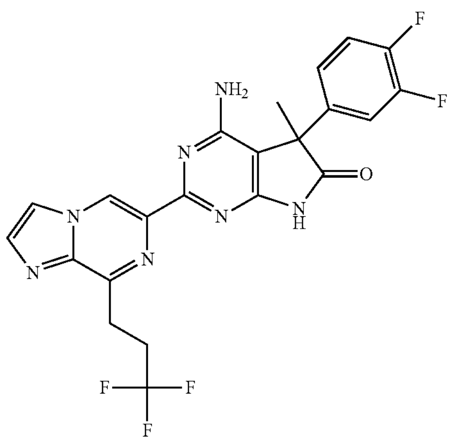 [SMILES: CC1(c2ccc(F)c(F)c2)C(=O)Nc2nc(-c3cn4ccnc4c(CCC(F)(F)F)n3)nc(N)c21] | 4-amino-5-(3,4-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-94B* | 490.1 |
| 184A | 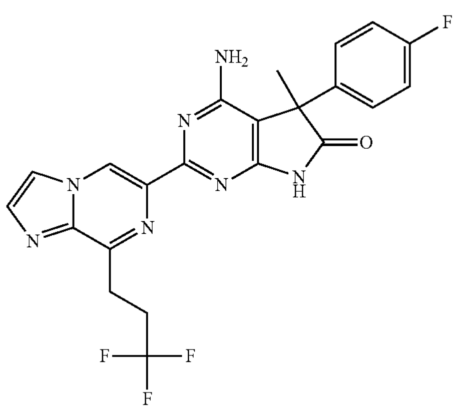 [SMILES: CC1(c2ccc(F)cc2)C(=O)Nc2nc(-c3cn4ccnc4c(CCC(F)(F)F)n3)nc(N)c21] | 4-amino-5-(4-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-85A* | 472.0 |
| 185A & B | 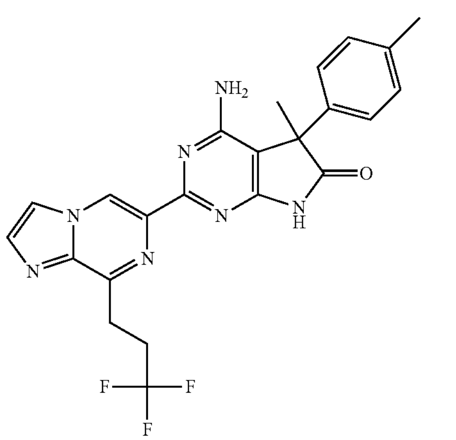 [SMILES: Cc1ccc(C2(C)C(=O)Nc3nc(-c4cn5ccnc5c(CCC(F)(F)F)n4)nc(N)c32)cc1] | 4-amino-5-methyl-5-(p-tolyl)-2-(8-(3,3,3-trifluoropropyl)imidazo[1,2-a]pyrazin-6-yl)-5H-pyrrolo[2,3-d]pyrimidin-6(7H)-one | CHIRALPAK IA | 468.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 186A & B | 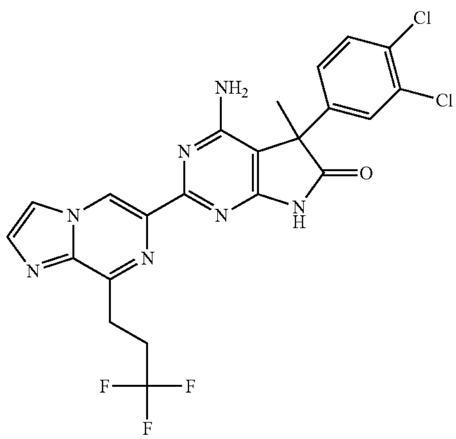 | 4-amino-5-(3,4-dichlorophenyl)-5-methyl-2-(8-(3,3,3-trifluoropropyl)imidazo[1,2-a]pyrazin-6-yl)-5H-pyrrolo[2,3-d]pyrimidin-6(7H)-one | CHIRALPAK IA | 522.0 |
| 187A | 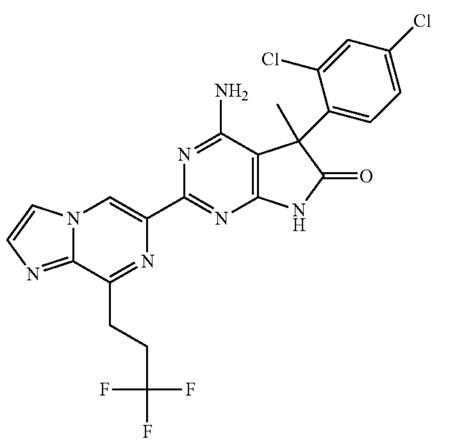 [SMILES: CC1(c2ccc(Cl)cc2Cl)C(=O)Nc2nc(-c3cn4ccnc4c(CCC(F)(F)F)n3)nc(N)c21] | 4-amino-5-(2,4-dichlorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-43A* | 521.9 |
| 188B | 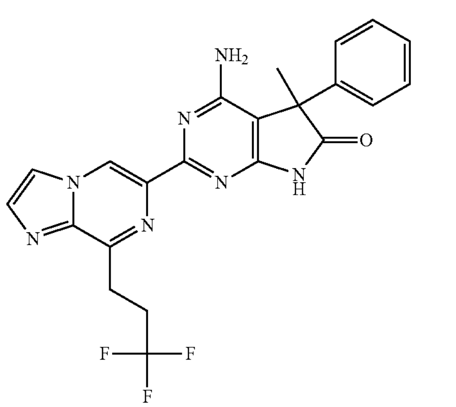 [SMILES: CC1(c2ccccc2)C(=O)Nc2nc(-c3cn4ccnc4c(CCC(F)(F)F)n3)nc(N)c21] | 4-amino-5-methyl-5-phenyl-2-(8-(3,3,3-trifluoropropyl)imidazo[1,2-a]pyrazin-6-yl)-5H-pyrrolo[2,3-d]pyrimidin-6(7H)-one | I-41B* | 454.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 189A & B | 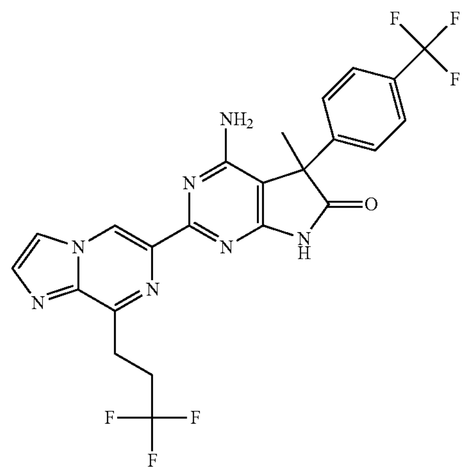 [SMILES: CC1(c2ccc(C(F)(F)F)cc2)C(=O)Nc2nc(-c3cn4ccnc4c(CCC(F)(F)F)n3)nc(N)c21] | 4-amino-5-methyl-5-(4-(trifluoromethyl)phenyl)-2-(8-(3,3,3-trifluoropropyl)imidazo[1,2-a]pyrazin-6-yl)-5H-pyrrolo[2,3-d]pyrimidin-6(7H)-one | CHIRALPAK IA | 522.0 |
| 190A | 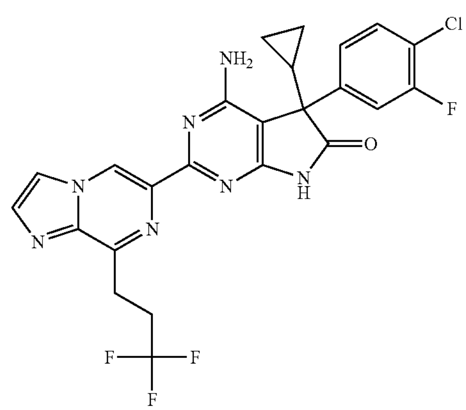 [SMILES: Nc1nc(-c2cn3ccnc3c(CCC(F)(F)F)n2)nc2c1C(c1ccc(Cl)c(F)c1)(C1CC1)C(=O)N2] | 4-amino-5-(4-chloro-3-fluorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one | I-81A* | 532.0 |
| 191A & B | 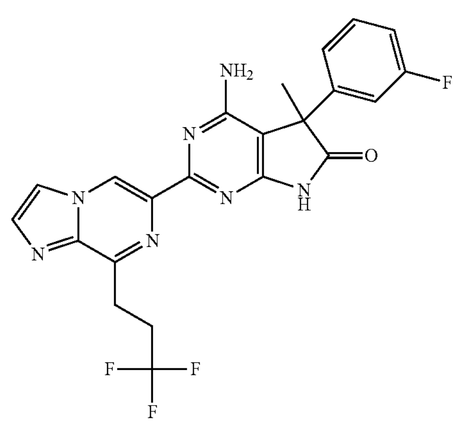 [SMILES: CC1(c2cccc(F)c2)C(=O)Nc2nc(-c3cn4ccnc4c(CCC(F)(F)F)n3)nc(N)c21] | 4-amino-5-(3-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one | CHIRALPAK IA | 472.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 192A & B | 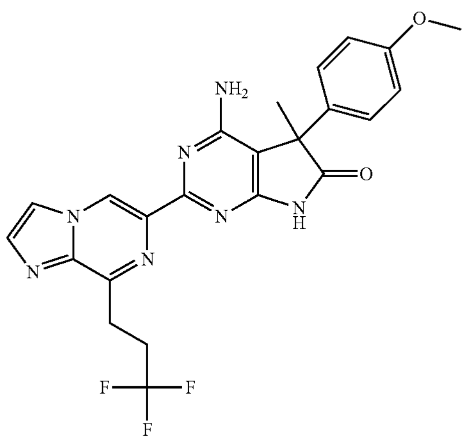 [SMILES: COc1ccc(C2(C)C(=O)Nc3nc(-c4cn5ccnc5c(CCC(F)(F)F)n4)nc(N)c32)cc1] | 4-amino-5-(4-methoxyphenyl)-5-methyl-2-(8-(3,3,3-trifluoropropyl)imidazo[1,2-a]pyrazin-6-yl)-5H-pyrrolo[2,3-d]pyrimidin-6(7H)-one | CHIRALPAK IB | 484.4 |
| 193B | 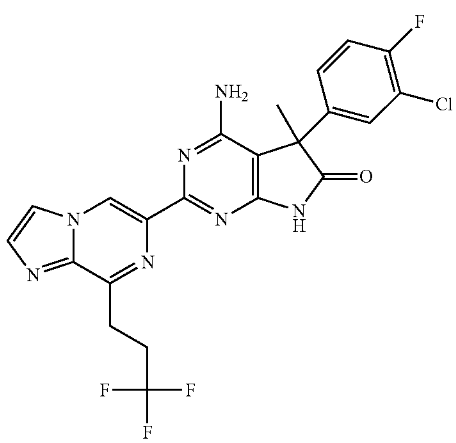 [SMILES: CC1(c2ccc(F)c(Cl)c2)C(=O)Nc2nc(-c3cn4ccnc4c(CCC(F)(F)F)n3)nc(N)c21] | 4-amino-5-(3-chloro-4-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-93B* | 506.0 |
| 194A & B | 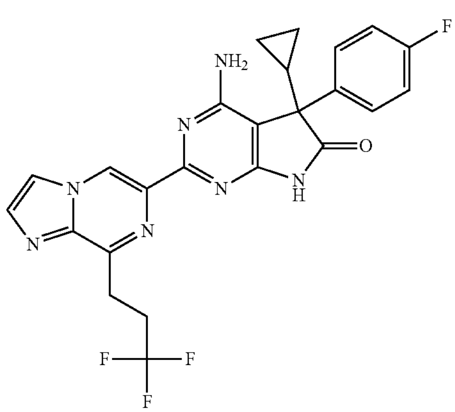 [SMILES: Nc1nc(-c2cn3ccnc3c(CCC(F)(F)F)n2)nc2c1C(c1ccc(F)cc1)(C1CC1)C(=O)N2] | 4-amino-5-cyclopropyl-5-(4-fluorophenyl)-2-(8-(3,3,3-trifluoropropyl)imidazo[1,2-a]pyrazin-6-yl)-5H-pyrrolo[2,3-d]pyrimidin-6(7H)-one | CHIRALPAK AD | 498.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 195B | 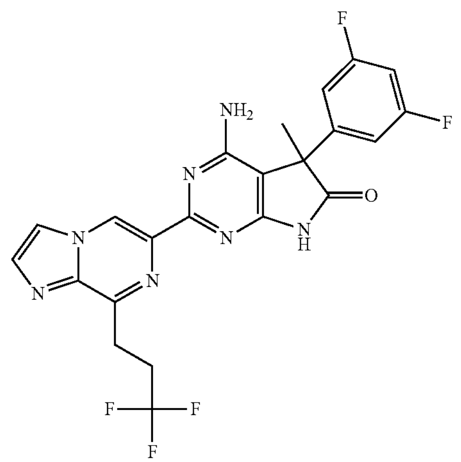 [SMILES: CC1(c2cc(F)cc(F)c2)C(=O)Nc2nc(-c3cn4ccnc4c(CCC(F)(F)F)n3)nc(N)c21] | 4-amino-5-(3,5-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one | I-45B* | 490.0 |
| 196A & B | 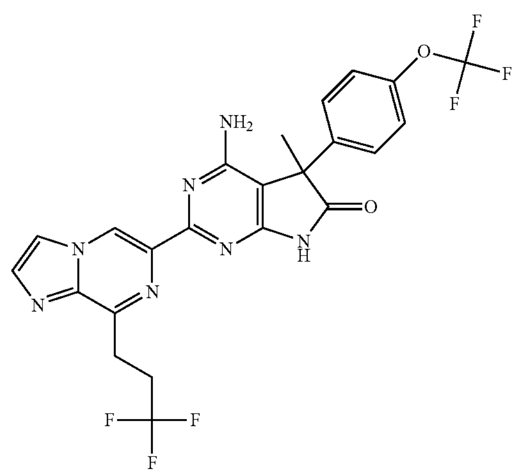 [SMILES: CC1(c2ccc(OC(F)(F)F)cc2)C(=O)Nc2nc(-c3cn4ccnc4c(CCC(F)(F)F)n3)nc(N)c21] | 4-amino-5-methyl-5-(4-(trifluoromethoxy)phenyl)-2-(8-(3,3,3-trifluoropropyl)imidazo[1,2-a]pyrazin-6-yl)-5H-pyrrolo[2,3-d]pyrimidin-6(7H)-one | CHIRALPAK IC | 538 |
| 197A | 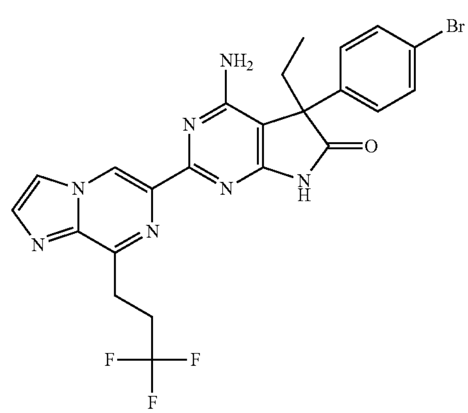 [SMILES: CCC1(c2ccc(Br)cc2)C(=O)Nc2nc(-c3cn4ccnc4c(CCC(F)(F)F)n3)nc(N)c21] | 4-amino-5-(4-bromophenyl)-5-ethyl-2-(8-(3,3,3-trifluoropropyl)imidazo[1,2-a]pyrazin-6-yl)-5H-pyrrolo[2,3-d]pyrimidin-6(7H)-one | I-73A* | 546.2 548.2 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 198B | 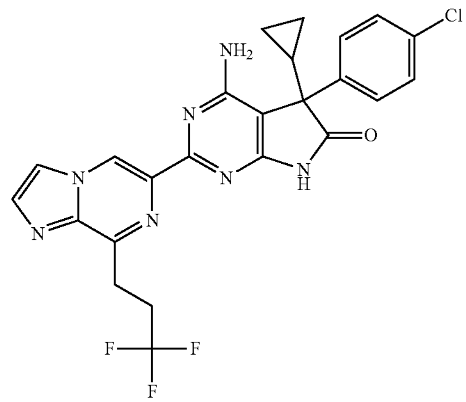 [SMILES: Nc1nc(-c2cn3ccnc3c(CCC(F)(F)F)n2)nc2c1C(c1ccc(Cl)cc1)(C1CC1)C(=O)N2] | 4-amino-5-(4-chlorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one | I-79B* | 514 |
| 199A | 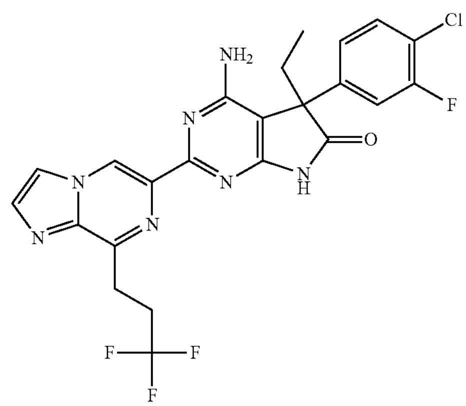 [SMILES: CCC1(c2ccc(Cl)c(F)c2)C(=O)Nc2nc(-c3cn4ccnc4c(CCC(F)(F)F)n3)nc(N)c21] | 4-amino-5-(4-chloro-3-fluorophenyl)-5-ethyl-2-(8-(3,3,3-trifluoropropyl)imidazo[1,2-a]pyrazin-6-yl)-5H-pyrrolo[2,3-d]pyrimidin-6(7H)-one | I-74A* | 520.2 |
| 200A | 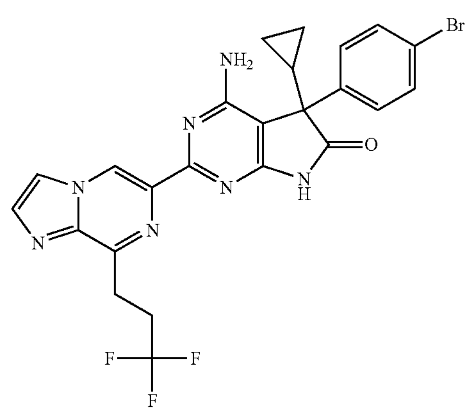 [SMILES: Nc1nc(-c2cn3ccnc3c(CCC(F)(F)F)n2)nc2c1C(c1ccc(Br)cc1)(C1CC1)C(=O)N2] | 4-amino-5-(4-bromophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one | I-80A* | 558.3 560.3 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 201A | 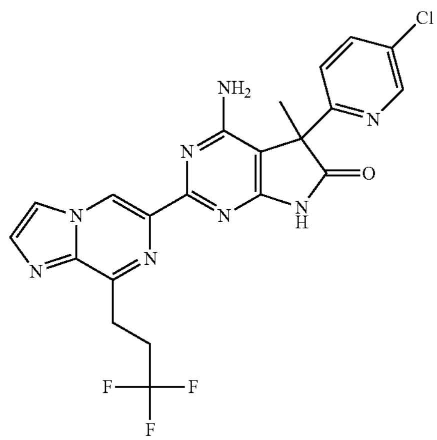 | 4-amino-5-(5-chloropyridin-2-yl)-5-methyl-2-(8-(3,3,3-trifluoropropyl)imidazo[1,2-a]pyrazin-6-yl)-5H-pyrrolo[2,3-d]pyrimidin-6(7H)-one | I-52A* | 489.1 |
| 202B | 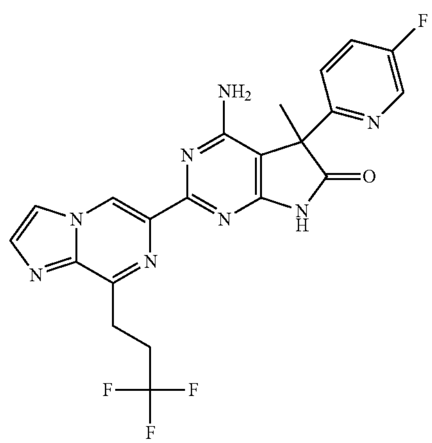 [SMILES: CC1(c2ccc(F)cn2)C(=O)Nc2nc(-c3cn4ccnc4c(CCC(F)(F)F)n3)nc(N)c21] | 4-amino-5-(5-fluoropyridin-2-yl)-5-methyl-2-(8-(3,3,3-trifluoropropyl)imidazo[1,2-a]pyrazin-6-yl)-5H-pyrrolo[2,3-d]pyrimidin-6(7H)-one | I-39B* | 473.1 |
| 203A & B | 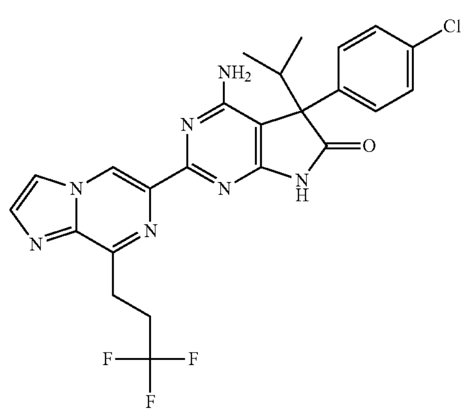 [SMILES: CC(C)C1(c2ccc(Cl)cc2)C(=O)Nc2nc(-c3cn4ccnc4c(CCC(F)(F)F)n3)nc(N)c21] | 4-amino-5-(4-chlorophenyl)-5-isopropyl-2-(8-(3,3,3-trifluoropropyl)imidazo[1,2-a]pyrazin-6-yl)-5H-pyrrolo[2,3-d]pyrimidin-6(7H)-one | CHIRALPAK IA | 516.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 204B | 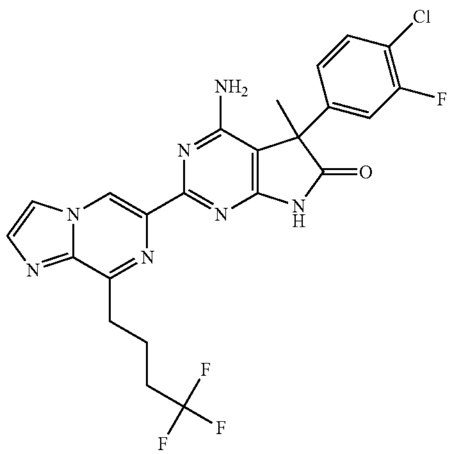 [SMILES: CC1(c2ccc(Cl)c(F)c2)C(=O)Nc2nc(-c3cn4ccnc4c(CCCC(F)(F)F)n3)nc(N)c21] | 4-amino-5-(4-chloro-3-fluorophenyl)-5-methyl-2-(8-(4,4,4-trifluorobutyl)imidazo[1,2-a]pyrazin-6-yl)-5H-pyrrolo[2,3-d]pyrimidin-6(7H)-one | I-91B* | 520.2 |
| 205B | 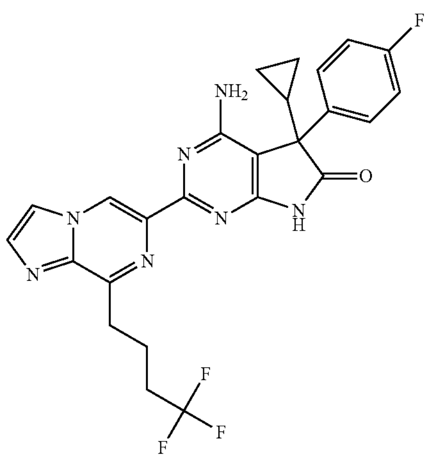 [SMILES: Nc1nc(-c2cn3ccnc3c(CCCC(F)(F)F)n2)nc2c1C(c1ccc(F)cc1)(C1CC1)C(=O)N2] | 4-amino-5-cyclopropyl-5-(4-fluorophenyl)-2-(8-(4,4,4-trifluorobutyl)imidazo[1,2-a]pyrazin-6-yl)-5H-pyrrolo[2,3-d]pyrimidin-6(7H)-one | I-78B* | 512.3 |
| 206A | 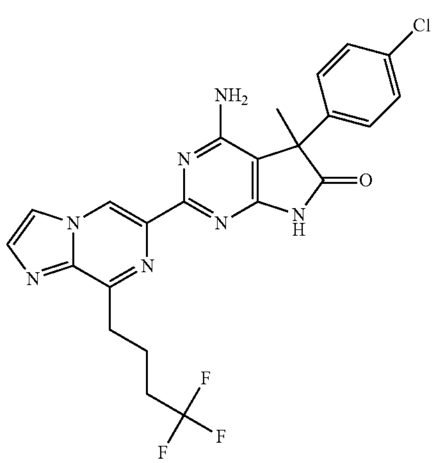 | 4-amino-5-(4-chlorophenyl)-5-methyl-2-(8-(4,4,4-trifluorobutyl)imidazo[1,2-a]pyrazin-6-yl)-5H-pyrrolo[2,3-d]pyrimidin-6(7H)-one | I-86A* | 502.3 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 207B | 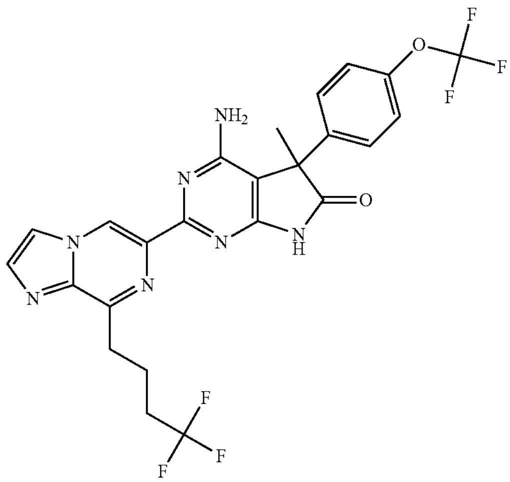 [SMILES: CC1(c2ccc(OC(F)(F)F)cc2)C(=O)Nc2nc(-c3cn4ccnc4c(CCCC(F)(F)F)n3)nc(N)c21] | 4-amino-5-methyl-2-(8-(4,4,4-trifluorobutyl)imidazo[1,2-a]pyrazin-6-yl)-5-(4-(trifluoromethoxy)phenyl)-5H-pyrrolo[2,3-d]pyrimidin-6(7H)-one | I-87B* | 552.1 |
| 208A | 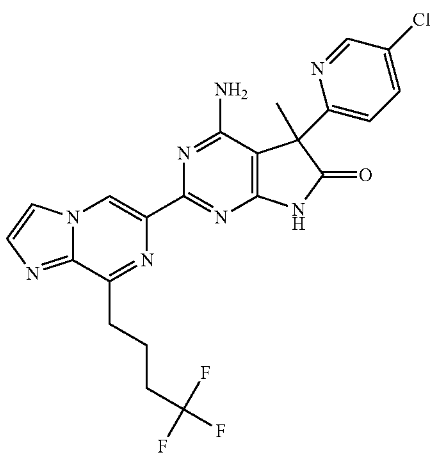 [SMILES: CC1(c2ccc(Cl)cn2)C(=O)Nc2nc(-c3cn4ccnc4c(CCCC(F)(F)F)n3)nc(N)c21] | 4-amino-5-(5-chloropyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one | I-52A* | 503.1 |
| 209B | 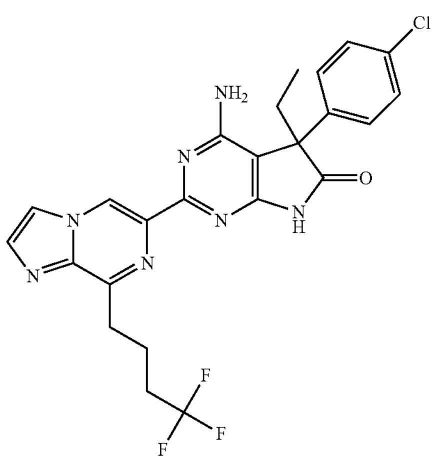 [SMILES: CCC1(c2ccc(Cl)cc2)C(=O)Nc2nc(-c3cn4ccnc4c(CCCC(F)(F)F)n3)nc(N)c21] | 4-amino-5-(4-chlorophenyl)-5-ethyl-2-(8-(4,4,4-trifluorobutyl)imidazo[1,2-a]pyrazin-6-yl)-5H-pyrrolo[2,3-d]pyrimidin-6(7H)-one | I-95B* | 516.3 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 210B | 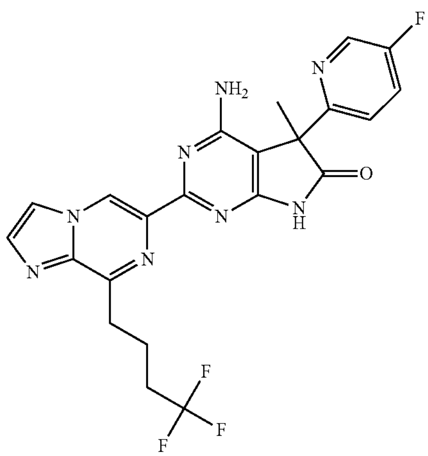 [SMILES: CC1(c2ccc(F)cn2)C(=O)Nc2nc(-c3cn4ccnc4c(CCCC(F)(F)F)n3)nc(N)c21] | 4-amino-5-(5-fluoropyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one | I-39B* | 487.1 |
| 211A | 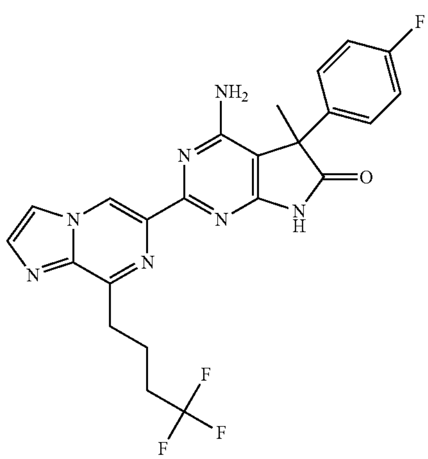 [SMILES: CC1(c2ccc(F)cc2)C(=O)Nc2nc(-c3cn4ccnc4c(CCCC(F)(F)F)n3)nc(N)c21] | 4-amino-5-(4-fluorophenyl)-5-methyl-2-(8-(4,4,4-trifluorobutyl)imidazo[1,2-a]pyrazin-6-yl)-5H-pyrrolo[2,3-d]pyrimidin-6(7H)-one | I-85A* | 486.1 |
| 212A & B | 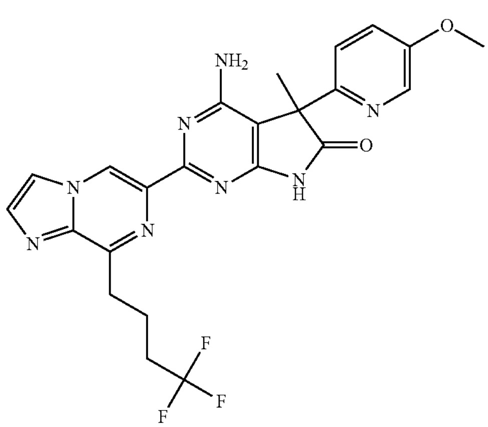 [SMILES: COc1ccc(C2(C)C(=O)Nc3nc(-c4cn5ccnc5c(CCCC(F)(F)F)n4)nc(N)c32)nc1] | 4-amino-5-(5-methoxypyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one | CHIRALPAK IA | 499.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 213B | 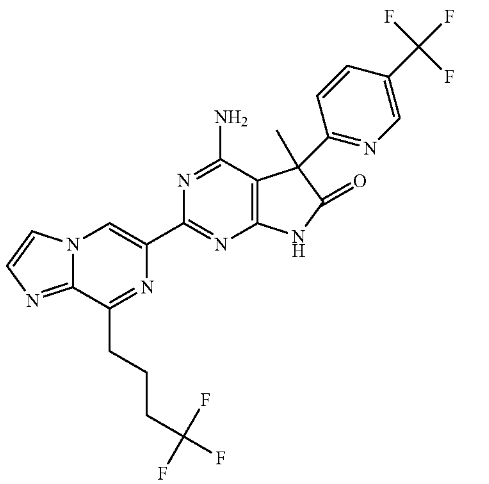 [SMILES: CC1(c2ccc(C(F)(F)F)cn2)C(=O)Nc2nc(-c3cn4ccnc4c(CCCC(F)(F)F)n3)nc(N)c21] | 4-amino-5-methyl-2-(8-(4,4,4-trifluorobutyl)imidazo[1,2-a]pyrazin-6-yl)-5-(5-(trifluoromethyl)pyridin-2-yl)-5H-pyrrolo[2,3-d]pyrimidin-6(7H)-one | I-61B* | 537.0 |
| 214A | 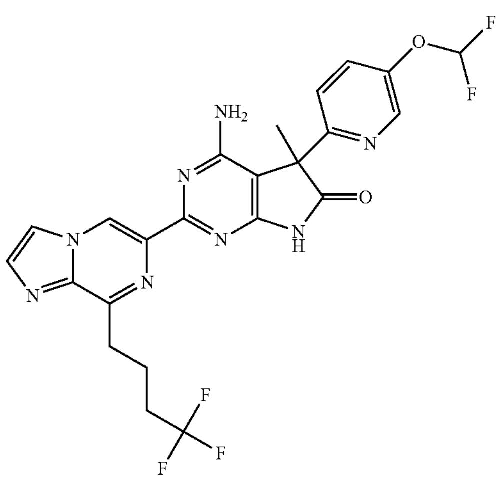 [SMILES: CC1(c2ccc(OC(F)F)cn2)C(=O)Nc2nc(-c3cn4ccnc4c(CCCC(F)(F)F)n3)nc(N)c21] | 4-amino-5-(5-(difluoromethoxy)pyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one | I-55A* | 535.0 |
| 215A | 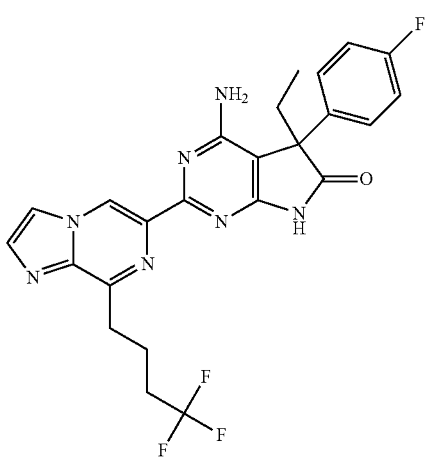 [SMILES: CCC1(c2ccc(F)cc2)C(=O)Nc2nc(-c3cn4ccnc4c(CCCC(F)(F)F)n3)nc(N)c21] | 4-amino-5-ethyl-5-(4-fluorophenyl)-2-(8-(4,4,4-trifluorobutyl)imidazo[1,2-a]pyrazin-6-yl)-5H-pyrrolo[2,3-d]pyrimidin-6(7H)-one | I-96A* | 500.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 216A | 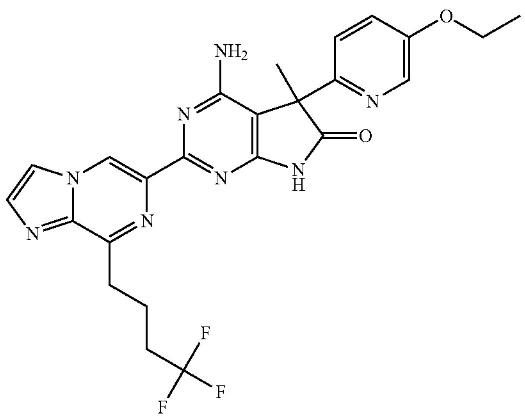 [SMILES: CCOc1ccc(C2(C)C(=O)Nc3nc(-c4cn5ccnc5c(CCCC(F)(F)F)n4)nc(N)c32)nc1] | 4-amino-5-(5-ethoxypyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one | I-54A* | 513.2 |
| 217A | 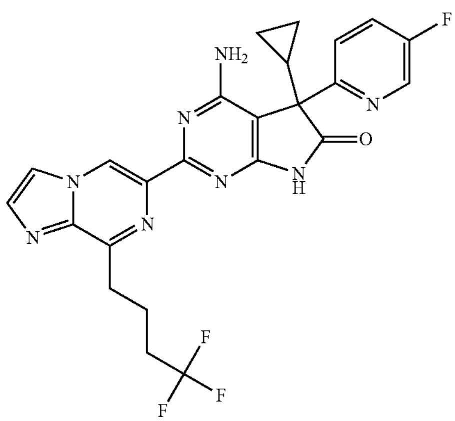 [SMILES: Nc1nc(-c2cn3ccnc3c(CCCC(F)(F)F)n2)nc2c1C(c1ccc(F)cn1)(C1CC1)C(=O)N2] | 4-amino-5-cyclopropyl-5-(5-fluoropyridin-2-yl)-2-(8-(4,4,4-trifluorobutyl)imidazo[1,2-a]pyrazin-6-yl)-5H-pyrrolo[2,3-d]pyrimidin-6(7H)-one | I-82A* | 513.4 |
| 218A & B | 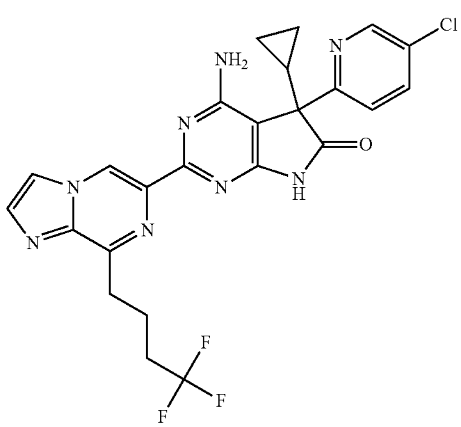 [SMILES: Nc1nc(-c2cn3ccnc3c(CCCC(F)(F)F)n2)nc2c1C(c1ccc(Cl)cn1)(C1CC1)C(=O)N2] | 4-amino-5-(5-chloropyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | CHIRALPAK IC | 529.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 219A | 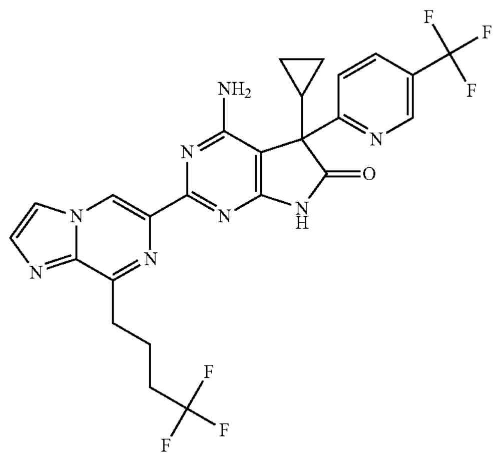 [SMILES: Nc1nc(-c2cn3ccnc3c(CCCC(F)(F)F)n2)nc2c1C(c1ccc(C(F)(F)F)cn1)(C1CC1)C(=O)N2] | 4-amino-5-cyclopropyl-2-(8-(4,4,4-trifluorobutyl)imidazo[1,2-a]pyrazin-6-yl)-5-(5-(trifluoromethyl)pyridin-2-yl)-5H-pyrrolo[2,3-d]pyrimidin-6(7H)-one | I-84A* | 563.1 |
| 220B | 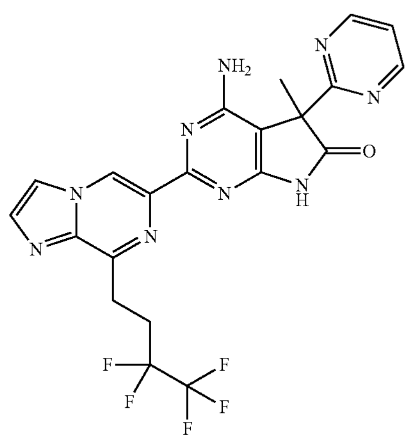 [SMILES: CC1(c2ncccn2)C(=O)Nc2nc(-c3cn4ccnc4c(CCC(F)(F)C(F)(F)F)n3)nc(N)c21] | 4-amino-5-methyl-2-(8-(3,3,4,4,4-pentafluorobutyl)imidazo[1,2-a]pyrazin-6-yl)-5-(pyrimidin-2-yl)-5H-pyrrolo[2,3-d]pyrimidin-6(7H)-one | I-48B* | 506.1 |
| 221A & B | 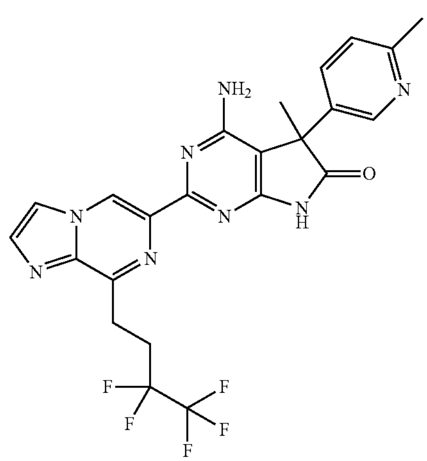 [SMILES: Cc1ccc(C2(C)C(=O)Nc3nc(-c4cn5ccnc5c(CCC(F)(F)C(F)(F)F)n4)nc(N)c32)cn1] | 4-amino-5-methyl-5-(6-methylpyridin-3-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 519.3 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 222B | 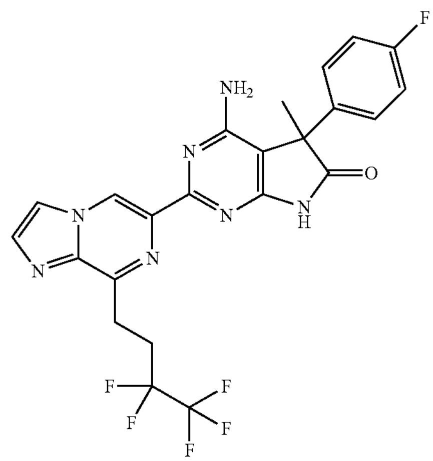 [SMILES: CC1(c2ccc(F)cc2)C(=O)Nc2nc(-c3cn4ccnc4c(CCC(F)(F)C(F)(F)F)n3)nc(N)c21] | 4-amino-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-85B* | 522.5 |
| 223A | 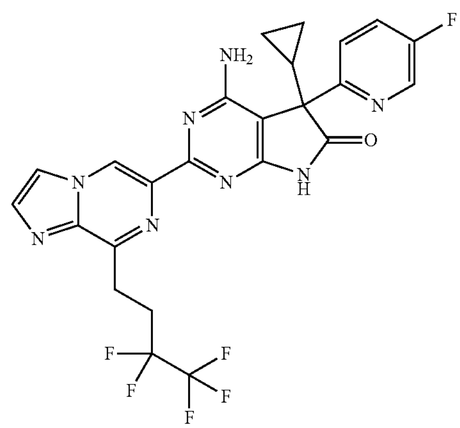 [SMILES: Nc1nc(-c2cn3ccnc3c(CCC(F)(F)C(F)(F)F)n2)nc2c1C(c1ccc(F)cn1)(C1CC1)C(=O)N2] | 4-amino-5-cyclopropyl-5-(5-fluoropyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | I-82A* | 549.0 |
| 224A | 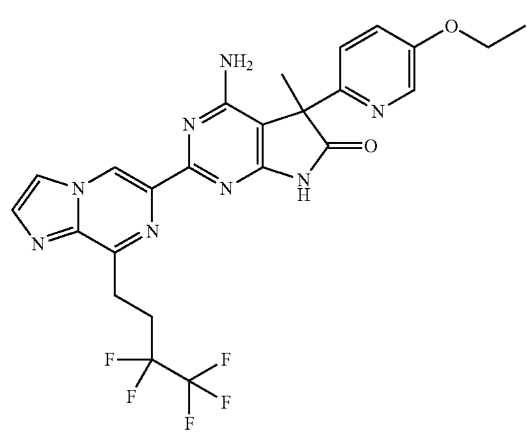 [SMILES: CCOc1ccc(C2(C)C(=O)Nc3nc(-c4cn5ccnc5c(CCC(F)(F)C(F)(F)F)n4)nc(N)c32)nc1] | 4-amino-5-(5-ethoxypyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-54A* | 549.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 225A | 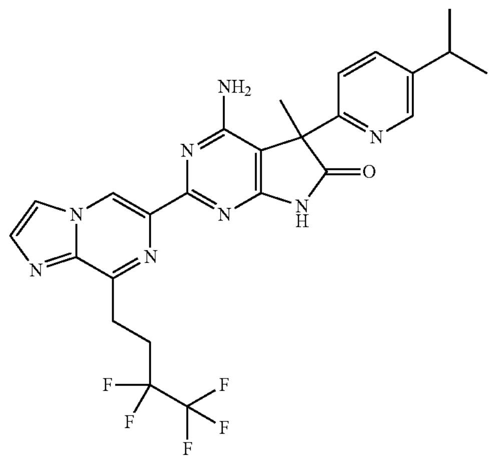 [SMILES: CC(C)c1ccc(C2(C)C(=O)Nc3nc(-c4cn5ccnc5c(CCC(F)(F)C(F)(F)F)n4)nc(N)c32)nc1] | 4-amino-5-(5-isopropylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-60A* | 547.1 |
| 226A | 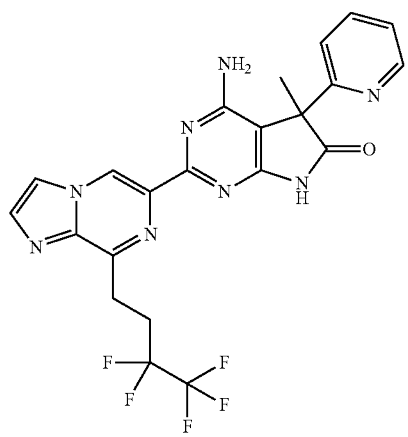 [SMILES: CC1(c2ccccn2)C(=O)Nc2nc(-c3cn4ccnc4c(CCC(F)(F)C(F)(F)F)n3)nc(N)c21] | 4-amino-5-methyl-2-(8-(3,3,4,4,4-pentafluorobutyl)imidazo[1,2-a]pyrazin-6-yl)-5-(pyridin-2-yl)-5H-pyrrolo[2,3-d]pyrimidin-6(7H)-one | I-44A* | 505.1 |
| 227B | 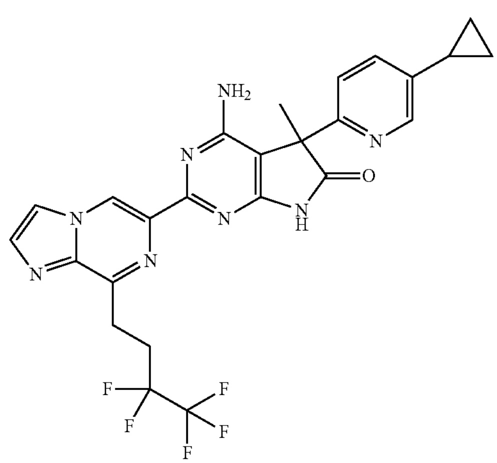 [SMILES: CC1(c2ccc(C3CC3)cn2)C(=O)Nc2nc(-c3cn4ccnc4c(CCC(F)(F)C(F)(F)F)n3)nc(N)c21] | 4-amino-5-(5-cyclopropylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-100B* | 545.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 228A | 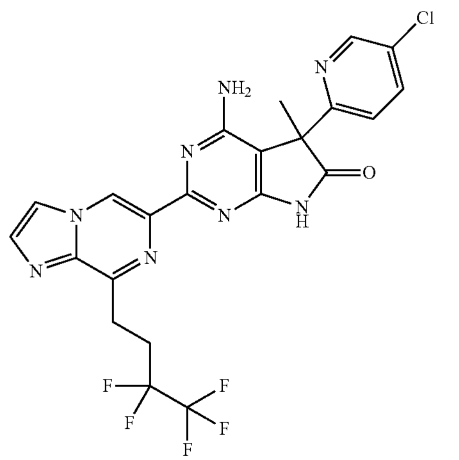 [SMILES: CC1(c2ccc(Cl)cn2)C(=O)Nc2nc(-c3cn4ccnc4c(CCC(F)(F)C(F)(F)F)n3)nc(N)c21] | 4-amino-5-(5-chloropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-52A* | 539.0 |
| 229A & B | 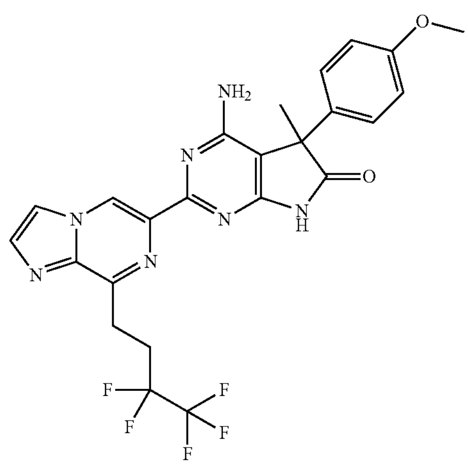 [SMILES: COc1ccc(C2(C)C(=O)Nc3nc(-c4cn5ccnc5c(CCC(F)(F)C(F)(F)F)n4)nc(N)c32)cc1] | 4-amino-5-(4-methoxyphenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IB | 534.0 |
| 230A & B | 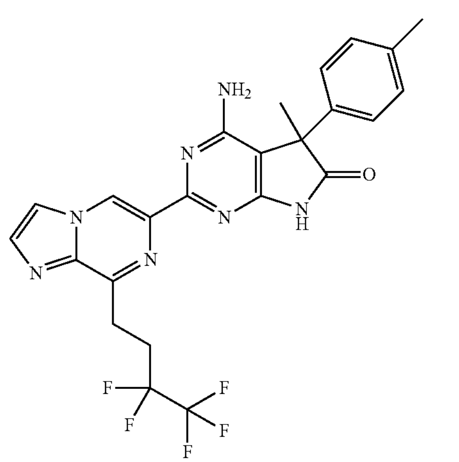 [SMILES: Cc1ccc(C2(C)C(=O)Nc3nc(-c4cn5ccnc5c(CCC(F)(F)C(F)(F)F)n4)nc(N)c32)cc1] | 4-amino-5-methyl-2-(8-(3,3,4,4,4-pentafluorobutyl)imidazo[1,2-a]pyrazin-6-yl)-5-(p-tolyl)-5H-pyrrolo[2,3-d]pyrimidin-6(7H)-one | CHIRALPAK IA | 518.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 231A & B | 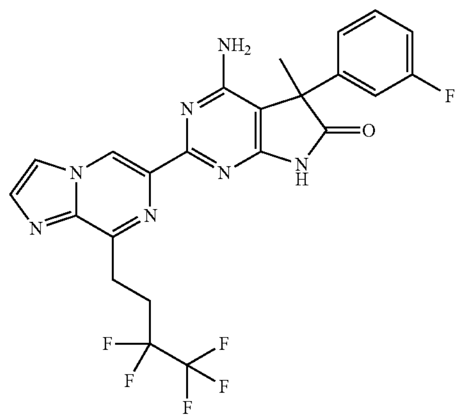 [SMILES: CC1(c2cccc(F)c2)C(=O)Nc2nc(-c3cn4ccnc4c(CCC(F)(F)C(F)(F)F)n3)nc(N)c21] | 4-amino-5-(3-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 522.3 |
| 232B | 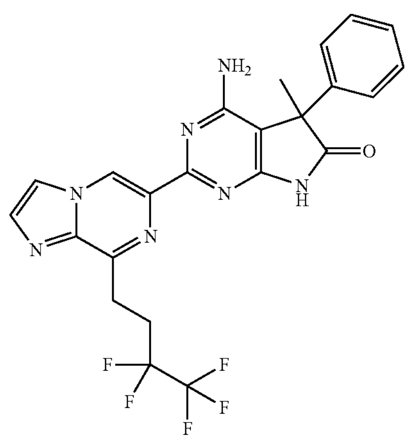 [SMILES: CC1(c2ccccc2)C(=O)Nc2nc(-c3cn4ccnc4c(CCC(F)(F)C(F)(F)F)n3)nc(N)c21] | 4-amino-5-methyl-2-(8-(3,3,4,4,4-pentafluorobutyl)imidazo[1,2-a]pyrazin-6-yl)-5-phenyl-5H-pyrrolo[2,3-d]pyrimidin-6(7H)-one | I-41B* | 504.0 |
| 233B | 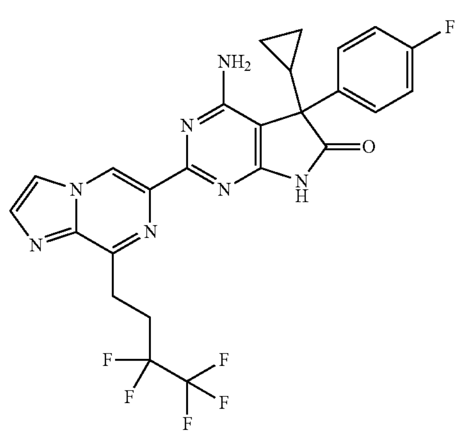 [SMILES: Nc1nc(-c2cn3ccnc3c(CCC(F)(F)C(F)(F)F)n2)nc2c1C(c1ccc(F)cc1)(C1CC1)C(=O)N2] | 4-amino-5-cyclopropyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one | I-78B* | 548.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 234A & B | 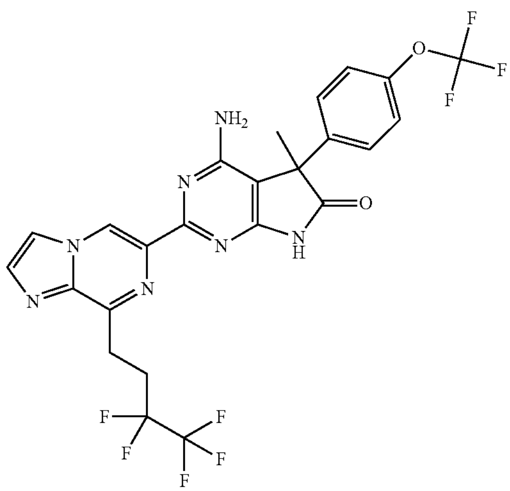 [SMILES: CC1(c2ccc(OC(F)(F)F)cc2)C(=O)Nc2nc(-c3cn4ccnc4c(CCC(F)(F)C(F)(F)F)n3)nc(N)c21] | 4-amino-5-methyl-2-(8-(3,3,4,4,4-pentafluorobutyl)imidazo[1,2-a]pyrazin-6-yl)-5-(4-(trifluoromethoxy)phenyl)-5H-pyrrolo[2,3-d]pyrimidin-6(7H)-one | CHIRALPAK IC | 588 |
| 235B | 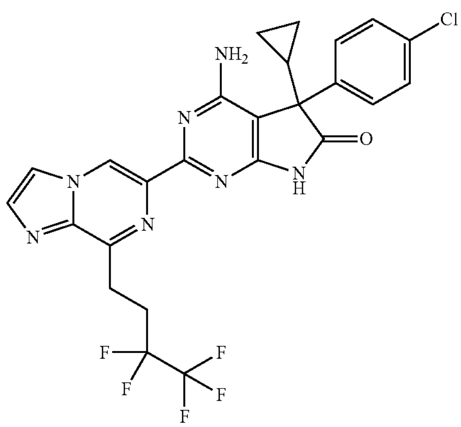 [SMILES: Nc1nc(-c2cn3ccnc3c(CCC(F)(F)C(F)(F)F)n2)nc2c1C(c1ccc(Cl)cc1)(C1CC1)C(=O)N2] | 4-amino-5-(4-chlorophenyl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one | I-79B* | 564.2 |
| 236B | 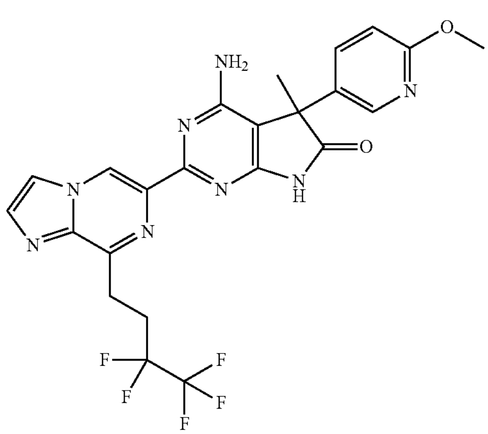 [SMILES: COc1ccc(C2(C)C(=O)Nc3nc(-c4cn5ccnc5c(CCC(F)(F)C(F)(F)F)n4)nc(N)c32)cn1] | 4-amino-5-(6-methoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-66B* | 535.3 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 237A & B | 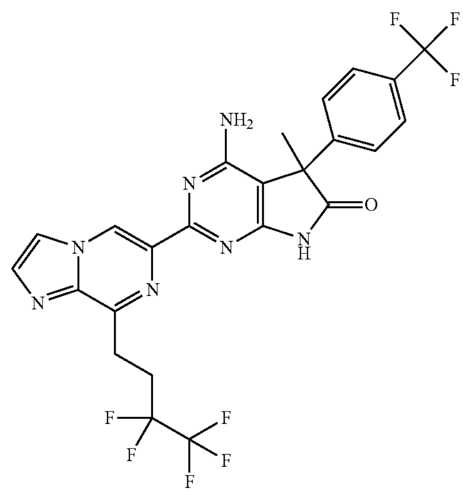 [SMILES: CC1(c2ccc(C(F)(F)F)cc2)C(=O)Nc2nc(-c3cn4ccnc4c(CCC(F)(F)C(F)(F)F)n3)nc(N)c21] | 4-amino-5-methyl-2-(8-(3,3,4,4,4-pentafluorobutyl)imidazo[1,2-a]pyrazin-6-yl)-5-(4-(trifluoromethyl)phenyl)-5H-pyrrolo[2,3-d]pyrimidin-6(7H)-one | CHIRALPAK IB | 572.0 |
| 238A | 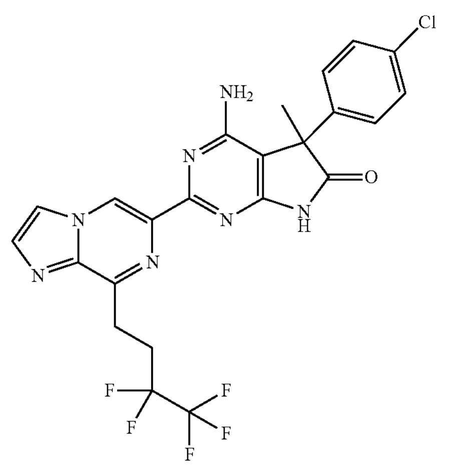 [SMILES: CC1(c2ccc(Cl)cc2)C(=O)Nc2nc(-c3cn4ccnc4c(CCC(F)(F)C(F)(F)F)n3)nc(N)c21] | 4-amino-5-(4-chlorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-86A* | 538.1 |
| 239A & B | 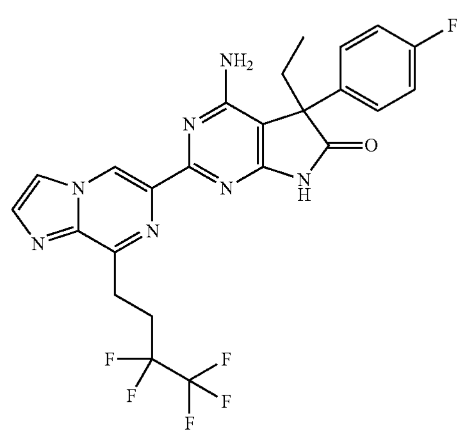 [SMILES: CCC1(c2ccc(F)cc2)C(=O)Nc2nc(-c3cn4ccnc4c(CCC(F)(F)C(F)(F)F)n3)nc(N)c21] | 4-amino-5-ethyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 536.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 240B | 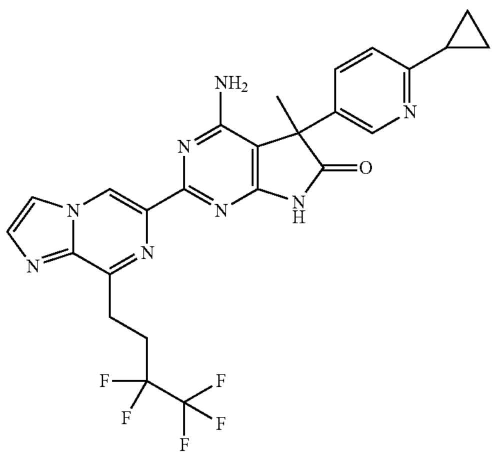 [SMILES: CC1(c2ccc(C3CC3)nc2)C(=O)Nc2nc(-c3cn4ccnc4c(CCC(F)(F)C(F)(F)F)n3)nc(N)c21] | 4-amino-5-(6-cyclopropylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-62B* | 545.2 |
| 241B | 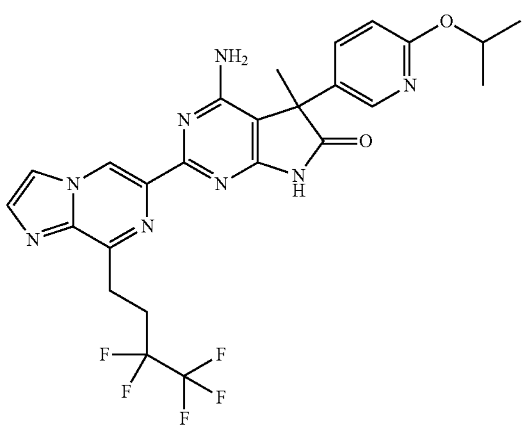 | 4-amino-5-(6-isopropoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-68B* | 563.4 |
| 242B | 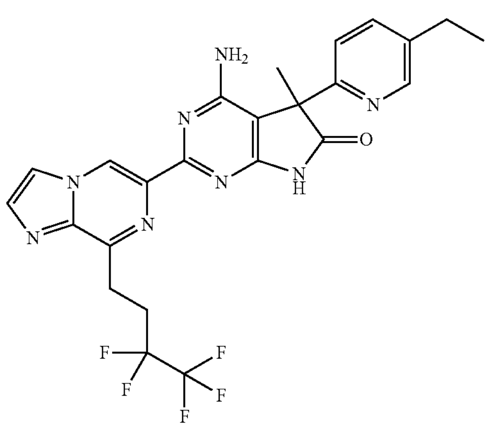 [SMILES: CCc1ccc(C2(C)C(=O)Nc3nc(-c4cn5ccnc5c(CCC(F)(F)C(F)(F)F)n4)nc(N)c32)nc1] | 4-amino-5-(5-ethylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-99B* | 533.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 243B | 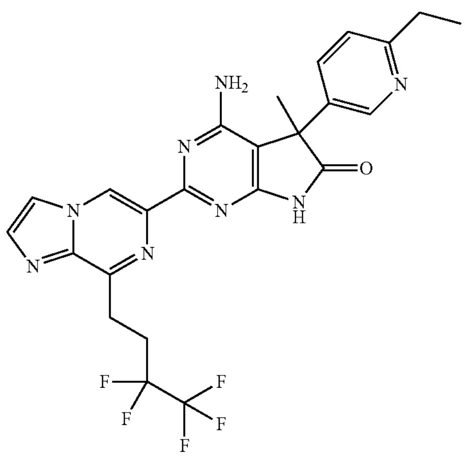 [SMILES: CCc1ccc(C2(C)C(=O)Nc3nc(-c4cn5ccnc5c(CCC(F)(F)C(F)(F)F)n4)nc(N)c32)cn1] | 4-amino-5-(6-ethylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-63B* | 533.1 |
| 244B | 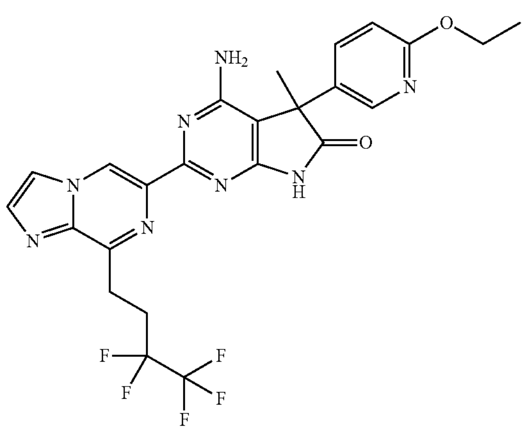 [SMILES: CCOc1ccc(C2(C)C(=O)Nc3nc(-c4cn5ccnc5c(CCC(F)(F)C(F)(F)F)n4)nc(N)c32)cn1] | 4-amino-5-(6-ethoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-67B* | 549.1 |
| 245A & B | 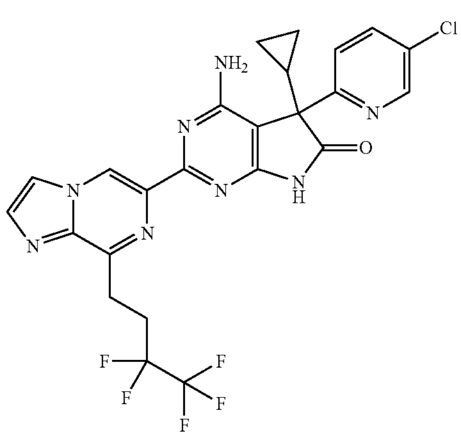 [SMILES: Nc1nc(-c2cn3ccnc3c(CCC(F)(F)C(F)(F)F)n2)nc2c1C(c1ccc(Cl)cn1)(C1CC1)C(=O)N2] | 4-amino-5-(5-chloropyridin-2-yl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 565.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 246B | 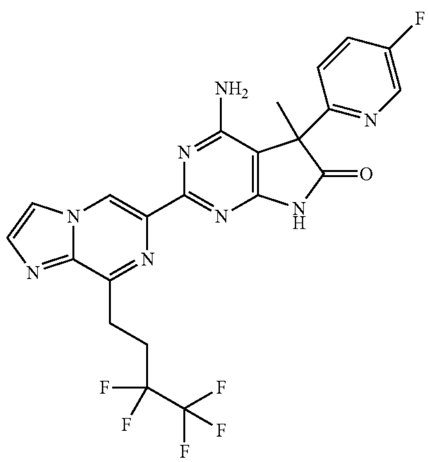 [SMILES: CC1(c2ccc(F)cn2)C(=O)Nc2nc(-c3cn4ccnc4c(CCC(F)(F)C(F)(F)F)n3)nc(N)c21] | 4-amino-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-39B* | 523.1 |
| 247B | 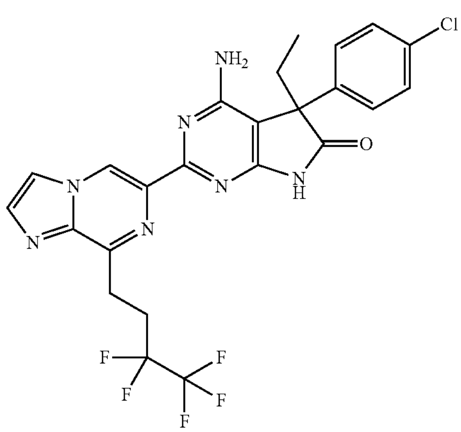 [SMILES: CCC1(c2ccc(Cl)cc2)C(=O)Nc2nc(-c3cn4ccnc4c(CCC(F)(F)C(F)(F)F)n3)nc(N)c21] | 4-amino-5-(4-chlorophenyl)-5-ethyl-2-(8-(3,3,4,4,4-pentafluorobutyl)imidazo[1,2-a]pyrazin-6-yl)-5H-pyrrolo[2,3-d]pyrimidin-6(7H)-one | I-95B* | 552.1 |
| 248A & B | 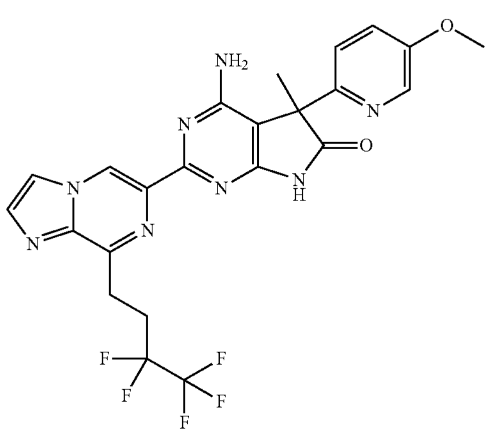 [SMILES: COc1ccc(C2(C)C(=O)Nc3nc(-c4cn5ccnc5c(CCC(F)(F)C(F)(F)F)n4)nc(N)c32)nc1] | 4-amino-5-(5-methoxypyridin-2-yl)-5-methyl-2-(8-(3,3,4,4,4-pentafluorobutyl)imidazo[12-a]pyrazin-6-yl)-5H-pyrrolo[2,3-d]pyrimidin-6(7H)-one | CHIRALPAK IA | 535.4 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 249A | 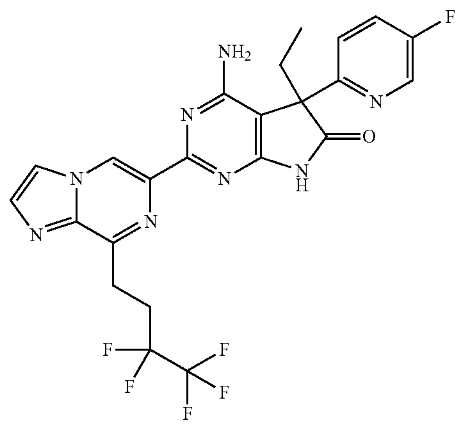 [SMILES: CCC1(c2ccc(F)cn2)C(=O)Nc2nc(-c3cn4ccnc4c(CCC(F)(F)C(F)(F)F)n3)nc(N)c21] | 4-amino-5-ethyl-5-(5-fluoropyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | I-75A* | 537.1 |
| 250B | 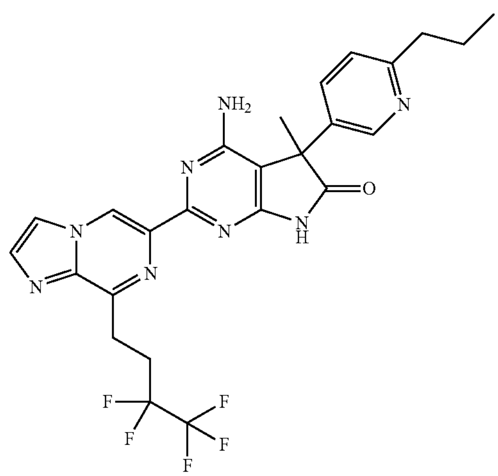 [SMILES: CCCc1ccc(C2(C)C(=O)Nc3nc(-c4cn5ccnc5c(CCC(F)(F)C(F)(F)F)n4)nc(N)c32)cn1] | 4-amino-5-methyl-2-(8-(3,3,4,4,4-pentafluorobutyl)imidazo[1,2-a]pyrazin-6-yl)-5-(6-propylpyridin-3-yl)-5H-pyrrolo[2,3-d]pyrimidin-6(7H)-one | I-65B* | 547.4 |
| 251B | 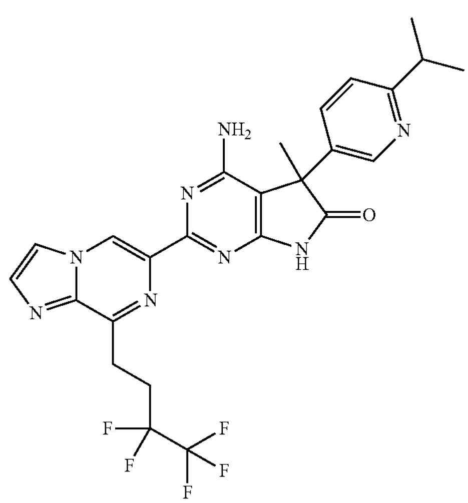 [SMILES: CC(C)c1ccc(C2(C)C(=O)Nc3nc(-c4cn5ccnc5c(CCC(F)(F)C(F)(F)F)n4)nc(N)c32)cn1] | 4-amino-5-(6-isopropylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-64B* | 547.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 252A & B | 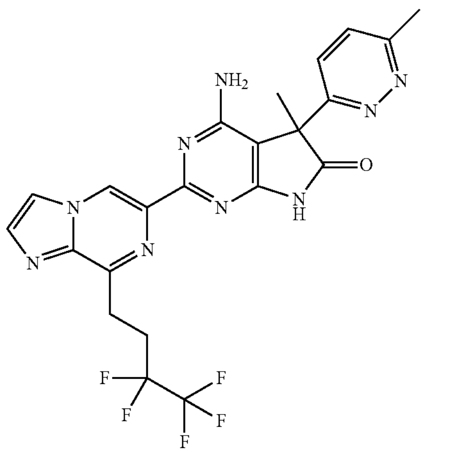 | 4-amino-5-methyl-5-(6-methylpyridazin-3-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 520.3 |
| 253A & B | 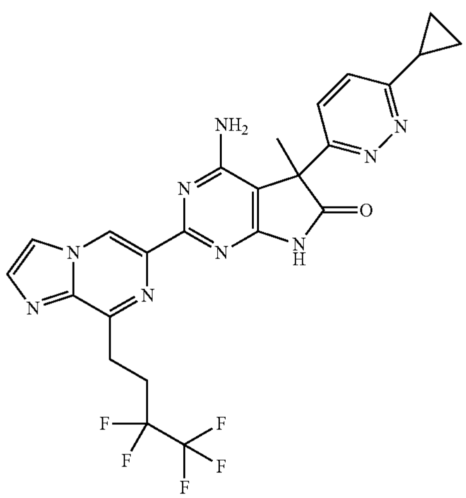 [SMILES: CC1(c2ccc(C3CC3)nn2)C(=O)Nc2nc(-c3cn4ccnc4c(CCC(F)(F)C(F)(F)F)n3)nc(N)c21] | 4-amino-5-(6-cyclopropylpyridazin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 546.4 |
| 254A | 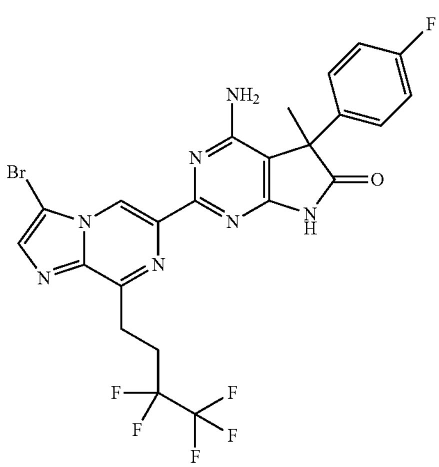 | 4-amino-2-(3-bromo-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 602.1 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 255A | 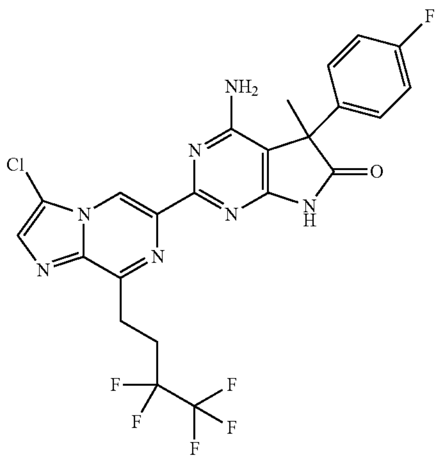 [SMILES: CC1(c2ccc(F)cc2)C(=O)Nc2nc(-c3cn4c(Cl)cnc4c(CCC(F)(F)C(F)(F)F)n3)nc(N)c21] | 4-amino-2-(3-chloro-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | I-85A* | 556.0 |
| 256B | 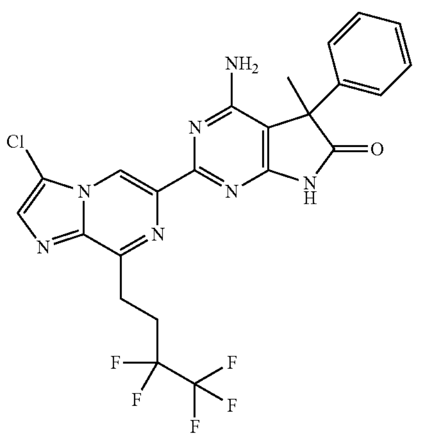 [SMILES: CC1(c2ccccc2)C(=O)Nc2nc(-c3cn4c(Cl)cnc4c(CCC(F)(F)C(F)(F)F)n3)nc(N)c21] | 4-amino-2-(3-chloro-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one | I-41B* | 538.0 |
| 257 | 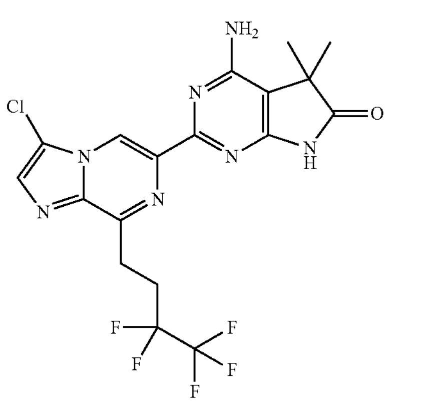 [SMILES: CC1(C)C(=O)Nc2nc(-c3cn4c(Cl)cnc4c(CCC(F)(F)C(F)(F)F)n3)nc(N)c21] | 4-amino-2-(3-chloro-8-(3,3,4,4,4-pentafluorobutyl)imidazo[1,2-a]pyrazin-6-yl)-5,5-dimethyl-5H-pyrrolo[2,3-d]pyrimidin-6(7H)-one | | 476.0 |

TABLE 14-continued

Using similar procedures to that described in Examples 68-69, the following compounds in Table 14 were prepared.

| Ex. | Structure | IUPAC Name | Chiral separation conditions or Starting Material | MS (M + 1) |
|---|---|---|---|---|
| 258A | 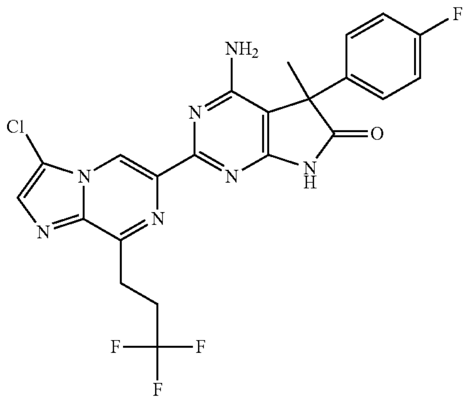 [SMILES: CC1(c2ccc(F)cc2)C(=O)Nc2nc(-c3cn4c(Cl)cnc4c(CCC(F)(F)F)n3)nc(N)c21] | 4-amino-2-(3-chloro-8-(3,3,3-trifluoropropyl)imidazo[1,2-a]pyrazin-6-yl)-5-(4-fluorophenyl)-5-methyl-5H-pyrrolo[2,3-d]pyrimidin-6(7H)-one | I-85A* | 506.0 |
| 259B | 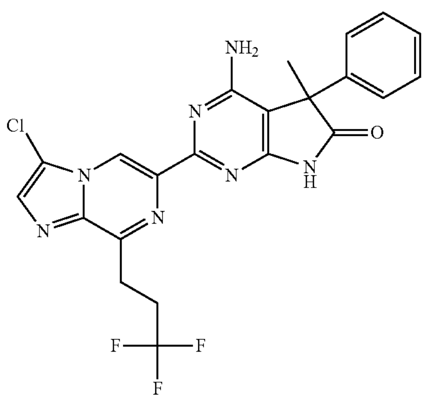 [SMILES: CC1(c2ccccc2)C(=O)Nc2nc(-c3cn4c(Cl)cnc4c(CCC(F)(F)F)n3)nc(N)c21] | 4-amino-2-(3-chloro-8-(3,3,3-trifluoropropyl)imidazo[1,2-a]pyrazin-6-yl)-5-methyl-5-phenyl-5H-pyrrolo[2,3-d]pyrimidin-6(7H)-one | I-41B* | 488.0 |

Example 260A

4-Amino-2-(3-benzyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one and the S or R Isomers Thereof

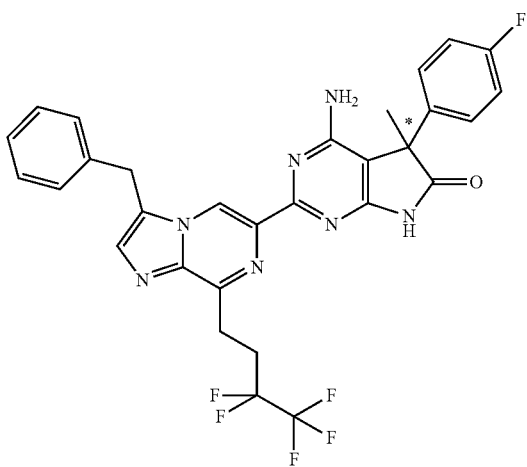 [SMILES: CC1(c2ccc(F)cc2)C(=O)Nc2nc(-c3cn4c(Cc5ccccc5)cnc4c(CCC(F)(F)C(F)(F)F)n3)nc(N)c21]

Example 254A (50.0 mg, 0.08 mmol) and Pd(PPh$_3$)$_2$Cl$_2$ (11.7 mg, 0.02 mmol) were added to an oven dried vial which was capped, evacuated and refilled with nitrogen three times. A 1.0 M solution of benzylzinc(II) bromide in DMA (0.17 mL, 0.17 mmol) was added and the reaction was warmed at 70° C. for 0.5 h. The reaction mixture was cooled, diluted with EtOAc and washed with 1N HCl and brine. The aqueous layer was extracted with EtOAc (3×). The organic layers were combined and dried over anhydrous sodium sulfate. The solid was filtered and the filtrate was concentrated in vacuo to dryness. The crude residue was purified by RP-HPLC with 20-75% acetonitrile:water (0.1% formic acid), followed by basifying with saturated aqueous NaHCO$_3$ and extraction with EtOAc to afford the title compound. $^1$H NMR: (600 MHz, DMSO-d$_6$): δ 11.16 (1H, s), 8.93 (1H, s), 7.65 (1H, s), 7.34 (2H, t, J=7.5 Hz), 7.29-7.25 (5H, m), 7.16 (2H, t, J=8.7 Hz), 6.54 (2H, br s), 4.41 (2H, s), 3.47 (2H, t, J=8.0 Hz), 2.94-2.85 (2H, m), 1.77 (3H, s); m/z=612.0 (M+H).

Example 261A

4-Amino-2-(3-(2-cyclohexylethyl)imidazo[1,2-a]pyrazin-6-yl)-5-(4-fluorophenyl)-5-methyl-5H-pyrrolo[2,3-d]pyrimidin-6(7H)-one and the S or R Isomers Thereof

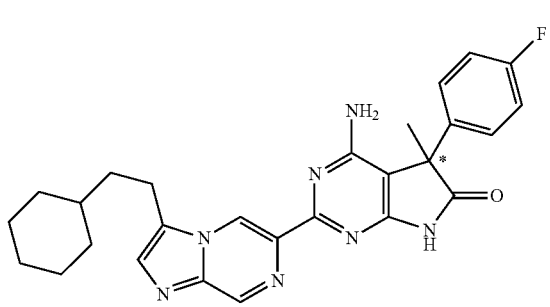 [SMILES: CC1(c2ccc(F)cc2)C(=O)Nc2nc(-c3cn4c(CCC5CCCCC5)cnc4cn3)nc(N)c21]

Using essentially the same procedures described in Example 260, the title compound was prepared from the brominated species of Example 134A. $^1$H NMR: (600 MHz, DMSO-$d_6$): δ 9.10 (1H, s), 9.02 (1H, s), 7.71 (1H, s), 7.23-7.38 (2H, m), 7.18-7.23 (2H, m), 2.95-3.01 (2H, m), 2.42-2.58 (4H, m), 1.80 (3H, s), 1.60-1.78 (5H, m), 1.10-1.22 (2H, m), 0.90-1.05 (2H, m); m/z=486.2 (M+H).

Example 262B

4-Amino-2-(3-bromo-8-(3,3,4,4,4-pentafluorobutyl)imidazo[1,2-a]pyrazin-6-yl)-5-(5-fluoropyridin-2-yl)-5-methyl-5H-pyrrolo[2,3-d]pyrimidin-6(7H)-one and the S or R Isomers Thereof

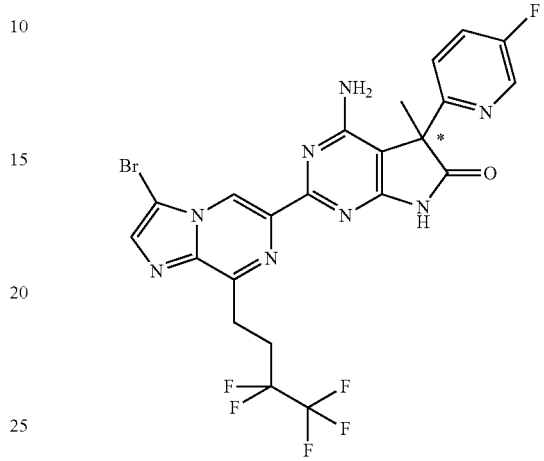

To a mixture of Example 246B (106 mg, 0.20 mmol) in CHCl$_3$ (1.4 mL) was added NBS (40 mg, 0.22 mmol), and the mixture was stirred at ambient temperature for 0.5 h. Upon completion, the reaction mixture was diluted with DCM, washed with water and brine, dried over anhydrous sodium sulfate and concentrated in vacuo to dryness. The residue was triturated with DCM:hexanes to afford the title compound. $^1$H NMR (500 MHz, acetone-$d_6$): δ 9.02 (1H s), 8.56 (1H, d, J=2.9 Hz), 7.87 (1H, s), 7.66-7.67 (1H, m), 7.60-7.66 (1H, m), 6.51 (2H, br s), 3.56-3.75 (2H, m), 2.88-2.99 (2H, m), 1.90 (3H, s); m/z=601.0 (M+H), 603.0 (M+3).

TABLE 15

Using a simlar procedure to that described in Example 262, the following compounds in Table 15 were prepared.

| Ex. | Structure | IUPAC Name | Derived from Ex | MS (M + 1) |
|---|---|---|---|---|
| 263 | 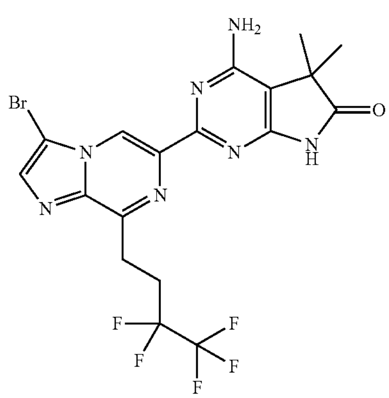 [SMILES: CC1(C)C(=O)Nc2nc(-c3cn4c(Br)cnc4c(CCC(F)(F)C(F)(F)F)n3)nc(N)c21] | 4-amino-2-(3-bromo-8-(3,3,4,4,4-pentafluorobutyl)imidazo[1,2-a]pyrazin-6-yl)-5,5-dimethyl-5H-pyrrolo[2,3-d]pyrimidin-6(7H)-one | Ex-87 | 521.9 |

TABLE 15-continued

Using a simlar procedure to that described in Example 262, the following compounds in Table 15 were prepared.

| Ex. | Structure | IUPAC Name | Derived from Ex | MS (M + 1) |
|---|---|---|---|---|
| 264A | 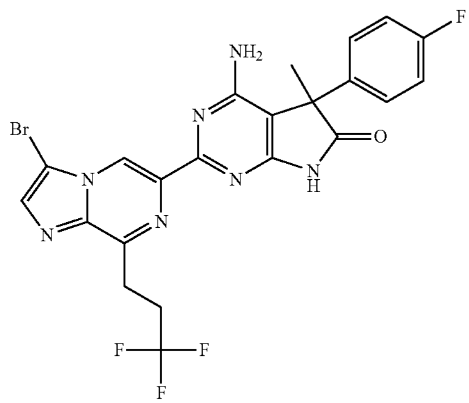 [SMILES: CC1(c2ccc(F)cc2)C(=O)Nc2nc(-c3cn4c(Br)cnc4c(CCC(F)(F)F)n3)nc(N)c21] | 4-amino-2-(3-bromo-8-(3,3,3-trifluoropropyl)imidazo[1,2-a]pyrazin-6-yl)-5-(4-fluorophenyl)-5-methyl-5H-pyrrolo[2,3-d]pyrimidin-6(7H)-one | Ex-184A | 551.9 |
| 265B | 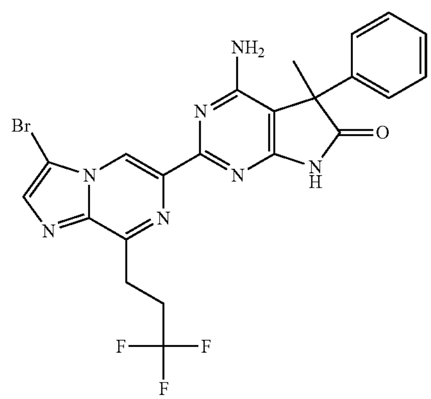 | 4-amino-2-(3-bromo-8-(3,3,3-trifluoropropyl)imidazo[1,2-a]pyrazin-6-yl)-5-methyl-5-phenyl-5H-pyrrolo[2,3-d]pyrimidin-6(7H)-one | Ex-188B | 533.9 |
| 266A | 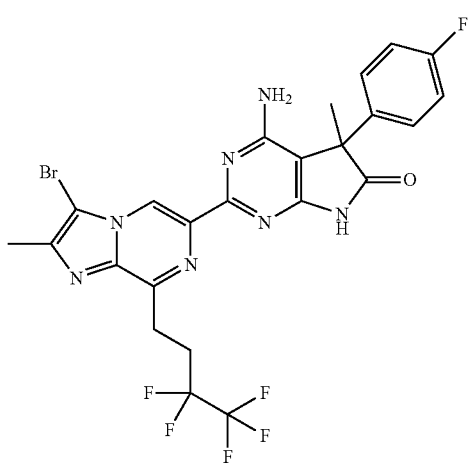 [SMILES: Cc1nc2c(CCC(F)(F)C(F)(F)F)nc(-c3nc(N)c4c(n3)NC(=O)C4(C)c3ccc(F)cc3)cn2c1Br] | 4-amino-2-(3-bromo-2-methyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one | Ex-170A | 613.9 |

Example 267A

4-Amino-2-(3-amino-8-(3,3,4,4,4-pentafluorobutyl) imidazo[1,2-a]pyrazin-6-yl)-5-(4-fluorophenyl)-5-methyl-5H-pyrrolo[2,3-d]pyrimidin-6(7H)-one and the S or R Isomers Thereof

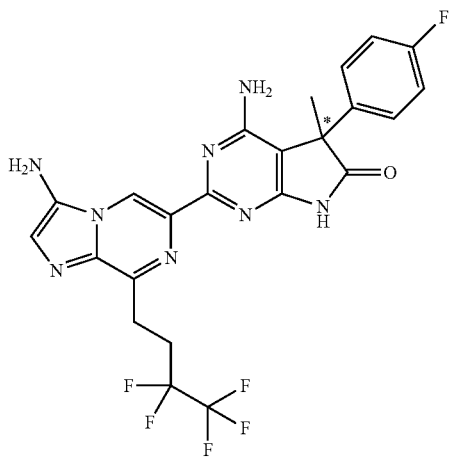

Step A—4-Amino-2-(3-((diphenylmethylene) amino)-8-(3,3,4,4,4-pentafluorobutyl)imidazo[1,2-a] pyrazin-6-yl)-5-(4-fluorophenyl)-5-methyl-5H-pyrrolo[2,3-d]pyrimidin-6(7H)-one To dioxane (0.75 mL) under nitrogen was added Example 254A (60 mg, 0.10 mmol), benzophenone imine (25 µl, 0.150 mmol), sodium t-butoxide (14 mg, 0.14 mmol), and Xantphos generation II precatalyst (9.0 mg, 0.10 mmol). The vessel was degassed, sealed, and heated by microwave irradiation at 140° C. for 30 min. After 30 min, more Xantphos generation II precatalyst (9.0 mg, 0.10 mmol) was added, and the vessel was again degassed, and heated by microwave irradiation at 150° C. for 30 min. Upon completion, the reaction was diluted with EtOAc and washed with water. The aqueous layer was further extracted with EtOAc, and the combined organic layers were dried over anhydrous magnesium sulfate, filtered, concentrated in vacuo, and purified by silica gel chromatography using EtOAc:hexanes (5-50%) to afford the title compound.

Step B—4-Amino-2-(3-amino-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one To the intermediate from Step A (41 mg, 0.059 mmol) in THF (0.25 mL) and MeOH (0.25 mL) was added sodium acetate (14.4 mg, 0.176 mmol) and hydroxylamine hydrochloride (12.2 mg, 0.176 mmol) and the reaction mixture warmed at 50° C. for 2 h. Additional hydroxylamine hydrochloride (12.2 mg, 0.176 mmol) and sodium acetate (14.4 mg, 0.176 mmol) were added and heating continued for 2 h. The reaction was allowed to cool to RT, diluted with EtOAc, washed with water, extracted with EtOAc, and the combined organic layers were concentrated in vacuo and purified by silica gel chromatography using 3:1 EtOAc:EtOH/hexanes (2-50%) to afford the title compound. $^1$H-NMR: (400 MHz, DMSO-$d_6$): δ 11.09 (1H, s), 8.81 (1H, s), 7.30-7.19 (2H, m), 7.18-7.07 (2H, m), 7.02 (1H, s), 6.45 (2H, s), 5.56 (2H, s), 3.40-3.15 (2H, m), 2.92-2.74 (2H, m), 1.75 (3H, s); m/z=537.0 (M+H).

TABLE 16

Using simlar procedures to that described in Examples 262 and Examples 267, the following compounds in Table 16 were prepared.

| EX. | Structure | Name | Derived from Ex | MS (M + 1) |
|---|---|---|---|---|
| 268B | 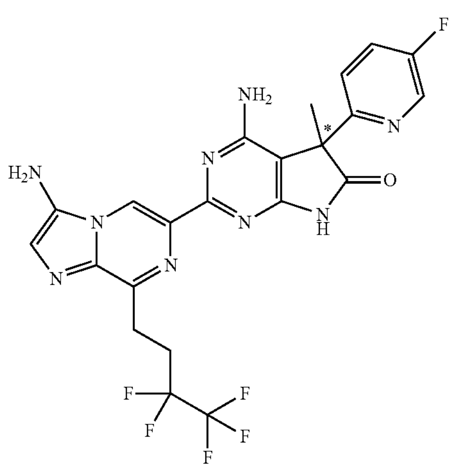 [SMILES: CC1(c2ccc(F)cn2)C(=O)Nc2nc(-c3cn4c(N)cnc4c(CCC(F)(F)C(F)(F)F)n3)nc(N)c21] | 4-Amino-2-(3-amino-8-(3,3,4,4,4-pentafluorobutyl)imidazo[1,2-a]pyrazin-6-yl)-5-(5-fluoropyridin-2-yl)-5-methyl-5H-pyrrolo[2,3-d]pyrimidin-6(7H)-one | Ex-262B | 538.1 |

TABLE 16-continued

Using simlar procedures to that described in Examples 262 and Examples 267, the following compounds in Table 16 were prepared.

| EX. | Structure | Name | Derived from Ex | MS (M + 1) |
|---|---|---|---|---|
| 269A | 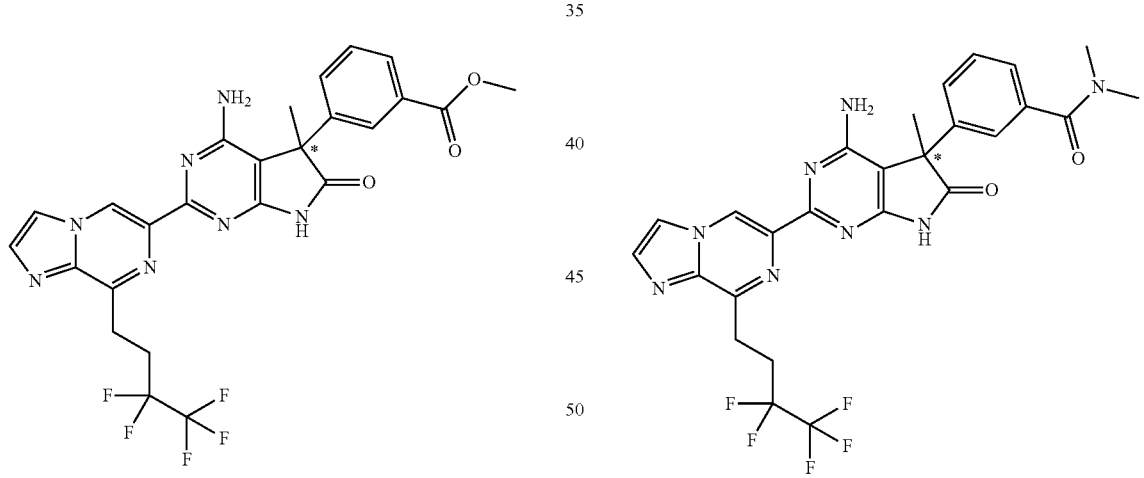 | 4-amino-2-(3-amino-8-(3,3,4,4,4-pentafluorobutyl)imidazo[1,2-a]pyrazin-6-yl)-5-(5-chloropyridin-2-yl)-5-methyl-5H-pyrrolo[2,3-d]pyrimidin-6(7H)-one | Ex-228A | 554.1 |

Example 270, 270A, & 270B

Methyl 3-(4-amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl)benzoate and the S or R Isomers Thereof

Example 271B 3-(4-Amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl)-N,N-dimethylbenzamide and the S or R Isomers Thereof The title compound in the racemic form was prepared using the procedure described in Example 30 Step A, through the reaction of 1-15 (200 mg, 0.65 mmol) with 1-69 (235 mg, 0.78 mmol) to afford the title compound. The racemic material was resolved using chiral SFC (AS-H column) to afford isomers Ex-270A (faster eluting) and Ex-270B (slower eluting) of the title compound. $^1$H-NMR (500 MHz, CD$_3$OD): δ 9.39 (1H, s), 8.13 (1H, s), 7.93-7.96 (2H, m), 7.83 (1H, s), 7.62 (1H, d, J=8.0 Hz), 7.48 (1H, t, J=7.9 Hz), 3.87 (3H, s), 3.58-3.61 (2H, m), 2.90-2.96 (2H, m), 1.92 (3H, s); m/z=562.1 (M+H).

Step A—3-(4-Amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl) benzoic acid To a solution of Ex-270B (120 mg, 0.21 mmol) in MeOH (3 mL) was added 1 N aqueous NaOH (2 mL, 2 mmol). The mixture was stirred at RT for 2 h. The reaction mixture was acidified with 1N aqueous HCl to pH 4 and extracted with EtOAc. The organic phase was washed with water and brine, dried over anhydrous sodium sulfate and concentrated in vacuo to afford the title compound, which was used without further purification.

Step B—3-(4-Amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl)-N,N-dimethylbenzamide The intermediate from Step A (10 mg, 0.018 mmol) was mixed with dimethylamine hydrochloride (3 mg, 0.04 mmol), PyBOP (14 mg, 0.027 mmol), HOBt (4 mg, 0.03 mmol) and DIEA (0.013 mL, 0.073 mmol) in DMF (0.2 mL). The mixture was stirred at ambient temperature for 2 h. The reaction mixture was partitioned between EtOAc and water. The organic phase was washed with brine and then concentrated in vacuo to dryness. The crude residue was purified by RP-HPLC with 10-50% acetonitrile:water (0.1% TFA), followed by basifying with saturated aqueous NaHCO$_3$ and extraction with EtOAc to afford the title compound. $^1$H NMR δ (500 MHz, CD$_3$OD): 9.41 (1H, s), 8.14 (1H, s), 7.83 (1H, s), 7.46-7.48 (2H, m), 7.37-7.39 (2H, m), 3.59-3.62 (2H, m), 3.07 (3H, s), 2.96 (3H, s), 2.88-2.95 (2H, m), 1.90 (3H, s); m/z=575.1 (M+H).

Example 272

3-((6-(4-Amino-5,5-dimethyl-6-oxo-6,7-dihydro-5H-pyrrolo[2,3-d]pyrimidin-2-yl)imidazo[1,2-a]pyrazin-8-yl)methyl)benzonitrile

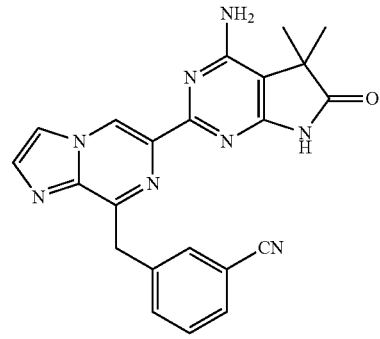

Ex-74 (200 mg, 0.48 mmol), dicyanozinc (136 mg, 1.16 mmol), zinc metal (24 mg, 0.37 mmol), Pd$_2$(dba)$_3$ (100 mg, 0.10 mmol), dppf (104 mg, 0.19 mmol) and DMF (1 mL) were added to a microwave vial under an atmosphere of nitrogen. The resulting mixture was irradiated with microwave radiation for 18 h at 150° C. The reaction mixture was quenched by the addition of DCM:MeOH (1:1). The solid was filtered and the filtrate was concentrated in vacuo to dryness. The residue was dissolved in EtOAc, washed with water and brine, dried over anhydrous sodium sulfate and concentrated in vacuo to dryness. The residue was purified by silica gel chromatography with MeOH:DCM (10%) to afford the title compound. $^1$H NMR (300 MHz, CD$_3$OD): δ 9.38 (1H s), 8.13 (1H, d, J=1.2 Hz), 7.93 (1H, s), 7.87-7.85 (2H, m), 7.56 (1H, d, J=7.8 Hz), 7.47-7.42 (1H, m), 4.70 (2H, s), 1.48 (6H, s); m/z=411.3 (M+H).

TABLE 17

Using similar procedures to that described in example 272, the following compounds in Table 17 were prepared.

| Ex. | Structure | IUPAC Name | Derived from Ex | MS (M + 1) |
|---|---|---|---|---|
| 273A | 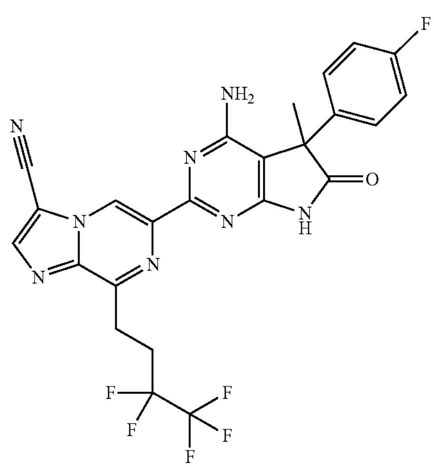 [SMILES: CC1(c2ccc(F)cc2)C(=O)Nc2nc(-c3cn4c(C#N)cnc4c(CCC(F)(F)C(F)(F)F)n3)nc(N)c21] | 6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-3a]pyrazine-3-carbonitrile | Ex-254A | 547.0 |

TABLE 17-continued

Using simlar procedures to that described in example 272, the following compounds in Table 17 were prepared.

| Ex. | Structure | IUPAC Name | Derived from Ex | MS (M + 1) |
|---|---|---|---|---|
| 274A | 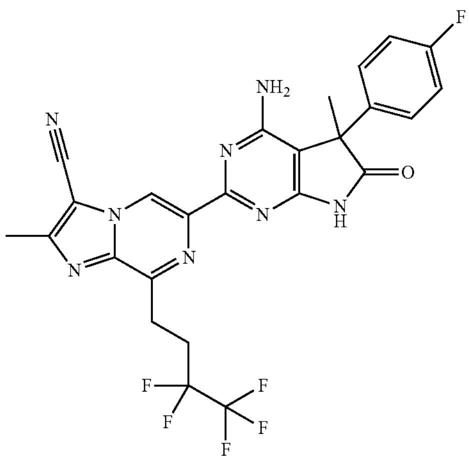 [SMILES: Cc1nc2c(CCC(F)(F)C(F)(F)F)nc(-c3nc(N)c4c(n3)NC(=O)C4(C)c3ccc(F)cc3)cn2c1C#N] | 6-(4-amino-5-(4-fluorophenyl)-5-methyl-6-oxo-6,7-dihydro-5H-pyrrolo[2,3-d]pyrimidin-2-yl)-2-methyl-8-(3,3,4,4,4-pentafluorobutyl)imidazo[1,2-a]pyrazine-3-carbonitrile | Ex-266A | 561.0 |

Example 275A 6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-2-carbonitrile and the S or R Isomers Thereof

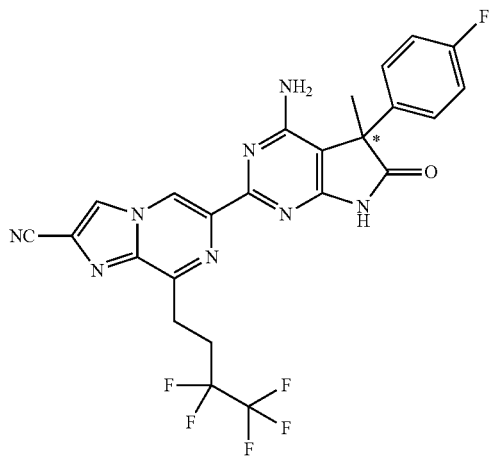 [SMILES: CC1(c2ccc(F)cc2)C(=O)Nc2nc(-c3cn4cc(C#N)nc4c(CCC(F)(F)C(F)(F)F)n3)nc(N)c21]

Step A—Ethyl 6-cyano-8-(3,3,4,4,4-pentafluorobutyl)imidazo[1,2-a]pyrazine-2-carboxylate To an oven-dried vial containing the product of 1-27 Step A (1.5 g, 5.6 mmol) was added ethyl 3-bromo-2-oxopropanoate (1.1 g, 5.6 mmol) and dimethylcarbonate (8 mL). The resulting mixture was stirred at 110° C. for 2 h. The mixture was diluted with EtOAc, washed with saturated aqueous NaHCO$_3$ and brine, dried over anhydrous sodium sulfate, and concentrated in vacuo to dryness. Purification by silica gel chromatography using EtOAc:hexanes (0-30%) afforded the title compound. m/z=363.0 (M+H).

Step B—Methyl 6-carbamimidoyl-8-(3,3,4,4,4-pentafluorobutyl)imidazo[1,2-a]pyrazine-2-carboxylate To a solution of the intermediate from Step A (1.2 g, 3.3 mmol) in methanol (5 mL) was added sodium methoxide in MeOH (25% w/w, 1.1 mL, 4 mmol), and the mixture was stirred at ambient temperature for 2 h. Ammonium chloride (0.25 g, 4.6 mmol) and acetic acid (0.76 ml, 13.3 mmol) were added and the mixture was warmed at 70° C. for 3h. The reaction mixture was basified with 1N aqueous NaOH, and extracted with EtOAc. The organic phase was dried over anhydrous sodium sulfate and concentrated in vacuo to afford the title compound which was used without further purification.

Step C—Methyl 6-(4-amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-2-carboxylate Using the procedure described in Example 30 Step A, reacting the intermediate from Step B (200 mg, 0.55 mmol) with Intermediate 85A (135 mg, 0.55 mmol) afforded the title compound. m/z 579.9 (M+H).

Step D—6-(4-amino-5-(4-fluorophenyl)-5-methyl-6-oxo-6,7-dihydro-5H-pyrrolo[2,3-d]-pyrimidin-2-yl)-8-(3,3,4,4,4-pentafluorobutyl)imidazo[1,2-a]pyrazine-2-carboxylic acid A solution of the intermediate from Step C (120 mg, 0.21 mmol) in methanol (5 mL) was treated with 2M aqueous NaOH (0.52 mL, 1.04 mmol) at ambient temperature for 4 h. The mixture was acidified with 1N HCl, extracted with EtOAc, and the organic phase was dried over anhydrous sodium sulfate and concentrated to afford the title compound. m/z 566.0 (M+H).

Step E—6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-2-carboxamide The intermediate from Step D (53 mg, 0.08 mmol) was mixed with ammonium chloride (8.0 mg, 0.15 mmol), HATU (43 mg, 0.11 mmol), and DIEA (0.04 mL, 0.23 mmol) in DMF (1 mL), and the mixture was stirred at ambient temperature for 16 h. The reaction mixture was diluted with EtOAc, washed with water and brine, dried over anhydrous sodium sulfate, and concentrated in vacuo to afford the title compound, which was used without further purification. m/z 565.0 (M+H).

Step F—6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-2-carbonitrile The intermediate from Step E (5 mg, 8.9 μmol) was dissolved in THF (0.5 mL). To this was added pyridine (100 μl, 1.24 mmol) and TFAA (100 μl, 0.71 mmol). The mixture was stirred at ambient temperature for 2 h. The volatiles were removed, and the residue was dissolved in EtOAc. The organic layer was washed with water and brine, dried over anhydrous sodium sulfate and concentrated in vacuo. Purification by RP-HPLC with 10-50% acetonitrile:water (0.1% TFA), followed by basifying with saturated aqueous NaHCO$_3$ and extraction with EtOAc to afford the title compound. $^1$H-NMR: (500 MHz, CD$_3$OD): δ 9.40 (1H, s), 8.53 (1H, s), 7.35-7.38 (2H, m), 7.06-7.12 (2H, m), 3.61-3.68 (2H, m), 2.90-3.03 (2H, m), 1.87 (3H, s); m/z=546.9 (M+H).

Example 276

4-Amino-5-ethyl-2-(3-fluoro-8-(3,3,4,4,4-pentafluorobutyl)imidazo[1,2-a]pyrazin-6-yl)-5-(4-fluorophenyl)-5H-pyrrolo[2,3-d]pyrimidin-6(7H)-one and the S or R Isomers Thereof

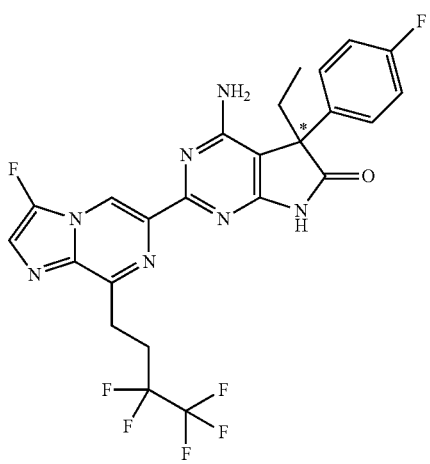 [SMILES: CCC1(c2ccc(F)cc2)C(=O)Nc2nc(-c3cn4c(F)cnc4c(CCC(F)(F)C(F)(F)F)n3)nc(N)c21]

To a sample of Ex-239 (40 mg, 0.075 mmol) in acetonitrile (1.5 ml) was added SELECTFLUOR, a fluorinating reagent, (53 mg, 0.15 mmol), and the mixture was warmed at 50° C. for 48 h. The reaction was allowed to cool to ambient temperature and partitioned between EtOAc and water. The organic layer was washed with brine, dried over anhydrous sodium sulfate, filtered, concentrated in vacuo, and purified by MS-RP-HPLC using 10-65% acetonitrile: water (0.1% TFA) to afford the title compound. $^1$H-NMR (500 MHz, CD$_3$CN): δ 9.01 (1H, s), 7.51 (1H, d, J=6.5 Hz), 7.41 (2H, dd, J=5.0, 9.0 Hz), 7.12 (2H, t, J=9.0 Hz), 3.55 (2H, t, J=8.0 Hz), 3.04-2.96 (2H, m), 2.55-2.51 (1H, m), 2.35-2.30 (1H, m), 0.81 (3H, t, J=7.5 Hz); m/z=554.1 (M+H).

Example 277A 5-(4-Chlorophenyl)-4-(3,3-difluorocyclobutyl)-2-(imidazo[1,2-a]pyrazin-6-yl)-5-methyl-5H-pyrrolo[2,3-d]pyrimidin-6(7H)-one and the S or R Isomers Thereof

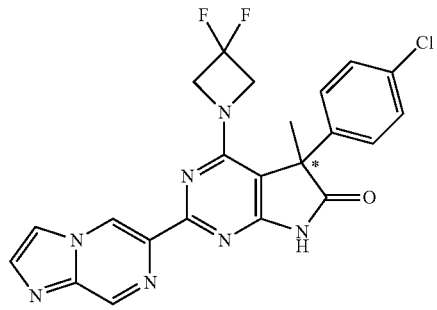 [SMILES: CC1(c2ccc(Cl)cc2)C(=O)Nc2nc(-c3cn4ccnc4cn3)nc(N3CC(F)(F)C3)c21]

Step A—4-Bromo-5-(4-chlorophenyl)-2-(imidazo[1,2-a]pyrazin-6-yl)-5-methyl-5H-pyrrolo[2,3-d]pyrimidin-6(7H)-one Into a flask, purged with an inert atmosphere of nitrogen, was placed a sample of Example 144A (850 mg, 2.17 mmol), copper(II) bromide (2.91 g, 13.0 mmol) and DMF (10 mL). Tert-butyl nitrite (0.77 mL, 6.51 mmol) was added dropwise and the reaction was warmed at 65° C. for 40 min. The reaction mixture was cooled to ambient temperature and any solids were filtered. The filtrate was purified by RP-MPLC with 20-50% acetonitrile:water (0.05% TFA), to afford the title compound as the TFA salt. m/z=454.9, 456.9 (M+H).

Step B—5-(4-Chlorophenyl)-4-(3,3-difluoroazetidin-1-yl)-2-(imidazo[1,2-a]pyrazin-6-yl)-5-methyl-5H-pyrrolo[2,3-d]pyrimidin-6(7H)-one Into a vial was placed the intermediate from Step A (56 mg, 0.10 mmol), 3,3-difluoroazetidine hydrochloride (38.2 mg, 0.30 mmol), DIEA (0.08 mL, 0.44 mmol) and DMA (0.75 mL). The resulting mixture was warmed at 80° C. for 6 h. Upon completion, the reaction was cooled to ambient temperature and any solids were filtered. The filtrate was purified by RP-HPLC with 20-80% acetonitrile:water (0.05% TFA), followed by basifying with saturated aqueous NaHCO$_3$ and extraction with EtOAc to afford the title compound. $^1$H NMR (400 MHz, CD$_3$OD): δ 9.57 (1H, s), 9.12 (1H, s), 8.21 (1H, s), 7.91 (1H, s), 7.41 (2H, d, J=7.2 Hz), 7.30 (2H, d, J=8.5 Hz), 4.56-4.44 (2H, m), 4.01-3.91 (2H, m), 1.87 (3H, s); m/z=468.1 (M+H).

TABLE 18

*Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.*

| Ex. No. | Structure | IUPAC Name | Chiral amine source or separation conditions | MS (M + 1) | Starting material |
|---|---|---|---|---|---|
| 278A | 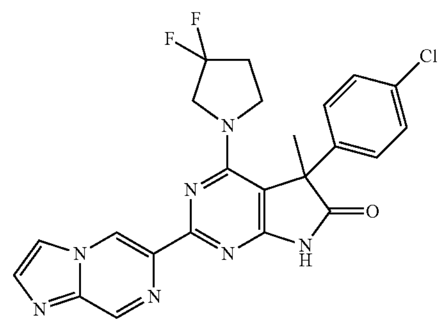 [SMILES: CC1(c2ccc(Cl)cc2)C(=O)Nc2nc(-c3cn4ccnc4cn3)nc(N3CCC(F)(F)C3)c21] | 5-(4-chlorophenyl)-4-(3,3-difluoroazetidin-1-yl)-2-(imidazo[1,2-a]pyrazin-6-yl)-5-methyl-5H-pyrrolo[2,3-d]pyrimidin-6(7H)-one | | 482.1 | Ex-144A |
| 279A | 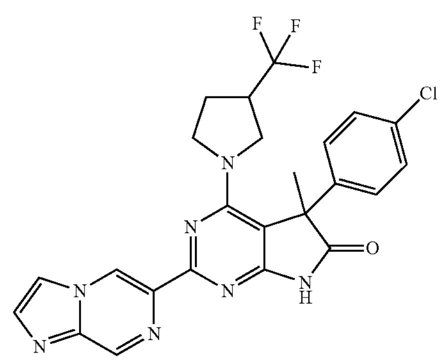 [SMILES: CC1(c2ccc(Cl)cc2)C(=O)Nc2nc(-c3cn4ccnc4cn3)nc(N3CCC(C(F)(F)F)C3)c21] | 5-(4-chlorophenyl)-2-(imidazo[1,2-a]pyrazin-6-yl)-5-methyl-4-(3-(trifluoromethyl)pyrrolidin-1-yl)-5H-pyrrolo[2,3-d]pyrimidin-6(7H)-one | (rac) 3-(trifluromethyl)pyrrolidine | 514 | Ex-144A |
| 280A | 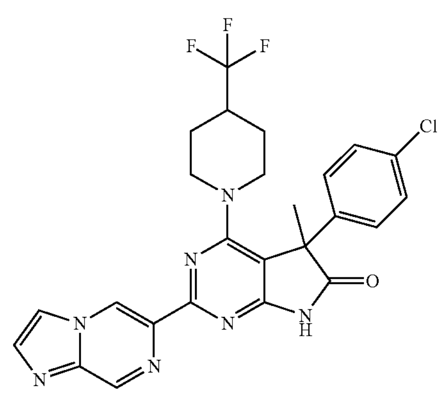 [SMILES: CC1(c2ccc(Cl)cc2)C(=O)Nc2nc(-c3cn4ccnc4cn3)nc(N3CCC(C(F)(F)F)CC3)c21] | 5-(4-chlorophenyl)-2-(imidazo[1,2-a]pyrazin-6-yl)-5-methyl-4-(4-(trifluromethyl)piperdin-1-yl)-5H-pyrrolo[2,3-d]pyrimidin-6(7H)-one | | 528.1 | Ex-144A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 281A | 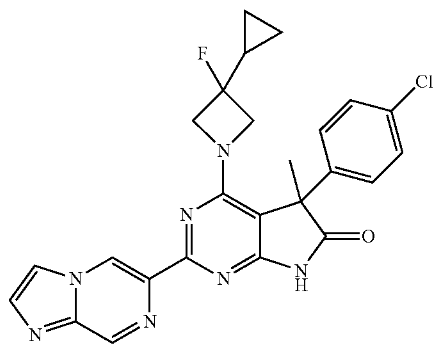 [SMILES: CC1(c2ccc(Cl)cc2)C(=O)Nc2nc(-c3cn4ccnc4cn3)nc(N3CC(F)(C4CC4)C3)c21] | 5-(4-chlorophenyl)-4-(3-cyclopropyl-3-fluoroazetidin-1-yl)-2-(imidazo[1,2-a]pyrazin-6-yl)-5-methyl-5H-pyrrolo[2,3-d]pyrimidin-6(7H)-one | | 490.1 | Ex-144A |
| 282A | 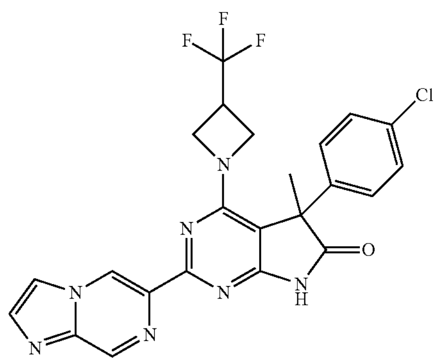 [SMILES: CC1(c2ccc(Cl)cc2)C(=O)Nc2nc(-c3cn4ccnc4cn3)nc(N3CC(C(F)(F)F)C3)c21] | 5-(4-chlorophenyl)-2-(imidazo[1,2-a]pyrazin-6-yl)-5-methyl-4-(3-(trifluromethyl)azetidin-1-yl)-5H-pyrrolo[2,3-d]pyrimidin-6(7H)-one | | 500.1 | Ex-144A |
| 283A | 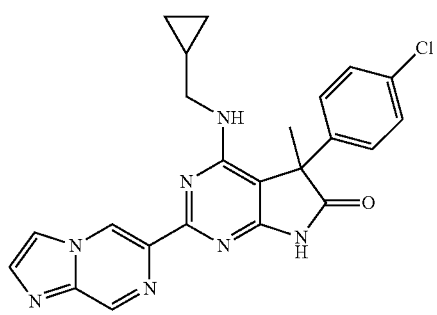 [SMILES: CC1(c2ccc(Cl)cc2)C(=O)Nc2nc(-c3cn4ccnc4cn3)nc(NCC3CC3)c21] | 5-(4-chlorophenyl)-4-((cyclopropylmethyl)amino)-2-(imidazo[1,2-a]pyrazin-6-yl)-5-methyl-5H-pyrrolo[2,3-d]pyrimidin-6(7H)-one | | 446.1 | Ex-144A |
| 284A | 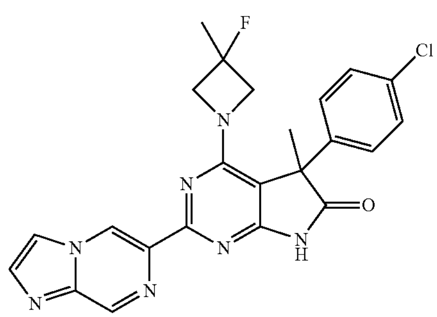 [SMILES: CC1(F)CN(c2nc(-c3cn4ccnc4cn3)nc3c2C(C)(c2ccc(Cl)cc2)C(=O)N3)C1] | 5-(4-chlorophenyl)-4-(3-fluoro-3-methylazetidin-1-yl)-2-(imidazo[1,2-a]pyrazin-6-yl)-5-methyl-5H-pyrrolo[2,3-d]pyrimidin-6(7H)-one | | 464.1 | Ex-144A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et$_3$N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 285A | 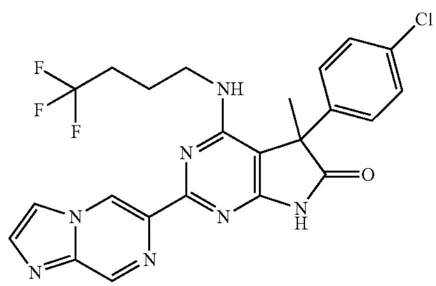 [SMILES: CC1(c2ccc(Cl)cc2)C(=O)Nc2nc(-c3cn4ccnc4cn3)nc(NCCCC(F)(F)F)c21] | 5-(4-chlorophenyl)-2-(imidazo[1,2-a]pyrazin-6-yl)-5-methyl-4-((4,4,4-trifluorobutyl)amino)-5H-pyrrolo[2,3-d]pyrimidin-6(7H)-one | | 502.1 | Ex-144A |
| 286A | 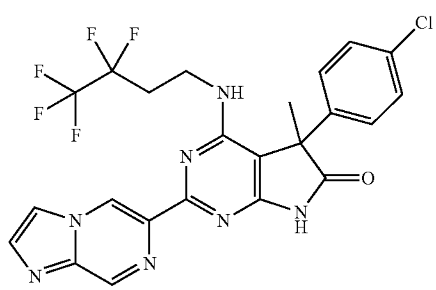 [SMILES: CC1(c2ccc(Cl)cc2)C(=O)Nc2nc(-c3cn4ccnc4cn3)nc(NCCC(F)(F)C(F)(F)F)c21] | 5-(4-chlorophenyl)-2-(imidazo[1,2-a]pyrazin-6-yl)-5-methyl-4-((3,3,4,4,4-pentafluorobutyl)amino)-5H-pyrrolo[2,3-d]pyrimidin-6(7H)-one | | 538.2 | Ex-144A |
| 287A | 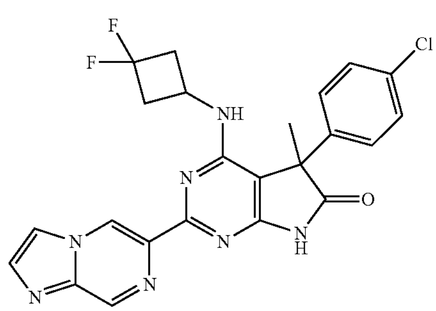 [SMILES: CC1(c2ccc(Cl)cc2)C(=O)Nc2nc(-c3cn4ccnc4cn3)nc(NC3CC(F)(F)C3)c21] | 5-(4-chlorophenyl)-4-((3,3-difluorocyclobutyl)amino)-2-(imidazo[1,2-a]pyrazin-6-yl)-5-methyl-5H-pyrrolo[2,3-d]pyrimidin-6(7H)-one | | 482.2 | Ex-144A |
| 288A | 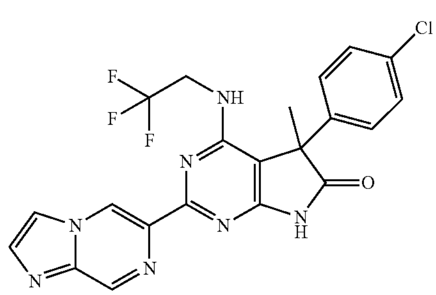 [SMILES: CC1(c2ccc(Cl)cc2)C(=O)Nc2nc(-c3cn4ccnc4cn3)nc(NCC(F)(F)F)c21] | 5-(4-chlorophenyl)-2-(imidazo[1,2-a]pyrazin-6-yl)-5-methyl-4-((2,2,2-trifluoroethyl)amino)-5H-pyrrolo[2,3-d]pyrimidin-6(7H)-one | | 474.2 | Ex-144A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 289A | 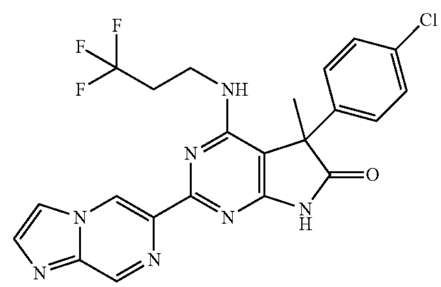 [SMILES: CC1(c2ccc(Cl)cc2)C(=O)Nc2nc(-c3cn4ccnc4cn3)nc(NCCC(F)(F)F)c21] | 5-(4-chlorophenyl)-2-(imidazo[1,2-a]pyrazin-6-yl)-5-methyl-4-((3,3,3-trifluoropropyl)amino)-5H-pyrrolo[2,3-d]pyrimidin-6(7H)-one | | 488.2 | Ex-144A |
| 290B | 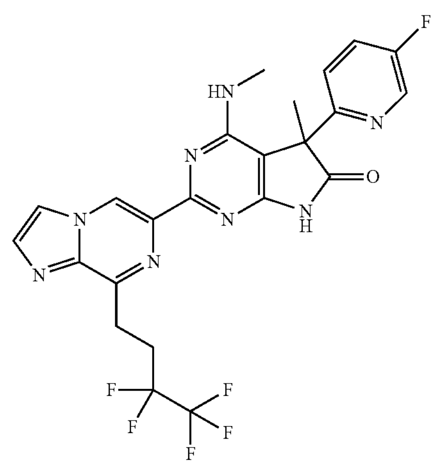 [SMILES: CNc1nc(-c2cn3ccnc3c(CCC(F)(F)C(F)(F)F)n2)nc2c1C(C)(c1ccc(F)cn1)C(=O)N2] | 5-(5-fluoropyridin-2-yl)-5-methyl-4-(methylamino)-2-(8-(3,3,4,4,4-pentafluorobutyl)imidazo[1,2-a]pyrazin-6-yl)-5H-pyrrolo[2,3-d]pyrimidin-6(7H)-one | | 537.1 | Ex-246B |
| 291B | 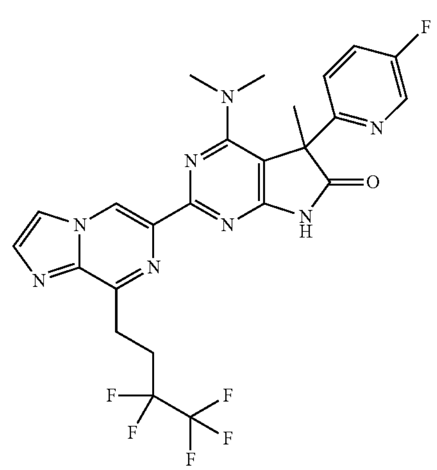 [SMILES: CN(C)c1nc(-c2cn3ccnc3c(CCC(F)(F)C(F)(F)F)n2)nc2c1C(C)(c1ccc(F)cn1)C(=O)N2] | 4-(dimethylamino)-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 551.2 | Ex-246B |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et$_3$N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 292B | 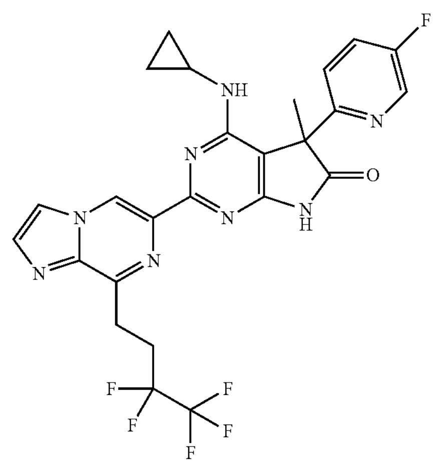 [SMILES: CC1(c2ccc(F)cn2)C(=O)Nc2nc(-c3cn4ccnc4c(CCC(F)(F)C(F)(F)F)n3)nc(NC3CC3)c21] | 4-(cyclopropylamino)-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 563.3 | Ex-246B |
| 293B | 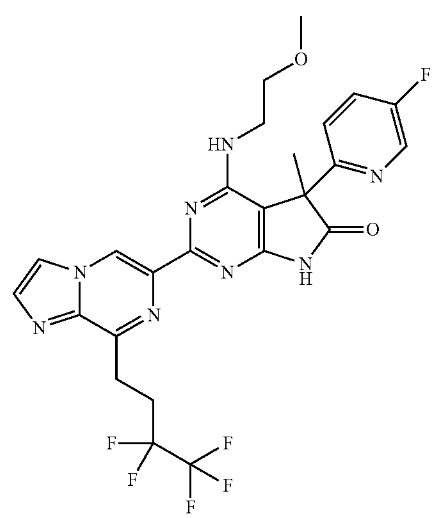 [SMILES: COCCNc1nc(-c2cn3ccnc3c(CCC(F)(F)C(F)(F)F)n2)nc2c1C(C)(c1ccc(F)cn1)C(=O)N2] | 5-(5-fluoropyridin-2-yl)-4-((2-methoxyethyl)amino)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 581.2 | Ex-246B |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 294B | 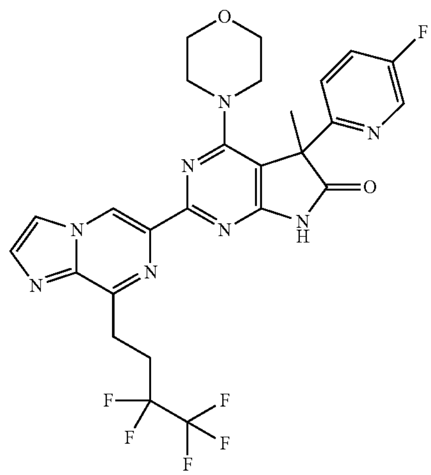 [SMILES: CC1(c2ccc(F)cn2)C(=O)Nc2nc(-c3cn4ccnc4c(CCC(F)(F)C(F)(F)F)n3)nc(N3CCOCC3)c21] | 5-(5-fluoropyridin-2-yl)-5-methyl-4-morpholino-2-(8-(3,3,4,4,4-pentafluorobutyl)imidazo[1,2-a]pyrazin-6-yl)-5H-pyrrolo[2,3-d]pyrimidin-6(7H)-one | | 593.1 | Ex-246B |
| 295B | 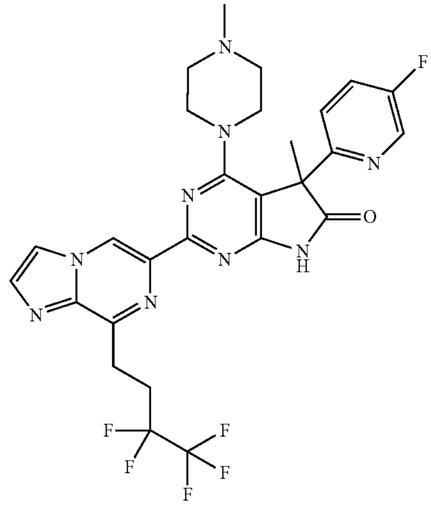 [SMILES: CN1CCN(c2nc(-c3cn4ccnc4c(CCC(F)(F)C(F)(F)F)n3)nc3c2C(C)(c2ccc(F)cn2)C(=O)N3)CC1] | 5-(5-fluoropyridin-2-yl)-5-methyl-4-(4-methylpiperazin-1-yl)-2-(8-(3,3,4,4,4-pentafluorobutyl)imidazo[1,2-a]pyrazin-6-yl)-5H-pyrrolo[2,3-d]pyrimidin-6(7H)-one | | 606.2 | Ex-246B |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 296A | 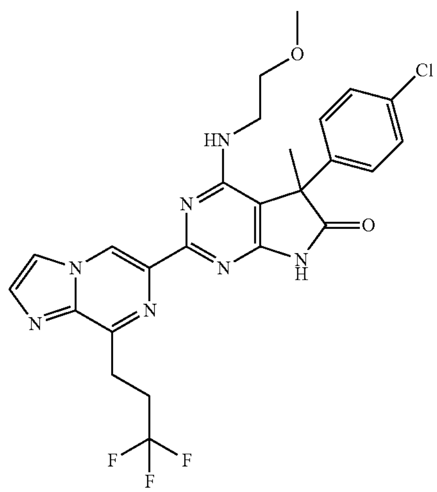 [SMILES: COCCNc1nc(-c2cn3ccnc3c(CCC(F)(F)F)n2)nc2c1C(C)(c1ccc(Cl)cc1)C(=O)N2] | 5-(4-chlorophenyl)-4-((2-methyoxyethyl)amino)-5-methyl-2-(8-(3,3,3-trifluoropropyl)imidazo[1,2-a]pyrazin-6-yl)-5H-pyrrolo[2,3-d]pyrimidin-6(7H)-one | | 546.2 | Ex-182A |
| 297A | 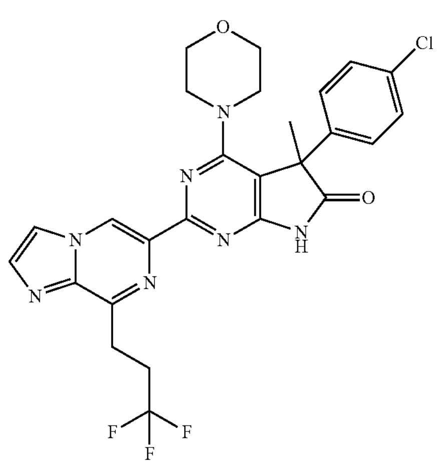 [SMILES: CC1(c2ccc(Cl)cc2)C(=O)Nc2nc(-c3cn4ccnc4c(CCC(F)(F)F)n3)nc(N3CCOCC3)c21] | 5-(4-chlorophenyl)-5-methyl-4-morpholino-2-(8-(3,3,3-trifluoropropyl)imidazo[1,2-a]pyrazin-6-yl)-5H-pyrrolo[2,3-d]pyrimidin-6(7H)-one | | 558.1 | Ex-182A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 298A | 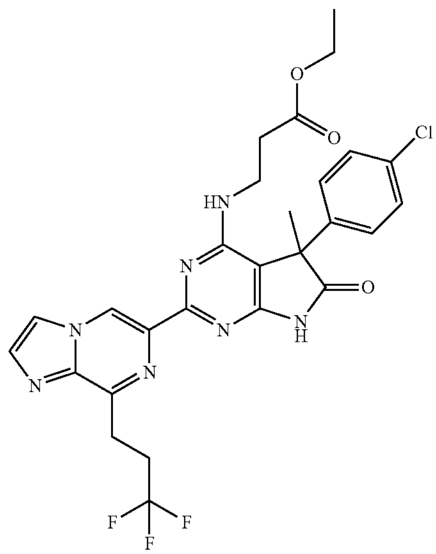 [SMILES: CCOC(=O)CCNc1nc(-c2cn3ccnc3c(CCC(F)(F)F)n2)nc2c1C(C)(c1ccc(Cl)cc1)C(=O)N2] | ethyl 3-((5-(4-chlorophenyl)-5-methyl-6-oxo-2-(8-(3,3,3-trifluoropropyl)imidazo[1,2-a]pyrazin-6-yl)-6,7-dihydro-5H-pyrrolo[2,3-d]pyrimidin-4-yl)amino)propanoate | | 588.1 | Ex-182A |
| 299A | 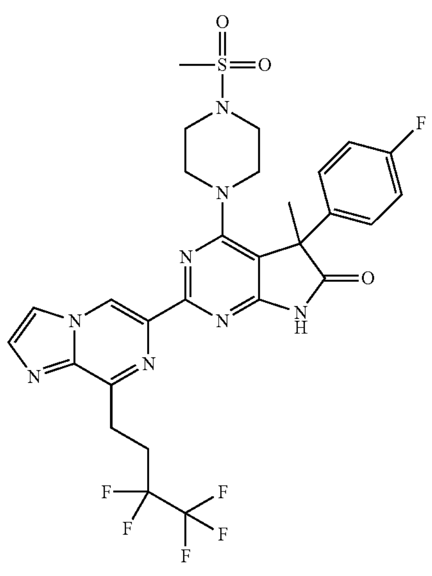 [SMILES: CC1(c2ccc(F)cc2)C(=O)Nc2nc(-c3cn4ccnc4c(CCC(F)(F)C(F)(F)F)n3)nc(N3CCN(S(C)(=O)=O)CC3)c21] | 5-(4-fluorophenyl)-5-methyl-4-(4-(methylsulfonyl)piperazin-1-yl)-2-(8-(3,3,4,4,4-pentafluorobutyl)imidazo[1,2-a]pyrazin-6-yl)-5H-pyrrolo[2,3-d]pyrimidin-6(7H)-one | | 669.3 | Ex-68A |

TABLE 18-continued

*Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.*

| Ex. No. | Structure | IUPAC Name | Chiral amine source or separation conditions | MS (M + 1) | Starting material |
|---|---|---|---|---|---|
| 300A | 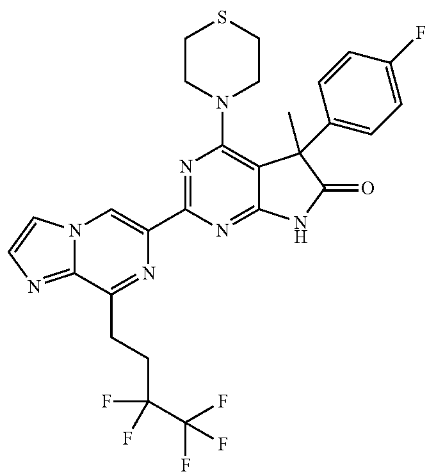 [SMILES: CC1(c2ccc(F)cc2)C(=O)Nc2nc(-c3cn4ccnc4c(CCC(F)(F)C(F)(F)F)n3)nc(N3CCSCC3)c21] | 5-(4-fluorophenyl)-5-methyl-2-(8-(3,3,4,4,4-pentafluorobutyl)imidazo[1,2-a]pyrazin-6-yl)-4-thiomorpholine-5H-pyrrolo[2,3-d]pyrimidin-6(7H)-one | | 608.4 | Ex-68A |
| 301A | 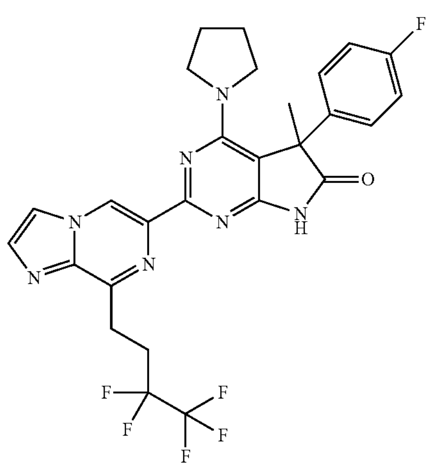 [SMILES: CC1(c2ccc(F)cc2)C(=O)Nc2nc(-c3cn4ccnc4c(CCC(F)(F)C(F)(F)F)n3)nc(N3CCCC3)c21] | 5-(4-fluorophenyl)-5-methyl-2-(8-(3,3,4,4,4-pentafluorobutyl)imidazo[1,2-a]pyrazin-6-yl)-4-(pyrrolidin-1-yl)-5H-pyrrolo[2,3-d]pyrimidin-6(7H)-one | | 576.3 | Ex-68A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 302A | 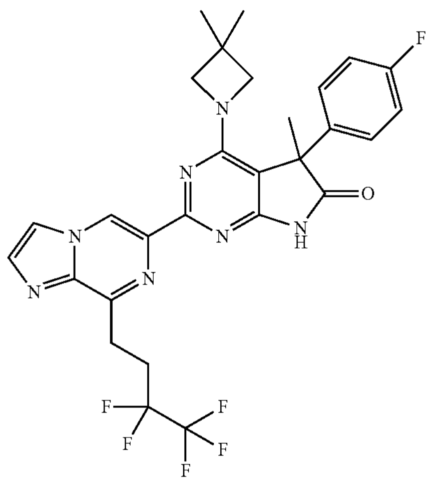 [SMILES: CC1(C)CN(c2nc(-c3cn4ccnc4c(CCC(F)(F)C(F)(F)F)n3)nc3c2C(C)(c2ccc(F)cc2)C(=O)N3)C1] | 4-(3,3-dimethylazetidin-1-yl)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 590.3 | Ex-68A |
| 303A | 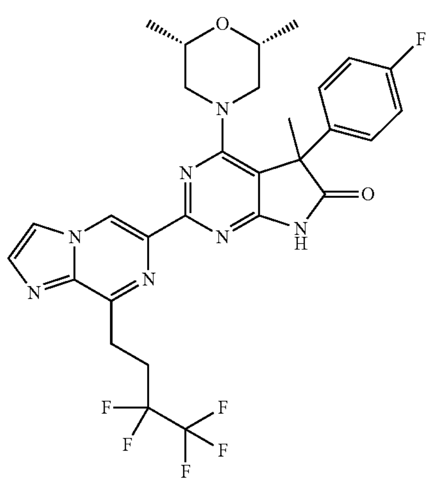 [SMILES: C[C@@H]1CN(c2nc(-c3cn4ccnc4c(CCC(F)(F)C(F)(F)F)n3)nc3c2C(C)(c2ccc(F)cc2)C(=O)N3)C[C@H](C)O1] | 4-((2R,6S)-2,6-dimethylmorpholino)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | (2R,6S)-dimethylmorpholine | 620.3 | Ex-68A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et$_3$N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 304A | 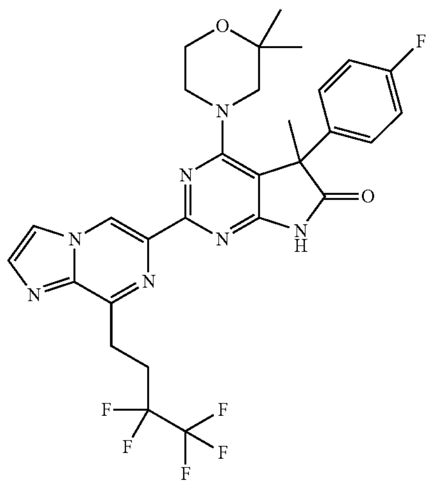 [SMILES: CC1(C)CN(c2nc(-c3cn4ccnc4c(CCC(F)(F)C(F)(F)F)n3)nc3c2C(C)(c2ccc(F)cc2)C(=O)N3)CCO1] | 4-(2,2-dimethylmorpholino)-5-(4-fluorophenyl)-5-mehtyl-2-(8-(3,3,4,4,4-pentafluorobutyl)imidazo[1,2-a]pyrazin-6-yl)-5H-pyrrolo[2,3-d]pyrimidin-6(7H)-one | | 620.5 | Ex-68A |
| 305A | 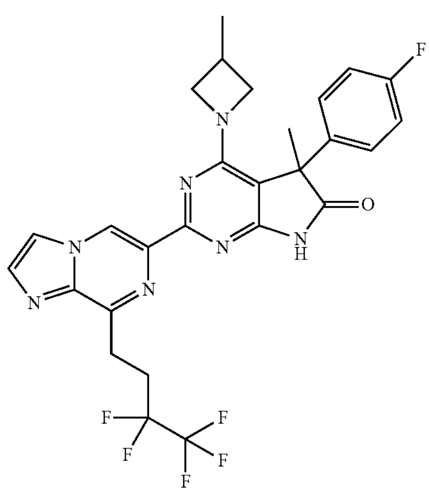 [SMILES: CC1CN(c2nc(-c3cn4ccnc4c(CCC(F)(F)C(F)(F)F)n3)nc3c2C(C)(c2ccc(F)cc2)C(=O)N3)C1] | 5-(4-fluorophenyl)-5-methyl-4-(3-methylazetidin-1-yl)-2-(8-(3,3,4,4,4-pentafluorobutyl)imidazo[1,2-a]pyrazin-6-yl)-5H-pyrrolo[2,3-d]pyrimidin-6(7H)-one | | 576.3 | Ex-68A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et$_3$N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 306A | 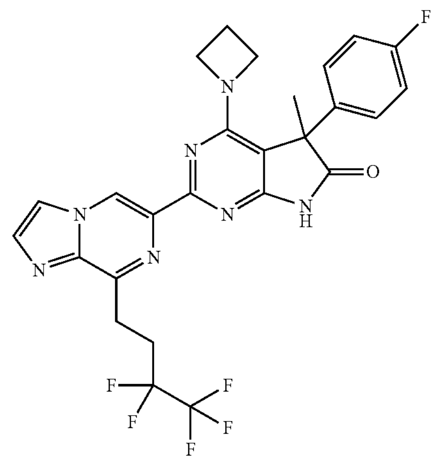 [SMILES: CC1(c2ccc(F)cc2)C(=O)Nc2nc(-c3cn4ccnc4c(CCC(F)(F)C(F)(F)F)n3)nc(N3CCC3)c21] | 4-(azetidin-1-yl)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 562.3 | Ex-68A |
| 307A | 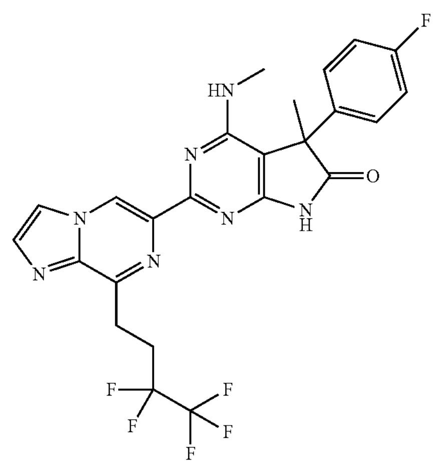 [SMILES: CNc1nc(-c2cn3ccnc3c(CCC(F)(F)C(F)(F)F)n2)nc2c1C(C)(c1ccc(F)cc1)C(=O)N2] | 5-(4-fluorophenyl)-5-methyl-4-(methylamino)-2-(8-(3,3,4,4,4-pentafluorobutyl)imidazo[1,2-a]pyrazin-6-yl)-5H-pyrrolo[2,3-d]pyrimidin-6(7H)-one | | 535.9 | Ex-68A |
| 308A | 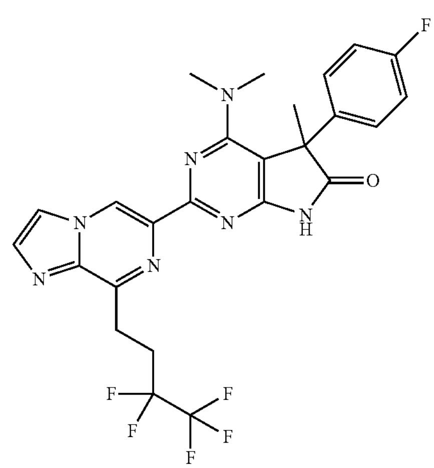 [SMILES: CN(C)c1nc(-c2cn3ccnc3c(CCC(F)(F)C(F)(F)F)n2)nc2c1C(C)(c1ccc(F)cc1)C(=O)N2] | 4-(dimethylamino)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 550.1 | Ex-68A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 309A | 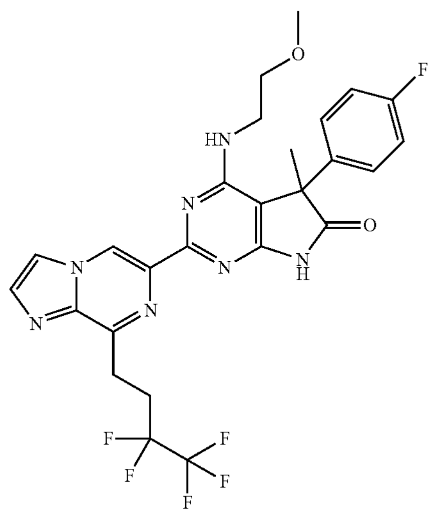 [SMILES: COCCNc1nc(-c2cn3ccnc3c(CCC(F)(F)C(F)(F)F)n2)nc2c1C(C)(c1ccc(F)cc1)C(=O)N2] | 5-(4-fluorophenyl)-4-((2-methoxyethyl)amino)-5-methyl-2-(8-(3,3,4,4,4-pentafluorobutyl)imidazo[1,2-a]pyrazin-6-yl)-5H-pyrrolo[2,3-d]pyrimidin-6(7H)-one | | 580.3 | Ex-68A |
| 310A | 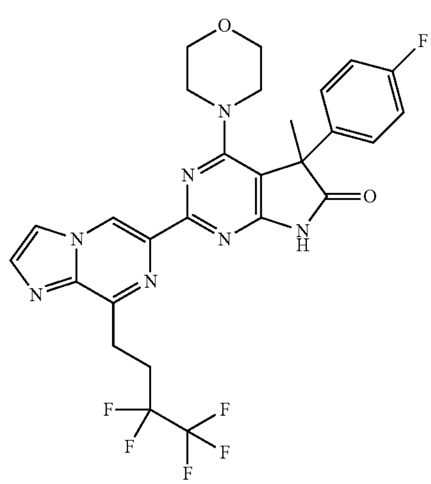 [SMILES: CC1(c2ccc(F)cc2)C(=O)Nc2nc(-c3cn4ccnc4c(CCC(F)(F)C(F)(F)F)n3)nc(N3CCOCC3)c21] | 5-(4-fluorophenyl)-5-methyl-4-morpholino-2-(8-(3,3,4,4,4-pentafluorobutyl)imidazo[1,2-a]pyrazin-6-yl)-5H-pyrrolo[2,3-d]pyrimidin-6(7H)-one | | 592.2 | Ex-68A |

TABLE 18-continued

Using essentially the same procedures described in Examples 277, the following compounds in Table 18 were prepared. The conditions employed may utilize slight variations of reagents such as tert-butyl nitrite in conjunction with copper(II) bromide or copper(II) chloride at varying amounts of excess (4-10X) in 1,2-DCE or DMF at elevated temperatures of 40-80 °C.. The displacement of the halogen with an amine may utilize the amine salt or the free amine in conjunction with a base such as DIEA or Et₃N, in a solvent such as DMA, 1,2-DCE, or THF under thermal or microwave irradiation conditions.

| Ex. No. | Structure | IUPAC Name | Chiral amine source or separation conditions | MS (M + 1) | Starting material |
|---|---|---|---|---|---|
| 311A | 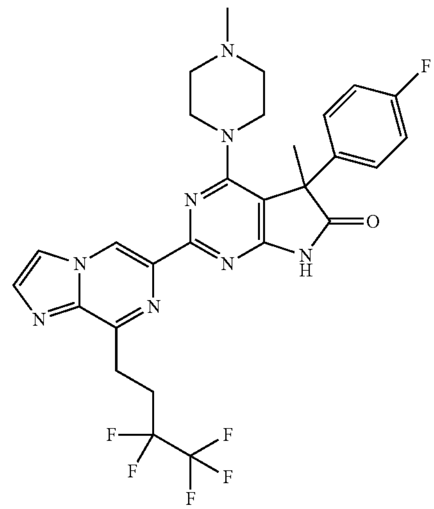 [SMILES: CN1CCN(c2nc(-c3cn4ccnc4c(CCC(F)(F)C(F)(F)F)n3)nc3c2C(C)(c2ccc(F)cc2)C(=O)N3)CC1] | 5-(4-fluorophenyl)-5-methyl-4-(4-methylpiperazin-1-yl)-2-(8-(3,3,4,4,4-pentafluorobutyl)imidazo[1,2-a]pyrazin-6-yl)-5H-pyrrolo[2,3-d]pyrimidin-6(7H)-one | | 605.2 | Ex-68A |
| 312A | 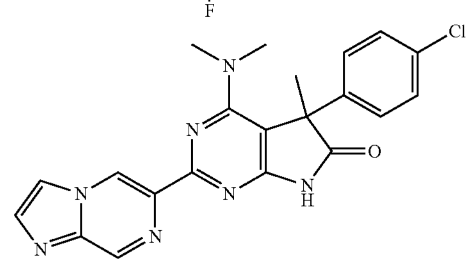 | 5-(4-chlorophenyl)-4-(dimehtylamino)-2-imidazo[1,2-a]pyrazin-6-yl)-5-methyl-5H-pyrrolo[2,3-d]pyrimidin-6(7H)-one | | 420.2 | Ex-144A |

Example 313

4-((2-Methoxyethyl)amino)-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one

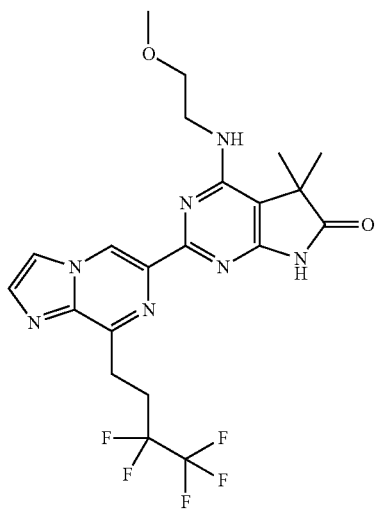 [SMILES: COCCNc1nc(-c2cn3ccnc3c(CCC(F)(F)C(F)(F)F)n2)nc2c1C(C)(C)C(=O)N2]

Step A—4-Chloro-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one Into a flask, purged with an inert atmosphere of nitrogen, was placed a sample of Ex-87 (582 mg, 1.32 mmol), copper(II) chloride (1241 mg, 9.23 mmol), and 1,2-DCE (24 mL). Tert-butyl nitrite (0.627 mL, 5.27 mmol) was added and the mixture was warmed at 65° C. for 1 h. The reaction mixture was cooled to ambient temperature and diluted with EtOAc. The reaction was washed with a 9:1 solution of saturated NH₄Cl:NH₄OH (2×). The organic layer was extracted, dried over anhydrous magnesium sulfate, filtered, and the filtrate was concentrated in vacuo to dryness. The residue was purified by silica gel chromatography with MeOH:DCM (0-7%) to afford the title compound. m/z=461.1 (M+H).

Step B—4-((2-Methoxyethyl)amino)-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one Into a microwave vial, purged with an inert atmosphere of nitrogen, was placed the intermediate from Step A (100 mg, 0.22 mmol) and 2-methoxyethanamine (0.19 mL, 2.17 mmol). The resulting mixture was irradiated with microwave radiation for 0.5 h at 150° C. The reaction mixture was concentrated in vacuo and then diluted with DCM. The reaction was washed with a 9:1 solution of saturated NH₄Cl: NH₄OH (2×). The organic layer was extracted, dried over anhydrous magnesium sulfate, filtered, and the filtrate was concentrated in vacuo to dryness. The residue was purified by silica gel chromatography with MeOH:DCM (0-7%) to afford the title compound. $^1$H NMR (400 MHz, DMSO-$d_6$): δ 10.97 (1H, brs), 9.23 (1H, s), 8.26 (1H, s), 7.77 (1H, s), 6.62 (1H, br s), 3.72-3.63 (2H, m), 3.57-3.50 (2H, m), 3.48-3.39 (2H, m), 3.24 (3H, s), 2.97-2.80 (2H, m), 1.31 (6H, s); m/z=500.1 (M+H).

TABLE 19

Using similar procedures as described in all the above examples from Examples 1-334, the following compounds in Table 19 were also made.

| Ex. No. | Structure | IUPAC Name | Chiral separation column or Starting Material | MS [M + 1] |
| --- | --- | --- | --- | --- |
| 314B | 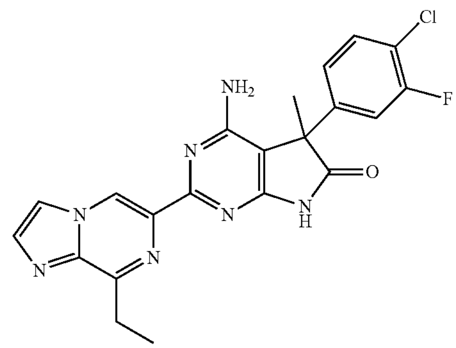 [SMILES: CCc1nc(-c2nc(N)c3c(n2)NC(=O)C3(C)c2ccc(Cl)c(F)c2)cn2ccnc12] | 4-amino-5-(4-chloro-3-fluorophenyl)-2-(8-ethylimidazo[1,2-a]pyrazin-6-yl)-5-methyl-5H-pyrrolo[2,3-d]pyrimidin-6(7H)-one | I-91B* | 438.2 |
| 315A | 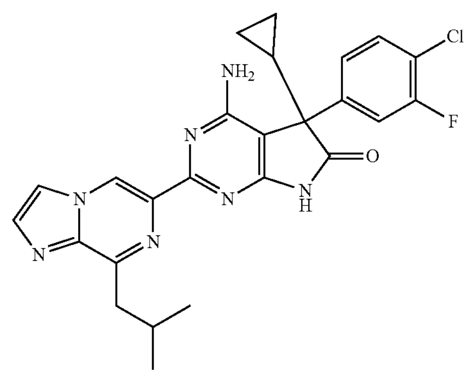 [SMILES: CC(C)Cc1nc(-c2nc(N)c3c(n2)NC(=O)C3(c2ccc(Cl)c(F)c2)C2CC2)cn2ccnc12] | 4-amino-5-(4-chloro-3-fluorophenyl)-5-cyclopropyl-2-(8-isobutylimidazo[1,2-a]pyrazin-6-yl)-5H-pyrrolo[2,3-d]pyrimidin-6(7H)-one | I-81A* | 492.2 |
| 316B | 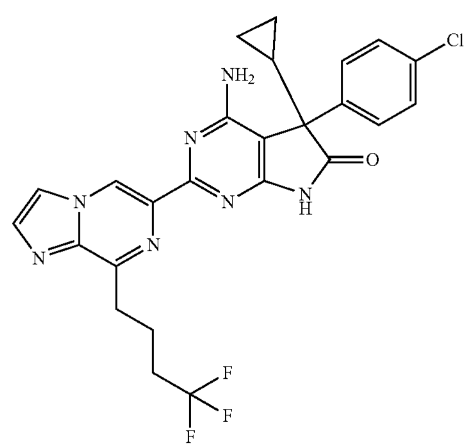 [SMILES: Nc1nc(-c2cn3ccnc3c(CCCC(F)(F)F)n2)nc2c1C(c1ccc(Cl)cc1)(C1CC1)C(=O)N2] | 4-amino-5-(4-chlorophenyl)-5-cyclopropyl-2-(8-(4,4,4-trifluorobutyl)imidazo[1,2-a]pyrazin-6-yl)-5H-pyrrolo[2,3-d]pyrimidin-6(7H)-one | I-79B* | 528.3 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 317A | 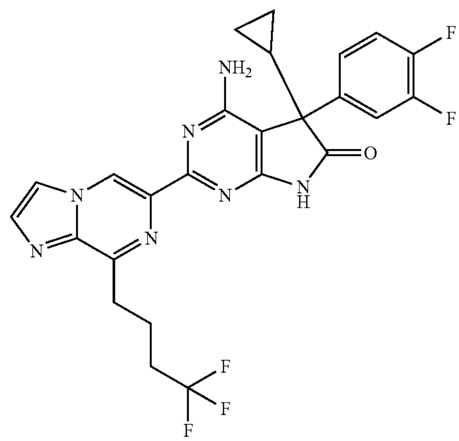 [SMILES: Nc1nc(-c2cn3ccnc3c(CCCC(F)(F)F)n2)nc2c1C(c1ccc(F)c(F)c1)(C1CC1)C(=O)N2] | 4-amino-5-cyclopropyl-5-(3,4-difluorophenyl)-2-(8-(4,4,4-trifluorobutyl)imidazo[1,2-a]pyrazin-6-yl)-5H-pyrrolo[2,3-d]pyrimidin-6(7H)-one | I-113 A* | 530.4 |
| 318A | 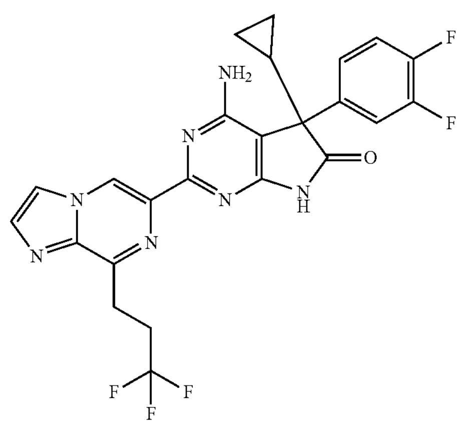 [SMILES: Nc1nc(-c2cn3ccnc3c(CCC(F)(F)F)n2)nc2c1C(c1ccc(F)c(F)c1)(C1CC1)C(=O)N2] | 4-amino-5-cyclopropyl-5-(3,4-difluorophenyl)-2-(8-(3,3,3-trifluoropropyl)imidazo[1,2-a]pyrazin-6-yl)-5H-pyrrolo[2,3-d]pyrimidin-6(7H)-one | I-113A* | 516.3 |
| 319A & B | 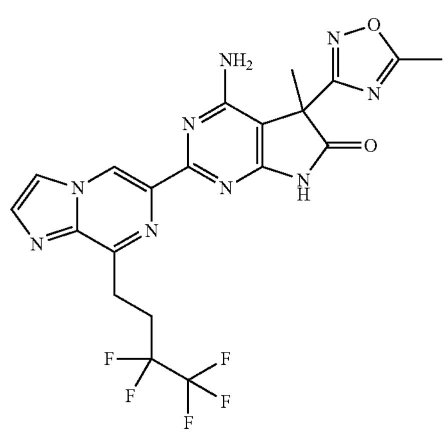 [SMILES: Cc1nc(C2(C)C(=O)Nc3nc(-c4cn5ccnc5c(CCC(F)(F)C(F)(F)F)n4)nc(N)c32)no1] | 4-amino-5-ethynyl-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IA | 510.3 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 320B | 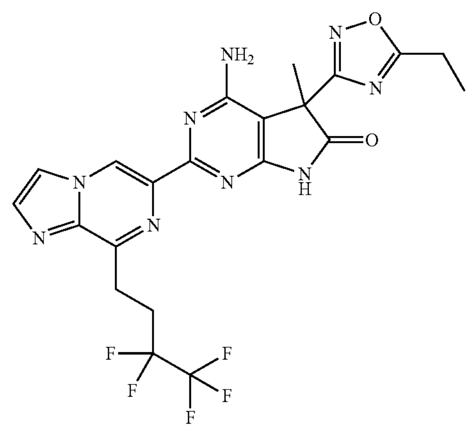 [SMILES: CCc1nc(C2(C)C(=O)Nc3nc(-c4cn5ccnc5c(CCC(F)(F)C(F)(F)F)n4)nc(N)c32)no1] | 4-amino-5-(5-ethyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | I-109B | 524.1 |
| 321A & B | 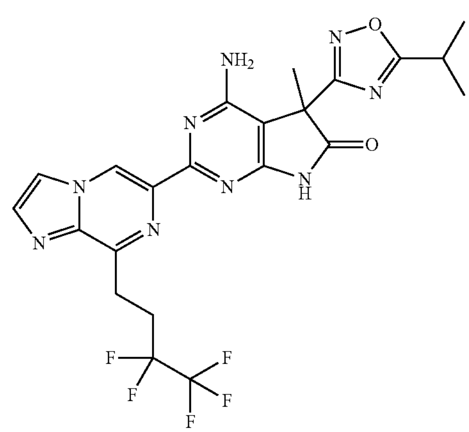 [SMILES: CC(C)c1nc(C2(C)C(=O)Nc3nc(-c4cn5ccnc5c(CCC(F)(F)C(F)(F)F)n4)nc(N)c32)no1] | 4-amino-5-(5-isopropyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AS | 538.4 |
| 325A & B | 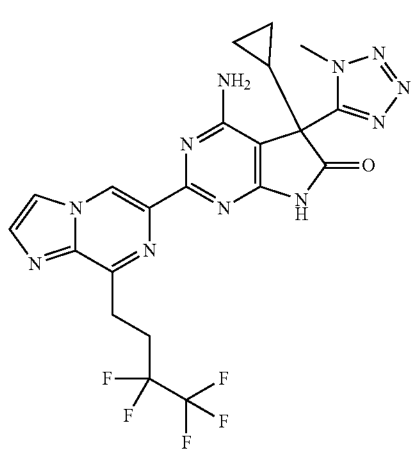 [SMILES: Cn1nnnc1C1(C2CC2)C(=O)Nc2nc(-c3cn4ccnc4c(CCC(F)(F)C(F)(F)F)n3)nc(N)c21] | 4-amino-5-cyclopropyl-5-(1-methyl-1H-tetrazol-5-yl)-2-(8-(3,3,4,4,4-pentafluorobutyl)imidazo[1,2-a]pyrazin-6-yl]-5H-pyrrolo[2,3-d]pyrimidin-6(7H)-one | CHIRALPAK IC A* | 536.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 327A | 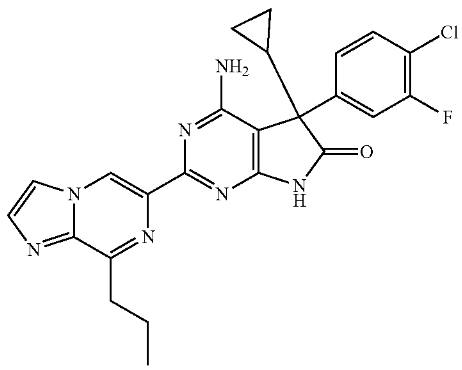 [SMILES: CCCc1nc(-c2nc(N)c3c(n2)NC(=O)C3(c2ccc(Cl)c(F)c2)C2CC2)cn2ccnc12] | 4-amino-5-(4-chloro-3-fluorophenyl)-5-cyclopropyl-2-(8-propylimidazo[1,2-a]pyrazin-6-yl)-5H-pyrrolo[2,3-d]pyrimidin-6(7H)-one | I-81A* | 478.1 |
| 328A | 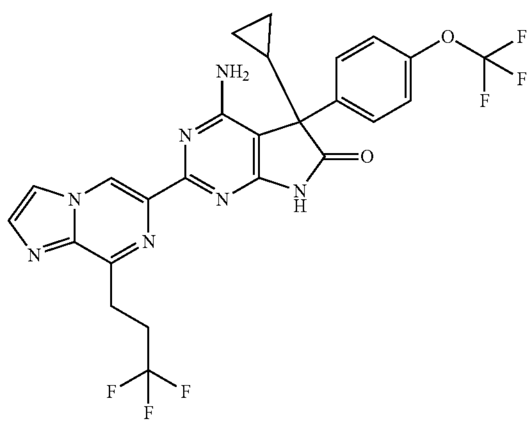 [SMILES: Nc1nc(-c2cn3ccnc3c(CCC(F)(F)F)n2)nc2c1C(c1ccc(OC(F)(F)F)cc1)(C1CC1)C(=O)N2] | 4-amino-5-cyclopropyl-5-(4-(trifluoromethoxy)phenyl)-2-(8-(3,3,3-trifluoropropyl)imidazo[1,2-a]pyrazin-6-yl)-5H-pyrrolo[2,3-d]pyrimidin-6(7H)-one | I-87A* | 564.4 |
| 329A | 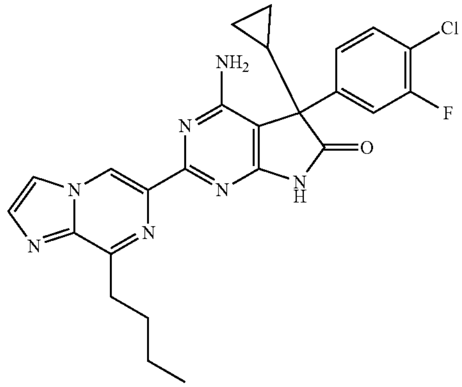 [SMILES: CCCCc1nc(-c2nc(N)c3c(n2)NC(=O)C3(c2ccc(Cl)c(F)c2)C2CC2)cn2ccnc12] | 4-amino-2-(8-butylimidazo[1,2-a]pyrazin-6-yl)-5-(4-chloro-3-fluorophenyl)-5-cyclopropyl-5H-pyrrolo[2,3-d]pyrimidin-6(7H)-one | I-81A* | 492.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 330A | 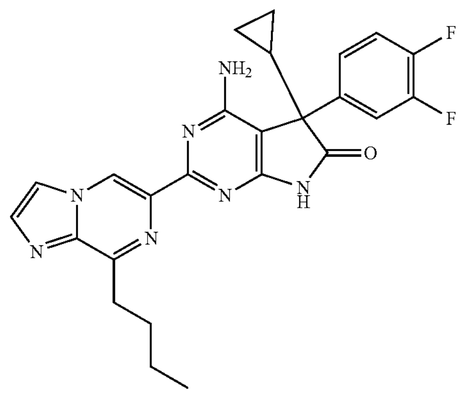 [SMILES: CCCCc1nc(-c2nc(N)c3c(n2)NC(=O)C3(c2ccc(F)c(F)c2)C2CC2)cn2ccnc12] | 4-amino-2-(8-butylimidazo[1,2-a]pyrazin-6-yl)-5-cyclopropyl-5-(3,4-difluorophenyl)-5H-pyrrolo[2,3-d]pyrimidin-6(7H)-one | I-113A* | 476.3 |
| 331A & B | 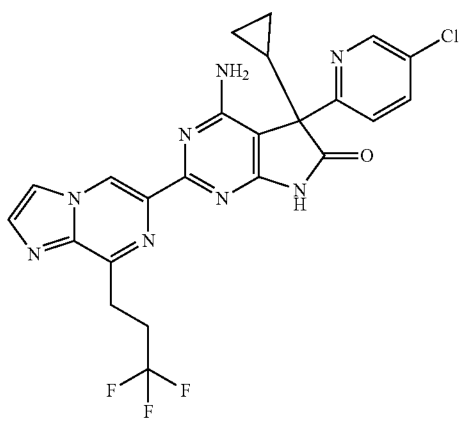 [SMILES: Nc1nc(-c2cn3ccnc3c(CCC(F)(F)F)n2)nc2c1C(c1ccc(Cl)cn1)(C1CC1)C(=O)N2] | 4-amino-5-(5-chloropyridin-2-yl)-5-cyclopropyl-2-(8-(3,3,3-trifluoropropyl)imidazo[1,2-a]pyrazin-6-yl)-5H-pyrrolo[2,3-d]pyrimidin-6(7H)-one | CHIRALPAK IC | 515.0 |
| 332B | 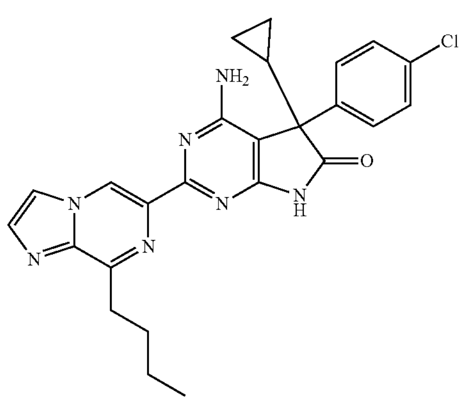 [SMILES: CCCCc1nc(-c2nc(N)c3c(n2)NC(=O)C3(c2ccc(Cl)cc2)C2CC2)cn2ccnc12] | 4-amino-2-(8-butylimidazo[1,2-a]pyrazin-6-yl)-5-(4-chlorophenyl)-5-cyclopropyl-5H-pyrrolo[2,3-d]pyrimidin-6(7H)-one | I-79B* | 474.3 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 333A & B | 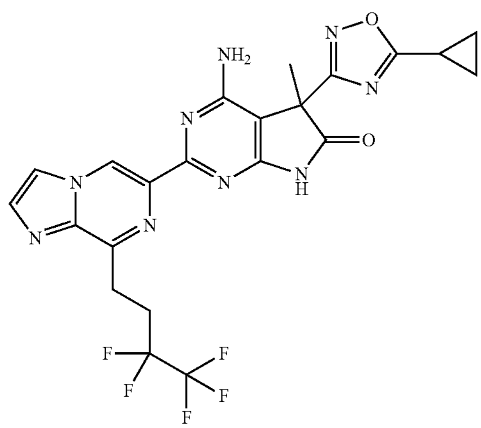 [SMILES: CC1(c2noc(C3CC3)n2)C(=O)Nc2nc(-c3cn4ccnc4c(CCC(F)(F)C(F)(F)F)n3)nc(N)c21] | 4-amino-5-(5-cyclopropyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | CHIRALCEL AS | 536.2 |
| 334A | 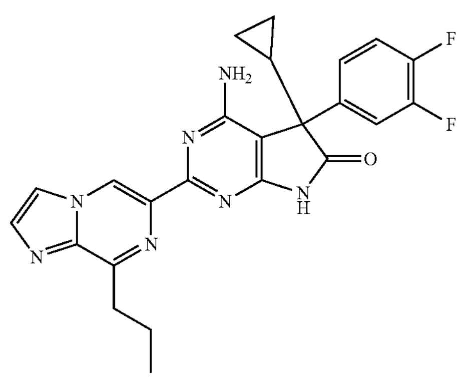 [SMILES: CCCc1nc(-c2nc(N)c3c(n2)NC(=O)C3(c2ccc(F)c(F)c2)C2CC2)cn2ccnc12] | 4-amino-5-cyclopropyl-5-(3,4-difluorophenyl)-2-(8-propylimidazo[1,2-a]pyrazin-6-yl)-5H-pyrrolo[2,3-d]pyrimidin-6(7H)-one | I-113A* | 462.2 |
| 335A | 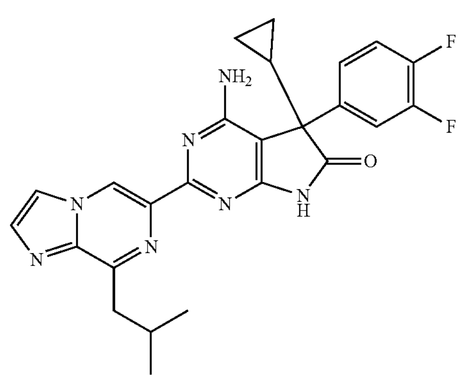 [SMILES: CC(C)Cc1nc(-c2nc(N)c3c(n2)NC(=O)C3(c2ccc(F)c(F)c2)C2CC2)cn2ccnc12] | 4-amino-5-cyclopropyl-5-(3,4-difluorophenyl)-2-(8-isobutylimidazo[1,2-a]pyrazin-6-yl)-5H-pyrrolo[2,3-d]pyrimidin-6(7H)-one | I-113A* | 476.4 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 336B | 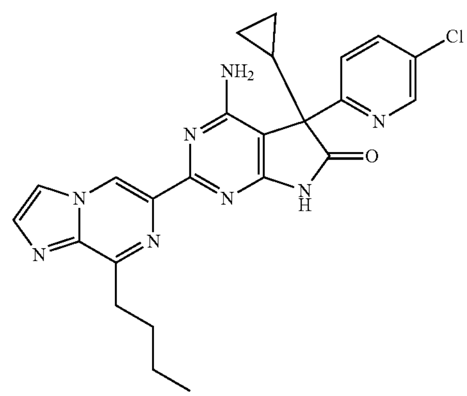 [SMILES: CCCCc1nc(-c2nc(N)c3c(n2)NC(=O)C3(c2ccc(Cl)cn2)C2CC2)cn2ccnc12] | 4-amino-2-(8-butylimidazo[1,2-a]pyrazin-6-yl)-5-(5-chloropyridin-2-yl)-5-cyclopropyl-5H-pyrrolo[2,3-d]pyrimidin-6(7H)-one | I-83B | 475.2 |
| 337A & B | 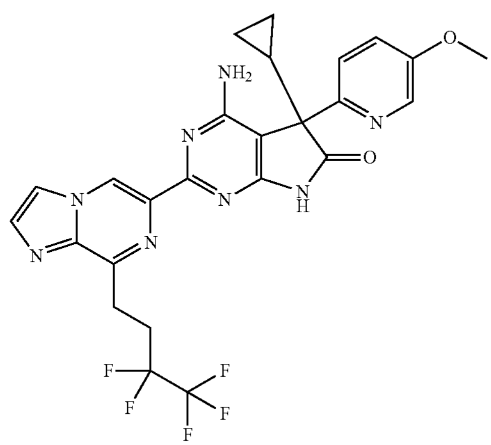 [SMILES: COc1ccc(C2(C3CC3)C(=O)Nc3nc(-c4cn5ccnc5c(CCC(F)(F)C(F)(F)F)n4)nc(N)c32)nc1] | 4-amino-5-cyclopropyl-5-(5-methoxypyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALCEL OJ A* | 561.2 |
| 338A | 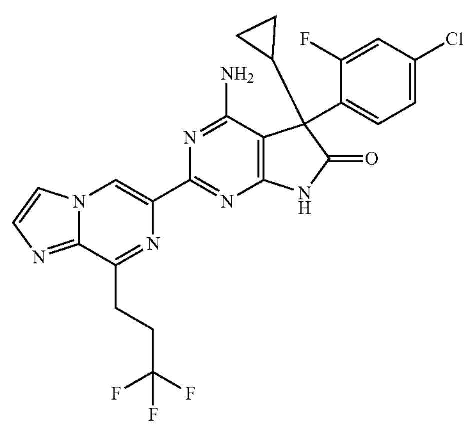 [SMILES: Nc1nc(-c2cn3ccnc3c(CCC(F)(F)F)n2)nc2c1C(c1ccc(Cl)cc1F)(C1CC1)C(=O)N2] | 4-amino-5-(4-chloro-2-fluorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one | I-116A* | 532.3 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 339A | 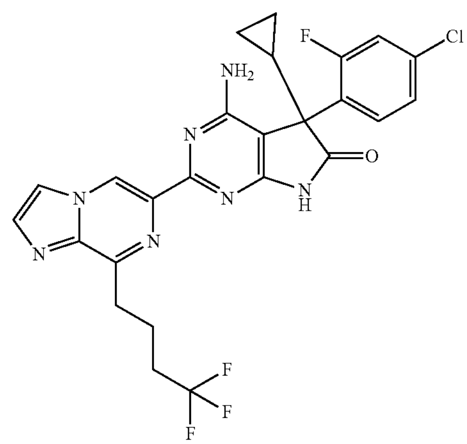 [SMILES: Nc1nc(-c2cn3ccnc3c(CCCC(F)(F)F)n2)nc2c1C(c1ccc(Cl)cc1F)(C1CC1)C(=O)N2] | 4-amino-5-(4-chloro-2-fluorophenyl)-5-cyclopropyl-2-(8-(4,4,4-trifluorobutyl)imidazo[1,2-a]pyrazin-6-yl)-5H-pyrrolo[2,3-d]pyrimidin-6(7H)-one | I-116A* | 546.2 |
| 340A | 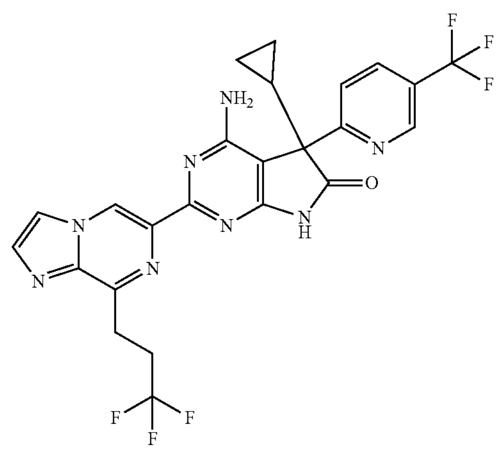 [SMILES: Nc1nc(-c2cn3ccnc3c(CCC(F)(F)F)n2)nc2c1C(c1ccc(C(F)(F)F)cn1)(C1CC1)C(=O)N2] | 4-amino-5-cyclopropyl-5-(5-(trifluoromethyl)pyridin-2-yl)-2-(8-(3,3,3-trifluoropropyl)imidazo[1,2-a]pyrazin-6-yl)-5H-pyrrolo[2,3-d]pyrimidin-6(7H)-one | I-84A* | 549.3 |
| 341A | 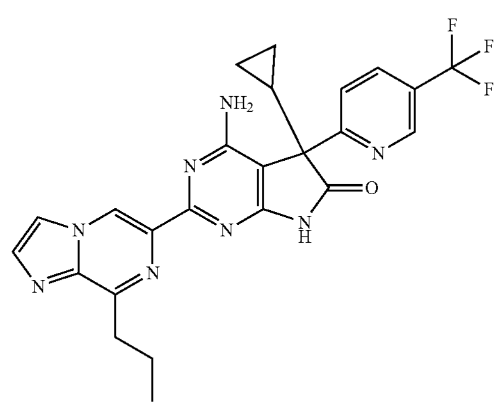 [SMILES: CCCc1nc(-c2nc(N)c3c(n2)NC(=O)C3(c2ccc(C(F)(F)F)cn2)C2CC2)cn2ccnc12] | 4-amino-5-cyclopropyl-2-(8-propylimidazo[1,2-a]pyrazin-6-yl)-5-(5-(trifluoromethyl)pyridin-2-yl)-5H-pyrrolo[2,3-d]pyrimidin-6(7H)-one | I-84A* | 495.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 342A & B | 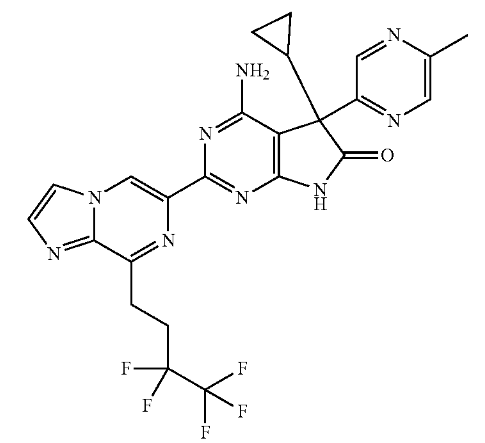 [SMILES: Cc1cnc(C2(C3CC3)C(=O)Nc3nc(-c4cn5ccnc5c(CCC(F)(F)C(F)(F)F)n4)nc(N)c32)cn1] | 4-amino-5-cyclopropyl-5-(5-methylpyrazin-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 546.4 |
| 343A | 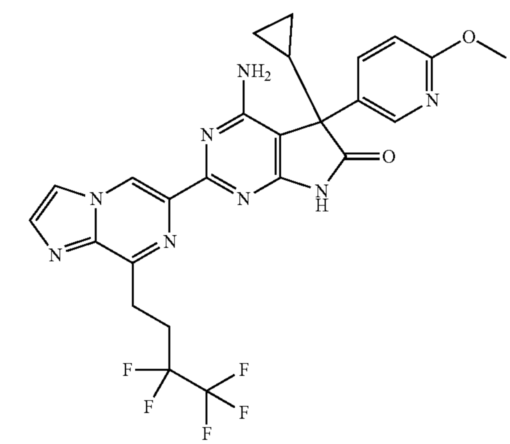 [SMILES: COc1ccc(C2(C3CC3)C(=O)Nc3nc(-c4cn5ccnc5c(CCC(F)(F)C(F)(F)F)n4)nc(N)c32)cn1] | 4-amino-5-cyclopropyl-5-(6-methoxypyridin-3-yl)-2-(8-(3,3,4,4,4-pentafluorobutyl)imidazo[1,2-a]pyrazin-6-yl)-5H-pyrrolo[2,3-d]pyrimidin-6(7H)-one | I-118A* | 561.3 |
| 344A & B | 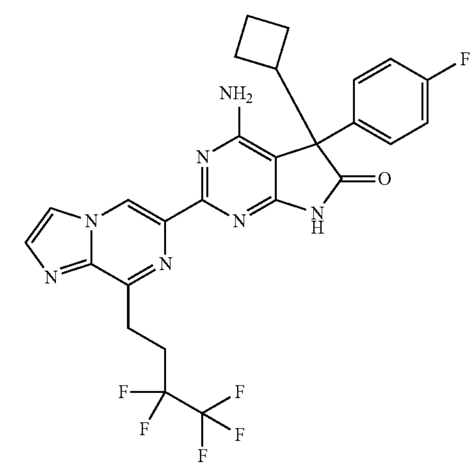 [SMILES: Nc1nc(-c2cn3ccnc3c(CCC(F)(F)C(F)(F)F)n2)nc2c1C(c1ccc(F)cc1)(C1CCC1)C(=O)N2] | 4-amino-5-cyclobutyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AD | 562.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 345A & B | 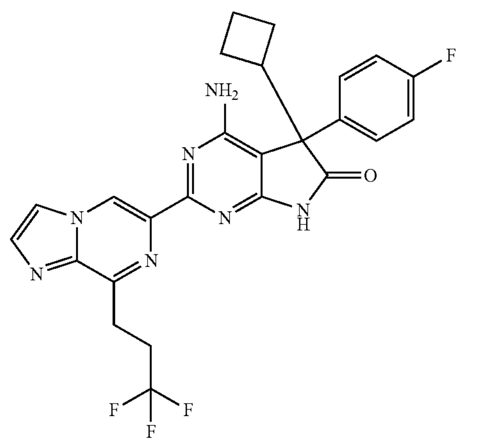 [SMILES: Nc1nc(-c2cn3ccnc3c(CCC(F)(F)F)n2)nc2c1C(c1ccc(F)cc1)(C1CCC1)C(=O)N2] | 4-amino-5-cyclobutyl-5-(4-fluorophenyl)-2-(8-(3,3,3-trifluoropropyl)imidazo[1,2-a]pyrazin-6-yl)-5H-pyrrolo[2,3-d]pyrimidin-6(7H)-one | CHIRALPAK AD | 512.2 |
| 346A | 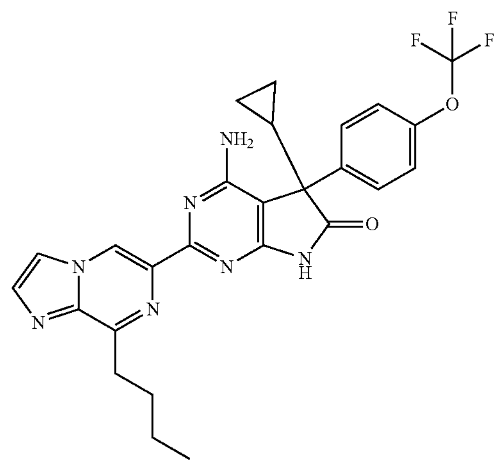 [SMILES: CCCCc1nc(-c2nc(N)c3c(n2)NC(=O)C3(c2ccc(OC(F)(F)F)cc2)C2CC2)cn2ccnc12] | 4-amino-2-(8-butylimidazo[1,2-a]pyrazin-6-yl)-5-cyclopropyl-5-(4-trifluoromethoxy)phenyl)-5H-pyrrolo[2,3-d]pyrimidin-6(7H)-one | I-112A* | 524.4 |
| 347A | 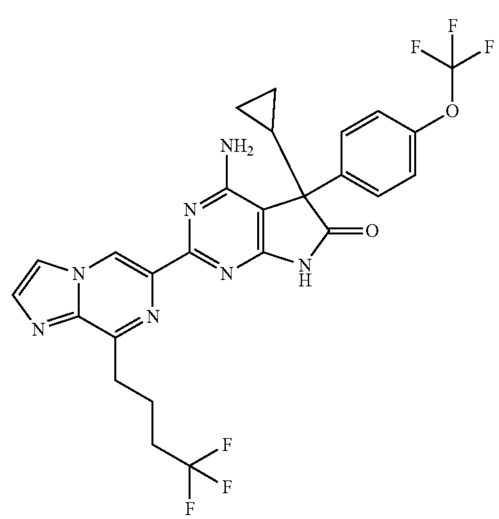 [SMILES: Nc1nc(-c2cn3ccnc3c(CCCC(F)(F)F)n2)nc2c1C(c1ccc(OC(F)(F)F)cc1)(C1CC1)C(=O)N2] | 4-amino-5-cyclopropyl-2-(8-(4,4,4-trifluorobutyl)imidazo[1,2-a]pyrazin-6-yl)-5-(4-(trifluoromethoxy)phenyl)-5H-pyrrolo[2,3-d]pyrimidin-6(7H)-one | I-112A* | 548.4 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 348A & B | 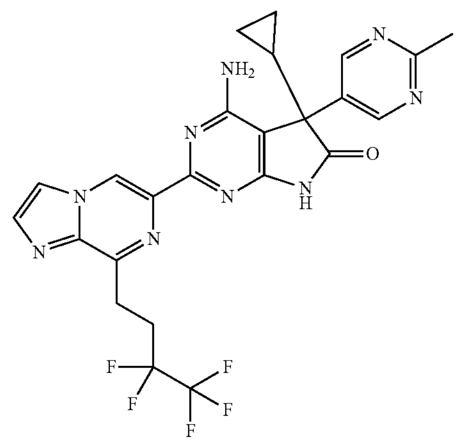 [SMILES: Cc1ncc(C2(C3CC3)C(=O)Nc3nc(-c4cn5ccnc5c(CCC(F)(F)C(F)(F)F)n4)nc(N)c32)cn1] | 4-amino-5-cyclopropyl-5-(2-methylpyrimidin-5-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AD | 546.1 |
| 349A | 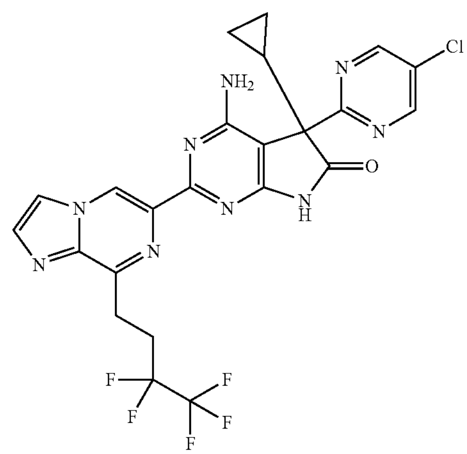 [SMILES: Nc1nc(-c2cn3ccnc3c(CCC(F)(F)C(F)(F)F)n2)nc2c1C(c1ncc(Cl)cn1)(C1CC1)C(=O)N2] | 4-amino-5-(5-chloropyrimidin-2-yl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one | I-106A* | 566.4 |
| 350A & B | 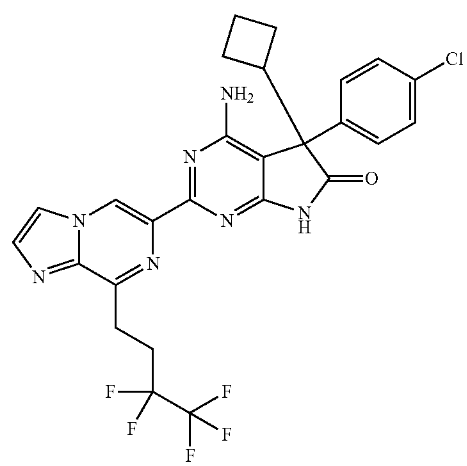 [SMILES: Nc1nc(-c2cn3ccnc3c(CCC(F)(F)C(F)(F)F)n2)nc2c1C(c1ccc(Cl)cc1)(C1CCC1)C(=O)N2] | 4-amino-5-(4-chlorophenyl)-5-cyclobutyl-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AS | 578.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 351A & B | 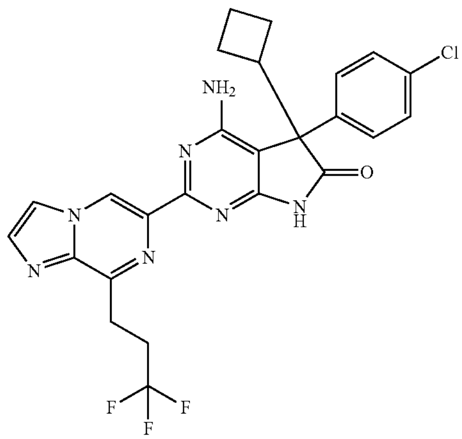 [SMILES: Nc1nc(-c2cn3ccnc3c(CCC(F)(F)F)n2)nc2c1C(c1ccc(Cl)cc1)(C1CCC1)C(=O)N2] | 4-amino-5-(4-chlorophenyl)-5-cyclobutyl-2-(8-(3,3,3-trifluoropropyl)imidazo[1,2-a]pyrazin-6-yl)-5H-pyrrolo[2,3-d]pyrimidin-6(7H)-one | CHIRALPAK AD | 528.1 |
| 352A & B | 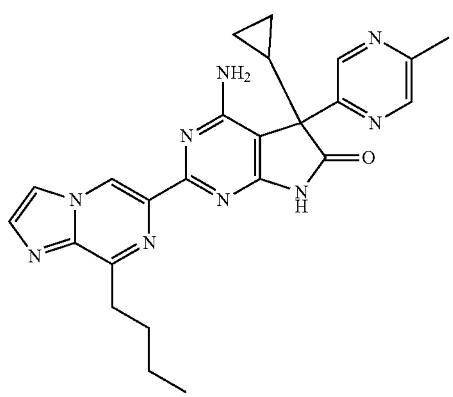 [SMILES: CCCCc1nc(-c2nc(N)c3c(n2)NC(=O)C3(c2cnc(C)cn2)C2CC2)cn2ccnc12] | 4-amino-2-(8-butylimidazo[1,2-a]pyrazin-6-yl)-5-cyclopropyl-5-(5-methylpyrazin-2-yl)-5H-pyrrolo[2,3-d]pyrimidin-6(7H)-one | CHIRALPAK IA | 456.2 |
| 353B | 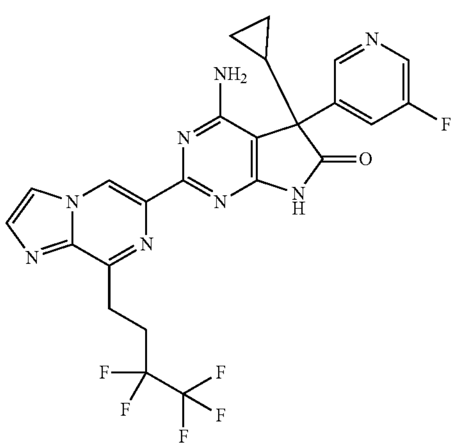 [SMILES: Nc1nc(-c2cn3ccnc3c(CCC(F)(F)C(F)(F)F)n2)nc2c1C(c1cncc(F)c1)(C1CC1)C(=O)N2] | 4-amino-5-cyclopropyl-5-(5-fluoropyridin-3-yl)-2-(8-(3,3,4,4,4-pentafluorobutyl)imidazo[1,2-a]pyrazin-6-yl)-5H-pyrrolo[2,3-d]pyrimidin-6(7H)-one | I-114B* | 549.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 354A & B | 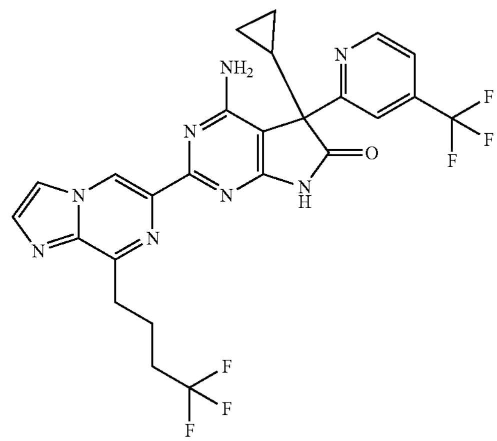 [SMILES: Nc1nc(-c2cn3ccnc3c(CCCC(F)(F)F)n2)nc2c1C(c1cc(C(F)(F)F)ccn1)(C1CC1)C(=O)N2] | 4-amino-5-cyclopropyl-2-(8-(4,4,4-trifluorobutyl)imidazo[1,2-a]pyrazin-6-yl)-5-(4-(trifluoromethyl)pyridin-2-yl)-5H-pyrrolo[2,3-d]pyrimidin-6(7H)-one | CHIRALPAK AS | 563.2 |
| 355A & B | 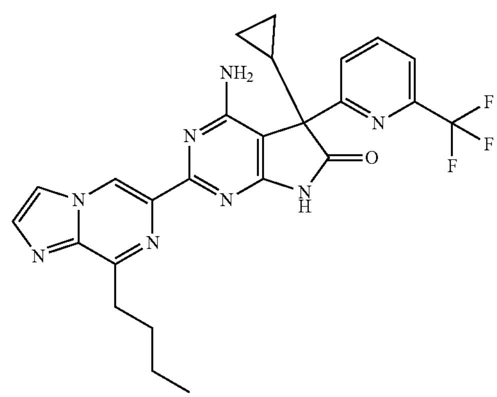 [SMILES: CCCCc1nc(-c2nc(N)c3c(n2)NC(=O)C3(c2cccc(C(F)(F)F)n2)C2CC2)cn2ccnc12] | 4-amino-2-(8-butylimidazo[1,2-a]pyrazin-6-yl)-5-cyclopropyl-5-(6-(trifluoromethyl)pyridin-2-yl)-5H-pyrrolo[2,3-d]pyrimidin-6(7H)-one | CHIRALPAK AD | 509.2 |
| 356B | 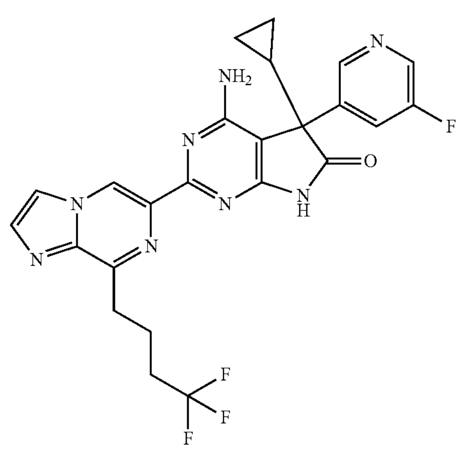 [SMILES: Nc1nc(-c2cn3ccnc3c(CCCC(F)(F)F)n2)nc2c1C(c1cncc(F)c1)(C1CC1)C(=O)N2] | 4-amino-5-cyclopropyl-5-(5-fluoropyridin-3-yl)-2-(8-(4,4,4-trifluorobutyl)imidazo[1,2-a]pyrazin-6-yl)-5H-pyrrolo[2,3-d]pyrimidin-6(7H)-one | I-114B* | 513.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 357A & B | 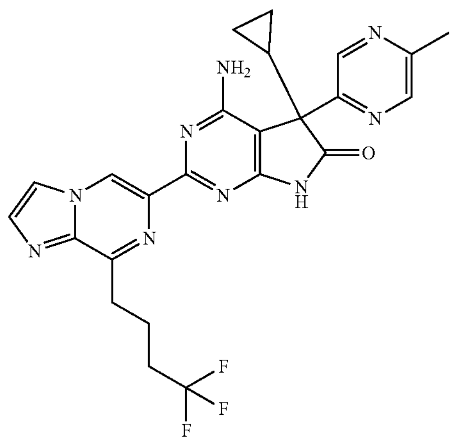 [SMILES: Cc1cnc(C2(C3CC3)C(=O)Nc3nc(-c4cn5ccnc5c(CCCC(F)(F)F)n4)nc(N)c32)cn1] | 4-amino-5-cyclopropyl-5-(5-methylpyrazin-2-yl)-2-(8-(4,4,4-trifluorobutyl)imidazo[1,2-a]pyrazin-6-yl)-5H-pyrrolo[2,3-d]pyrimidin-6(7H)-one | CHIRALPAK OD | 510.2 |
| 358A & B | 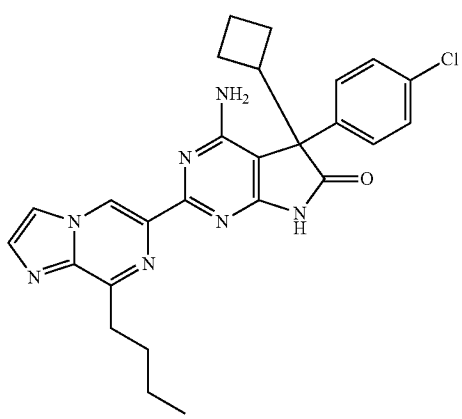 [SMILES: CCCCc1nc(-c2nc(N)c3c(n2)NC(=O)C3(c2ccc(Cl)cc2)C2CCC2)cn2ccnc12] | 4-amino-2-(8-butylimidazo[1,2-a]pyrazin-6-yl)-5-(4-chlorophenyl)-5-cyclobutyl-5H-pyrrolo[2,3-d]pyrimidin-6(7H)-one | CHIRALPAK IA | 488.2 |
| 359A & B | 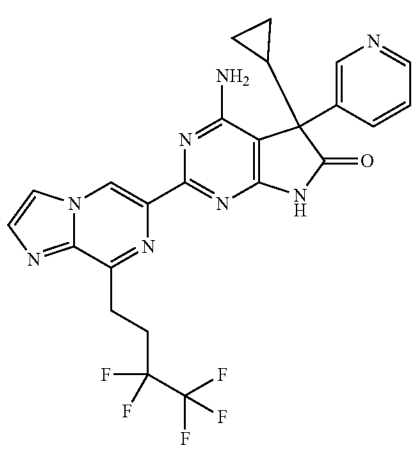 [SMILES: Nc1nc(-c2cn3ccnc3c(CCC(F)(F)C(F)(F)F)n2)nc2c1C(c1cccnc1)(C1CC1)C(=O)N2] | 4-amino-5-cyclopropyl-2-(8-(3,3,4,4,4-pentafluorobutyl)imidazo[1,2-a]pyrazin-6-yl)-5-(pyridin-3-yl)-5H-pyrrolo[2,3-d]pyrimidin-6(7H)-one | CHIRALPAK AS | 531.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 360A | 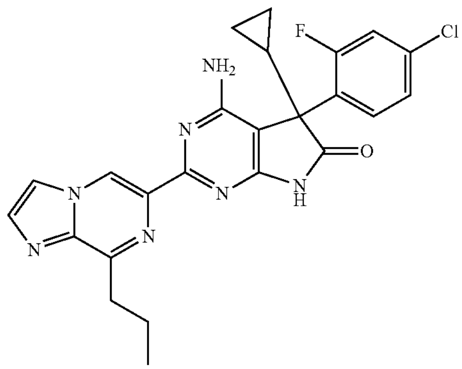 [SMILES: CCCc1nc(-c2nc(N)c3c(n2)NC(=O)C3(c2ccc(Cl)cc2F)C2CC2)cn2ccnc12] | 4-amino-5-(4-chloro-2-fluorophenyl)-5-cyclopropyl-2-(8-propylimidazo[1,2-a]pyrazin-6-yl)-5H-pyrrolo[2,3-d]pyrimidin-6(7H)-one | I-116A* | 478.0 |
| 361A & B | 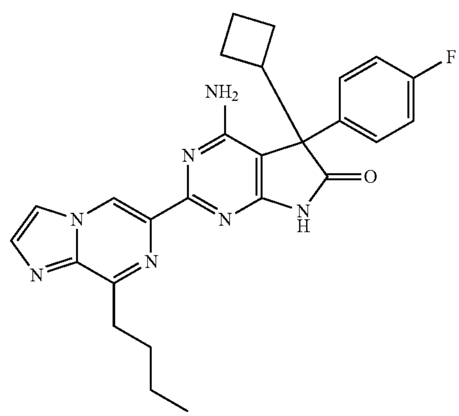 [SMILES: CCCCc1nc(-c2nc(N)c3c(n2)NC(=O)C3(c2ccc(F)cc2)C2CCC2)cn2ccnc12] | 4-amino-2-(8-butylimidazo[1,2-a]pyrazin-6-yl)-5-cyclobutyl-5-(4-fluorophenyl)-5H-pyrrolo[2,3-d]pyrimidin-6(7H)-one | CHIRALPAK AD | 472.2 |
| 362A & B | 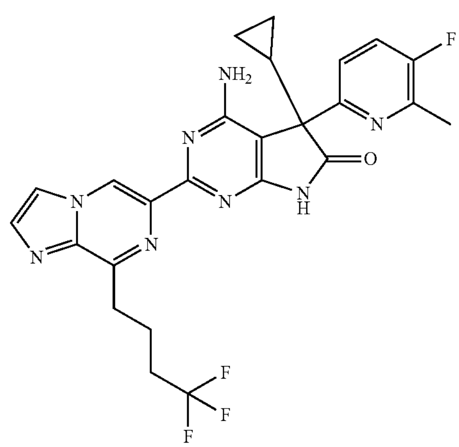 [SMILES: Cc1nc(C2(C3CC3)C(=O)Nc3nc(-c4cn5ccnc5c(CCCC(F)(F)F)n4)nc(N)c32)ccc1F] | 4-amino-5-cyclopropyl-5-(5-fluoro-6-methylpyridin-2-yl)-2-(8-(4,4,4-trifluorobutyl)imidazo[1,2-a]pyrazin-6-yl)-5H-pyrrolo[2,3-d]pyrimidin-6(7H)-one | CHIRALPAK IC | 527.3 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 363A & B | 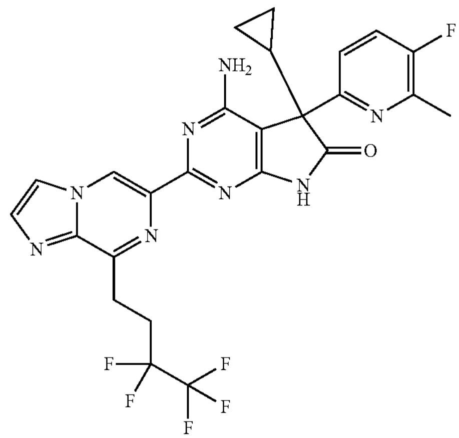 [SMILES: Cc1nc(C2(C3CC3)C(=O)Nc3nc(-c4cn5ccnc5c(CCC(F)(F)C(F)(F)F)n4)nc(N)c32)ccc1F] | 4-amino-5-cyclopropyl-5-(5-fluoro-6-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK IC | 563.2 |
| 364A & B | 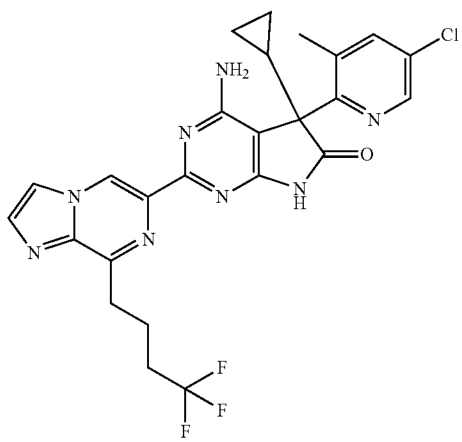 [SMILES: Cc1cc(Cl)cnc1C1(C2CC2)C(=O)Nc2nc(-c3cn4ccnc4c(CCCC(F)(F)F)n3)nc(N)c21] | 4-amino-5-(5-chloro-3-methylpyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | CHIRALPAK IC | 543.3 |
| 365A & B | 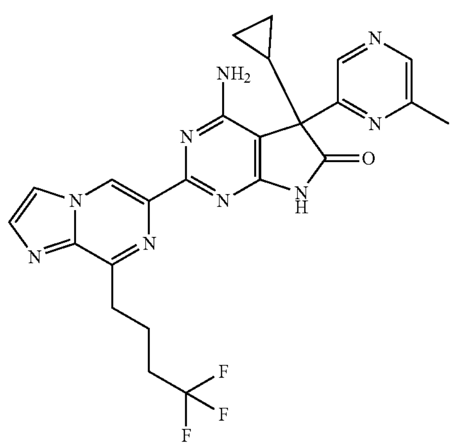 [SMILES: Cc1cncc(C2(C3CC3)C(=O)Nc3nc(-c4cn5ccnc5c(CCCC(F)(F)F)n4)nc(N)c32)n1] | 4-amino-5-cyclopropyl-5-(6-methylpyrazin-2-yl)-2-(8-(4,4,4-trifluorobutyl)imidazo[1,2-a]pyrazin-6-yl)-5H-pyrrolo[2,3-d]pyrimidin-6(7H)-one | CHIRALPAK AD | 510.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 366A & B | 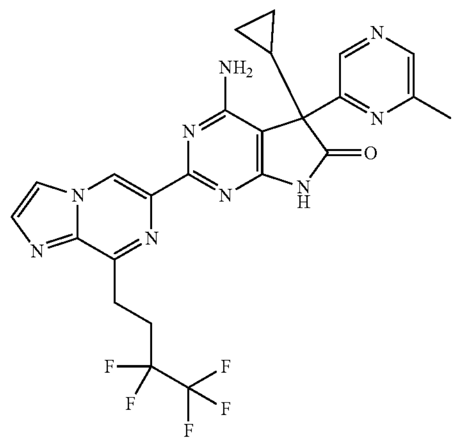 [SMILES: Cc1cncc(C2(C3CC3)C(=O)Nc3nc(-c4cn5ccnc5c(CCC(F)(F)C(F)(F)F)n4)nc(N)c32)n1] | 4-amino-5-cyclopropyl-5-(6-methylpyrazin-2-yl)-2-(8-(3,3,4,4,4-pentafluorobutyl)imidazo[1,2-a]pyrazin-6-yl)-5H-pyrrolo[2,3-d]pyrimidin-6(7H)-one | CHIRALPAK AD | 546.2 |
| 367A & B | 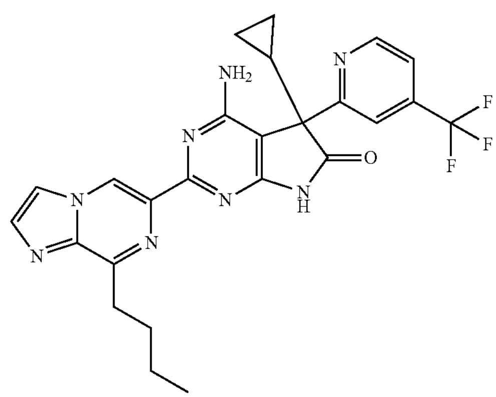 [SMILES: CCCCc1nc(-c2nc(N)c3c(n2)NC(=O)C3(c2cc(C(F)(F)F)ccn2)C2CC2)cn2ccnc12] | 4-amino-2-(8-butylimidazo[1,2-a]pyrazin-6-yl)-5-cyclopropyl-5-(4-(trifluoromethyl)pyridin-2-yl)-5H-pyrrolo[2,3-d]pyrimidin-6(7H)-one | CHIRALPAK AS | 509.3 |
| 368A & B | 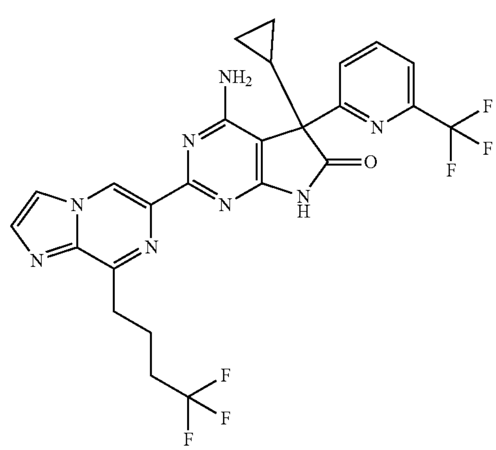 [SMILES: Nc1nc(-c2cn3ccnc3c(CCCC(F)(F)F)n2)nc2c1C(c1cccc(C(F)(F)F)n1)(C1CC1)C(=O)N2] | 4-amino-5-cyclopropyl-2-(8-(4,4,4-trifluorobutyl)imidazo[1,2-a]pyrazin-6-yl)-5-(6-(trifluoromethyl)pyridin-2-yl)-5H-pyrrolo[2,3-d]pyrimidin-6(7H)-one | CHIRALPAK IC | 563.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 369A | 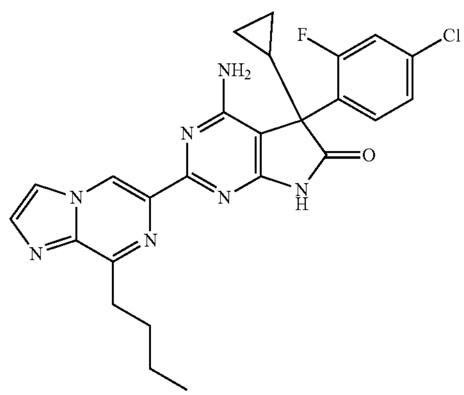 [SMILES: CCCCc1nc(-c2nc(N)c3c(n2)NC(=O)C3(c2ccc(Cl)cc2F)C2CC2)cn2ccnc12] | 4-amino-2-(8-butylimidazo[1,2-a]pyrazin-6-yl)-5-(4-chloro-2-fluorophenyl)-5-cyclopropyl-5H-pyrrolo[2,3-d]pyrimidin-6(7H)-one | I-116A* | 492.1 |
| 370A & B | 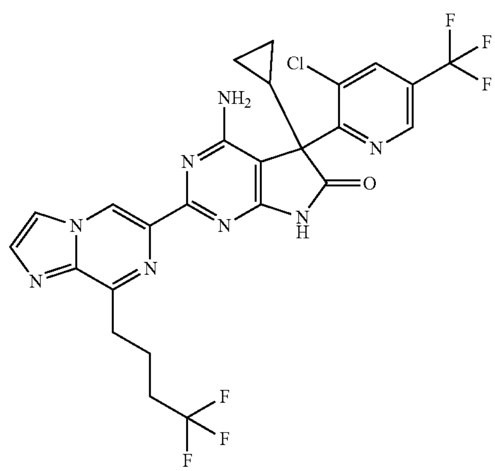 [SMILES: Nc1nc(-c2cn3ccnc3c(CCCC(F)(F)F)n2)nc2c1C(c1ncc(C(F)(F)F)cc1Cl)(C1CC1)C(=O)N2] | 4-amino-5-(3-chloro-5-(trifluoromethyl)pyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | CHIRALPAK IC | 597.2 |
| 371A & B | 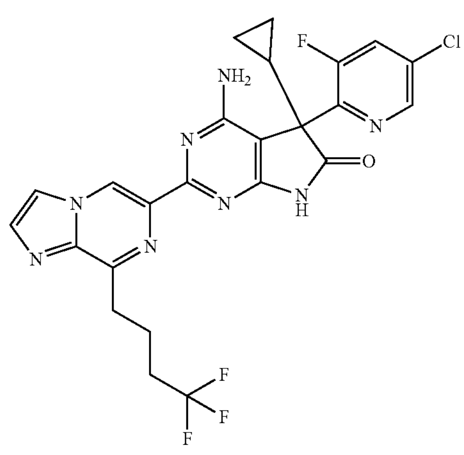 [SMILES: Nc1nc(-c2cn3ccnc3c(CCCC(F)(F)F)n2)nc2c1C(c1ncc(Cl)cc1F)(C1CC1)C(=O)N2] | 4-amino-5-(5-chloro-3-fluoropyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | CHIRALPAK IA | 547.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 372A | 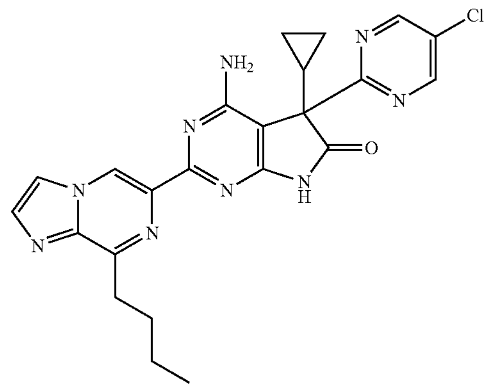 [SMILES: CCCCc1nc(-c2nc(N)c3c(n2)NC(=O)C3(c2ncc(Cl)cn2)C2CC2)cn2ccnc12] | 4-amino-2-(8-butylimidazo[1,2-a]pyrazin-6-yl)-5-(5-chloropyrimidin-2-yl)-5-cyclopropyl-5H-pyrrolo[2,3-d]pyrimidin-6(7H)-one | I-106A | 476.2 |
| 373A | 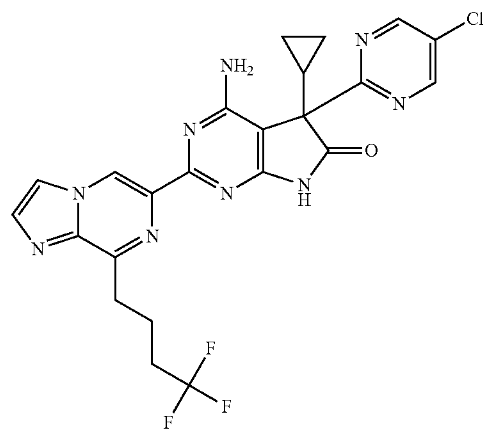 [SMILES: Nc1nc(-c2cn3ccnc3c(CCCC(F)(F)F)n2)nc2c1C(c1ncc(Cl)cn1)(C1CC1)C(=O)N2] | 4-amino-5-(5-chloropyrimidin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | I-106A | 530.4 |
| 374A | 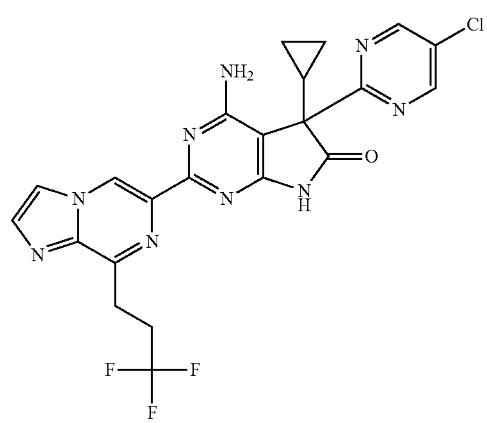 [SMILES: Nc1nc(-c2cn3ccnc3c(CCC(F)(F)F)n2)nc2c1C(c1ncc(Cl)cn1)(C1CC1)C(=O)N2] | 4-amino-5-(5-chloropyrimidin-2-yl)-5-cyclopropyl-2-(8-(3,3,3-trifluoropropyl)imidazo[1,2-a]pyrazin-6-yl)-5H-pyrrolo[2,3-d]pyrimidin-6(7H)-one | I-106A | 516.1 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 375A & B | 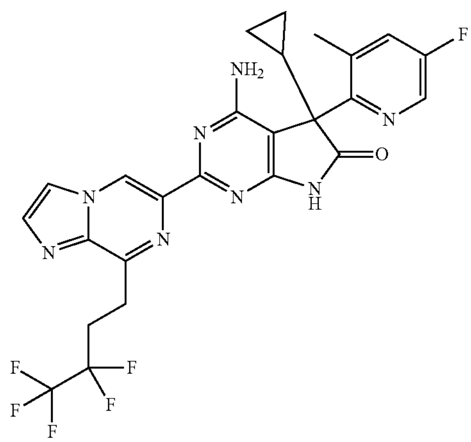 [SMILES: Cc1cc(F)cnc1C1(C2CC2)C(=O)Nc2nc(-c3cn4ccnc4c(CCC(F)(F)C(F)(F)F)n3)nc(N)c21] | 4-amino-5-cyclopropyl-5-(5-fluoro-3-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | Chiralpak IC | 563.2 |
| 376A & B | 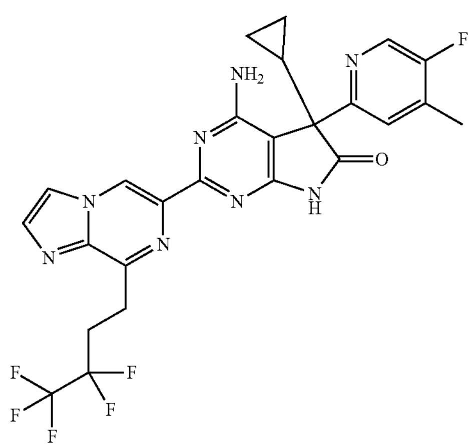 [SMILES: Cc1cc(C2(C3CC3)C(=O)Nc3nc(-c4cn5ccnc5c(CCC(F)(F)C(F)(F)F)n4)nc(N)c32)ncc1F] | 4-amino-5-cyclopropyl-5-(5-fluoro-4-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one | Chiralpak IC-B* | |
| 377A & B | 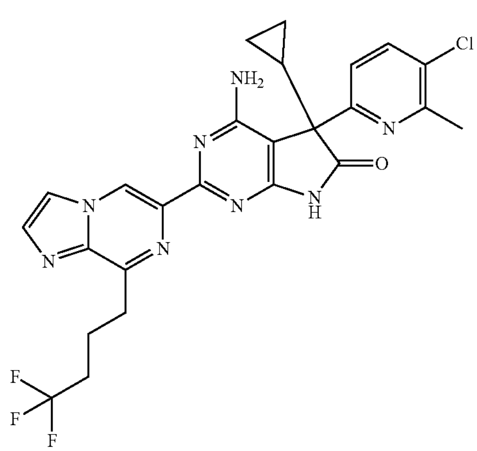 [SMILES: Cc1nc(C2(C3CC3)C(=O)Nc3nc(-c4cn5ccnc5c(CCCC(F)(F)F)n4)nc(N)c32)ccc1Cl] | 4-amino-5-(5-chloro-6-methylpyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one | Chiralpak IC-B* | 543.2 |

TABLE 19-continued

Using similar procedures as described in all the above examples from Examples 1-334, the following compounds in Table 19 were also made.

| Ex. No. | Structure | IUPAC Name | Chiral separation column or Starting Material | MS [M + 1] |
|---|---|---|---|---|
| 378A & B | 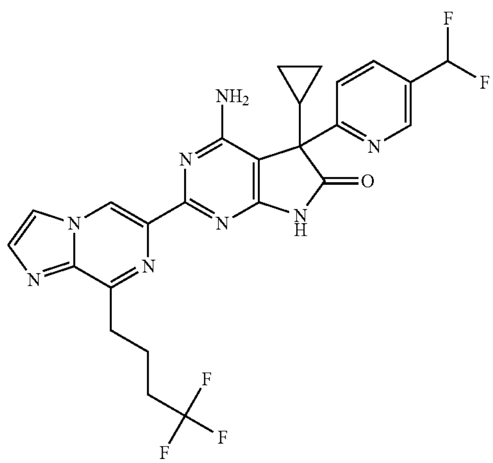 [SMILES: Nc1nc(-c2cn3ccnc3c(CCCC(F)(F)F)n2)nc2c1C(c1ccc(C(F)F)cn1)(C1CC1)C(=O)N2] | 4-amino-5-cyclopropyl-5-(5-(difluoromethyl)pyridin-2-yl)-2-(8-(4,4,4-trifluorobutyl)imidazo[1,2-a]pyrazin-6-yl)-5H-pyrrolo[2,3-d]pyrimidin-6(7H)-one | Chiralpak IA-B* | 545.2 |
| 379A & B | 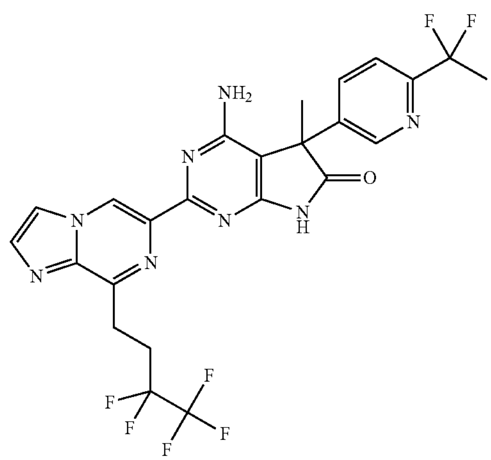 [SMILES: CC(F)(F)c1ccc(C2(C)C(=O)Nc3nc(-c4cn5ccnc5c(CCC(F)(F)C(F)(F)F)n4)nc(N)c32)cn1] | 4-amino-5-(6-(1,1-difluoroethyl)pyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one | Chiralpak IA | 569.1 |
| 380A & B | 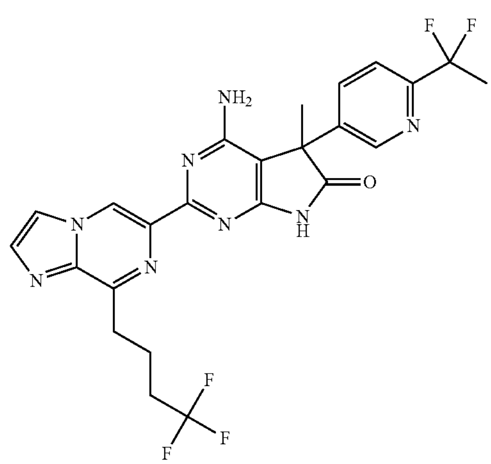 [SMILES: CC(F)(F)c1ccc(C2(C)C(=O)Nc3nc(-c4cn5ccnc5c(CCCC(F)(F)F)n4)nc(N)c32)cn1] | 4-amino-5-(6-(1,1-difluoroethyl)pyridin-3-yl)-5-methyl-2-(8-(4,4,4-trifluorobutyl)imidazo[1,2-a]pyrazin-6-yl)-5H-pyrrolo[2,3-d]pyrimidin-6(7H)-one | Chiralcel ODH | 533.6 |

Example 381A

Methyl 6-[4-amino-5-(4-fluorophenyl)-5-methyl-6-oxo-6,7-dihydro-5H-pyrrolo[2,3-d]pyrimidin-2-yl]-2-methyl-8-(3,3,4,4,4-pentafluorobutyl)imidazo[1,2-a]pyrazine-3-carboxylate

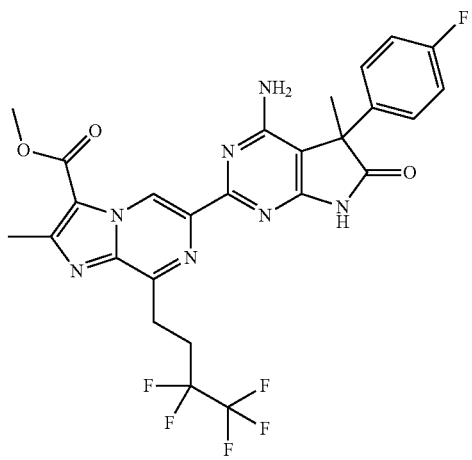 [SMILES: COC(=O)c1c(C)nc2c(CCC(F)(F)C(F)(F)F)nc(-c3nc(N)c4c(n3)NC(=O)C4(C)c3ccc(F)cc3)cn12]

To Ex-274A (28 mg, 0.05 mmol) in methanol (0.5 ml) was slowly bubbled in HCl (gas) over several minutes, saturating the mixture. The reaction was sealed and stirred at room temperature overnight, then increased to 50° C. for 4 h. The reaction was diluted with water, extracted with EtOAc, and the combined organic layers was dried over MgSO₄, filtered and concentrated in vacuo. The crude residue was purified by silica gel chromatography using 10-100% EtOAc/hexanes to afford the title compound. ¹HNMR 500 mHz (d₆-DMSO) δ 11.18 (1H, s), 9.84 (1H, s), 7.30-7.20 (2H, m), 7.18-7.09 (2H, m), 3.91 (3H, s), 3.52-3.38 (2H, m), 2.92-2.75 (2H, m), 2.63 (3H, s), 1.74 (3H, s). m/z=594.0 (M+H).

Example 382B

4-Amino-5-cyclopropyl-2-(8-(3,3,4,4,4-pentafluorobutyl)imidazo[1,2-a]pyrazin-6-yl)-5-(pyridin-2-yl)-5H-pyrrolo[2,3-d]pyrimidin-6(7H)-one

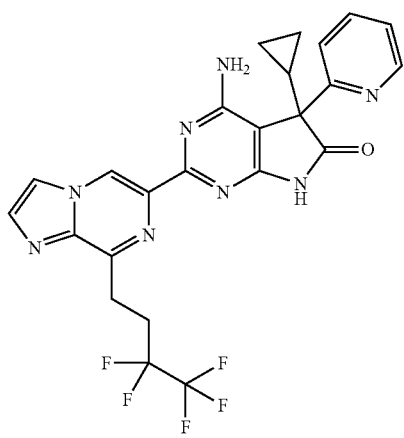 [SMILES: Nc1nc(-c2cn3ccnc3c(CCC(F)(F)C(F)(F)F)n2)nc2c1C(c1ccccn1)(C1CC1)C(=O)N2]

Into a 40-mL vial were placed a sample of Ex-245B, (120 mg, 0.21 mmol), Pd/C (120 mg, 1.13 mmol), ammonium formate (67.0 mg, 1.06 mmol) and MeOH (12 ml). The resulting mixture was stirred at 1 h at 60° C. It was cooled, and the catalyst was filtered off. The filtrate was concentrated, and the residue was purified by silica gel chromatography 10% MeOH/DCM. Further purification by Prep-HPLC on affords the title compound. ¹H NMR (300 MHz, CD3OD): δ 9.40 (1H, s), 8.54 (1H, d, J=4.8 Hz), 8.15 (1H, s), 7.81 (1H, s), 7.80-7.90 (2H, m) 3.55-3.60 (2H, m), 2.80-2.98 (2H, m), 1.84-1.97 (1H, m), 0.51-0.71 (4H, m); LCMS m/z=531.2 (M+1).

Example 383B

4-Amino-5-cyclopropyl-5-(pyridin-2-yl)-2-(8-(4,4,4-trifluorobutyl)imidazo[1,2-a]pyrazin-6-yl)-5H-pyrrolo[2,3-d]pyrimidin-6(7H)-one

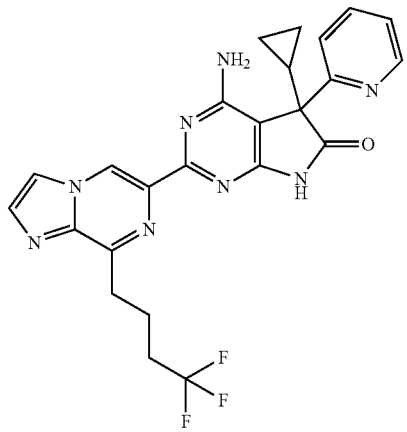 [SMILES: Nc1nc(-c2cn3ccnc3c(CCCC(F)(F)F)n2)nc2c1C(c1ccccn1)(C1CC1)C(=O)N2]

Using method similarly described for Ex-382B, the title compound was made from Ex-218B. ¹H NMR (300 MHz, CD3OD): δ 9.31 (1H, s), 8.55 (1H, d, J=4.8 Hz), 8.08 (1H, s), 7.75-7.88 (2H, m), 7.32 (1H, m), 3.20-3.30 (2H, m), 2.25-2.38 (2H, m), 2.10-2.21 (2H, m), 1.90 (1H, m), 0.50-0.71 (4H, m); LCMS m/z=495.4 (M+1).

Biological Assay 1: Cell-Based sGC Functional Assay (CASA Assay)

Rationale sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for 2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in LN2. On the day of the assay, cells thawed and resuspended in EBSS Assay Buffer (Sigma, E3024) supplemented with 5 mM $MgCl_2$, 10 mM HEPES (4-(2-hydroxyethyl)piperazine-1-ethanesulfonic acid) and 0.05% BSA (bovine serum albumin) (EAB) and cell density was then adjusted to 4×105/mL with EAR IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were incubated with compounds in the presence and absence of 1 μM of Diethylenetriamine/nitric oxide adduct (DETA-NO; Sigma, 17018) for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation.) of the published sGC-HDA Compound A:

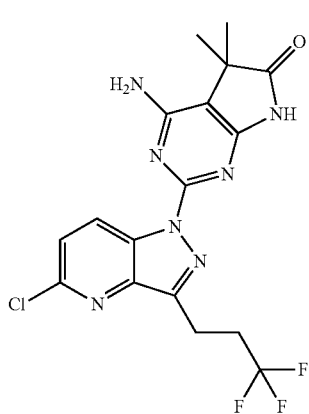

Compound A (Example 1 in WO 2010/065275, published Jun. 10, 2010). The test compounds' activities were then expressed as a percentage of Compound A, the standard in every experiment. This percent activation was calculated either in the presence or absence of DETA-NO which was then plotted. IP and maximum fold induction was derived using ADA analysis software for 4P fit.

The compounds in the Examples of the instant invention had inflection points (IP) less than or equal to 10 μM and more particularly less than or equal to about 1 μM. Most preferred compounds had an IP of less than or equal to about 500 nM. Data for the compounds of the Examples is provided in Table 20.

TABLE 20

| EX | IP (nM) | % Act. |
|---|---|---|
| 1A | 894 | 124 |
| 2A | 105 | 74 |
| 3A | 19 | 139 |

TABLE 20-continued

| EX | IP (nM) | % Act. |
|---|---|---|
| 4A | 32 | 123 |
| 5A | 849 | 109 |
| 6A | 559 | 115 |
| 7A | 583 | 63 |
| 8A | 45 | 137 |
| 9A | 60 | 134 |
| 10A | 56 | 120 |
| 11B | 46 | 135 |
| 12A | 53 | 142 |
| 13A | 42 | 114 |
| 14A | 111 | 113 |
| 15A | 82 | 119 |
| 16B | 134 | 117 |
| 17A | 157 | 124 |
| 18B | 145 | 106 |
| 19A | 387 | 113 |
| 20A | 231 | 108 |
| 21A | 197 | 95 |
| 22B | 150 | 91 |
| 23B | 257 | 96 |
| 24A | 410 | 104 |
| 25A | 324 | 87 |
| 26B | 253 | 81 |
| 27B | 441 | 85 |
| 28A | 652 | 82 |
| 29A | 299 | 102 |
| 30A | 358 | 113 |
| 31A | 46 | 141 |
| 32A | 58 | 137 |
| 33A | 129 | 135 |
| 34A | 339 | 150 |
| 35A | 16 | 129 |
| 36A | 304 | 151 |
| 36B | 959 | 154 |
| 38B | 7 | 103 |
| 38A | 61 | 124 |
| 40B | 27 | 127 |
| 40A | 53 | 138 |
| 42B | 32 | 103 |
| 43A | 182 | 86 |
| 44B | 286 | 88 |
| 45A | 668 | 86 |
| 45B | 217 | 75 |
| 46A | 570 | 124 |
| 47B | 735 | 118 |
| 48B | 442 | 93 |
| 50B | 829 | 86 |
| 51A | 890 | 93 |
| 52A | 950 | 93 |
| 53A | 132 | 104 |
| 54A | 144 | 91 |
| 55A | 634 | 93 |
| 56B | 772 | 89 |
| 57A | 920 | 101 |
| 58A | 636 | 93 |
| 59A | 67 | 97 |
| 60A | 88 | 41 |
| 61A | 424 | 95 |
| 61B | 450 | 83 |
| 63A | 109 | 99 |
| 64A | 196 | 115 |
| 65A | 256 | 108 |
| 66A | 252 | 127 |
| 67A | 746 | 120 |
| 68A | 37 | 112 |
| 69B | 9 | 116 |
| 70 | 21 | 109 |
| 71 | 44 | 109 |
| 72 | 342 | 126 |
| 73 | 44 | 111 |
| 74 | 138 | 94 |
| 75 | 862 | 99 |
| 76 | 91 | 119 |
| 77B | 30 | 176 |
| 77A | 90 | 151 |
| 79 | 36 | 112 |
| 80A | 66 | 125 |
| 80B | 253 | 88 |

TABLE 20-continued

| EX | IP (nM) | % Act. |
|---|---|---|
| 82A | 90 | 120 |
| 82B | 473 | 114 |
| 84A | 58 | 90 |
| 84B | 180 | 100 |
| 86B | 201 | 102 |
| 87 | 399 | 54 |
| 88B | 224 | 79 |
| 89A | 4 | 141 |
| 90A | 32 | 122 |
| 90B | 140 | 129 |
| 92A | 9 | 97 |
| 93A | 12 | 109 |
| 94A | 5 | 108 |
| 95A | 4 | 109 |
| 96A | 4 | 106 |
| 97A | 5 | 145 |
| 98A | 13 | 110 |
| 99A | 11 | 119 |
| 100B | 13 | 96 |
| 101B | 34 | 116 |
| 102B | 15 | 89 |
| 103B | 18 | 85 |
| 104A | 396 | 132 |
| 105A | 384 | 102 |
| 106A | 252 | 83 |
| 107A | 86 | 171 |
| 108A | 12 | 121 |
| 108B | 16 | 79 |
| 110A | 51 | 154 |
| 110B | 11 | 151 |
| 112A | 289 | 89 |
| 113B | 5 | 138 |
| 114A | 57 | 94 |
| 115B | 14 | 111 |
| 116A | 10 | 79 |
| 117A | 33 | 103 |
| 118A | 33 | 76 |
| 119B | 161 | 121 |
| 120A | 31 | 112 |
| 121A | 56 | 145 |
| 122B | 92 | 119 |
| 123A | 61 | 105 |
| 124B | 34 | 103 |
| 125A | 41 | 97 |
| 126B | 242 | 160 |
| 127A | 518 | 105 |
| 128B | 164 | 108 |
| 129A | 107 | 94 |
| 130A | 324 | 119 |
| 131B | 178 | 88 |
| 132B | 949 | 99 |
| 133A | 37 | 129 |
| 134A | 627 | 118 |
| 135A | 57 | 148 |
| 136A | 77 | 129 |
| 137B | 135 | 108 |
| 138A | 369 | 151 |
| 139A | 222 | 118 |
| 140B | 217 | 107 |
| 141B | 236 | 112 |
| 142B | 667 | 166 |
| 143B | 252 | 78 |
| 144A | 400 | 117 |
| 145A | 385 | 96 |
| 146B | 461 | 95 |
| 147A | 12 | 120 |
| 148A | 24 | 148 |
| 149A | 22 | 111 |
| 150A | 29 | 122 |
| 151A | 19 | 106 |
| 152A | 43 | 129 |
| 153A | 37 | 110 |
| 154A | 85 | 120 |
| 155A | 130 | 112 |
| 156A | 163 | 92 |
| 157A | 227 | 90 |
| 158B | 296 | 109 |
| 159A | 552 | 103 |
| 160B | 978 | 102 |
| 161A | 354 | 76 |
| 162B | 168 | 88 |
| 163B | 230 | 84 |
| 164B | 81 | 93 |
| 165B | 43 | 81 |
| 166B | 120 | 94 |
| 167B | 41 | 99 |
| 168A | 150 | 97 |
| 169A | 19 | 75 |
| 170A | 57 | 104 |
| 171A | 80 | 126 |
| 172A | 637 | 124 |
| 173B | 156 | 92 |
| 174A | 107 | 139 |
| 175B | 501 | 88 |
| 176A | 79 | 107 |
| 177A | 129 | 107 |
| 178B | 17 | 106 |
| 179A | 45 | 129 |
| 180A | 39 | 115 |
| 181A | 56 | 132 |
| 182A | 55 | 120 |
| 183B | 61 | 113 |
| 184A | 176 | 134 |
| 185A | 235 | 132 |
| 186A | 207 | 129 |
| 187A | 1072 | 126 |
| 188B | 304 | 154 |
| 189B | 211 | 143 |
| 190A | 114 | 90 |
| 191A | 130 | 90 |
| 192B | 923 | 168 |
| 193B | 355 | 111 |
| 194B | 268 | 116 |
| 195B | 312 | 114 |
| 196B | 267 | 106 |
| 197A | 163 | 66 |
| 198B | 492 | 112 |
| 199A | 544 | 101 |
| 200A | 457 | 96 |
| 201A | 928 | 140 |
| 202B | 870 | 91 |
| 203B | 1174 | 115 |
| 204B | 14 | 110 |
| 205B | 20 | 127 |
| 206A | 21 | 116 |
| 207B | 44 | 121 |
| 208A | 36 | 88 |
| 209B | 49 | 111 |
| 210B | 40 | 97 |
| 211A | 75 | 122 |
| 212B | 87 | 83 |
| 213B | 100 | 89 |
| 214A | 247 | 92 |
| 215A | 351 | 107 |
| 216A | 146 | 77 |
| 217A | 288 | 82 |
| 218B | 253 | 126 |
| 219A | 53 | 124 |
| 220B | 409 | 100 |
| 221A | 496 | 107 |
| 222B | 578 | 121 |
| 223A | 177 | 84 |
| 224A | 153 | 77 |
| 225A | 166 | 82 |
| 226A | 287 | 124 |
| 227B | 249 | 111 |
| 228A | 20 | 108 |
| 229B | 26 | 122 |
| 230B | 32 | 117 |
| 231A | 50 | 156 |
| 232B | 17 | 60 |
| 233B | 43 | 131 |
| 234B | 27 | 105 |
| 235B | 36 | 148 |
| 236B | 35 | 91 |
| 237B | 53 | 119 |

TABLE 20-continued

| EX | IP (nM) | % Act. |
| --- | --- | --- |
| 238A | 71 | 131 |
| 239A | 53 | 97 |
| 240B | 53 | 105 |
| 241B | 58 | 99 |
| 242B | 127 | 133 |
| 243B | 208 | 106 |
| 244B | 81 | 109 |
| 245B | 77 | 118 |
| 246B | 128 | 114 |
| 247B | 152 | 117 |
| 248B | 82 | 88 |
| 249A | 759 | 96 |
| 250B | 169 | 87 |
| 251B | 100 | 85 |
| 252B | 175 | 121 |
| 253B | 51 | 83 |
| 254A | 57 | 126 |
| 255A | 32 | 142 |
| 256B | 24 | 86 |
| 257 | 614 | 146 |
| 258A | 89 | 116 |
| 259B | 112 | 99 |
| 260A | 504 | 90 |
| 261A | 822 | 116 |
| 262B | 236 | 105 |
| 263 | 314 | 20 |
| 264A | 239 | 123 |
| 265B | 648 | 121 |
| 266A | 141 | 101 |
| 267A | 212 | 91 |
| 268B | 338 | 79 |
| 269A | 5087 | 198 |
| 270B | 319 | 101 |
| 271B | 622 | 95 |
| 272 | 367 | 114 |
| 273A | 61 | 81 |
| 274A | 238 | 100 |
| 275A | 89 | 98 |
| 276A | 22 | 80 |
| 277A | 469 | 106 |
| 278A | 181 | 115 |
| 279A | 58 | 69 |
| 280A | 124 | 102 |
| 281A | 102 | 120 |
| 282A | 197 | 153 |
| 283A | 56 | 163 |
| 284A | 102 | 120 |
| 285A | 20 | 130 |
| 286A | 124 | 83 |
| 287A | 376 | 133 |
| 288A | 12 | 119 |
| 289A | 289 | 106 |
| 290B | 280 | 106 |
| 291B | 786 | 126 |
| 292B | 951 | 148 |
| 293B | 509 | 107 |
| 294B | 444 | 89 |
| 295B | 671 | 96 |
| 296A | 142 | 77 |
| 297A | 466 | 101 |
| 298A | 121 | 114 |
| 299A | 624 | 114 |
| 300A | 492 | 136 |
| 301A | 317 | 116 |
| 302A | 551 | 105 |
| 303A | 425 | 101 |
| 304A | 415 | 89 |
| 305A | 147 | 158 |
| 306A | 108 | 108 |
| 307A | 152 | 93 |
| 308A | 281 | 126 |
| 309A | 39 | 97 |
| 310A | 45 | 77 |
| 311A | 29 | 92 |
| 312A | 25 | 93 |
| 313 | 25 | 93 |
| 314B | 434 | 104 |
| 315A | 119 | 113 |
| 316B | 29 | 156 |
| 317A | 75 | 156 |
| 318A | 2178 | 127 |
| 319B | 262 | 161 |
| 320B | 85 | 204 |
| 321B | 237 | 126 |
| 322A | 119 | 113 |
| 323B | 29 | 156 |
| 324A | 75 | 156 |
| 325A | 1206 | 83 |
| 326A | 2178 | 127 |
| 327A | 134 | 112 |
| 328A | 1039 | 106 |
| 329A | 16 | 93 |
| 330A | 22 | 142 |
| 331B | 1313 | 157 |
| 332B | 30 | 141 |
| 333B | 84 | 81 |
| 334A | 278 | 111 |
| 335A | 303 | 140 |
| 336B | 22 | 131 |
| 337A | 486 | 189 |
| 338A | 178 | 158 |
| 339A | 122 | 325 |
| 340A | 808 | 129 |
| 341A | 2098 | 106 |
| 342B | 695 | 177 |
| 343A | 46 | 121 |
| 344B | 51 | 163 |
| 345B | 949 | 148 |
| 346A | 65 | 132 |
| 347A | 131 | 107 |
| 348B | 1552* | 175 |
| 349A | 213 | 107 |
| 350B | 105 | 239 |
| 351B | 985 | 182 |
| 352B | 302 | 96 |
| 353B | 1032 | 168 |
| 354B | 170 | 137 |
| 355A | 202 | 126 |
| 356B | 487 | 108 |
| 357B | 680 | 113 |
| 358B | 20 | 120 |
| 359B | 302 | 108 |
| 360A | 43 | 129 |
| 361B | 47 | 157 |
| 362B | 384 | 140 |
| 363B | 244 | 186 |
| 364A | 273 | 138 |
| 365B | 704 | 108 |
| 366B | 843 | 122 |
| 367B | 155 | 170 |
| 368B | 148 | 151 |
| 369A | 13 | 109 |
| 370B | 262 | 99 |
| 371A | 194 | 82 |
| 372A | 239 | 187 |
| 373A | 26 | 114 |
| 374A | 387 | 126 |
| 375B | 931 | 41 |
| 376B | 180 | 127 |
| 377B | 86 | 90 |
| 378B | 373 | 92 |
| 379A | 152 | 87 |
| 380B | 35 | 181 |
| 381B | 1694 | 92 |
| 382B | 453 | 149 |
| 383B | 98 | 137 |

Acute Efficacy in Spontaneously Hypertensive Rats (SHR)

Spontaneously hypertensive rats (SHR, male, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following representative compounds are provided. Category A=SBP in SHRs<20 mmHg; Category B=SBP in SHRs 20-40 mmHg; Category C=SBP in SHRs>40 mmHg

| Ex. | Dose, P.O. mpk | Cat. |
|---|---|---|
| 1A | 1.0 | B |
| 2A | 1.0 | C |
| 8A | 0.3 | C |
| 10A | 0.3 | C |
| 11B | 1.0 | B |
| 14A | 1.0 | C |
| 15A | 1.0 | C |
| 16B | 0.3 | C |
| 20A | 1.0 | C |
| 26B | 3.0 | B |
| 29A | 3.0 | B |
| 30A | 3.0 | C |
| 32A | 1.0 | B |
| 33A | 1.0 | B |
| 34A | 3.0 | B |
| 38B | 0.3 | B |
| 39A | 0.3 | A |
| 53A | 3.0 | C |
| 59A | 1.0 | A |
| 60A | 1.0 | A |
| 61A | 3.0 | B |
| 68A | 0.3 | C |
| 69B | 0.3 | C |
| 70 | 0.3 | B |
| 71 | 1.0 | C |
| 76 | 1.0 | B |
| 86B | 3.0 | A |
| 90A | 0.3 | C |
| 100B | 0.3 | A |
| 112A | 3.0 | B |
| 114A | 0.3 | C |
| 115B | 0.3 | C |
| 118A | 0.3 | C |
| 124B | 0.3 | B |
| 129A | 1.0 | B |
| 131B | 1.0 | B |
| 132B | 3.0 | B |
| 134A | 3.0 | B |
| 135A | 1.0 | B |
| 136A | 1.0 | B |
| 137B | 1.0 | B |
| 138A | 3.0 | B |
| 139A | 3.0 | C |
| 140B | 0.3 | B |
| 141B | 3.0 | B |
| 143B | 3.0 | B |
| 144A | 1.0 | B |
| 154A | 1.0 | A |
| 157A | 3.0 | B |
| 159A | 3.0 | A |

-continued

| Ex. | Dose, P.O. mpk | Cat. |
|---|---|---|
| 166B | 1.0 | A |
| 168A | 1.0 | B |
| 170A | 1.0 | B |
| 171A | 1.0 | B |
| 172A | 3.0 | B |
| 173B | 1.0 | B |
| 174A | 1.0 | B |
| 175B | 1.0 | A |
| 176A | 1.0 | B |
| 178B | 0.3 | B |
| 179A | 1.0 | C |
| 181A | 1.0 | B |
| 182A | 1.0 | B |
| 183B | 1.0 | B |
| 184A | 1.0 | B |
| 185A | 3.0 | C |
| 186A | 1.0 | B |
| 188B | 3.0 | B |
| 189B | 3.0 | B |
| 190A | 3.0 | C |
| 193B | 3.0 | B |
| 194B | 3.0 | C |
| 197A | 3.0 | B |
| 198B | 1.0 | B |
| 199A | 3.0 | B |
| 201A | 3.0 | C |
| 202B | 3.0 | B |
| 205B | 0.3 | C |
| 207B | 0.3 | B |
| 208A | 0.3 | C |
| 209B | 0.3 | B |
| 250A | 3.0 | A |
| 251B | 3.0 | B |
| 253B | 1.0 | A |
| 210B | 0.3 | A |
| 211A | 0.3 | A |
| 213B | 0.3 | B |
| 214A | 1.0 | B |
| 215A | 0.3 | B |
| 216A | 1.0 | B |
| 217A | 1.0 | C |
| 218B | 1.0 | C |
| 219A | 1.0 | B |
| 220B | 3.0 | A |
| 221A | 1.0 | A |
| 222B | 3.0 | B |
| 223A | 1.0 | B |
| 225A | 1.0 | A |
| 228A | 0.3 | B |
| 231A | 0.3 | A |
| 232B | 1.0 | C |
| 233B | 0.3 | B |
| 234B | 0.3 | A |
| 235B | 0.3 | B |
| 238A | 0.3 | C |
| 239A | 0.3 | B |
| 240B | 1.0 | A |
| 243B | 1.0 | A |
| 244B | 3.0 | C |
| 245B | 1.0 | C |
| 246B | 1.0 | B |
| 247B | 0.3 | A |
| 249A | 3.0 | B |
| 254A | 1.0 | C |
| 255A | 1.0 | C |
| 264A | 1.0 | A |
| 278A | 2.0 | B |
| 286A | 3.0 | A |
| 290B | 3.0 | B |
| 311A | 0.3 | A |
| 314B | 3.0 | B |
| 315A | 3.0 | B |
| 316B | 0.3 | B |
| 317A | 0.1 | B |
| 318A | 2.0 | A |
| 319B | 3.0 | B |
| 327A | 1.0 | A |

-continued

| Ex. | Dose, P.O. mpk | Cat. |
|---|---|---|
| 328A | 3.0 | A |
| 329A | 0.3 | B |
| 330A | 0.3 | B |
| 331B | 3.0 | B |
| 332B | 0.3 | B |
| 333B | 2.0 | B |
| 334A | 3.0 | A |
| 335A | 3.0 | B |
| 336B | 0.3 | B |
| 338A | 2.0 | B |
| 339A | 0.3 | B |
| 342B | 1.0 | A |
| 344B | 0.3 | A |
| 345B | 3.0 | A |
| 346A | 1.0 | B |
| 347A | 1.0 | B |
| 349A | 2.0 | B |
| 353B | 3.0 | A |
| 354B | 1.0 | A |
| 355A | 1.0 | A |
| 356B | 3.0 | A |
| 360A | 3.0 | B |
| 369A | 0.3 | B |
| 372A | 1.0 | C |
| 373A | 0.3 | A |
| 378B | 1.0 | B |
| 383B | 1.0 | B |

What is claimed is:

1. A compound having structural Formula I:

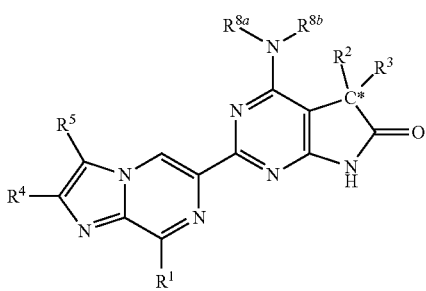

or a pharmaceutically acceptable salt thereof wherein:
C* indicates a potential chiral carbon atom;
$R^1$ is
  (1) hydrogen,
  (2) $(C_{1-6})$alkyl,
  (3) halo$(C_{1-6})$alkyl,
  (4) $(C_{1-6})$alkyl-$(C_{3-7})$cycloalkyl,
  (5) $(C_{1-6})$alkyl-aryl, wherein aryl is unsubstituted or substituted by cyano, $(C_{3-6})$cycloalkyl, $(C_{1-6})$alkoxy, or one to three halo,
  (6) aryl unsubstituted or substituted by cyano, $(C_{3-6})$cycloalkyl, $(C_{1-6})$alkoxy, or one to three halo, or
  (7) $(C_{3-6})$cycloalkyl;
$R^2$ is
  (1) $(C_{1-6})$alkyl,
  (2) $(C_{1-6})$alkoxy, or
  (3) $(C_{3-7})$cycloalkyl;
$R^3$ is
  (1) $(C_{1-6})$alkyl,
  (2) $(C_{3-6})$cycloalkyl,
  (3) $CO_2(C_{1-6})$alkyl,
  (4) $CONR^{6a}R^{6b}$,
  (5) —N(H)C(O)$(C_{1-6})$alkyl,
  (6) —N(H)$(C_{1-6})$alkyl,
  (7) aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo,
  (8) five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo, or
  (9) $(C_{2-6})$alkynyl;
$R^4$ is
  (1) hydrogen,
  (2) $(C_{1-6})$alkyl,
  (3) halo$(C_{1-6})$alkyl,
  (4) halo$(C_{1-6})$alkoxy,
  (5) $(C_{1-6})$alkoxy,
  (6) $(C_{3-7})$cycloalkyl, or
  (7) cyano;
$R^5$ is
  (1) hydrogen,
  (2) $(C_{1-6})$alkyl,
  (3) halo$(C_{1-6})$alkyl,
  (4) halo,
  (5) amino,
  (6) $(C_{1-3})$alkyl-aryl,
  (7) $(C_{1-3})$alkyl-$(C_{3-6})$cycloalkyl, or
  (8) cyano;
each $R^{6a}$ and $R^{6b}$ are independently
  (1) hydrogen,
  (2) $(C_{1-3})$alkyl, or
  (3) $(C_{3-6})$cycloalkyl;
$R^{8a}$ and $R^{8b}$ are independently
  (1) hydrogen,
  (2) $(C_{1-6})$alkyl,
  (3) halo$(C_{1-6})$alkyl,
  (4) $(C_{1-6})$alkyl-C(O)—O—$(C_{1-6})$alkyl,
  (5) $(C_{3-6})$cycloalkyl, unsubstituted or substituted by halo, or
  (6) $(C_{1-3})$alkyl-$(C_{3-6})$cycloalkyl;
or $R^{8a}$ and $R^{8b}$ along with the nitrogen atom to which they are attached cyclize to form a 4- to 6-membered heterocyclyl containing one or two heteroatoms independently selected from N, O and S, wherein the heterocyclyl is unsubstituted or substituted by one to three $R^9$; and
$R^9$ is
  (1) $(C_{1-3})$alkyl,
  (2) halo,
  (3) halo$(C_{1-3})$alkyl,
  (4) $(C_{3-6})$cycloalkyl, or
  (5) —S(O)$_2$—$(C_{1-3})$alkyl.

2. A compound having structural Formula II:

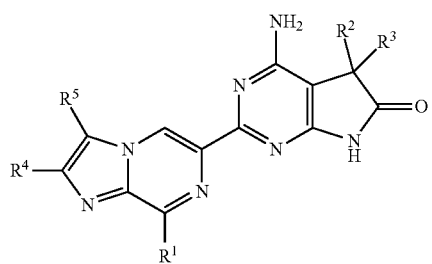

or a pharmaceutically acceptable salt thereof wherein R¹ is
(1) hydrogen,
(2) $(C_{1-6})$alkyl,
(3) halo$(C_{1-6})$alkyl,
(4) $(C_{1-6})$alkyl-$(C_{3-7})$cycloalkyl,
(5) $(C_{1-6})$alkyl-aryl, wherein aryl is unsubstituted or substituted by cyano, $(C_{3-6})$cycloalkyl, $(C_{1-6})$alkoxy, or one to three halo,
(6) aryl unsubstituted or substituted by cyano, $(C_{3-6})$cycloalkyl, $(C_{1-6})$alkoxy, or one to three halo, or
(7) $(C_{3-6})$cycloalkyl;
R² is
(1) $(C_{1-6})$alkyl,
(2) $(C_{1-6})$alkoxy, or
(3) $(C_{3-7})$cycloalkyl;
R³ is
(1) $(C_{1-6})$alkyl,
(2) $(C_{3-6})$cycloalkyl,
(3) $CO_2(C_{1-6})$alkyl,
(4) $CONR^{6a}R^{6b}$,
(5) —N(H)C(O)$(C_{1-6})$alkyl,
(6) —N(H)$(C_{1-6})$alkyl,
(7) aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo,
(8) five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo, or
(9) $(C_{2-6})$alkynyl,
R⁴ is
(1) hydrogen,
(2) $(C_{1-6})$alkyl,
(3) halo$(C_{1-6})$alkyl,
(4) halo$(C_{1-6})$alkoxy,
(5) $(C_{1-6})$alkoxy,
(6) $(C_{3-7})$cycloalkyl, or
(7) cyano;
R⁵ is
(1) hydrogen,
(2) $(C_{1-6})$alkyl,
(3) halo$(C_{1-6})$alkyl,
(4) halo,
(5) amino,
(6) $(C_{1-3})$alkyl-aryl,
(7) $(C_{1-3})$alkyl-$(C_{3-6})$cycloalkyl, or
(8) cyano; and
each $R^{6a}$ and $R^{6b}$ are independently
(1) hydrogen,
(2) $(C_{1-3})$alkyl, or
(3) $(C_{3-6})$cycloalkyl.

3. The compound of claim 1 or a pharmaceutically acceptable salt thereof wherein: R³ is $(C_{1-3})$alkyl, $(C_{3-6})$cycloalkyl, $(C_{2-6})$alkynyl or $CONR^{6a}R^{6b}$.

4. The compound of claim 3 or a pharmaceutically acceptable salt thereof wherein: R³ is

, or

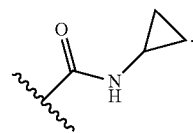.

5. The compound of claim 3 or a pharmaceutically acceptable salt thereof wherein: R² is methyl, ethyl, isopropyl or cyclopropyl.

6. The compound of claim 4 or a pharmaceutically acceptable salt thereof wherein:

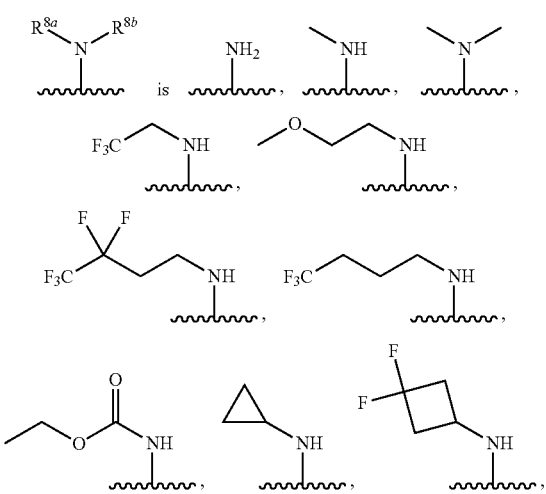

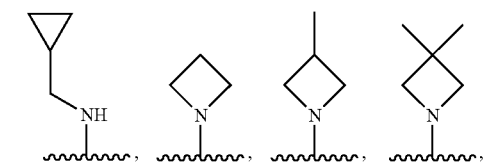

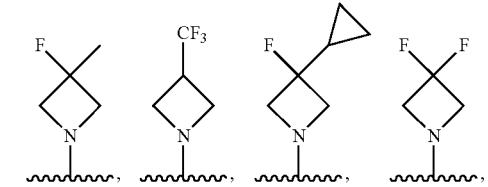

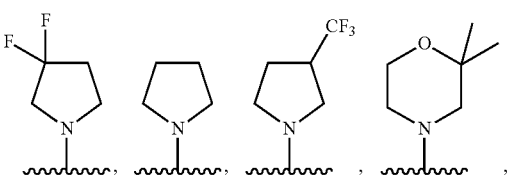

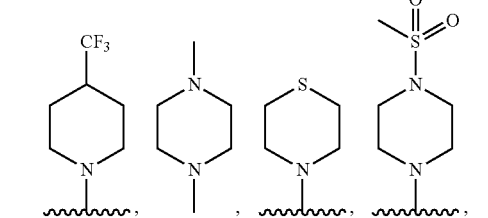

-continued

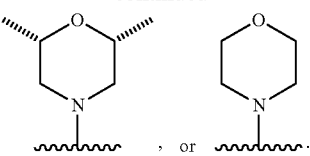, or

7. The compound of claim 1 or a pharmaceutically acceptable salt thereof wherein $R^3$ is aryl unsubstituted or substituted by $(C_{1-6})$alkyl, halo$(C_{1-3})$alkyl, $(C_{1-6})$alkoxy, halo$(C_{1-6})$alkoxy, $(C_{3-6})$cycloalkyl, $CO_2(C_{1-6})$alkyl, $CONR^{6a}R^{6b}$, or one to three halo; or five- or six-membered heteroaryl containing one to three N, O or S heteroatoms, wherein heteroaryl is unsubstituted or substituted by one to two $(C_{1-6})$alkyl, halo$(C_{1-6})$alkyl, $(C_{1-6})$alkoxy, halo$(C_{1-6})$alkoxy, $(C_{3-6})$cycloalkyl or halo.

8. The compound of claim 7 or a pharmaceutically acceptable salt thereof wherein $R^3$ is

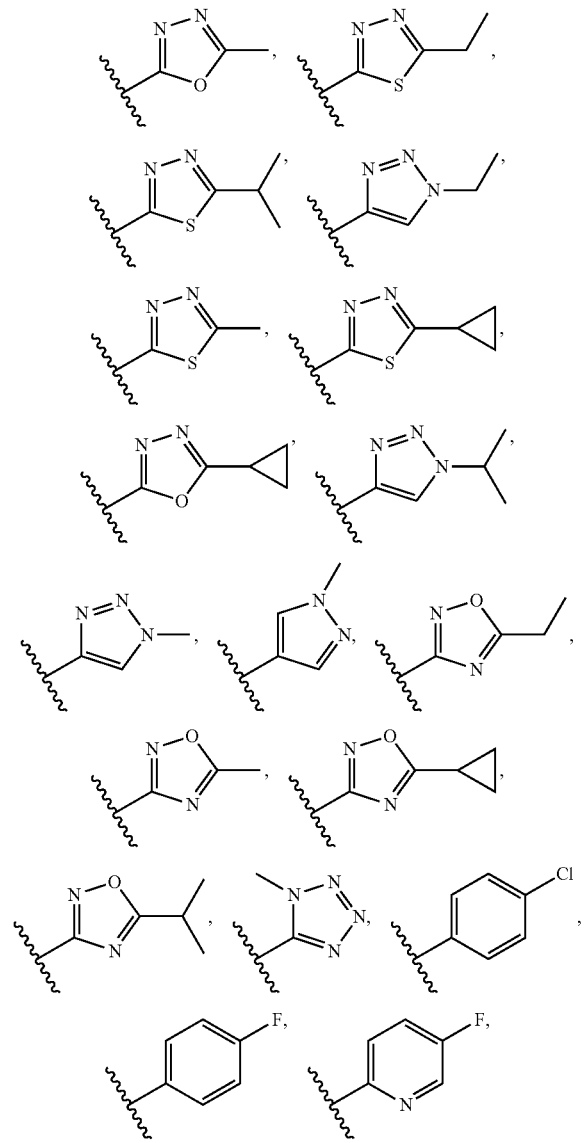

-continued

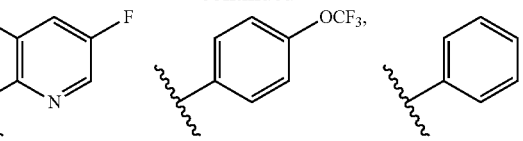

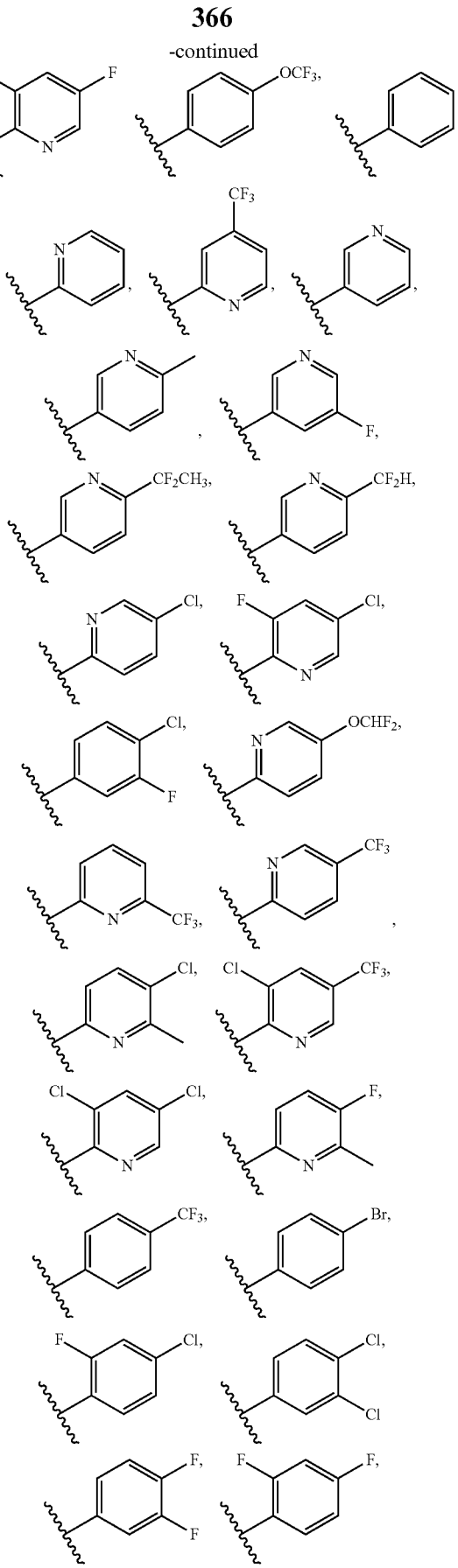

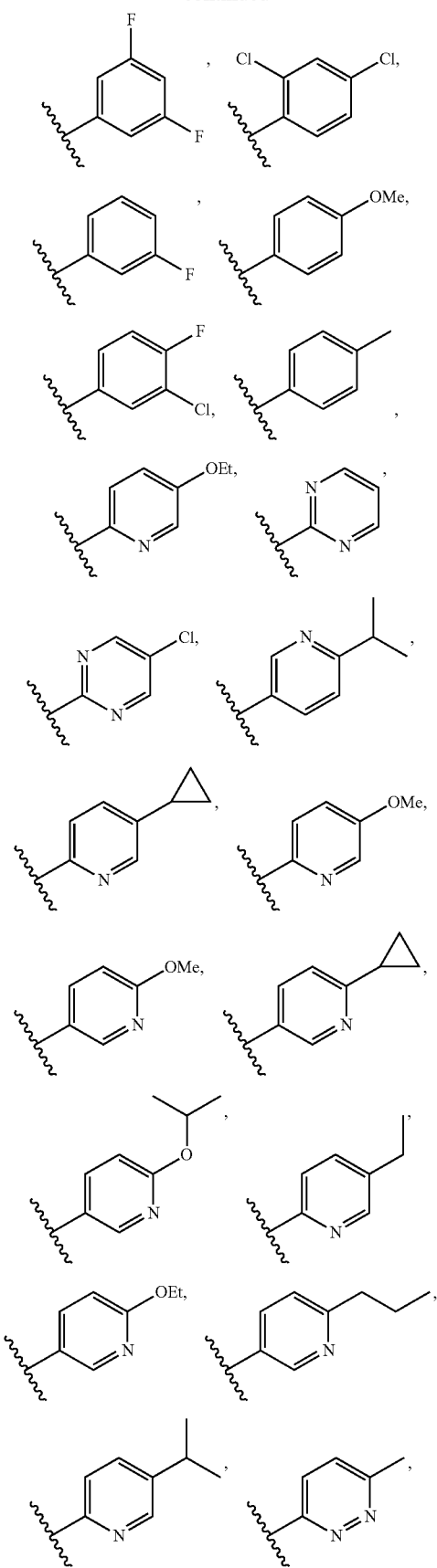

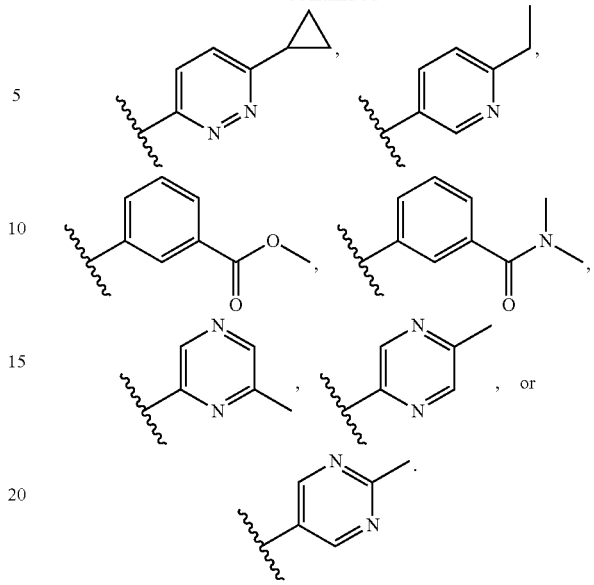

9. The compound of claim 7 or a pharmaceutically acceptable salt thereof wherein: $R^2$ is methyl, ethyl, isopropyl or cyclopropyl.

10. The compound of claim 1 or a pharmaceutically acceptable salt thereof wherein: $R^1$ is $(C_{1-6})$alkyl or halo $(C_{1-6})$alkyl.

11. The compound of claim 10 or a pharmaceutically acceptable salt thereof wherein: $R^2$ is methyl, ethyl, isopropyl or cyclopropyl.

12. The compound of claim 1 or a pharmaceutically acceptable salt thereof wherein: $R^1$ $(C_{1-3})$alkyl-aryl, wherein aryl is unsubstituted or substituted by cyano, $(C_{3-6})$cycloalkyl, $(C_{1-3})$alkoxy, or one to three fluoro.

13. The compound of claim 11 or a pharmaceutically acceptable salt thereof wherein: $R^2$ is methyl, ethyl, isopropyl or cyclopropyl.

14. The compound of claim 1, which is:
4-Amino-5-(4-chlorophenyl)-2-(8-ethylimidazo[1,2-a]pyrazin-6-yl)-5-methyl-5H-pyrrolo[2,3-d]pyrimidin-6(7H)-one;
4-Amino-5-(4-chlorophenyl)-5-methyl-2-(8-propylimidazo[1,2-a]pyrazin-6-yl)-5H-pyrrolo[2,3-d]pyrimidin-6(7H)-one;
4-amino-2-(8-(2-fluorophenethyl)imidazo[1,2-a]pyrazin-6-yl)-5-(4-fluorophenyl)-5-methyl-5H-pyrrolo[2,3-d]pyrimidin-6(7H)-one;
4-amino-2-(8-(3-fluorophenethyl)imidazo[1,2-a]pyrazin-6-yl)-5-(4-fluorophenyl)-5-methyl-5H-pyrrolo[2,3-d]pyrimidin-6(7H)-one;
6-(4-amino-5-(4-4-amino-5-(4-fluorophenyl)-5-methyl-2-(8-(3-phenylpropyl)imidazo[1,2-a]pyrazin-6-yl)-5H-pyrrolo[2,3-d]pyrimidin-6(7H)-one;
4-amino-2-(8-(4-cyclopropylphenyl)imidazo[1,2-a]pyrazin-6-yl)-5-(4-fluorophenyl)-5-methyl-5H-pyrrolo[2,3-d]pyrimidin-6(7H)-one;
4-amino-5-(4-fluorophenyl)-2-(8-(4-methoxyphenyl)imidazo[1,2-a]pyrazin-6-yl)-5-methyl-5H-pyrrolo[2,3-d]pyrimidin-6(7H)-one;
4-amino-2-(8-butylimidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-2-(8-(2-ethylbutyl)imidazo[1,2-a]pyrazin-6-yl)-5-methyl-5H-pyrrolo[2,3-d]pyrimidin-6(7H)-one;

4-amino-2-(8-butylimidazo[1,2-a]pyrazin-6-yl)-5-(4-chlorophenyl)-5-methyl-5H-pyrrolo[2,3-d]pyrimidin-6(7H)-one;

4-amino-5-(5-fluoropyridin-2-yl)-2-(8-isopentylimidazo[1,2-a]pyrazin-6-yl)-5-methyl-5H-pyrrolo[2,3-d]pyrimidin-6(7H)-one;

4-amino-2-(8-(2-cyclohexylethyl)imidazo[1,2-a]pyrazin-6-yl)-5-(4-fluorophenyl)-5-methyl-5H-pyrrolo[2,3-d]pyrimidin-6(7H)-one;

4-amino-2-(8-(2-ethylbutyl)imidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-2-(8-isopentylimidazo[1,2-a]pyrazin-6-yl)-5-methyl-5H-pyrrolo[2,3-d]pyrimidin-6(7H)-one;

4-amino-5-(4-chlorophenyl)-2-(8-cyclobutylimidazo[1,2-a]pyrazin-6-yl)-5-methyl-5H-pyrrolo[2,3-d]pyrimidin-6(7H)-one;

4-amino-2-(8-butylimidazo[1,2-a]pyrazin-6-yl)-5-(5-fluoropyridin-2-yl)-5-methyl-5H-pyrrolo[2,3-d]pyrimidin-6(7H)-one;

4-amino-5-(4-fluorophenyl)-5-methyl-2-(8-propylimidazo[1,2-a]pyrazin-6-yl)-5H-pyrrolo[2,3-d]pyrimidin-6(7H)-one;

4-amino-2-(8-(2-ethylbutyl)imidazo[1,2-a]pyrazin-6-yl)-5-(5-fluoropyridin-2-yl)-5-methyl-5H-pyrrolo[2,3-d]pyrimidin-6(7H)-one;

4-amino-5-(4-fluorophenyl)-2-(8-isobutylimidazo[1,2-a]pyrazin-6-yl)-5-methyl-5H-pyrrolo[2,3-d]pyrimidin-6(7H)-one;

4-amino-5-(4-chlorophenyl)-2-(8-isobutylimidazo[1,2-a]pyrazin-6-yl)-5-methyl-5H-pyrrolo[2,3-d]pyrimidin-6(7H)-one;

4-amino-2-(8-cyclobutylimidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-5-cyclopropyl-2-(8-isobutylimidazo[1,2-a]pyrazin-6-yl)-5H-pyrrolo[2,3-d]pyrimidin-6(7H)-one;

4-amino-2-(8-(5-fluoropyridin-2-yl)-2-(8-isobutylimidazo[1,2-a]pyrazin-6-yl)-5-methyl-5H-pyrrolo[2,3-d]pyrimidin-6(7H)-one;

4-amino-5-methyl-2-(8-propylimidazo[1,2-a]pyrazin-6-yl)-5-(4-(trifluoromethoxy)phenyl)-5H-pyrrolo[2,3-d]pyrimidin-6(7H)-one;

4-amino-2-(8-isobutylimidazo[1,2-a]pyrazin-6-yl)-5-methyl-5-(4-(trifluoromethoxy)phenyl)-5H-pyrrolo[2,3-d]pyrimidin-6(7H)-one;

4-amino-5-(4-chlorophenyl)-5-cyclopropyl-2-(8-propylimidazo[1,2-a]pyrazin-6-yl)-5H-pyrrolo[2,3-d]pyrimidin-6(7H)-one;

4-amino-2-(8-cyclobutylimidazo[1,2-a]pyrazin-6-yl)-5-(5-fluoropyridin-2-yl)-5-methyl-5H-pyrrolo[2,3-d]pyrimidin-6(7H)-one;

4-amino-2-(8-cyclopropylimidazo[1,2-a]pyrazin-6-yl)-5-(4-fluorophenyl)-5-methyl-5H-pyrrolo[2,3-d]pyrimidin-6(7H)-one;

4-Amino-2-(8-(4-fluorobenzyl)imidazo[1,2-a]pyrazin-6-yl)-5-methyl-5-(5-methyl-1,3,4-oxadiazol-2-yl)-5H-pyrrolo[2,3-d]pyrimidin-6(7H)-one;

4-Amino-5-cyclopropyl-5-(5-ethyl-1,3,4-thiadiazol-2-yl)-2-(8-(3,3,4,4,4-pentafluorobutyl) imidazo[1,2-a]pyrazin-6-yl)-5H-pyrrolo[2,3-d]pyrimidin-6(7H)-one;

4-Amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide;

4-amino-5-(5-cyclopropyl-1,3,4-thiadiazol-2-yl)-2-(8-(4-fluorobenzyl)imidazo[1,2-a]pyrazin-6-yl)-5-methyl-5H-pyrrolo[2,3-d]pyrimidin-6(7H)-one;

4-amino-2-(8-(4-fluorobenzyl)imidazo[1,2-a]pyrazin-6-yl)-5-methyl-5-(5-methyl-1,3,4-thiadiazol-2-yl)-5H-pyrrolo[2,3-d]pyrimidin-6(7H)-one;

4-amino-5-(5-cyclopropyl-1,3,4-oxadiazol-2-yl)-2-(8-(4-fluorobenzyl)imidazo[1,2-a]pyrazin-6-yl)-5-methyl-5H-pyrrolo[2,3-d]pyrimidin-6(7H)-one;

4-amino-N-cyclopropyl-2-(8-(2-fluorobenzyl)imidazo[1,2-a]pyrazin-6-yl)-5-methyl-6-oxo-6,7-dihydro-5H-pyrrolo[2,3-d]pyrimidine-5-carboxamide;

4-amino-N-cyclopropyl-2-(8-(3-fluorobenzyl)imidazo[1,2-a]pyrazin-6-yl)-5-methyl-6-oxo-6,7-dihydro-5H-pyrrolo[2,3-d]pyrimidine-5-carboxamide;

4-amino-N,5-dicyclopropyl-2-(8-(3-fluorobenzyl)imidazo[1,2-a]pyrazin-6-yl)-6-oxo-6,7-dihydro-5H-pyrrolo[2,3-d]pyrimidine-5-carboxamide;

4-amino-2-(8-benzylimidazo[1,2-a]pyrazin-6-yl)-N,5-dicyclopropyl-6-oxo-6,7-dihydro-5H-pyrrolo[2,3-d]pyrimidine-5-carboxamide;

4-amino-5-cyclopropyl-2-(8-(3-fluorobenzyl)imidazo[1,2-a]pyrazin-6-yl)-6-oxo-6,7-dihydro-5H-pyrrolo[2,3-d]pyrimidine-5-carboxamide;

4-amino-N-cyclopropyl-2-(8-(2,3-difluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide;

4-amino-N,5-dicyclopropyl-2-(8-(3-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide;

4-amino-N,5-dicyclopropyl-2-(8-(2-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide;

4-amino-N-cyclopropyl-2-(8-(3-fluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide;

4-amino-N-cyclopropyl-2-(8-(2-fluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide;

4-amino-N,5-dicyclopropyl-2-(8-(2,3-difluorobenzyl)-2-(trifluoromethyl)imidazo[1,2-a]pyrazin-6-yl)-6-oxo-6,7-dihydro-5H-pyrrolo[2,3-d]pyrimidine-5-carboxamide;

4-amino-N,5-dicyclopropyl-2-(8-(4-fluorobenzyl)-2-(trifluoromethyl)imidazo[1,2-a]pyrazin-6-yl)-6-oxo-6,7-dihydro-5H-pyrrolo[2,3-d]pyrimidine-5-carboxamide;

4-amino-2-(8-benzyl-2-(trifluoromethyl)imidazo[1,2-a]pyrazin-6-yl)-N,5-dicyclopropyl-6-oxo-6,7-dihydro-5H-pyrrolo[2,3-d]pyrimidine-5-carboxamide;

4-amino-N-cyclopropyl-2-(8-(3,4-difluorobenzyl)-2-(trifluoromethyl)imidazo[1,2-a]pyrazin-6-yl)-5-methyl-6-oxo-6,7-dihydro-5H-pyrrolo[2,3-d]pyrimidine-5-carboxamide;

4-amino-5-cyclopropyl-5-(5-methyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(5-cyclopropyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(5-isopropyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(5-cyclopropyl-1,3,4-oxadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-5-(5-methyl-1,3,4-oxadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-5-(5-methyl-1,3,4-thiadiazol-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-cyclopropyl-1,3,4-thiadiazol-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-N-cyclopropyl-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidine-5-carboxamide;

4-amino-N,5-dicyclopropyl-6-oxo-2-(8-(3,3,4,4,4-pentafluorobutyl)imidazo[1,2-a]pyrazin-6-yl)-6,7-dihydro-5H-pyrrolo[2,3-d]pyrimidine-5-carboxamide;

4-Amino-2-(8-(4-fluorobenzyl)imidazo[1,2-a]pyrazin-6-yl)-5-(1-isopropyl-1H-1,2,3-triazol-4-yl)-5-methyl-5H-pyrrolo[2,3-d]pyrimidin-6(7H)-one;

4-amino-5-(1-ethyl-1H-1,2,3-triazol-4-yl)-2-(8-(4-fluorobenzyl)imidazo[1,2-a]pyrazin-6-yl)-5-methyl-5H-pyrrolo[2,3-d]pyrimidin-6(7H)-one;

4-amino-2-(8-(4-fluorobenzyl)imidazo[1,2-a]pyrazin-6-yl)-5-methyl-5-(1-methyl-1H-1,2,3-triazol-4-yl)-5H-pyrrolo[2,3-d]pyrimidin-6(7H)-one;

4-amino-5-ethynyl-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(1-isopropyl-1H-1,2,3-triazol-4-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-Amino-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-Amino-2-(8-(4-fluorobenzyl)imidazo[1,2-a]pyrazin-6-yl)-5-(5-fluoropyridin-2-yl)-5-methyl-5H-pyrrolo[2,3-d]pyrimidin-6(7H)-one;

4-amino-2-(8-(2-fluorobenzyl)imidazo[1,2-a]pyrazin-6-yl)-5,5-dimethyl-5H-pyrrolo[2,3-d]pyrimidin-6(7H)-one;

4-amino-2-(8-(3-fluorobenzyl)imidazo[1,2-a]pyrazin-6-yl)-5,5-dimethyl-5H-pyrrolo[2,3-d]pyrimidin-6(7H)-one;

4-amino-2-(8-(4-fluorobenzyl)imidazo[1,2-a]pyrazin-6-yl)-5,5-dimethyl-5H-pyrrolo[2,3-d]pyrimidin-6(7H)-one;

4-amino-2-(8-(3,4-difluorobenzyl)imidazo[1,2-a]pyrazin-6-yl)-5,5-dimethyl-5H-pyrrolo[2,3-d]pyrimidin-6(7H)-one;

4-amino-2-(8-(3-chlorobenzyl)imidazo[1,2-a]pyrazin-6-yl)-5,5-dimethyl-5H-pyrrolo[2,3-d]pyrimidin-6(7H)-one;

4-amino-2-(8-(3-fluorobenzyl)-2-(trifluoromethyl)imidazo[1,2-a]pyrazin-6-yl)-5,5-dimethyl-5H-pyrrolo[2,3-d]pyrimidin-6(7H)-one;

4-amino-2-(8-benzylimidazo[1,2-a]pyrazin-6-yl)-5,5-dimethyl-5H-pyrrolo[2,3-d]pyrimidin-6(7H)-one;

4-amino-2-(8-benzylimidazo[1,2-a]pyrazin-6-yl)-5-cyclopropyl-5-ethyl-5H-pyrrolo[2,3-d]pyrimidin-6(7H)-one;

4-amino-2-(8-benzylimidazo[1,2-a]pyrazin-6-yl)-5,5-diethyl-5H-pyrrolo[2,3-d]pyrimidin-6(7H)-one;

4-amino-2-(8-benzylimidazo[1,2-a]pyrazin-6-yl)-5-isopropyl-5-methyl-5H-pyrrolo[2,3-d]pyrimidin-6(7H)-one;

4-amino-2-(8-benzylimidazo[1,2-a]pyrazin-6-yl)-5-cyclopropyl-5-methyl-5H-pyrrolo[2,3-d]pyrimidin-6(7H)-one;

4-amino-2-(8-benzylimidazo[1,2-a]pyrazin-6-yl)-5-ethyl-5-methyl-5H-pyrrolo[2,3-d]pyrimidin-6(7H)-one;

4-amino-5-cyclopropyl-5-ethyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one;

4-amino-2-(8-(4-fluorobenzyl)imidazo[1,2-a]pyrazin-6-yl)-5-methyl-5-(1-methyl-1H-pyrazol-4-yl)-5H-pyrrolo[2,3-d]pyrimidin-6(7H)-one;

4-amino-2-(8-(2-fluorobenzyl)imidazo[1,2-a]pyrazin-6-yl)-5-(4-fluorophenyl)-5-methyl-5H-pyrrolo[2,3-d]pyrimidin-6(7H)-one;

4-amino-2-(8-(3-fluorobenzyl)imidazo[1,2-a]pyrazin-6-yl)-5-(4-fluorophenyl)-5-methyl-5H-pyrrolo[2,3-d]pyrimidin-6(7H)-one;

4-amino-2-(8-(4-fluorobenzyl)imidazo[1,2-a]pyrazin-6-yl)-5-(4-fluorophenyl)-5-methyl-5H-pyrrolo[2,3-d]pyrimidin-6(7H)-one;

4-amino-2-(8-benzylimidazo[1,2-a]pyrazin-6-yl)-5-(4-fluorophenyl)-5-methyl-5H-pyrrolo[2,3-d]pyrimidin-6(7H)-one;

4-amino-2-(8-(3-chlorobenzyl)imidazo[1,2-a]pyrazin-6-yl)-5-(4-fluorophenyl)-5-methyl-5H-pyrrolo[2,3-d]pyrimidin-6(7H)-one;

4-amino-2-(8-(3-chlorobenzyl)imidazo[1,2-a]pyrazin-6-yl)-5-(4-chlorophenyl)-5-methyl-5H-pyrrolo[2,3-d]pyrimidin-6(7H)-one;

4-amino-2-(8-(3,4-difluorobenzyl)imidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-2-(8-(3,4-difluorobenzyl)imidazo[1,2-a]pyrazin-6-yl)-5-methyl-5H-pyrrolo[2,3-d]pyrimidin-6(7H)-one;

4-amino-5-(4-fluorophenyl)-5-methyl-2-(8-(2,3,6-trifluorobenzyl)imidazo[1,2-a]pyrazin-6-yl)-5H-pyrrolo[2,3-d]pyrimidin-6(7H)-one;

4-amino-5-(4-chlorophenyl)-2-(8-(4-fluorobenzyl)imidazo[1,2-a]pyrazin-6-yl)-5-methyl-5H-pyrrolo[2,3-d]pyrimidin-6(7H)-one;

4-amino-5-methyl-5-phenyl-2-(8-(2,3,6-trifluorobenzyl)imidazo[1,2-a]pyrazin-6-yl)-5H-pyrrolo[2,3-d]pyrimidin-6(7H)-one;

4-amino-2-(8-(3-fluorobenzyl)imidazo[1,2-a]pyrazin-6-yl)-5-methyl-5-phenyl-5H-pyrrolo[2,3-d]pyrimidin-6(7H)-one;

4-amino-2-(8-benzylimidazo[1,2-a]pyrazin-6-yl)-5-methyl-5-phenyl-5H-pyrrolo[2,3-d]pyrimidin-6(7H)-one;

4-amino-2-(8-(4-fluorobenzyl)imidazo[1,2-a]pyrazin-6-yl)-5-methyl-5-(pyridin-2-yl)-5H-pyrrolo[2,3-d]pyrimidin-6(7H)-one;

4-amino-5-cyclopropyl-2-(8-(4-fluorobenzyl)imidazo[1,2-a]pyrazin-6-yl)-5-(5-fluoropyridin-2-yl)-5H-pyrrolo[2,3-d]pyrimidin-6(7H)-one;

4-amino-2-(8-(4-fluorobenzyl)imidazo[1,2-a]pyrazin-6-yl)-5-methyl-5-(6-methylpyridin-3-yl)-5H-pyrrolo[2,3-d]pyrimidin-6(7H)-one;

4-amino-5-ethyl-2-(8-(4-fluorobenzyl)imidazo[1,2-a]pyrazin-6-yl)-5-(5-fluoropyridin-2-yl)-5H-pyrrolo[2,3-d]pyrimidin-6(7H)-one;

4-amino-5-(5-chloropyridin-2-yl)-2-(8-(4-fluorobenzyl)imidazo[1,2-a]pyrazin-6-yl)-5-methyl-5H-pyrrolo[2,3-d]pyrimidin-6(7H)-one;

4-amino-5-(5-chloropyridin-2-yl)-cyclopropyl-2-(8-(4-fluorobenzyl)imidazo[1,2-a]pyrazin-6-yl)-5H-pyrrolo[2,3-d]pyrimidin-6(7H)-one;

4-amino-5-(5-chloropyridin-2-yl)-cyclopropyl-2-(8-(4-fluorobenzyl)imidazo[1,2-a]pyrazin-6-yl)-5H-pyrrolo[2,3-d]pyrimidin-6(7H)-one;

4-amino-5-(5-chloropyridin-2-yl)-cyclopropyl-2-(8-(2-fluorobenzyl)imidazo[1,2-a]pyrazin-6-yl)-5H-pyrrolo[2,3-d]pyrimidin-6(7H)-one;

4-amino-5-(5-chloropyridin-2-yl)-cyclopropyl-2-(8-(2-fluorobenzyl)imidazo[1,2-a]pyrazin-6-yl)-5H-pyrrolo[2,3-d]pyrimidin-6(7H)-one;

4-amino-5-(4-fluorophenyl)-5-methyl-2-(8-phenylimidazo[1,2-a]pyrazin-6-yl)-5H-pyrrolo[2,3-d]pyrimidin-6(7H)-one;

4-amino-5-(4-chloro-3-fluorophenyl)-2-(8-(cyclobutylmethyl)imidazo[1,2-a]pyrazin-6-yl)-5-methyl-5H-pyrrolo[2,3-d]pyrimidin-6(7H)-one;

4-amino-2-(8-(cyclobutylmethyl)imidazo[1,2-a]pyrazin-6-yl)-5-(4-fluorophenyl)-5-methyl-5H-pyrrolo[2,3-d]pyrimidin-6(7H)-one;

4-amino-2-(8-(cyclobutylmethyl)imidazo[1,2-a]pyrazin-6-yl)-5-(5-fluoropyridin-2-yl)-5-methyl-5H-pyrrolo[2,3-d]pyrimidin-6(7H)-one;

4-amino-5-(5-chloropyridin-2-yl)-2-(8-(cyclobutylmethyl)imidazo[1,2-a]pyrazin-6-yl)-5-methyl-5H-pyrrolo[2,3-d]pyrimidin-6(7H)-one;

4-amino-2-(8-(cyclobutylmethyl)imidazo[1,2-a]pyrazin-6-yl)-5-(5-(difluoromethoxy)pyridin-2-yl)-5-methyl-5H-pyrrolo[2,3-d]pyrimidin-6(7H)-one;

4-amino-5-(4-chlorophenyl)-2-(8-(cyclobutylmethyl)imidazo[1,2-a]pyrazin-6-yl)-5-methyl-5H-pyrrolo[2,3-d]pyrimidin-6(7H)-one;

4-amino-2-(8-(cyclobutylmethyl)imidazo[1,2-a]pyrazin-6-yl)-5-methyl-5-(5-(trifluoromethyl)pyridin-2-yl)-5H-pyrrolo[2,3-d]pyrimidin-6(7H)-one;

4-amino-5-(4-chlorophenyl)-2-(8-(3,3-dimethylbutyl)imidazo[1,2-a]pyrazin-6-yl)-5-methyl-5H-pyrrolo[2,3-d]pyrimidin-6(7H)-one;

4-amino-2-(8-(3,3-dimethylbutyl)imidazo[1,2-a]pyrazin-6-yl)-5-(4-fluorophenyl)-5-methyl-5H-pyrrolo[2,3-d]pyrimidin-6(7H)-one;

4-amino-2-(8-(3,3-dimethylbutyl)imidazo[1,2-a]pyrazin-6-yl)-5-(5-fluoropyridin-2-yl)-5-methyl-5H-pyrrolo[2,3-d]pyrimidin-6(7H)-one;

4-amino-5-(5-chloropyridin-2-yl)-2-(8-(3,3-dimethylbutyl)imidazo[1,2-a]pyrazin-6-yl)-5-methyl-5H-pyrrolo[2,3-d]pyrimidin-6(7H)-one;

4-amino-5-(4-chloro-3-fluorophenyl)-5-methyl-2-(8-propylimidazo[1,2-a]pyrazin-6-yl)-5H-pyrrolo[2,3-d]pyrimidin-6(7H)-one;

4-amino-5-(5-chloropyridin-2-yl)-2-(8-isobutylimidazo[1,2-a]pyrazin-6-yl)-5-methyl-5H-pyrrolo[2,3-d]pyrimidin-6(7H)-one;

4-amino-5-(5-chloropyridin-2-yl)-5-cyclopropyl-2-(8-isobutylimidazo[1,2-a]pyrazin-6-yl)-5H-pyrrolo[2,3-d]pyrimidin-6(7H)-one;

4-amino-5-cyclopropyl-2-(8-isobutylimidazo[1,2-a]pyrazin-6-yl)-5-(5-(trifluoromethyl)pyridin-2-yl)-5H-pyrrolo[2,3-d]pyrimidin-6(7H)-one;

4-amino-2-(8-isobutylimidazo[1,2-a]pyrazin-6-yl)-5-methyl-5-(4-(trifluoromethyl)phenyl)-5H-pyrrolo[2,3-d]pyrimidin-6(7H)-one;

4-amino-5-(5-chloropyridin-2-yl)-5-methyl-2-(8-propylimidazo[1,2-a]pyrazin-6-yl)-5H-pyrrolo[2,3-d]pyrimidin-6(7H)-one;

4-amino-5-(5-(difluoromethoxy)pyridin-2-yl)-2-(8-isobutylimidazo[1,2-a]pyrazin-6-yl)-5-methyl-5H-pyrrolo[2,3-d]pyrimidin-6(7H)-one;

4-amino-5-methyl-2-(8-propylimidazo[1,2-a]pyrazin-6-yl)-5-(4-(trifluoromethyl)phenyl)-5H-pyrrolo[2,3-d]pyrimidin-6(7H)-one;

4-amino-5-methyl-2-(8-propylimidazo[1,2-a]pyrazin-6-yl)-5-(5-(trifluoromethyl)pyridin-2-yl)-5H-pyrrolo[2,3-d]pyrimidin-6(7H)-one;

4-amino-2-(8-butylimidazo[1,2-a]pyrazin-6-yl)-5-cyclopropyl-5-(5-(trifluoromethyl)pyridin-2-yl)-5H-pyrrolo[2,3-d]pyrimidin-6(7H)-one;

4-amino-5-(4-fluorophenyl)-2-(imidazo[1,2-a]pyrazin-6-yl)-5-methyl-5H-pyrrolo[2,3-d]pyrimidin-6(7H)one;

4-amino-5-(4-bromophenyl)-2-(imidazo[1,2-a]pyrazin-6-yl)-5-methyl-5H-pyrrolo[2,3-d]pyrimidin-6(7H)-one;

4-amino-5-(4-chloro-2-fluorophenyl)-2-(imidazo[1,2-a]pyrazin-6-yl)-5-methyl-5H-pyrrolo[2,3-d]pyrimidin-6(7H)-one;

4-amino-5-(4-chloro-3-fluorophenyl)-5-cyclopropyl-2-(imidazo[1,2-a]pyrazin-6-yl)-5H-pyrrolo[2,3-d]pyrimidin-6(7H)-one;

4-amino-5-(3,4-dichlorophenyl)-2-(imidazo[1,2-a]pyrazin-6-yl)-5-methyl-5H-pyrrolo[2,3-d]pyrimidin-6(7H)-one;

4-amino-5-(2,4-difluorophenyl)-2-(imidazo[1,2-a]pyrazin-6-yl)-5-methyl-5H-pyrrolo[2,3-d]pyrimidin-6(7H)-one;

4-amino-5-(4-chloro-3-fluorophenyl)-2-(imidazo[1,2-a]pyrazin-6-yl)-5-methyl-5H-pyrrolo[2,3-d]pyrimidin-6(7H)-one;

4-amino-5-(3,4-difluorophenyl)-2-(imidazo[1,2-a]pyrazin-6-yl)-5-methyl-5H-pyrrolo[2,3-d]pyrimidin-6(7H)-one;

4-amino-5-(3,5-difluorophenyl)-2-(imidazo[1,2-a]pyrazin-6-yl)-5-methyl-5H-pyrrolo[2,3-d]pyrimidin-6(7H)-one;

4-amino-2-(imidazo[1,2-a]pyrazin-6-yl)-5-methyl-5-(4-(trifluoromethyl)phenyl)-5H-pyrrolo[2,3-d]pyrimidin-6(7H)-one;

4-amino-5-(4-chlorophenyl)-2-(imidazo[1,2-a]pyrazin-6-yl)-5-methyl-5H-pyrrolo[2,3-d]pyrimidin-6(7H)-one;

4-amino-2-(imidazo[1,2-a]pyrazin-6-yl)-5-methyl-5-(4-(trifluoromethoxy)phenyl)-5H-pyrrolo[2,3-d]pyrimidin-6(7H)-one;

4-amino-5-(4-chlorophenyl)-5-cyclopropyl-2-(imidazo[1,2-a]pyrazin-6-yl)-5H-pyrrolo[2,3-d]pyrimidin-6(7H)-one;

4-amino-2-(8-(2-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-2-(8-(2,3-difluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-2-(8-(3-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-2-(8-(3-fluorobenzyl)-2-(trifluoromethyl)imidazo[1,2-a]pyrazin-6-yl)-5-methyl-5H-pyrrolo[2,3-d]pyrimidin-6(7H)-one;

4-amino-5-(4-chlorophenyl)-2-(8-(2-fluorobenzyl)-2-(trifluoromethyl)imidazo[1,2-a]pyrazin-6-yl)-5-methyl-5H-pyrrolo[2,3-d]pyrimidin-6(7H)-one;

4-amino-2-(8-(3,4-difluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-5-(4-chlorophenyl)-2-(8-(4-fluorobenzyl)-2-(trifluoromethyl)imidazo[1,2-a]pyrazin-6-yl)-5-methyl-5H-pyrrolo[2,3-d]pyrimidin-6(7H)-one;

4-amino-2-(8-benzyl-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-2-(8-(4-fluorobenzyl)-2-(trifluoromethyl)imidazo[1,2-a]pyrazin-6-yl)-5-(4-fluorophenyl)-5-methyl-5H-pyrrolo[2,3-d]pyrimidin-6(7H)-one;

4-amino-5-(4-fluorophenyl)-5-methyl-2-(8-(3,3,4,4,4-pentafluorobutyl)-2-(trifluoromethyl)imidazo[1,2-a]pyrazin-6-yl)-5H-pyrrolo[2,3-d]pyrimidin-6(7H)-one;

4-amino-2-(2-cyclopropyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-2-(2-cyclopropyl-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one;

4-amino-2-(2-ethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-2-(2-ethyl-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one;

4-amino-2-(3-ethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-2-(8-(4-fluorobenzyl)-2-methylimidazo[1,2-a]pyrazin-6-yl)-5-(5-fluoropyridin-2-yl)-5-methyl-5H-pyrrolo[2,3-d]pyrimidin-6(7H)-one;

4-amino-2-(8-(4-fluorobenzyl)-3-methylimidazo[1,2-a]pyrazin-6-yl)-5-(5-fluoropyridin-2-yl)-5-methyl-5H-pyrrolo[2,3-d]pyrimidin-6(7H)-one;

4-amino-2-(8-butyl-2-methylimidazo[1,2-a]pyrazin-6-yl)-5-(5-fluoropyridin-2-yl)-5-methyl-5H-pyrrolo[2,3-d]pyrimidin-6(7H)-one;

4-amino-2-(8-butyl-3-methylimidazo[1,2-a]pyrazin-6-yl)-5-(5-fluoropyridin-2-yl)-5-methyl-5H-pyrrolo[2,3-d]pyrimidin-6(7H)-one;

4-amino-2-(8-butyl-2-methylimidazo[1,2-a]pyrazin-6-yl)-5-methyl-5-(5-(trifluoromethyl)pyridin-2-yl)-5H-pyrrolo[2,3-d]pyrimidin-6(7H)-one;

4-amino-2-(8-butyl-3-methylimidazo[1,2-a]pyrazin-6-yl)-5-methyl-5-(5-(trifluoromethyl)pyridin-2-yl)-5H-pyrrolo[2,3-d]pyrimidin-6(7H)-one;

4-amino-2-(8-butyl-2-methylimidazo[1,2-a]pyrazin-6-yl)-5-(5-chloropyridin-2-yl)-5-methyl-5H-pyrrolo[2,3-d]pyrimidin-6(7H)-one;

4-amino-2-(8-butyl-3-methylimidazo[1,2-a]pyrazin-6-yl)-5-(5-chloropyridin-2-yl)-5-methyl-5H-pyrrolo[2,3-d]pyrimidin-6(7H)-one;

4-amino-5-(4-fluorophenyl)-5-methyl-2-(2-methyl-8-(3,3,4,4,4-pentafluorobutyl)imidazo[1,2-a]pyrazin-6-yl)-5H-pyrrolo[2,3-d]pyrimidin-6(7H)-one;

4-amino-5-(4-fluorophenyl)-5-methyl-2-(3-methyl-8-(3,3,4,4,4-pentafluorobutyl)imidazo[1,2-a]pyrazin-6-yl)-5H-pyrrolo[2,3-d]pyrimidin-6(7H)-one;

4-amino-5-(5-fluoropyridin-2-yl)-5-methyl-2-(2-methyl-8-(3,3,4,4,4-pentafluorobutyl)imidazo[1,2-a]pyrazin-6-yl)-5H-pyrrolo[2,3-d]pyrimidin-6(7H)-one;

4-amino-5-(5-fluoropyridin-2-yl)-5-methyl-2-(3-methyl-8-(3,3,4,4,4-pentafluorobutyl)imidazo[1,2-a]pyrazin-6-yl)-5H-pyrrolo[2,3-d]pyrimidin-6(7H)-one;

4-amino-5-(4-fluorophenyl)-2-(2-methoxy-8-(3,3,4,4,4-pentafluorobutyl)imidazo[1,2-a]pyrazin-6-yl)-5-methyl-5H-pyrrolo[2,3-d]pyrimidin-6(7H)-one;

4-amino-5-(5-fluoropyridin-2-yl)-2-(2-methoxy-8-(3,3,4,4,4-pentafluorobutyl)imidazo[1,2-a]pyrazin-6-yl)-5-methyl-5H-pyrrolo[2,3-d]pyrimidin-6(7H)-one;

4-amino-5-(4-fluorophenyl)-2-(2-methoxy-8-(4,4,4-trifluorobutyl)imidazo[1,2-a]pyrazin-6-yl)-5-methyl-5H-pyrrolo[2,3-d]pyrimidin-6(7H)-one;

4-amino-2-(2,3-dimethyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-5-(4-chloro-3-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chloro-2-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(2,4-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-bromophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chlorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(3,4-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-methyl-5-(p-tolyl)-2-(8-(3,3,3-trifluoropropyl)imidazo[1,2-a]pyrazin-6-yl)-5H-pyrrolo[2,3-d]pyrimidin-6(7H)-one;

4-amino-5-(3,4-dichlorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(2,4-dichlorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-methyl-5-phenyl-2-(8-(3,3,3-trifluoropropyl)imidazo[1,2-a]pyrazin-6-yl)-5H-pyrrolo[2,3-d]pyrimidin-6(7H)-one;

4-amino-5-methyl-5-(4-(trifluoromethyl)phenyl)-2-(8-(3,3,3-trifluoropropyl)imidazo[1,2-a]pyrazin-6-yl)-5H-pyrrolo[2,3-d]pyrimidin-6(7H)-one;

4-amino-5-(4-chloro-3-fluorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-5-(3-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-methoxyphenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(3-chloro-4-fluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-cyclopropyl-5-(4-fluorophenyl)-2-(8-(3,3,3-trifluoropropyl)imidazo[1,2-a]pyrazin-6-yl)-5H-pyrrolo[2,3-d]pyrimidin-6(7H)-one;

4-amino-5-(3,5-difluorophenyl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-methyl-5-(4-(trifluoromethoxy)phenyl)-2-(8-(3,3,3-trifluoropropyl)imidazo[1,2-a]pyrazin-6-yl)-5H-pyrrolo[2,3-d]pyrimidin-6(7H)-one;

4-amino-5-(4-bromophenyl)-5-ethyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chlorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chloro-3-fluorophenyl)-5-ethyl-2-(8-(3,3,3-trifluoropropyl)imidazo[1,2-a]pyrazin-6-yl)-5H-pyrrolo[2,3-d]pyrimidin-6(7H)-one;

4-amino-5-(4-bromophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-5-(5-chloropyridin-2-yl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(5-fluoropyridin-2-yl)-5-methyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chlorophenyl)-5-isopropyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chloro-3-fluorophenyl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(4-fluorophenyl)-2-(8-(4,4,4-trifluorobutyl)imidazo[1,2-a]pyrazin-6-yl)-5H-pyrrolo[2,3-d]pyrimidin-6(7H)-one;

4-amino-5-(4-chlorophenyl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-methyl-2-(8-(4,4,4-trifluorobutyl)imidazo[1,2-a]pyrazin-6-yl)-5-(4-(trifluoromethoxy)phenyl)-5H-pyrrolo[2,3-d]pyrimidin-6(7H)-one;

4-amino-5-(5-chloropyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-(4-chlorophenyl)-5-ethyl-2-(8-(4,4,4-trifluorobutyl)imidazo[1,2-a]pyrazin-6-yl)-5H-pyrrolo[2,3-d]pyrimidin-6(7H)-one;

4-amino-5-(5-fluoropyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-(4-fluorophenyl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-(5-methoxypyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-methyl-2-(8-(4,4,4-trifluorobutyl)imidazo[1,2-a]pyrazin-6-yl)-5-(5-(trifluoromethyl)pyridin-2-yl)-5H-pyrrolo[2,3-d]pyrimidin-6(7H)-one;

4-amino-5-(5-(difluoromethoxy)pyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-ethyl-5-(4-fluorophenyl)-2-(8-(4,4,4-trifluorobutyl)imidazo[1,2-a]pyrazin-6-yl)-5H-pyrrolo[2,3-d]pyrimidin-6(7H)-one;

4-amino-5-(5-ethoxypyridin-2-yl)-5-methyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(5-fluoropyridin-2-yl)-2-(8-(4,4,4-trifluorobutyl)imidazo[1,2-a]pyrazin-6-yl)-5H-pyrrolo[2,3-d]pyrimidin-6(7H)-one;

4-amino-5-(5-chloropyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-2-(8-(4,4,4-trifluorobutyl)imidazo[1,2-a]pyrazin-6-yl)-5-(5-(trifluoromethyl)pyridin-2-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(pyrimidin-2-yl)-5H-pyrrolo[2,3-d]pyrimidin-6(7H)-one;

4-amino-5-methyl-5-(6-methylpyridin-3-yl)-2-(8-(3,3,4,4-pentafluorobutyl)imidazo[1,2-a]pyrazin-6-yl)-5H-pyrrolo[2,3-d]pyrimidin-6(7H)-one;

4-amino-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(5-fluoropyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-ethoxypyridin-2-yl)-5-methyl-2-(8-(3,3,4,4-pentafluorobutyl)imidazo[1,2-a]pyrazin-6-yl)-5H-pyrrolo[2,3-d]pyrimidin-6(7H)-one;

4-amino-5-(5-isopropylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(pyridin-2-yl)-5H-pyrrolo[2,3-d]pyrimidin-6(7H)-one;

4-amino-5-(5-cyclopropylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-chloropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-methoxyphenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(p-tolyl)-5H-pyrrolo[2,3-d]pyrimidin-6(7H)-one;

4-amino-5-(3-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-phenyl-5H-pyrrolo[2,3-d]pyrimidin-6(7H)-one;

4-amino-5-cyclopropyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(4-(trifluoromethoxy)phenyl)-5H-pyrrolo[2,3-d]pyrimidin-6(7H)-one;

4-amino-5-(4-chlorophenyl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-methoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(4-(trifluoromethyl)phenyl)-5H-pyrrolo[2,3-d]pyrimidin-6(7H)-one;

4-amino-5-(4-chlorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-ethyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-cyclopropylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-isopropoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-ethylpyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-ethylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-ethoxypyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-chloropyridin-2-yl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chlorophenyl)-5-ethyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-methoxypyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-ethyl-5-(5-fluoropyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-2-(8-(3,3,4,4,4-pentafluorobutyl)imidazo[1,2-a]pyrazin-6-yl)-5-(6-propylpyridin-3-yl)-5H-pyrrolo[2,3-d]pyrimidin-6(7H)-one;

4-amino-5-(6-isopropylpyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-methyl-5-(6-methylpyridazin-3-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-cyclopropylpyridazin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-2-(3-bromo-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-2-(3-chloro-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-amino-2-(3-chloro-8-(3,3,4,4,4-pentafluorobutyl)imidazo[1,2-a]pyrazin-6-yl)-5-methyl-5-phenyl-5H-pyrrolo[2,3-d]pyrimidin-6(7H)-one;

4-amino-2-(3-chloro-8-(3,3,4,4,4-pentafluorobutyl)imidazo[1,2-a]pyrazin-6-yl)-5,5-dimethyl-5H-pyrrolo[2,3-d]pyrimidin-6(7H)-one;

4-amino-2-(3-chloro-8-(3,3,3-trifluoropropyl)imidazo[1,2-a]pyrazin-6-yl)-5-(4-fluorophenyl)-5-methyl-5H-pyrrolo[2,3-d]pyrimidin-6(7H)-one;

4-amino-2-(3-chloro-8-(3,3,3-trifluoropropyl)imidazo[1,2-a]pyrazin-6-yl)-5-methyl-5-phenyl-5H-pyrrolo[2,3-d]pyrimidin-6(7H)-one;

4-Amino-2-(3-benzyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-Amino-2-(3-(2-cyclohexylethyl)imidazo[1,2-a]pyrazin-6-yl)-5-(4-fluorophenyl)-5-methyl-5H-pyrrolo[2,3-d]pyrimidin-6(7H)-one;

4-Amino-2-(3-bromo-8-(3,3,4,4,4-pentafluorobutyl)imidazo[1,2-a]pyrazin-6-yl)-5-(5-fluoropyridin-2-yl)-5-methyl-5H-pyrrolo[2,3-d]pyrimidin-6(7H)-one;

4-amino-2-(3-bromo-8-(3,3,4,4,4-pentafluorobutyl)imidazo[1,2-a]pyrazin-6-yl)-5,5-dimethyl-5H-pyrrolo[2,3-d]pyrimidin-6(7H)-one;

4-amino-2-(3-bromo-8-(3,3,3-trifluoropropyl)imidazo[1,2-a]pyrazin-6-yl)-5-(4-fluorophenyl)-5-methyl-5H-pyrrolo[2,3-d]pyrimidin-6(7H)-one;

4-amino-2-(3-bromo-8-(3,3,3-trifluoropropyl)imidazo[1,2-a]pyrazin-6-yl)-5-methyl-5-phenyl-5H-pyrrolo[2,3-d]pyrimidin-6(7H)-one;

4-amino-2-(3-bromo-2-methyl-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-Amino-2-(3-amino-8-(3,3,4,4,4-pentafluorobutyl)imidazo[1,2-a]pyrazin-6-yl)-5-(4-fluorophenyl)-5-methyl-5H-pyrrolo[2,3-d]pyrimidin-6(7H)-one;

4-Amino-2-(3-amino-8-(3,3,4,4,4-pentafluorobutyl)imidazo[1,2-a]pyrazin-6-yl)-5-(5-fluoropyridin-2-yl)-5-methyl-5H-pyrrolo[2,3-d]pyrimidin-6(7H)-one;

4-amino-2-(3-amino-8-(3,3,4,4,4-pentafluorobutyl)imidazo[1,2-a]pyrazin-6-yl)-5-(5-chloropyridin-2-yl)-5-methyl-5H-pyrrolo[2,3-d]pyrimidin-6(7H)-one;

Methyl 3-(4-amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl)benzoate;

3-(4-Amino-5-methyl-6-oxo-2-(8-(3,3,4,4,4-pentafluorobutyl)imidazo[1,2-a]pyrazin-6-yl)-6,7-dihydro-5H-pyrrolo[2,3-d]pyrimidin-5-yl)-N,N-dimethylbenzamide;

3-((6-(4-Amino-5,5-dimethyl-6-oxo-6,7-dihydro-5H-pyrrolo[2,3-d]pyrimidin-2-yl)imidazo[1,2-a]pyrazin-8-yl)methyl)benzonitrile;

6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-3-carbonitrile;

6-(4-amino-5-(4-fluorophenyl)-5-methyl-6-oxo-6,7-dihydro-5H-pyrrolo[2,3-d]pyrimidin-2-yl)-2-methyl-8-(3,3,4,4,4-pentafluorobutyl)imidazo[1,2-a]pyrazine-3-carbonitrile;

6-(4-Amino-5-(4-fluorophenyl)-5-methyl-6-oxo-6,7-dihydro-5H-pyrrolo[2,3-d]pyrimidin-2-yl)-8-(3,3,4,4,4-pentafluorobutyl)imidazo[1,2-a]pyrazine-2-carbonitrile;

4-Amino-5-ethyl-2-(3-fluoro-8-(3,3,4,4,4-pentafluorobutyl)imidazo[1,2-a]pyrazin-6-yl)-5-(4-fluorophenyl)-5H-pyrrolo[2,3-d]pyrimidin-6(7H)-one;

5-(4-Chlorophenyl)-4-(3,3-difluorocyclobutyl)-2-(imidazo[1,2-a]pyrazin-6-yl)-5-methyl-5H-pyrrolo[2,3-d]pyrimidin-6(7H)-one;

5-(4-chlorophenyl)-4-(3,3-difluoroazetidin-1-yl)-2-(imidazo[1,2-a]pyrazin-6-yl)-5-methyl-5H-pyrrolo[2,3-d]pyrimidin-6(7H)-one;

5-(4-chlorophenyl)-2-(imidazo[1,2-a]pyrazin-6-yl)-5-methyl-4-(3-(trifluoromethyl)pyrrolidin-1-yl)-5H-pyrrolo[2,3-d]pyrimidin-6(7H)-one;

5-(4-chlorophenyl)-2-(imidazo[1,2-a]pyrazin-6-yl)-5-methyl-4-(4-(trifluoromethyl)piperidin-1-yl)-5H-pyrrolo[2,3-d]pyrimidin-6(7H)-one;

5-(4-chlorophenyl)-4-(3-cyclopropyl-3-fluoroazetidin-1-yl)-2-(imidazo[1,2-a]pyrazin-6-yl)-5-methyl-5H-pyrrolo[2,3-d]pyrimidin-6(7H)-one;

5-(4-chlorophenyl)-2-(imidazo[1,2-a]pyrazin-6-yl)-5-methyl-4-(3-(trifluoromethyl)azetidin-1-yl)-5H-pyrrolo[2,3-d]pyrimidin-6(7H)-one;

5-(4-chlorophenyl)-4-((cyclopropylmethyl)amino)-2-(imidazo[1,2-a]pyrazin-6-yl)-5-methyl-5H-pyrrolo[2,3-d]pyrimidin-6(7H)-one;

5-(4-chlorophenyl)-4-(3-fluoro-3-methylazetidin-1-yl)-2-(imidazo[1,2-a]pyrazin-6-yl)-5-methyl-5H-pyrrolo[2,3-d]pyrimidin-6(7H)-one;

5-(4-chlorophenyl)-2-(imidazo[1,2-a]pyrazin-6-yl)-5-methyl-4-(4,4,4-trifluorobutyl)amino)-5H-pyrrolo[2,3-d]pyrimidin-6(7H)-one;

5-(4-chlorophenyl)-2-(imidazo[1,2-a]pyrazin-6-yl)-5-methyl-4-(3,3,4,4,4-pentafluorobutyl)amino)-5H-pyrrolo[2,3-d]pyrimidin-6(7H)-one;

5-(4-chlorophenyl)-4-(3,3-difluorocyclobutyl)amino)-2-(imidazo[1,2-a]pyrazin-6-yl)-5-methyl-5H-pyrrolo[2,3-d]pyrimidin-6(7H)-one;

5-(4-chlorophenyl)-2-(imidazo[1,2-a]pyrazin-6-yl)-5-methyl-4-(2,2,2-trifluoroethyl)amino)-5H-pyrrolo[2,3-d]pyrimidin-6(7H)-one;

5-(4-chlorophenyl)-2-(imidazo[1,2-a]pyrazin-6-yl)-5-methyl-4-(3,3,3-trifluoropropyl)amino)-5H-pyrrolo[2,3-d]pyrimidin-6(7H)-one;

5-(5-fluoropyridin-2-yl)-5-methyl-4-(methylamino)-2-(8-(3,3,4,4,4-pentafluorobutyl)imidazo[1,2-a]pyrazin-6-yl)-5H-pyrrolo[2,3-d]pyrimidin-6(7H)-one;

4-(dimethylamino)-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-(cyclopropylamino)-5-(5-fluoropyridin-2-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(5-fluoropyridin-2-yl)-4-(2-methoxyethyl)amino)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(5-fluoropyridin-2-yl)-5-methyl-4-morpholino-2-(8-(3,3,4,4,4-pentafluorobutyl)imidazo[1,2-a]pyrazin-6-yl)-5H-pyrrolo[2,3-d]pyrimidin-6(7H)-one;

5-(5-fluoropyridin-2-yl)-5-methyl-4-(4-methylpiperazin-1-yl)-2-(8-(3,3,4,4,4-pentafluorobutyl)imidazo[1,2-a]pyrazin-6-yl)-5H-pyrrolo[2,3-d]pyrimidin-6(7H)-one;

5-(4-chlorophenyl)-4-((2-methoxyethyl)amino)-5-methyl-2-(8-(3,3,3-trifluoropropyl)imidazo[1,2-a]pyrazin-6-yl)-5H-pyrrolo[2,3-d]pyrimidin-6(7H)-one;

5-(4-chlorophenyl)-5-methyl-4-morpholino-2-(8-(3,3,3-trifluoropropyl)imidazo[1,2-a]pyrazin-6-yl)-5H-pyrrolo[2,3-d]pyrimidin-6(7H)-one;

ethyl 3-((5-(4-chlorophenyl)-5-methyl-6-oxo-2-(8-(3,3,3-trifluoropropyl)imidazo[1,2-a]pyrazin-6-yl)-6,7-dihydro-5H-pyrrolo[2,3-d]pyrimidin-4-yl)amino)propanoate;

5-(4-fluorophenyl)-5-methyl-4-(4-(methylsulfonyl)piperazin-1-yl)-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-5-methyl-2-(8-(3,3,4,4,4-pentafluorobutyl)imidazo[1,2-a]pyrazin-6-yl)-4-thiomorpholino-5H-pyrrolo[2,3-d]pyrimidin-6(7H)-one;

5-(4-fluorophenyl)-5-methyl-2-(8-(3,3,4,4,4-pentafluorobutyl)imidazo[1,2-a]pyrazin-6-yl)-4-(pyrrolidin-1-yl)-5H-pyrrolo[2,3-d]pyrimidin-6(7H)-one;

4-(3,3-dimethylazetidin-1-yl)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-((2R,6S)-2,6-dimethylmorpholino)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-(2,2-dimethylmorpholino)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-5-methyl-4-(3-methylazetidin-1-yl)-2-(8-(3,3,4,4,4-pentafluorobutyl)imidazo[1,2-a]pyrazin-6-yl)-5H-pyrrolo[2,3-d]pyrimidin-6(7H)-one;

4-(azetidin-1-yl)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-5-methyl-4-(methylamino)-2-(8-(3,3,4,4,4-pentafluorobutyl)imidazo[1,2-a]pyrazin-6-yl)-5H-pyrrolo[2,3-d]pyrimidin-6(7H)-one;

4-(dimethylamino)-5-(4-fluorophenyl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-4-((2-methoxyethyl)amino)-5-methyl-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-5-methyl-4-morpholino-2-(8-(3,3,4,4,4-pentafluorobutyl)imidazo[1,2-a]pyrazin-6-yl)-5H-pyrrolo[2,3-d]pyrimidin-6(7H)-one;

5-(4-fluorophenyl)-5-methyl-4-(4-methylpiperazin-1-yl)-2-(8-(3,3,4,4,4-pentafluorobutyl)imidazo[1,2-a]pyrazin-6-yl)-5H-pyrrolo[2,3-d]pyrimidin-6(7H)-one;

5-(4-chlorophenyl)-4-(dimethylamino)-2-(imidazo[1,2-a]pyrazin-6-yl)-5-methyl-5H-pyrrolo[2,3-d]pyrimidin-6(7H)-one;

4-((2-Methoxyethyl)amino)-5,5-dimethyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chloro-3-fluorophenyl)-2-(8-ethylimidazo[1,2-a]pyrazin-6-yl)-5-methyl-5H-pyrrolo[2,3-d]pyrimidin-6(7H)-one;

4-amino-5-(4-chloro-3-fluorophenyl)-5-cyclopropyl-2-(8-isobutylimidazo[1,2-a]pyrazin-6-yl)-5H-pyrrolo[2,3-d]pyrimidin-6(7H)-one;

4-amino-5-(4-chlorophenyl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(3,4-difluorophenyl)-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(3,4-difluorophenyl)-2-(8-(3,3,3-trifluoropropyl)imidazo[1,2-a]pyrazin-6-yl)-5H-pyrrolo[2,3-d]pyrimidin-6(7H)-one;

4-amino-5-ethynyl-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-ethyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-isopropyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(1-methyl-1H-tetrazol-5-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chloro-3-fluorophenyl)-5-cyclopropyl-2-(8-propylimidazo[1,2-a]pyrazin-6-yl)-5H-pyrrolo[2,3-d]pyrimidin-6(7H)-one;

4-amino-5-cyclopropyl-5-(4-(trifluoromethoxy)phenyl)-2-(8-(3,3,3-trifluoropropyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-(4-chloro-3-fluorophenyl)-5-cyclopropyl-5H-pyrrolo[2,3-d]pyrimidin-6(7H)-one;

4-amino-2-(8-butylimidazo[1,2-a]pyrazin-6-yl)-5-cyclopropyl-5-(3,4-difluorophenyl)-5H-pyrrolo[2,3-d]pyrimidin-6(7H)-one;

4-amino-5-(5-chloropyridin-2-yl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-(4-chlorophenyl)-5-cyclopropyl-5H-pyrrolo[2,3-d]pyrimidin-6(7H)-one;

4-amino-5-(5-cyclopropyl-1,2,4-oxadiazol-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(3,4-difluorophenyl)-2-(8-propylimidazo[1,2-a]pyrazin-6-yl)-5H-pyrrolo[2,3-d]pyrimidin-6(7H)-one;

4-amino-5-cyclopropyl-5-(3,4-difluorophenyl)-2-(8-isobutylimidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-(5-chloropyridin-2-yl)-5-cyclopropyl-5H-pyrrolo[2,3-d]pyrimidin-6(7H)-one;

4-amino-5-cyclopropyl-5-(5-methoxypyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chloro-2-fluorophenyl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-5-(4-chloro-2-fluorophenyl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(5-(trifluoromethyl)pyridin-2-yl)-2-(8-(3,3,3-trifluoropropyl)imidazo[1,2-a]pyrazin-6-yl)-5H-pyrrolo[2,3-d]pyrimidin-6(7H)-one;

4-amino-5-cyclopropyl-2-(8-propylimidazo[1,2-a]pyrazin-6-yl)-5-(5-(trifluoromethyl)pyridin-2-yl)-5H-pyrrolo[2,3-d]pyrimidin-6(7H)-one;

4-amino-5-cyclopropyl-5-(5-methylpyrazin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(6-methoxypyridin-3-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclobutyl-5-(4-fluorophenyl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclobutyl-5-(4-fluorophenyl)-2-(8-(3,3,3-trifluoropropyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-cyclopropyl-5-(4-(trifluoromethoxy)phenyl)-5H-pyrrolo[2,3-d]pyrimidin-6(7H)-one;

4-amino-5-cyclopropyl-2-(8-(4,4,4-trifluorobutyl)imidazo[1,2-a]pyrazin-6-yl)-5-(4-(trifluoromethoxy)phenyl)-5H-pyrrolo[2,3-d]pyrimidin-6(7H)-one;

4-amino-5-cyclopropyl-5-(2-methylpyrimidin-5-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-chloropyrimidin-2-yl)-5-cyclopropyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chlorophenyl)-5-cyclobutyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(4-chlorophenyl)-5-cyclobutyl-2-(8-(3,3,3-trifluoropropyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-cyclopropyl-5-(5-methylpyrazin-2-yl)-5H-pyrrolo[2,3-d]pyrimidin-6(7H)-one;

4-amino-5-cyclopropyl-5-(5-fluoropyridin-3-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-2-(8-(4,4,4-trifluorobutyl)imidazo[1,2-a]pyrazin-6-yl)-5-(4-(trifluoromethyl)pyridin-2-yl)-5H-pyrrolo[2,3-d]pyrimidin-6(7H)-one;

4-amino-2-(8-butylimidazo[1,2-a]pyrazin-6-yl)-5-cyclopropyl-5-(6-(trifluoromethyl)pyridin-2-yl)-5H-pyrrolo[2,3-d]pyrimidin-6(7H)-one;

4-amino-5-cyclopropyl-5-(5-fluoropyridin-3-yl)-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(5-methylpyrazin-2-yl)-2-(8-(4,4,4-trifluorobutyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-(4-chlorophenyl)-5-cyclobutyl-5H-pyrrolo[2,3-d]pyrimidin-6(7H)-one;

4-amino-5-cyclopropyl-2-(8-(3,3,4,4,4-pentafluorobutyl)imidazo[1,2-a]pyrazin-6-yl)-5-(pyridin-3-yl)-5H-pyrrolo[2,3-d]pyrimidin-6(7H)-one;

4-amino-5-(4-chloro-2-fluorophenyl)-5-cyclopropyl-2-(8-propylimidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-cyclobutyl-5-(4-fluorophenyl)-5H-pyrrolo[2,3-d]pyrimidin-6(7H)-one;

4-amino-5-cyclopropyl-5-(5-fluoro-6-methylpyridin-2-yl)-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(5-fluoro-6-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-chloro-3-methylpyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(6-methylpyrazin-2-yl)-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(6-methylpyrazin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-cyclopropyl-5-(4-(trifluoromethyl)pyridin-2-yl)-5H-pyrrolo[2,3-d]pyrimidin-6(7H)-one;

4-amino-5-cyclopropyl-2-(8-(4,4,4-trifluorobutyl)imidazo[1,2-a]pyrazin-6-yl)-5-(6-(trifluoromethyl)pyridin-2-yl)-5H-pyrrolo[2,3-d]pyrimidin-6(7H)-one;

4-amino-2-(8-butylimidazo[1,2-a]pyrazin-6-yl)-5-(4-chloro-2-fluorophenyl)-5-cyclopropyl-5H-pyrrolo[2,3-d]pyrimidin-6(7H)-one;

4-amino-5-(3-chloro-5-(trifluoromethyl)pyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-(5-chloro-3-fluoropyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-2-(8-butylimidazo[1,2-a]pyrazin-6-yl)-5-(5-chloropyrimidin-2-yl)-5-cyclopropyl-5H-pyrrolo[2,3-d]pyrimidin-6(7H)-one;

4-amino-5-(5-chloropyrimidin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-(5-chloropyrimidin-2-yl)-5-cyclopropyl-2-(8-(3,3,3-trifluoropropyl)imidazo[1,2-a]pyrazin-6-yl)-5H-pyrrolo[2,3-d]pyrimidin-6(7H)-one;

4-amino-5-cyclopropyl-5-(5-fluoro-3-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-cyclopropyl-5-(5-fluoro-4-methylpyridin-2-yl)-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(5-chloro-6-methylpyridin-2-yl)-5-cyclopropyl-2-(8-(4,4,4-trifluorobutyl)imidazo[1,2-a]pyrazin-6-yl)-5H-pyrrolo[2,3-d]pyrimidin-6(7H)-one;

4-amino-5-cyclopropyl-5-(5-(difluoromethyl)pyridin-2-yl)-2-(8-(4,4,4-trifluorobutyl)imidazo[1,2-a]pyrazin-6-yl)-5H-pyrrolo[2,3-d]pyrimidin-6(7H)-one;

4-amino-5-(6-(1,1-difluoroethyl)pyridin-3-yl)-5-methyl-2-(8-(3,3,4,4,4-pentafluorobutyl)imidazo[1,2-a]pyrazin-6-yl)-5H-pyrrolo[2,3-d]pyrimidin-6(7H)-one;

4-amino-5-(6-(1,1-difluoroethyl)pyridin-3-yl)-5-methyl-2-(8-(4,4,4-trifluorobutyl)imidazo[1,2-a]pyrazin-6-yl)-5H-pyrrolo[2,3-d]pyrimidin-6(7H)-one;

Methyl 6-[4-amino-5-(4-fluorophenyl)-5-methyl-6-oxo-6,7-dihydro-5H-pyrrolo[2,3-d]pyrimidin-2-yl]-2-methyl-8-(3,3,4,4,4-pentafluorobutyl)imidazo[1,2-a]pyrazine-3-carboxylate;

4-Amino-5-cyclopropyl-2-(8-(3,3,4,4,4-pentafluorobutyl)imidazo[1,2-a]pyrazin-6-yl)-5-(pyridin-2-yl)-5H-pyrrolo[2,3-d]pyrimidin-6(7H)-one; or 4-Amino-5-cyclopropyl-5-(pyridin-2-yl)-2-(8-(4,4,4-trifluorobutyl)imidazo[1,2-a]pyrazin-6-yl)-5H-pyrrolo[2,3-d]pyrimidin-6(7H)-one, or a pharmaceutically acceptable salt thereof.

15. A method for the treatment of hypertension comprising administering a therapeutically effective amount of the compound of claim 1, or a pharmaceutically acceptable alt thereof, to a patient in need thereof.

16. A method for the treatment of heart failure comprising administering a therapeutically effective amount of the compound of claim 1, or a pharmaceutically acceptable salt thereof, to a patient in need thereof.

17. A pharmaceutical composition comprised of the compound of claim 1, or a pharmaceutically acceptable salt thereof, and a pharmaceutically acceptable carrier.

18. The pharmaceutical composition of claim 17 comprising one or more additional active agents selected from an angiotensin converting enzyme inhibitor, an angiotensin II receptor antagonist, a neutral endopeptidase inhibitor, an aldosterone antagonist, a renin inhibitor, an endothelin receptor antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent or a metabolic altering agent.

* * * * *

UNITED STATES PATENT AND TRADEMARK OFFICE
CERTIFICATE OF CORRECTION

PATENT NO. : 9,796,733 B2
APPLICATION NO. : 15/315428
DATED : October 24, 2017
INVENTOR(S) : Brian T. Campbell et al.

It is certified that error appears in the above-identified patent and that said Letters Patent is hereby corrected as shown below:

In item (75) in the Inventors field:
Please replace "Zhiquang Yang" with --Zhiqiang Yang--

Signed and Sealed this
Twentieth Day of February, 2018

Andrei Iancu
*Director of the United States Patent and Trademark Office*